United States Patent

Hatakeyama et al.

(10) Patent No.: US 11,460,772 B2
(45) Date of Patent: Oct. 4, 2022

(54) POSITIVE RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 341 days.

(21) Appl. No.: 16/717,022

(22) Filed: Dec. 17, 2019

(65) Prior Publication Data

US 2020/0209747 A1  Jul. 2, 2020

(30) Foreign Application Priority Data

Dec. 27, 2018  (JP) .............. JP2018-244436

(51) Int. Cl.
| | | |
|---|---|---|
| *G03F 7/004* | (2006.01) | |
| *G03F 7/039* | (2006.01) | |
| *G03F 7/20* | (2006.01) | |
| *C08L 33/08* | (2006.01) | |
| *C08L 33/14* | (2006.01) | |
| *C08L 25/06* | (2006.01) | |
| *C07D 333/76* | (2006.01) | |
| *C07C 381/12* | (2006.01) | |

(52) U.S. Cl.
CPC ............ *G03F 7/0392* (2013.01); *C08L 25/06* (2013.01); *C08L 33/08* (2013.01); *C08L 33/14* (2013.01); *G03F 7/0045* (2013.01); *G03F 7/0048* (2013.01); *G03F 7/2002* (2013.01); *C07C 381/12* (2013.01); *C07D 333/76* (2013.01)

(58) Field of Classification Search
CPC .... G03F 7/0045; G03F 7/0048; G03F 7/0392; C08F 16/24; C08L 27/10
See application file for complete search history.

(56) References Cited

U.S. PATENT DOCUMENTS

| | | | |
|---|---|---|---|
| 7,482,108 B2 | 1/2009 | Matsumaru et al. | |
| 9,122,153 B2 | 9/2015 | Echigo et al. | |
| 9,176,379 B2 | 11/2015 | Ichikawa et al. | |
| 9,448,475 B2 | 9/2016 | Masuyama et al. | |
| 9,563,123 B2 | 2/2017 | Masuyama et al. | |
| 10,295,904 B2 | 5/2019 | Hatakeyama et al. | |
| 10,495,968 B2 * | 12/2019 | Aqad | C08L 27/10 |
| 10,901,316 B2 * | 1/2021 | Aqad | C08F 16/24 |
| 10,915,021 B2 * | 2/2021 | Fukushima | C08F 212/24 |
| 2009/0311192 A1 * | 12/2009 | Margel | A61K 49/0442 424/9.4 |
| 2015/0374884 A1 * | 12/2015 | Goodrich | A61L 31/048 522/172 |
| 2020/0026188 A1 * | 1/2020 | Maruyama | C08F 220/1808 |

FOREIGN PATENT DOCUMENTS

| | | | | |
|---|---|---|---|---|
| JP | 5-204157 A | 8/1993 | | |
| JP | 2006-45311 A | 2/2006 | | |
| JP | 2006-178317 A | 7/2006 | | |
| JP | 2008-133312 A | 6/2008 | | |
| JP | 2009-181062 A | 8/2009 | | |
| JP | 2011-39266 A | 2/2011 | | |
| JP | 2015-161823 A | 9/2015 | | |
| JP | 2015161823 A | * 9/2015 | ........... G03F 7/0045 | |
| JP | 2015-172746 A | 10/2015 | | |
| JP | 2015-180928 A | 10/2015 | | |
| JP | 5852490 B2 | 2/2016 | | |
| JP | 2017-219836 A | 12/2017 | | |
| JP | 20184812 A | 1/2018 | | |
| WO | 2013/024777 A1 | 2/2013 | | |

OTHER PUBLICATIONS

Machine translation JP 2015-161823 (no date).*

* cited by examiner

*Primary Examiner* — Amanda C. Walke
(74) *Attorney, Agent, or Firm* — WHDA, LLP

(57) ABSTRACT

A positive resist composition comprising a base polymer comprising recurring units containing an optionally substituted amino group and iodine exhibits a high sensitivity, high resolution, low edge roughness (LER, LWR) and small size variation, and forms a pattern of good profile after exposure and development.

12 Claims, No Drawings

POSITIVE RESIST COMPOSITION AND PATTERNING PROCESS

CROSS-REFERENCE TO RELATED APPLICATION

This non-provisional application claims priority under 35 U.S.C. § 119(a) on Patent Application No. 2018-244436 filed in Japan on Dec. 27, 2018, the entire contents of which are hereby incorporated by reference.

TECHNICAL FIELD

This invention relates to a positive resist composition and a patterning process using the composition.

BACKGROUND ART

To meet the demand for higher integration density and operating speed of LSIs, the effort to reduce the pattern rule is in rapid progress. The logic devices used in smart phones or the like drive forward the miniaturization technology. Logic devices of 10-nm node are manufactured in a large scale using a multi-patterning lithography process based on ArF lithography.

In the application of lithography to next 7-nm or 5-nm node devices, the increased expense and overlay accuracy of multi-patterning lithography become tangible. The advent of EUV lithography capable of reducing the number of exposures is desired.

Since the wavelength (13.5 nm) of extreme ultraviolet (EUV) is shorter than $\frac{1}{10}$ of the wavelength (193 nm) of ArF excimer laser, the EUV lithography achieves a high light contrast, from which a high resolution is expectable. Because of the short wavelength and high energy density of EUV, an acid generator is sensitive to a small dose of photons. It is believed that the number of photons available with EUV exposure is $\frac{1}{14}$ of that of ArF exposure. In the EUV lithography, the phenomenon that the edge roughness (LWR) of line patterns or the critical dimension uniformity (CDU) of hole patterns is degraded by a variation of photon number is considered a problem.

Aiming to reduce a photon number variation, an attempt was made to render the resist more absorptive so that the number of photons absorbed in the resist film is increased. Patent Document 1 discloses a halogen-substituted styrene base resin. Among the halogen atoms, iodine is highly absorptive to EUV radiation of wavelength 13.5 nm. Recently Patent Documents 2 to 4 propose to use iodized resins as EUV resist material.

Patent Document 5 proposes a quencher of iodonium carboxylate type having a carboxylate ion bonded to an iodonium cation. Patent Documents 6 and 7 propose the use of hypervalent iodine compounds as the quencher. Patent Document 8 discloses a sulfonium salt of iodized benzoic acid. Since iodine has a large atomic weight, quenchers in the form of iodized compounds are fully effective for suppressing acid diffusion.

For the purpose of suppressing acid diffusion, Patent Documents 9 and 10 disclose resist compositions comprising a polymer comprising amino-containing recurring units. The polymeric amine is effective for suppressing acid diffusion. Moreover, Patent Document 11 proposes a resist composition comprising a polymer comprising recurring units of both acid generator and amine as the base polymer. It is a single component resist material in the sense that both acid generator and quencher are allocated to a common polymer and successful in minimizing the influence of acid diffusion.

The addition of an acid generator capable of generating a bulky acid is an effective means for suppressing acid diffusion. It was then proposed to incorporate in a polymer an acid generator of an onium salt having a polymerizable unsaturated bond. Patent Document 12 discloses a sulfonium salt having a polymerizable unsaturated bond capable of generating a specific sulfonic acid and a similar iodonium salt. Patent Document 13 discloses a sulfonium salt having sulfonic acid directly attached to the backbone.

CITATION LIST

Patent Document 1: JP-A H05-204157
Patent Document 2: JP-A 2015-161823
Patent Document 3: WO 2013/024777
Patent Document 4: JP-A 2018-004812
Patent Document 5: JP 5852490 (U.S. Pat. No. 9,176,379)
Patent Document 6: JP-A 2015-180928 (U.S. Pat. No. 9,563,123)
Patent Document 7: JP-A 2015-172746 (U.S. Pat. No. 9,448,475)
Patent Document 8: JP-A 2017-219836
Patent Document 9: JP-A 2008-133312
Patent Document 10: JP-A 2009-181062
Patent Document 11: JP-A 2011-039266
Patent Document 12: JP-A 2006-045311 (U.S. Pat. No. 7,482,108)
Patent Document 13: JP-A 2006-178317

SUMMARY OF INVENTION

An object of the present invention is to provide a positive resist composition which exhibits a higher sensitivity and resolution than conventional positive resist compositions, low edge roughness and small size variation, and forms a pattern of good profile after exposure and development, and a patterning process using the resist composition.

Making extensive investigations in search for a positive resist material capable of meeting the current requirements including high resolution, low edge roughness and small size variation, the inventors have found the following. To meet the requirements, the acid diffusion distance should be minimized. This invites a lowering of sensitivity and a drop of dissolution contrast, raising the problem that the resolution of a two-dimensional pattern such as hole pattern is reduced. Unexpectedly, when a polymer comprising recurring units containing iodine and amino is used as a base polymer, the efficiency of acid generation is increased by the furtherance of absorption and at the same time, the acid diffusion distance is minimized. Better results are obtainable using the polymer as a base polymer in a chemically amplified positive resist composition.

Further, for improving the dissolution contrast, recurring units having a carboxyl or phenolic hydroxyl group in which the hydrogen is substituted by an acid labile group are incorporated into the base polymer. There is obtained a positive resist composition having a high sensitivity, a significantly increased contrast of alkali dissolution rate before and after exposure, a remarkable acid diffusion-suppressing effect, a high resolution, a good pattern profile after exposure, improved edge roughness, and small size variation. The composition is thus suitable as a fine pattern forming material for the manufacture of VLSIs and photomasks.

In one aspect, the invention provides a positive resist composition comprising a base polymer comprising recurring units containing an optionally substituted amino group and iodine.

Preferably, the recurring units containing an optionally substituted amino group and iodine have the formula (a).

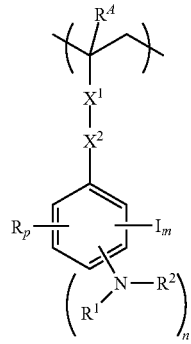

(a)

Herein $R^A$ is hydrogen or methyl, $X^1$ is a single bond, phenylene, naphthylene, or a $C_1$-$C_{12}$ linking group containing an ester bond, ether bond or lactone ring, $X^2$ is a single bond or a $C_1$-$C_{12}$ divalent hydrocarbon group which may contain hydroxyl, ether bond or ester bond, R is hydroxyl, carboxyl, $C_1$-$C_4$ straight or branched alkyl group, $C_1$-$C_4$ straight or branched alkoxy group, $C_2$-$C_5$ straight or branched alkoxycarbonyl group, $C_2$-$C_5$ straight or branched acyl group, $C_2$-$C_5$ straight or branched acyloxy group, or halogen exclusive of iodine, $R^1$ and $R^2$ are each independently hydrogen. $C_1$-$C_6$ alkyl group. $C_2$-$C_6$ alkenyl group, $C_2$-$C_6$ alkynyl group, $C_2$-$C_7$ acyl group, $C_2$-$C_7$ alkoxycarbonyl group, $C_2$-$C_7$ alkenyloxycarbonyl group, $C_2$-$C_7$ alkynyloxycarbonyl group, $C_7$-$C_{12}$ aryloxycarbonyl group, or $C_5$-$C_{12}$ aralkyloxycarbonyl group, $R^1$ and $R^2$ may bond together to form a ring with the nitrogen atom to which they are attached, the ring may contain an ether bond, m is an integer of 1 to 4, n is 1 or 2, p is an integer of 0 to 3, and 2≤m+n+p≤5.

In a preferred embodiment, the base polymer further comprises recurring units having a carboxyl group substituted with an acid labile group and/or recurring units having a phenolic hydroxyl group substituted with an acid labile group, which are more preferably recurring units having the formula (b1) and recurring units having the formula (b2), respectively.

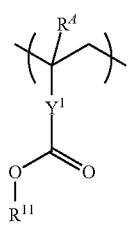

(b1)

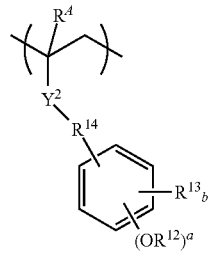

(b2)

Herein $R^A$ is each independently hydrogen or methyl, $Y^1$ is a single bond, phenylene, naphthylene, or a $C_1$-$C_{12}$ linking group containing an ester bond, ether bond or lactone ring, $Y^2$ is a single bond, ester bond or amide bond, $R^{11}$ and $R^{12}$ are each independently an acid labile group, $R^{13}$ is fluorine, trifluoromethyl, cyano, or a $C_1$-$C_6$ alkyl group, $R^{14}$ is a single bond or $C_1$-$C_6$ straight or branched alkanediyl group in which some carbon may be replaced by an ether or ester bond, a is 1 or 2, and b is an integer of 0 to 4.

The base polymer may further comprise recurring units (c) containing an adhesive group selected from the group consisting of hydroxyl, carboxyl, lactone ring, carbonate, thiocarbonate, carbonyl, cyclic acetal, ether bond, ester bond, sulfonic acid ester bond, cyano, amide, —O—C(=O)—S—, and —O—C(=O)—NH—.

The base polymer may further comprise recurring units of at least one type selected from recurring units having the formulae (d1) to (d3).

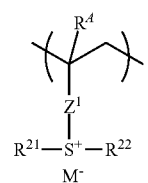

(d1)

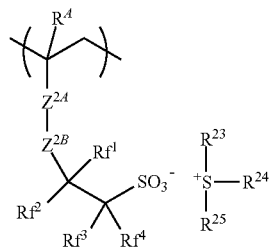

(d2)

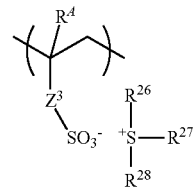

(d3)

Herein $R^A$ is each independently hydrogen or methyl; $Z^1$ is a single bond, phenylene, —O—$Z^{11}$—, —C(=O)—O—$Z^{11}$— or —C(O)—NH—$Z^{11}$—, $Z^{11}$ is a $C_1$-$C_6$ alkanediyl group, $C_2$-$C_6$ alkenediyl group or phenylene group, which may contain a carbonyl moiety, ester bond, ether bond or hydroxyl moiety; $Z^{2A}$ is a single bond or ester bond, $Z^{2B}$ is a single bond or $C_1$-$C_{12}$ divalent group which may contain an ester bond, ether bond, lactone ring, bromine or iodine: $Z^3$ is a single bond, methylene, ethylene, phenylene, fluorinated phenylene, —O—$Z^{31}$—, —C(O)—O—$Z^{31}$— or —C(=O)—NH—$Z^{31}$—, $Z^{31}$ is a $C_1$-$C_6$ alkanediyl group, $C_2$-$C_6$ alkenediyl group or phenylene group, which may contain a carbonyl moiety, ester bond, ether bond or hydroxyl moiety; $Rf^1$ to $Rf^4$ are each independently hydrogen, fluorine or trifluoromethyl, at least one thereof being fluorine; $R^{21}$ to $R^{28}$ are each independently a $C_1$-$C_{20}$ monovalent hydrocarbon group which may contain a heteroatom, any two of $R^{23}$, $R^{24}$ and R or any two of $R^{26}$, $R^{27}$ and $R^{28}$ may bond together to form a ring with the sulfur atom to which they are attached; and $M^-$ is a non-nucleophilic counter ion.

In a preferred embodiment, the resist composition may further comprise an acid generator, organic solvent, quencher, and/or surfactant.

In another aspect, the invention provides a pattern forming process comprising the steps of applying the resist composition defined above to form a resist film on a substrate, exposing the resist film to high-energy radiation, and developing the exposed resist film in a developer.

The high-energy radiation is typically i-line, KrF excimer laser, ArF excimer laser, EB or EUV of wavelength 3 to 15 nm.

Advantageous Effects of Invention

The positive resist composition has a high decomposition efficiency of the acid generator, a remarkable acid diffusion-suppressing effect, a high sensitivity, and a high resolution, and forms a pattern of good profile with improved edge roughness and size variation after exposure and development. By virtue of these properties, the resist composition is fully useful in commercial application and best suited as a micropatterning to material for photomasks by EB lithography or for VLSIs by EB or EUV lithography.

The resist composition may be used not only in the lithography for forming semiconductor circuits, but also in the formation of mask circuit patterns, micromachines, and thin-film magnetic head circuits.

DESCRIPTION OF EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. Me stands for methyl, and Ac for acetyl.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity Positive Resist Composition One embodiment of the invention is a positive resist composition comprising a base polymer comprising recurring units containing an optionally substituted amino group and iodine. Preferably, the recurring units containing an optionally substituted amino group and iodine have the formula (a). The recurring units having formula (a) are also referred to as recurring units (a).

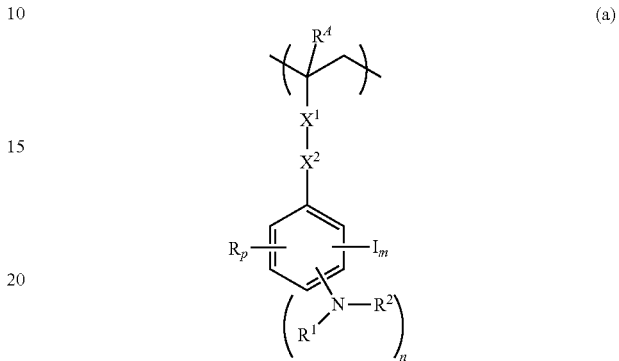

(a)

In formula (a), $R^A$ is hydrogen or methyl. $X^1$ is a single bond, phenylene, naphthylene, or a $C_1$-$C_{12}$ linking group containing an ester bond, ether bond or lactone ring. $X^2$ is a single bond or a $C_1$-$C_{12}$ divalent hydrocarbon group which may contain hydroxyl, ether bond or ester bond. R is hydroxyl, carboxyl, $C_1$-$C_4$ straight or branched alkyl group, $C_1$-$C_4$ straight or branched alkoxy group, $C_2$-$C_5$ straight or branched alkoxycarbonyl group, $C_2$-$C_5$ straight or branched acyl group, $C_2$-$C_5$ straight or branched acyloxy group, or halogen exclusive of iodine. $R^1$ and $R^2$ are each independently hydrogen, $C_1$-$C_6$ alkyl group, $C_2$-$C_6$ alkenyl group, $C_2$-$C_6$ alkynyl group, $C_2$-$C_7$ acyl group, $C_2$-$C_7$ alkoxycarbonyl group, $C_2$-$C_7$ alkenyloxycarbonyl group, $C_2$-$C_7$ alkynyloxycarbonyl group, $C_7$-$C_{12}$ aryloxycarbonyl group, or $C_8$-$C_{12}$ aralkyloxycarbonyl group, $R^1$ and $R^2$ may bond together to form a ring with the nitrogen atom to which they are attached, the ring may contain an ether bond, m is an integer of 1 to 4, n is 1 or 2, p is an integer of 0 to 3, and $2 \le m+n+p \le 5$.

The $C_1$-$C_{12}$ divalent hydrocarbon group represented by $X^2$ may be straight, branched or cyclic. Examples thereof include straight or branched alkanediyl groups such as methylene, ethylene, propane-1,2-diyl, propane-1,3-diyl, butane-1,2-diyl, butane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,1-diyl, dodecane-1,12-diyl; $C_3$-$C_{10}$ cyclic alkanediyl groups such as cyclopentanediyl, cyclohexanediyl, norbornanediyl, and adamantanediyl; and arylene groups such as phenylene and naphthylene, and mixtures thereof.

Examples of the $C_1$-$C_4$ straight or branched alkyl group represented by R include methyl, ethyl, propyl, isopropyl, n-butyl, isobutyl, sec-butyl, and tert-butyl.

Examples of the $C_1$-$C_4$ straight or branched alkoxy group represented by R include methoxy, ethoxy, n-propyloxy, isopropyloxy, n-butyloxy, isobutyloxy, sec-butyloxy, and tert-butyloxy.

Examples of the $C_2$-$C_5$ straight or branched alkoxycarbonyl group represented by R include methoxycarbonyl, ethoxycarbonyl, n-propyloxycarbonyl, isopropyloxycarbonyl, n-butyloxycarbonyl, isobutyloxycarbonyl, sec-butyloxycarbonyl, and tert-butyloxycarbonyl.

Examples of the $C_2$-$C_5$ straight or branched acyl group represented by R include acetyl, propionyl, butyryl and isobutyryl.

Examples of the $C_2$-$C_5$ straight or branched acyloxy group represented by R include methylcarbonyloxy, ethylcarbonyloxy, n-propylcarbonyloxy, isopropylcarbonyloxy, n-butylcarbonyloxy, isobutylcarbonyloxy, sec-butylcarbonyloxy, and tert-butylcarbonyloxy.

The $C_1$-$C_6$ alkyl group represented by $R^1$ and $R^2$ may be straight, branched or cyclic and examples thereof include methyl, ethyl, propyl, isopropyl, cyclopropyl n-butyl, isobutyl, sec-butyl, tert-butyl, cyclobutyl, n-pentyl, neopentyl, cyclopentyl, n-hexyl, and cyclohexyl.

The $C_2$-$C_6$ alkenyl group represented by $R^1$ and $R^2$ may be straight, branched or cyclic and examples thereof include vinyl, 1-propenyl, 2-propenyl, butenyl, pentenyl, hexenyl, and cyclohexenyl.

The $C_2$-$C_6$ alkynyl group represented by $R^1$ and $R^2$ may be straight, branched or cyclic and examples thereof include ethynyl, 1-propynyl, 2-propynyl, butynyl, pentynyl, hexynyl, and cyclohexynyl.

Examples of the $C_2$-$C_7$ acyl group represented by $R^1$ and $R^2$ include acetyl, propionyl, butyryl and isobutyryl.

The $C_2$-$C_7$ alkoxycarbonyl group represented by $R^1$ and $R^2$ may be straight, branched or cyclic and examples thereof include methoxycarbonyl, ethoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, neopentyloxycarbonyl, tert-pentyloxycarbonyl, cyclopentyloxycarbonyl, n-hexyloxycarbonyl, and cyclohexyloxycarbonyl.

The $C_2$-$C_7$ alkenyloxycarbonyl group represented by $R^1$ and $R^2$ may be straight, branched or cyclic and examples thereof include vinyloxycarbonyl, 1-propenyloxycarbonyl, 2-propenyloxycarbonyl, butenyloxycarbonyl, pentenyloxycarbonyl, hexenyloxycarbonyl, and cyclohexenyloxycarbonyl.

The $C_2$-$C_7$ alkynyloxycarbonyl group represented by $R^1$ and $R^2$ may be straight, branched or cyclic and examples thereof include ethynyloxycarbonyl, 1-propynyloxycarbonyl, 2-propynyloxycarbonyl, butynyloxycarbonyl, pentynyloxycarbonyl, hexynyloxycarbonyl, and cyclohexynyloxycarbonyl.

Examples of the $C_7$-$C_{12}$ aryloxycarbonyl group represented by $R^1$ and $R^2$ include phenyloxycarbonyl, tolyloxycarbonyl, xylyloxycarbonyl, 1-naphthyloxycarbonyl, and 2-naphthyloxycarbonyl.

Examples of the $C_8$-$C_{12}$ aralkyloxycarbonyl group represented by $R^1$ and $R^2$ include benzyloxycarbonyl and phenethyloxycarbonyl.

Inter alia, $R^1$ and $R^2$ are preferably selected from hydrogen, $C_1$-$C_6$ alkyl groups, $C_2$-$C_7$ acyl groups, $C_2$-$C_7$ alkoxycarbonyl groups, $C_2$-$C_7$ alkenyloxycarbonyl groups, and $C_5$-$C_{12}$ aralkyloxycarbonyl groups.

Examples of the monomer from which recurring units (a) are derived are shown below, but not limited thereto. Herein $R^A$ is as defined above.

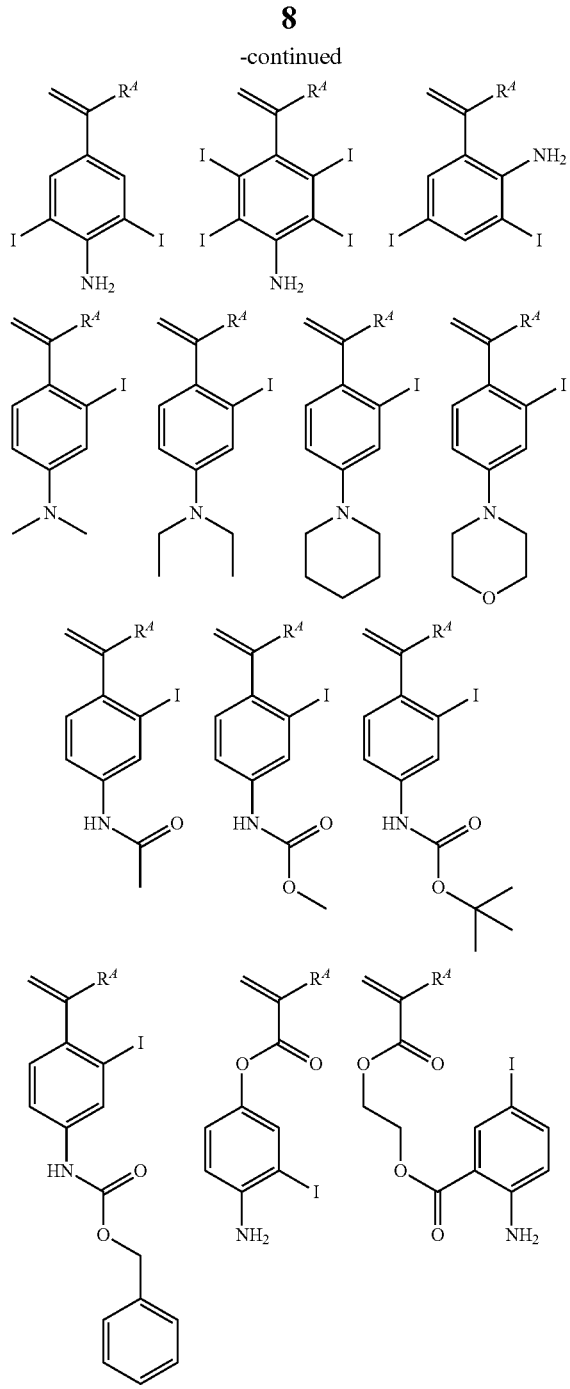

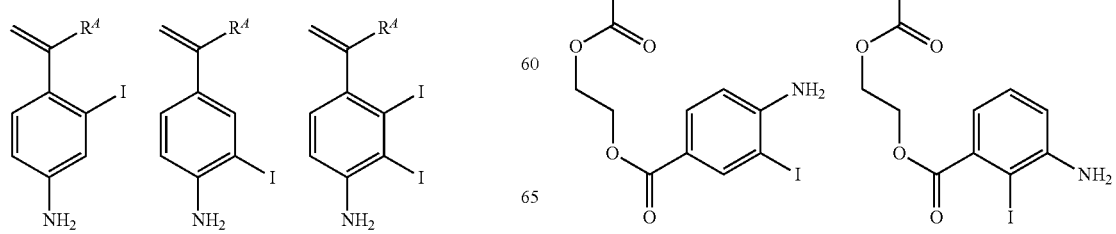

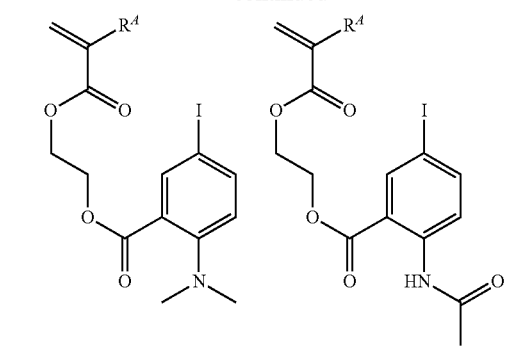
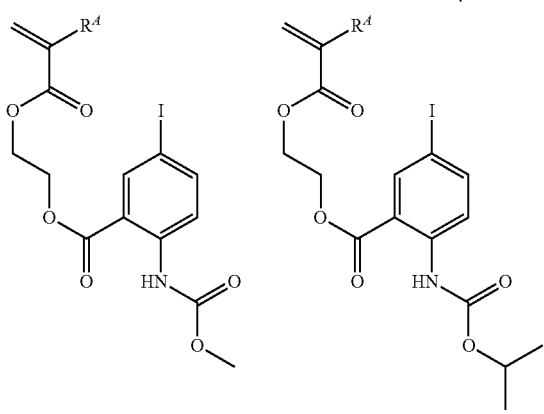
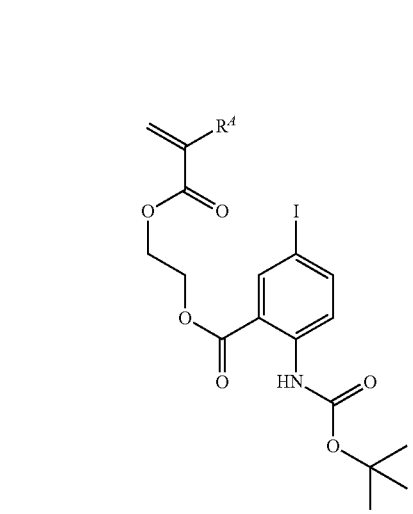
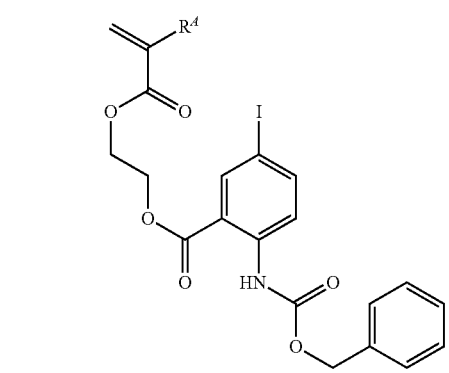

-continued

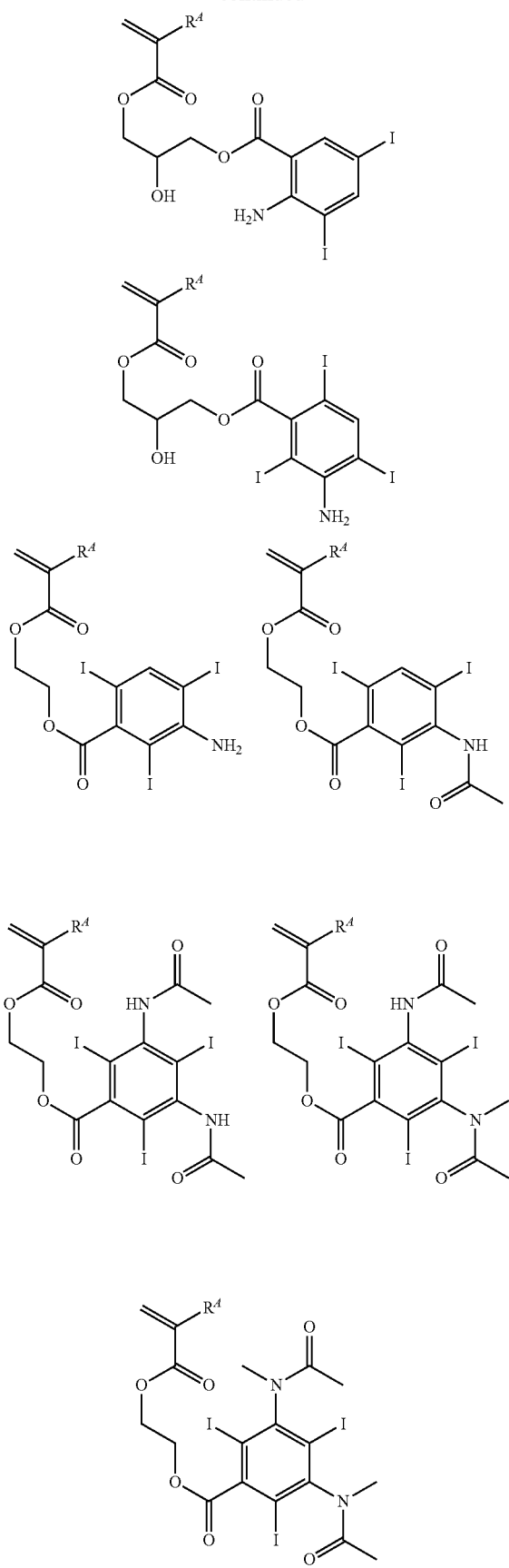

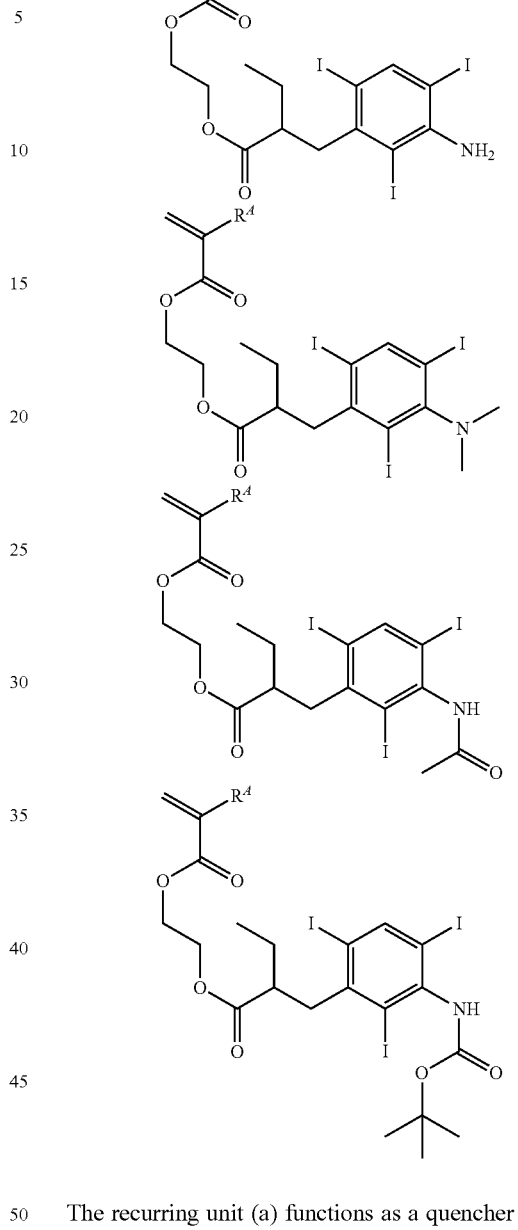

The recurring unit (a) functions as a quencher due to the inclusion of amino group. In this sense, the base polymer may be referred to as a quencher-bound polymer. The quencher-bound polymer has the advantages of a remarkable acid diffusion-suppressing effect and improved resolution. In addition, since the recurring unit (a) contains highly absorptive iodine atom, it generates secondary electrons to promote decomposition of the acid generator during exposure, leading to a high sensitivity. As a result, a high sensitivity, high resolution, and low LWR or improved CDU are achieved at the same time.

For further enhancing dissolution contrast, the base polymer may further comprise recurring units having a carboxyl group in which the hydrogen is substituted by an acid labile group, referred to as recurring units (b1), hereinafter, and/or recurring units having a phenolic hydroxyl group in which the hydrogen is substituted by an acid labile group, referred to as recurring units (b2), hereinafter.

The preferred recurring units (b1) and (b2) are recurring units having the formulae (b1) and (b2), respectively.

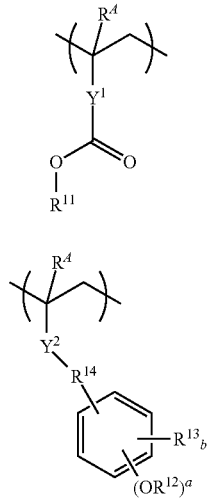

In formulae (b1) and (b2), $R^4$ is each independently hydrogen or methyl. $Y^1$ is a single bond, phenylene, naphthylene, or a $C_1$-$C_{12}$ linking group containing an ester bond, ether bond or lactone ring. $Y^2$ is a single bond, ester bond or amide bond. $R^{11}$ and $R^{12}$ each are an acid labile group. $R^{13}$ is fluorine, trifluoromethyl, cyano or a $C_1$-$C_6$ alkyl group. $R^{14}$ is a single bond or a $C_1$-$C_6$ straight or branched alkanediyl group in which some carbon may be replaced by an ether bond or ester bond. The subscript "a" is 1 or 2, and b is an integer of 0 to 4.

Examples of the monomer from which recurring units (b1) are derived are shown below, but not limited thereto. Herein $R^4$ and $R^{11}$ are as defined above.

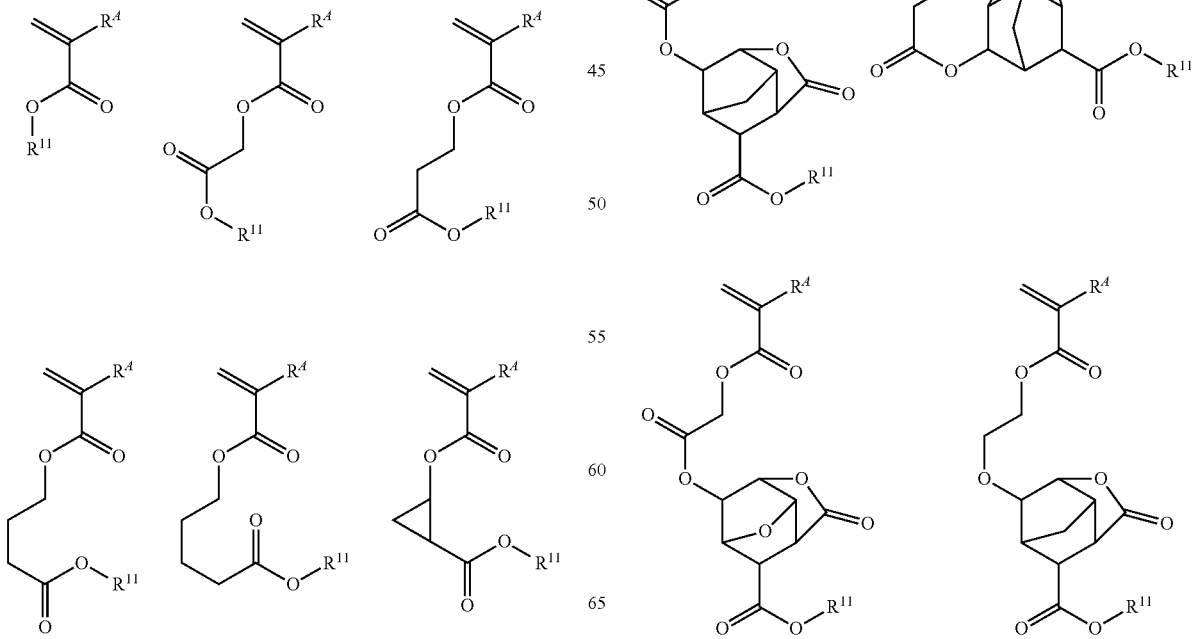

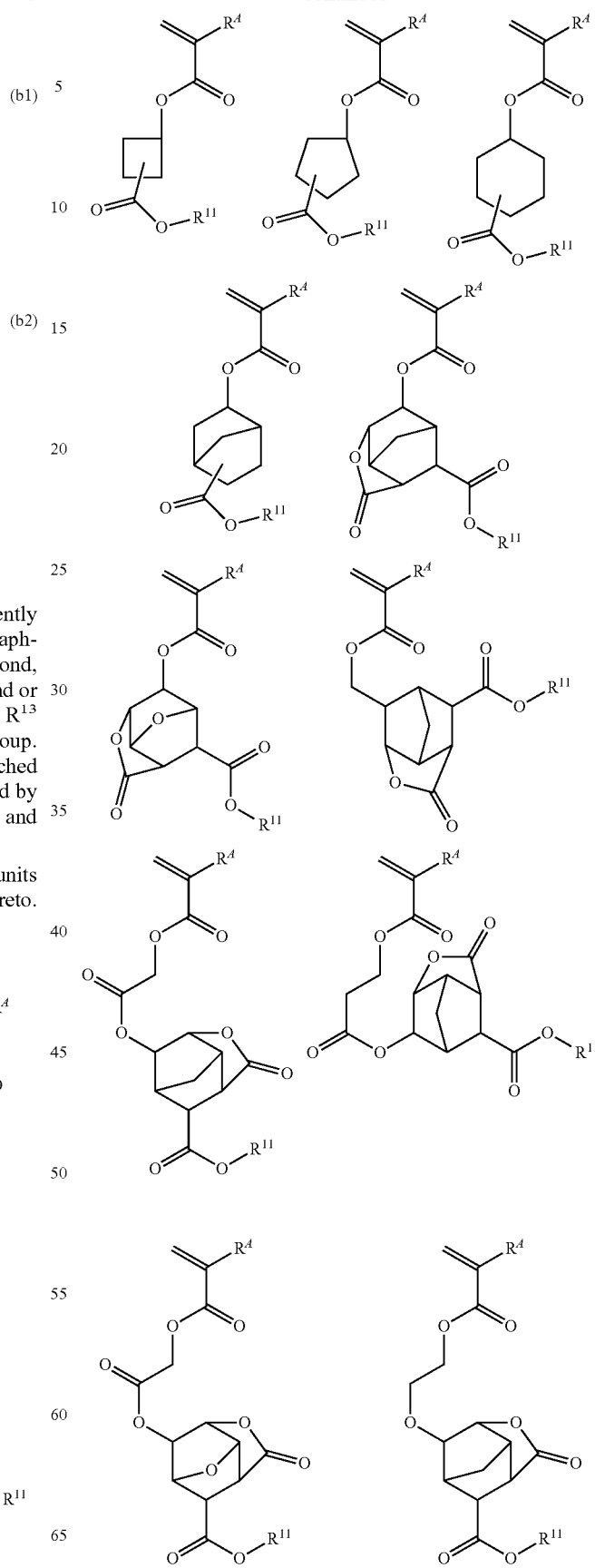

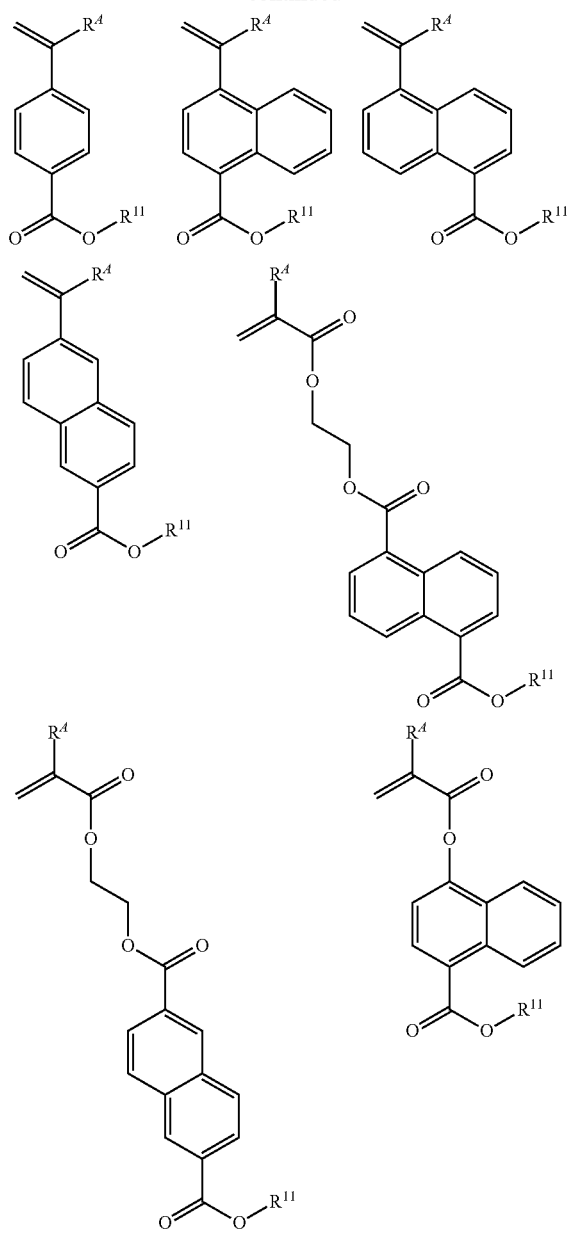
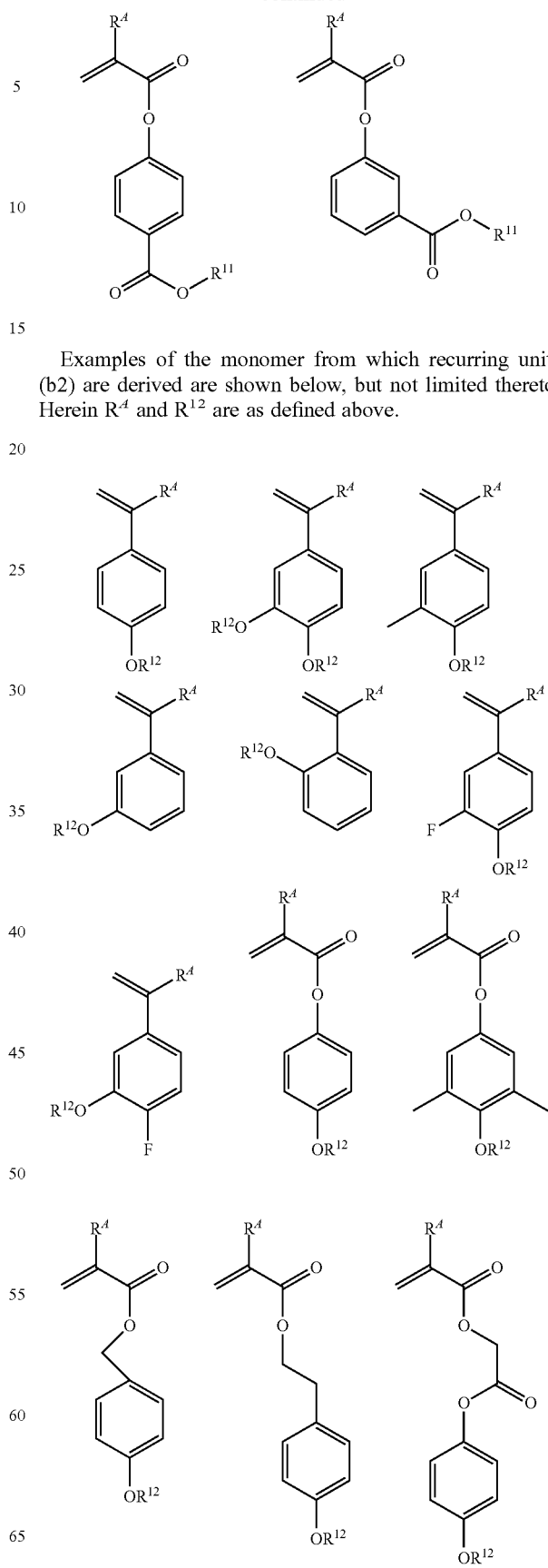
Examples of the monomer from which recurring units (b2) are derived are shown below, but not limited thereto. Herein $R^A$ and $R^{12}$ are as defined above.

-continued

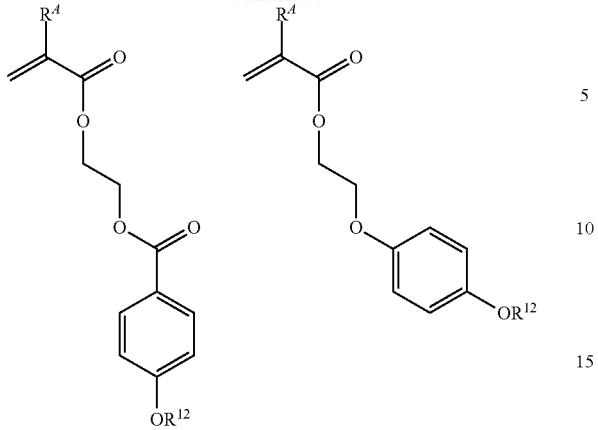

The acid labile groups represented by $R^{11}$ and $R^{12}$ may be selected from a variety of such groups, for example, groups of the following formulae (AL-1) to (AL-3).

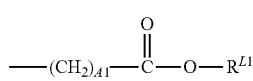 (AL-1)

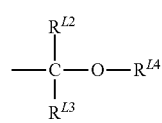 (AL-2)

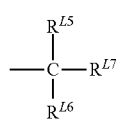 (AL-3)

In formula (AL-1), $R^{L1}$ is a $C_4$-$C_{20}$, preferably $C_4$-$C_5$ tertiary hydrocarbon group, a trialkylsilyl group in which each alkyl moiety has 1 to 6 carbon atoms, a $C_4$-$C_{20}$ alkyl group containing a carbonyl moiety or ester bond, or a group of formula (AL-3). A1 is an integer of 0 to 6.

The tertiary hydrocarbon group may be branched or cyclic, and examples thereof include tert-butyl, tert-pentyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-tetrahydropyranyl, and 2-tetrahydrofuranyl. Examples of the trialkylsilyl group include trimethylsilyl, triethylsilyl, and dimethyl-tert-butylsilyl. The alkyl group containing a carbonyl moiety or ester bond may be straight, branched or cyclic, preferably cyclic and examples thereof include 3-oxocyclohexyl, 4-methyl-2-oxooxan-4-yl, and 5-methyl-2-oxooxolan-5-yl.

Examples of the acid labile group having formula (AL-1) include tert-butoxycarbonyl, tert-butoxycarbonylmethyl, tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Other examples of the acid labile group having formula (AL-1) include groups having the formulae (AL-1)-1 to (AL-1)-10.

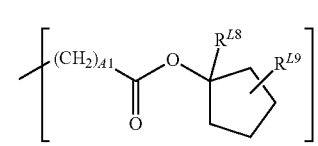 (AL-1)-1

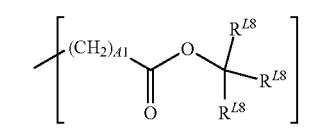 (AL-1)-2

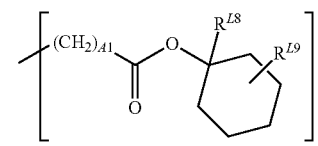 (AL-1)-3

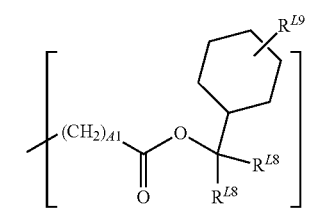 (AL-1)-4

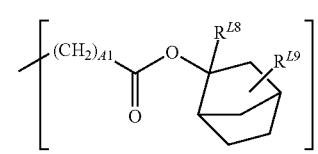 (AL-1)-5

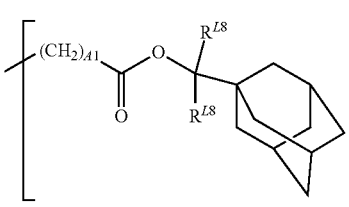 (AL-1)-6

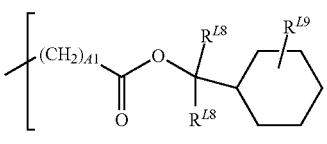 (AL-1)-7

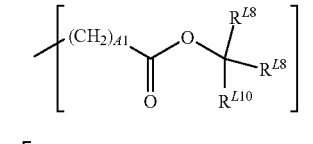 (AL-1)-8

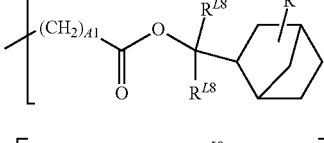 (AL-1)-9

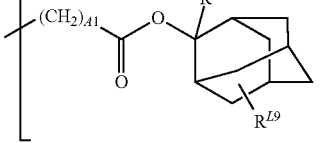 (AL-1)-10

Herein A1 is as defined above. $R^{L8}$ is each independently a $C_1$-$C_{10}$ alkyl group or $C_6$-$C_{20}$ aryl group. $R^{L9}$ is hydrogen or a $C_1$-$C_{10}$ alkyl group. $R^{L10}$ is a $C_1$-$C_{10}$ alkyl group or $C_6$-$C_{20}$ aryl group. The alkyl group may be straight, branched or cyclic.

In formula (AL-2), $R^{L2}$ and $R^{L3}$ are each independently hydrogen or a $C_1$-$C_{18}$, preferably $C_1$-$C_{10}$ alkyl group. The alkyl group may be straight, branched or cyclic and examples thereof include methyl, ethyl, propyl, isopropyl, n-butyl, sec-butyl, tert-butyl, cyclopentyl, cyclohexyl, 2-ethylhexyl and n-octyl. $R^{L4}$ is a $C_1$-$C_{18}$, preferably $C_1$-$C_{10}$ monovalent hydrocarbon group which may contain a heteroatom such as oxygen. The monovalent hydrocarbon group may be straight, branched or cyclic and typical examples thereof include $C_1$-$C_{18}$ alkyl groups, in which some hydrogen may be substituted by hydroxyl, alkoxy, oxo, amino or alkylamino. Examples of the substituted alkyl group are shown below.

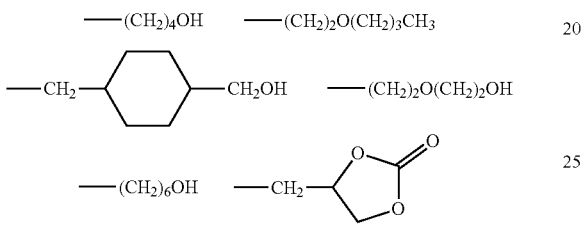

A pair of $R^{L2}$ and $R^{L3}$, $R^{L2}$ and $R^{L4}$, or $R^{L3}$ and $R^{L4}$ may bond together to form a ring with the carbon atom or carbon and oxygen atoms to which they are attached. A ring-forming combination of $R^{L2}$ and $R^{L3}$, $R^{L2}$ and $R^{L4}$, or $R^{L3}$ and $R^{L4}$ is each independently a $C_1$-$C_{18}$, preferably $C_1$-$C_{10}$ straight or branched alkanediyl group. The ring thus formed is preferably of 3 to 10, more preferably 4 to 10 carbon atoms.

Of the acid labile groups having formula (AL-2), suitable straight or branched groups include those having formulae (AL-2)-1 to (AL-2)-69, but are not limited thereto.

 (AL-2)-1

 (AL-2)-2

 (AL-2)-3

 (AL-2)-4

 (AL-2)-5

 (AL-2)-6

 (AL-2)-7

 (AL-2)-8

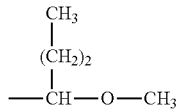 (AL-2)-9

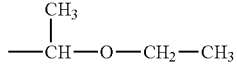 (AL-2)-10

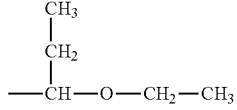 (AL-2)-11

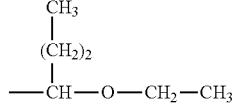 (AL-2)-12

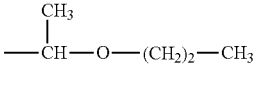 (AL-2)-13

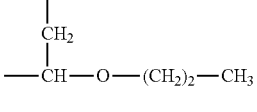 (AL-2)-14

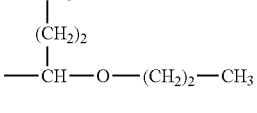 (AL-2)-15

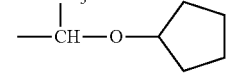 (AL-2)-16

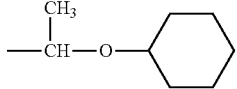 (AL-2)-17

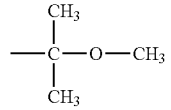 (AL-2)-18

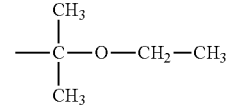 (AL-2)-19

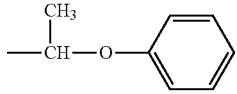 (AL-2)-20

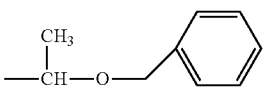 (AL-2)-21

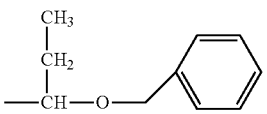 (AL-2)-22

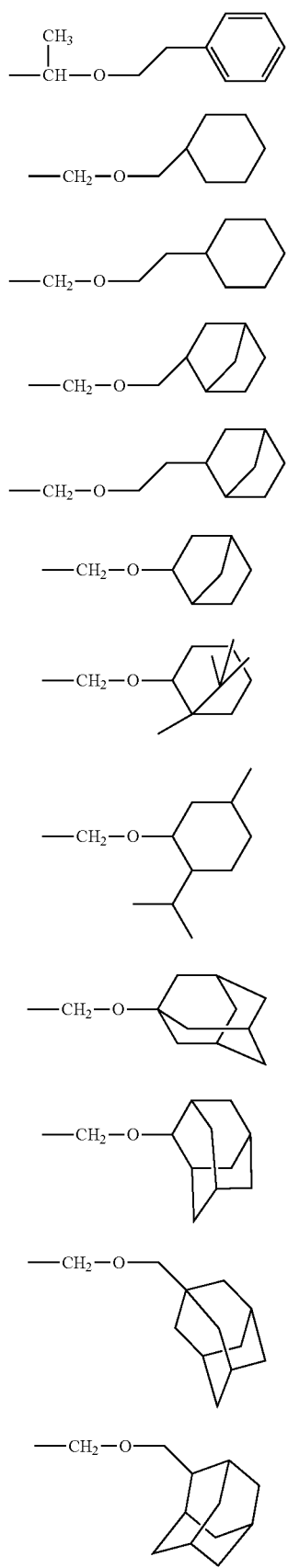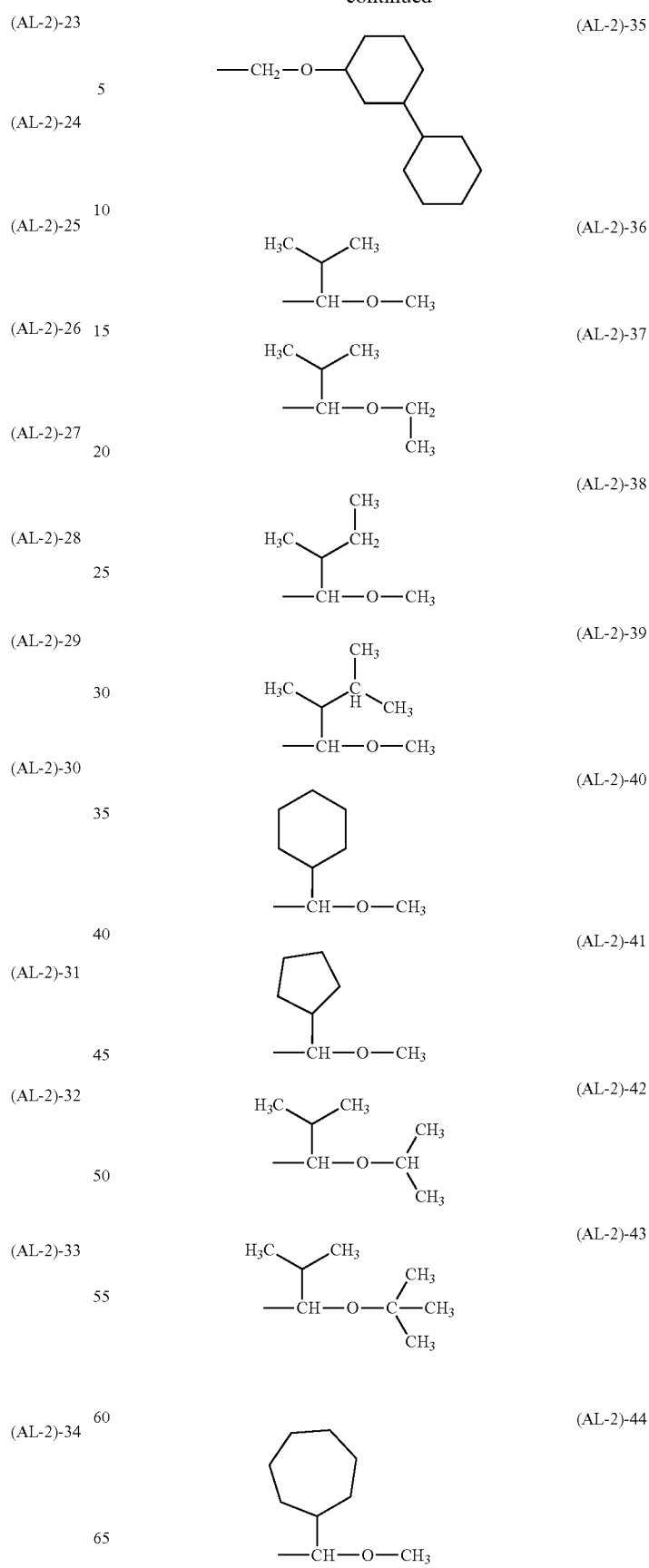

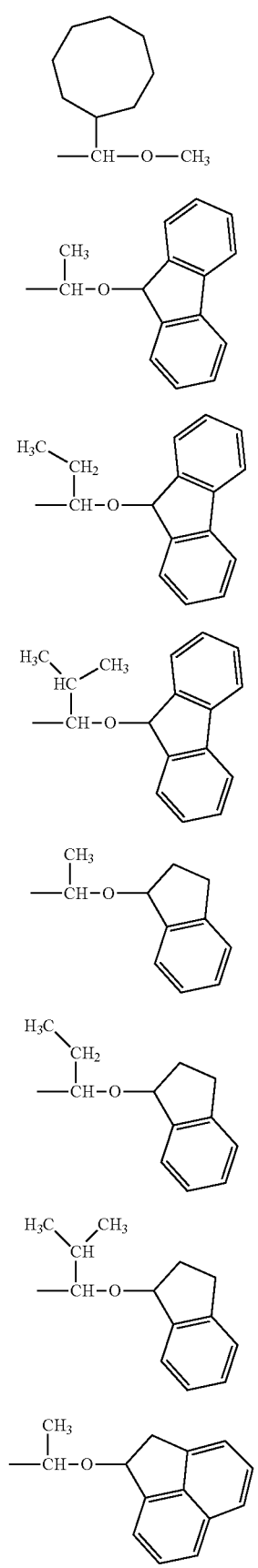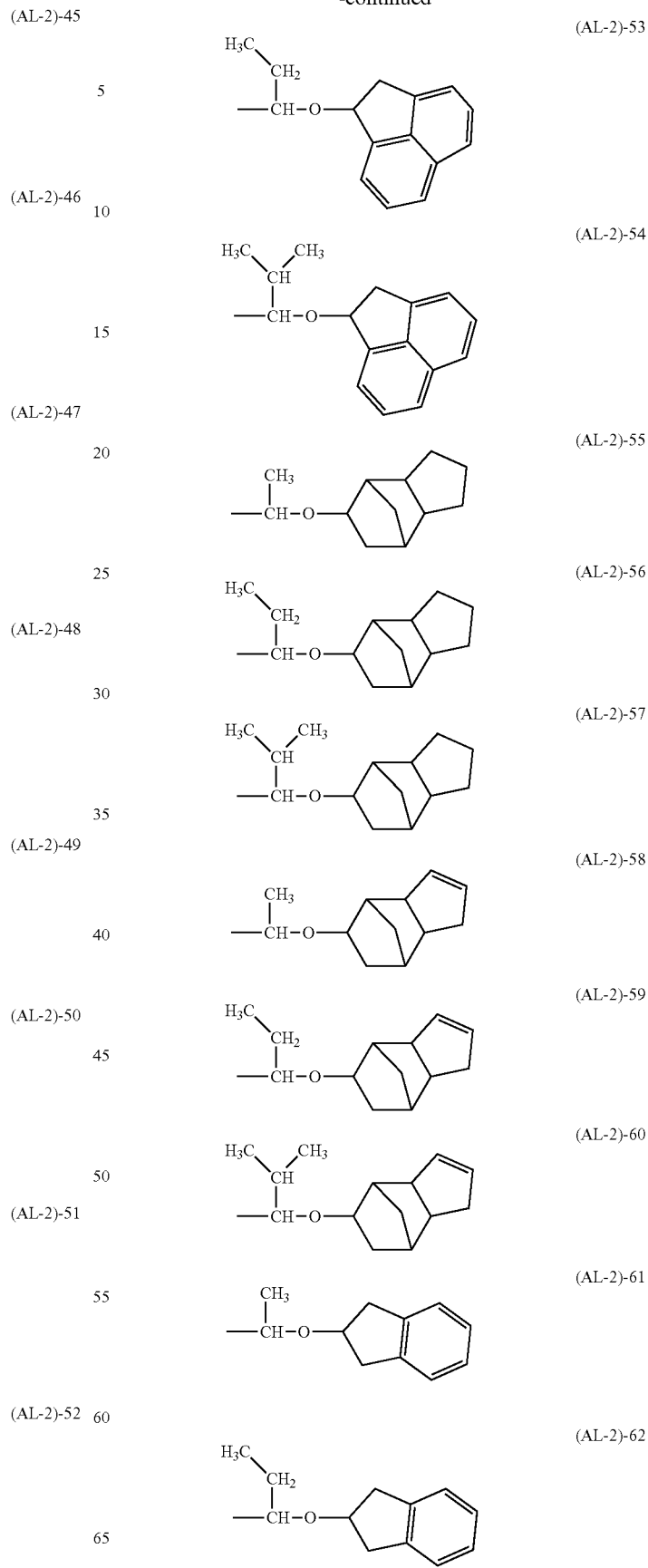

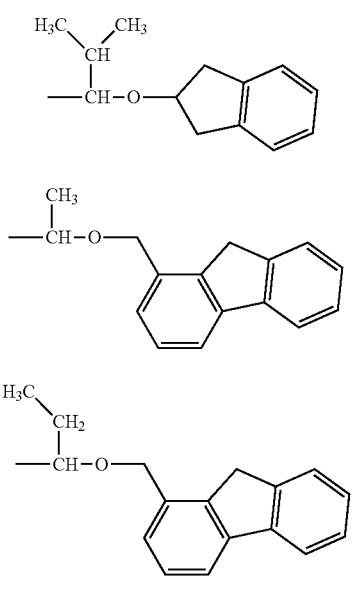
(AL-2)-63

(AL-2)-64

(AL-2)-65

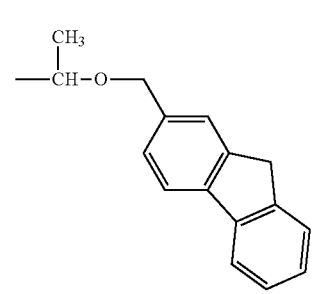
(AL-2)-66

(AL-2)-67

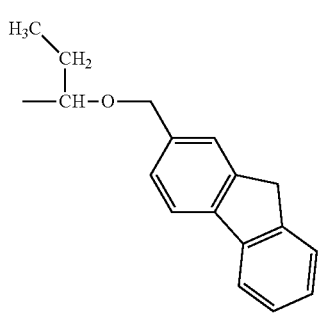
(AL-2)-68

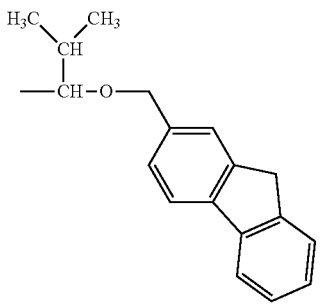
(AL-2)-69

Of the acid labile groups having formula (AL-2), suitable cyclic groups include tetrahydrofuran-2-yl 2-methyltetrahydrofuran-2-yl, tetrahydropyran-2-yl, and 2-methyltetrahydropyran-2-yl.

Also included are acid labile groups having the following formulae (AL-2a) and (AL-2b). The base polymer may be crosslinked within the molecule or between molecules with these acid labile groups.

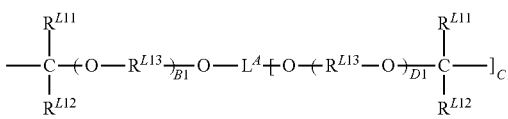
(AL-2a)

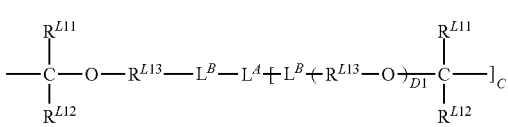
(AL-2b)

In formulae (AL-2a) and (AL-2b), $R^{L11}$ and $R^{L12}$ are each independently hydrogen or a $C_1$-$C_8$ alkyl group which may be straight, branched or cyclic. Also, $R^{L11}$ and $R^{L12}$ may bond together to form a ring with the carbon atom to which they are attached, and in this case, $R^{L11}$ and $R^{L12}$ are each independently a $C_1$-$C_8$ straight or branched alkanediyl group. $R^{L13}$ is each independently a $C_1$-$C_{10}$ alkanediyl group which may be straight, branched or cyclic. B1 and D1 are each independently an integer of 0 to 10, preferably 0 to 5, and C1 is an integer of 1 to 7, preferably 1 to 3.

In formulae (AL-2a) and (AL-2b), $L^A$ is a (Cl+1)-valent $C_1$-$C_{50}$ aliphatic or alicyclic saturated hydrocarbon group, aromatic hydrocarbon group or heterocyclic group. In these groups, some carbon may be replaced by a heteroatom-containing moiety, or some carbon-bonded hydrogen may be substituted by a hydroxyl, carboxyl acyl moiety or fluorine. $L^A$ is preferably a $C_1$-$C_{20}$ alkanediyl, alkanetriyl, alkanetetrayl, or $C_6$-$C_{30}$ arylene group. The alkanediyl, alkanetriyl, and alkanetetrayl groups may be straight, branched or cyclic. $L^B$ is —CO—O—, —NHCO—O— or —NHCONH—.

Examples of the crosslinking acetal groups having formulae (AL-2a) and (AL-2b) include groups having the formulae (AL-2)-70 to (AL-2)-77.

(AL-2)-70

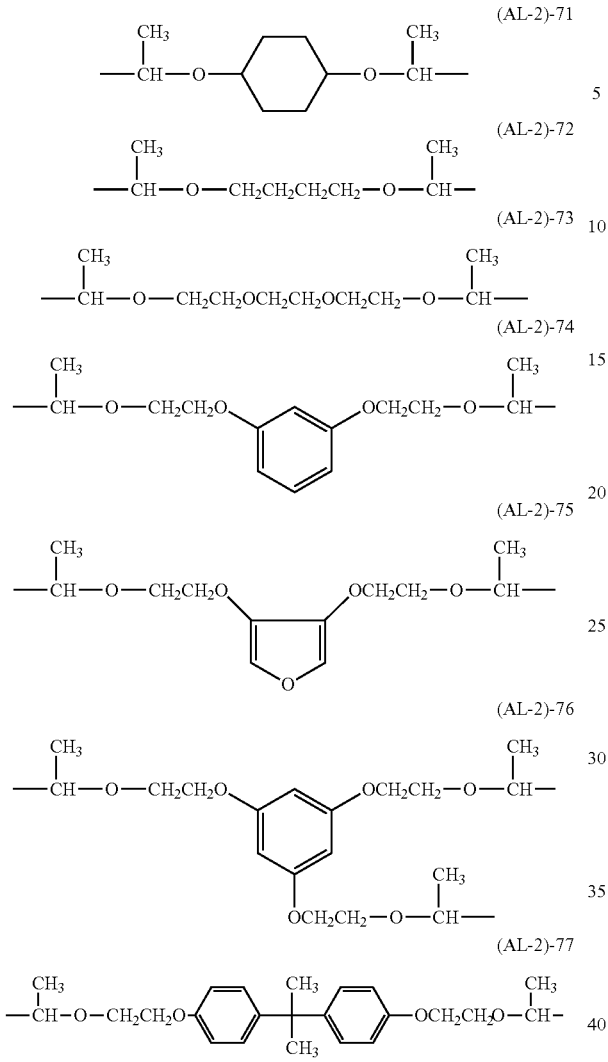

(AL-2)-71
(AL-2)-72
(AL-2)-73
(AL-2)-74
(AL-2)-75
(AL-2)-76
(AL-2)-77

In formula (AL-3), $R^{L5}$, $R^{L6}$ and $R^{L7}$ are each independently a $C_1$-$C_{20}$ monovalent hydrocarbon group which may contain a heteroatom such as oxygen, sulfur, nitrogen or fluorine. The monovalent hydrocarbon group may be straight, branched or cyclic and examples thereof include $C_1$-$C_{20}$ alkyl groups and $C_2$-$C_{20}$ alkenyl groups. A pair of $R^{L5}$ and $R^{L6}$, $R^{L5}$ and $R^{L7}$, or $R^{L6}$ and $R^{L7}$ may bond together to form a $C_3$-$C_{20}$ aliphatic ring with the carbon atom to which they are attached.

Examples of the group having formula (AL-3) include tert-butyl, 1,1-diethylpropyl, 1-ethylnorbornyl, 1-methylcyclohexyl, 1-methylcyclopentyl, 2-(2-methyl)adamantyl, 2-(2-ethyl)adamantyl, and tert-pentyl.

Examples of the group having formula (AL-3) also include groups having the formulae (AL-3)-1 to (AL-3)-18.

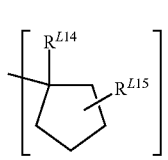

(AL-3)-1

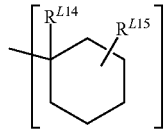

(AL-3)-2

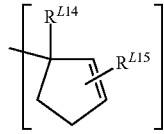

(AL-3)-3

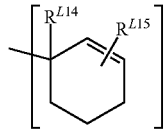

(AL-3)-4

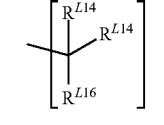

(AL-3)-5

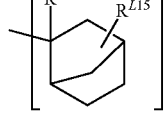

(AL-3)-6

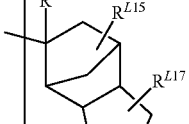

(AL-3)-7

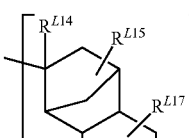

(AL-3)-8

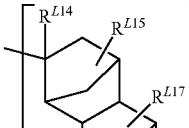

(AL-3)-9

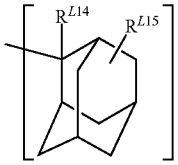

(AL-3)-10

(AL-3)-11
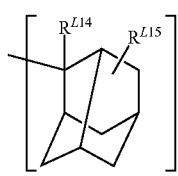

(AL-3)-12

(AL-3)-13
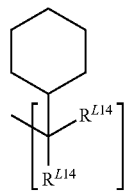

(AL-3)-14
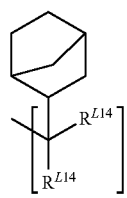

(AL-3)-15
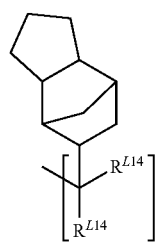

(AL-3)-16
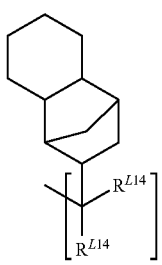

(AL-3)-17
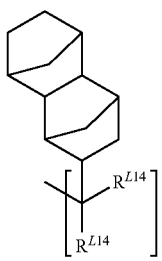

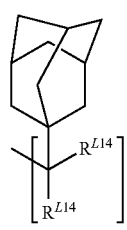

(AL-3)-18
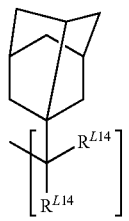

In formulae (AL-3)-1 to (AL-3)-18, $R^{L14}$ is each independently a $C_1$-$C_5$ alkyl group or $C_6$-$C_{20}$ aryl group. $R^{L15}$ and $R^{L17}$ are each independently hydrogen or a $C_1$-$C_{20}$ alkyl group. $R^{L16}$ is a $C_5$-$C_2$ aryl group. The alkyl group may be straight, branched or cyclic. Typical of the aryl group is phenyl.

Other examples of the group having formula (AL-3) include groups having the formulae (AL-3)-19 and (AL-3)-20. The base polymer may be crosslinked within the molecule or between molecules with these acid labile groups.

(AL-3)-19
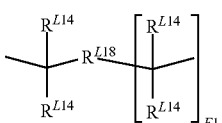

(AL-3)-20
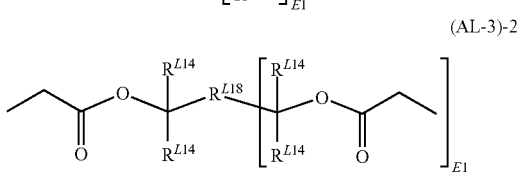

In formulae (AL-3)-19 and (AL-3)-20, $R^{L14}$ is as defined above. $R^{L18}$ is a (E1+1)-valent $C_1$-$C_{20}$ alkanediyl group or (E1+1)-valent $C_6$-$C_{20}$ arylene group, which may contain a heteroatom such as oxygen, sulfur or nitrogen. The alkanediyl group may be straight, branched or cyclic. E1 is an integer of 1 to 3.

Examples of the monomer from which recurring units containing an acid labile group of formula (AL-3) are derived include (meth)acrylates having an exo-form structure represented by the formula (AL-3)-21.

(AL-3)-21
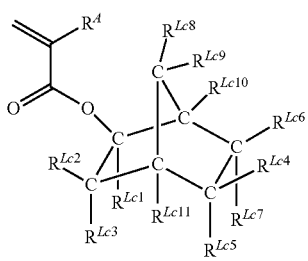

In formula (AL-3)-21, $R^A$ is as defined above. $R^{Lc1}$ is a $C_1$-$C_8$ alkyl group or an optionally substituted $C_6$-$C_{20}$ aryl group; the alkyl group may be straight, branched or cyclic. $R^{Lc2}$ to $R^{Lc11}$ are each independently hydrogen or a $C_1$-$C_{15}$ monovalent hydrocarbon group which may contain a heteroatom; oxygen is a typical heteroatom. Suitable monovalent hydrocarbon groups include $C_1$-$C_{15}$ alkyl groups and $C_6$-$C_{15}$ aryl groups. Alternatively, a pair of $R^{Lc2}$ and $R^{Lc3}$, $R^{Lc4}$ and $R^{Lc6}$, $R^{Lc4}$ and $R^{Lc7}$, $R^{Lc5}$ and $R^{Lc7}$, $R^{Lc5}$ and $R^{Lc11}$, $R^{Lc6}$ and $R^{Lc10}$, $R^{Lc8}$ and $R^{Lc9}$, or $R^{Lc9}$ and $R^{Lc10}$, taken together, may form a ring with the carbon atom to which they are attached, and in this event, the ring-forming combination is a $C_1$-$C_{15}$ divalent hydrocarbon group which may contain a heteroatom. Also, a pair of $R^{Lc2}$ and $R^{Lc11}$, $R^{Lc8}$ and $R^{Lc11}$, or $R^{Lc4}$ and $R^{Lc6}$ which are attached to vicinal carbon atoms may bond together directly to form a double bond. The formula also represents an enantiomer.

Examples of the monomer from which recurring units having formula (AL-3)-21 are derived are described in U.S. Pat. No. 6,448,420 (JP-A 2000-327633). Illustrative non-limiting examples of suitable monomers are given below. $R^A$ is as defined above.

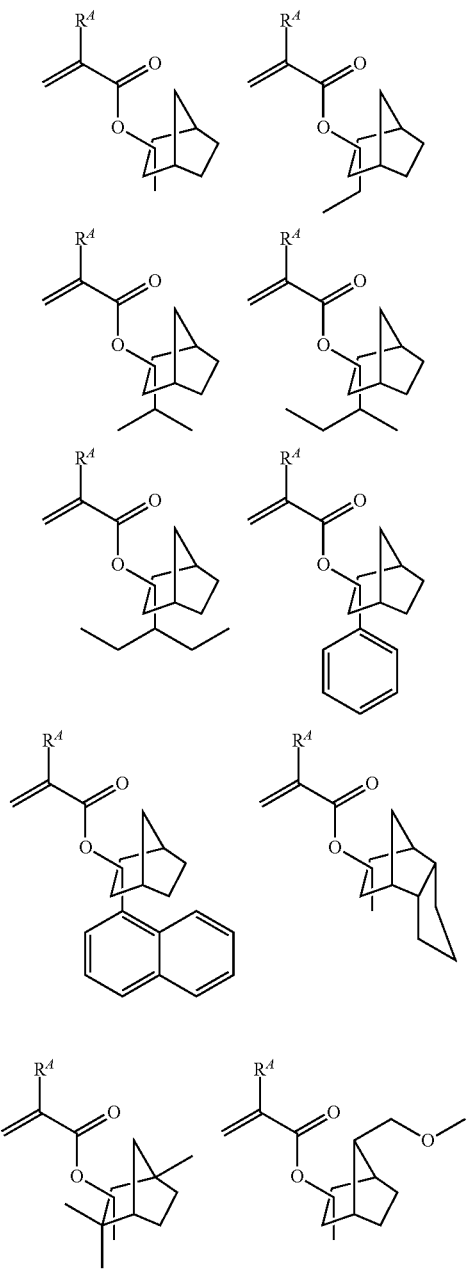

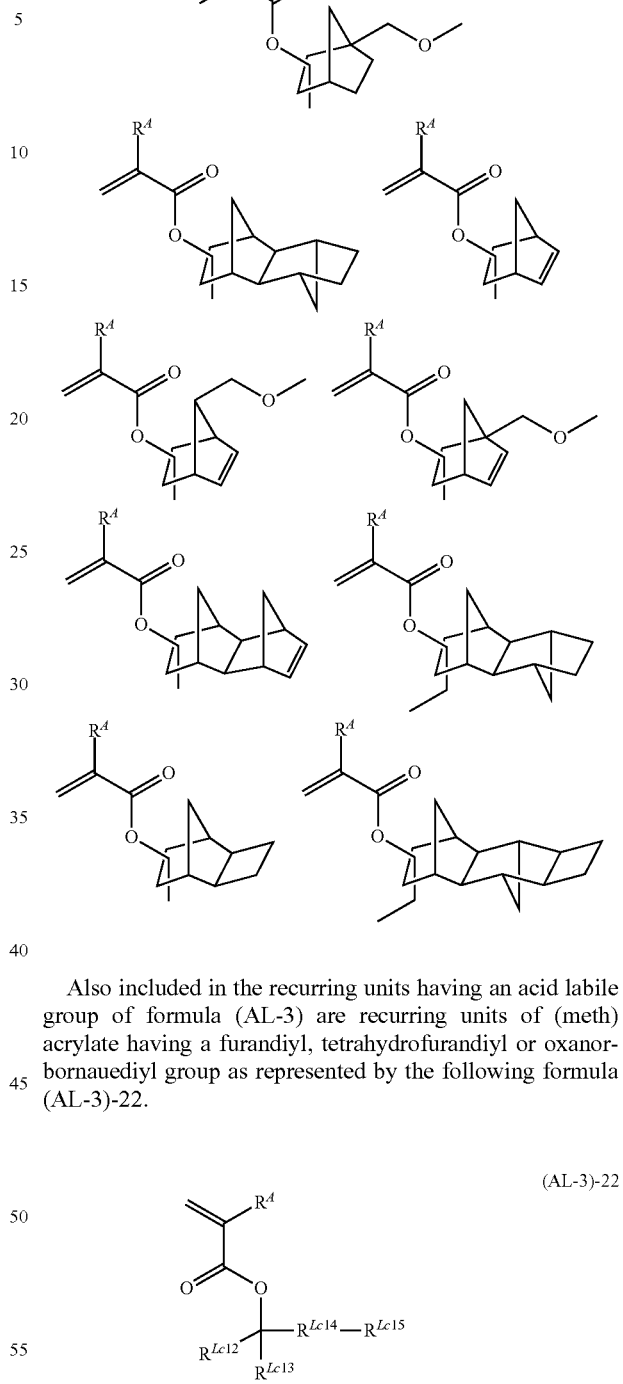

Also included in the recurring units having an acid labile group of formula (AL-3) are recurring units of (meth) acrylate having a furandiyl, tetrahydrofurandiyl or oxanorbornauediyl group as represented by the following formula (AL-3)-22.

(AL-3)-22

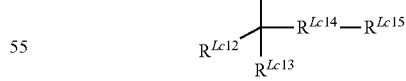

In formula (AL-3)-22, $R^A$ is as defined above. $R^{Lc12}$ and $R^{Lc13}$ are each independently a $C_1$-$C_{10}$ monovalent hydrocarbon group, or $R^{Lc12}$ and $R^{Lc13}$, taken together, may form an aliphatic ring with the carbon atom to which they are attached. $R^{Lc14}$ is furandiyl, tetrahydrofurandiyl or oxanorbornanediyl. $R^{Lc15}$ is hydrogen or a $C_1$-$C_{10}$ monovalent hydrocarbon group which may contain a heteroatom. The monovalent hydrocarbon group may be straight, branched or cyclic, and examples thereof include $C_1$-$C_{10}$ alkyl groups.

Examples of the monomer from which the recurring units having formula (AL-3)-22 are derived are shown below, but not limited thereto. Herein $R^A$ is as defined above.
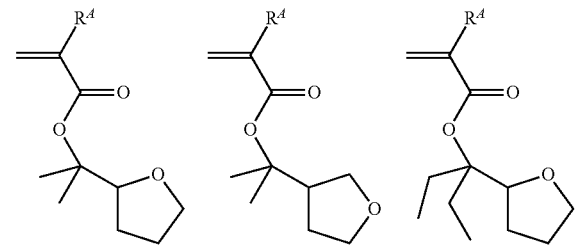
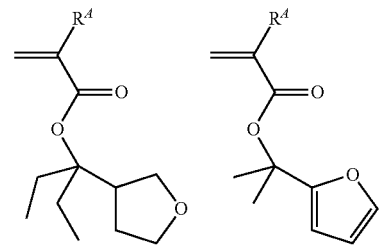
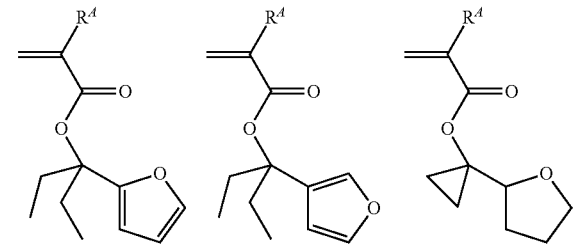
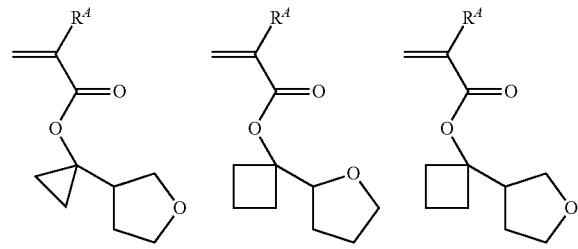
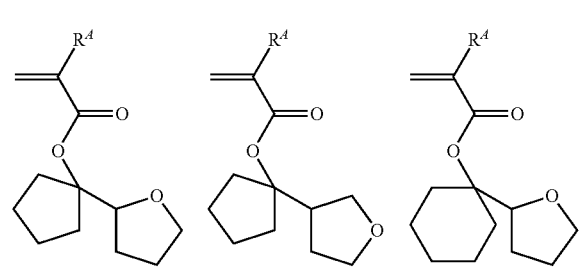
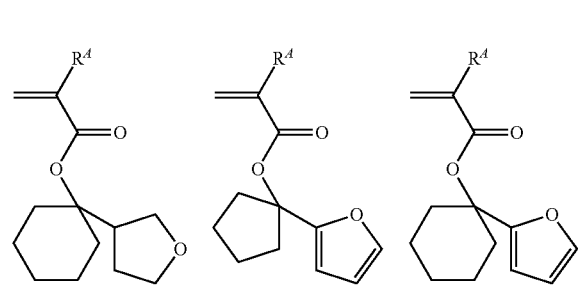
-continued
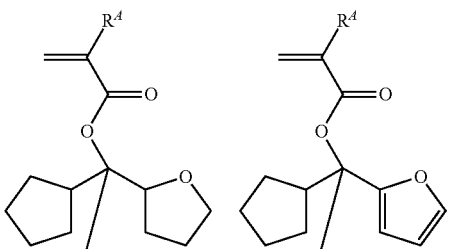
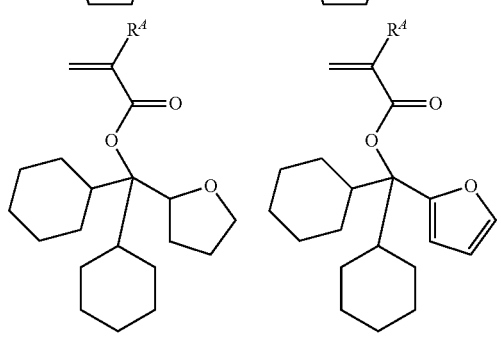
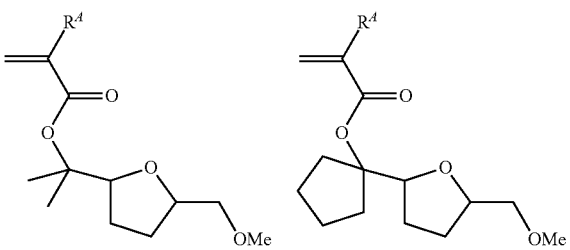
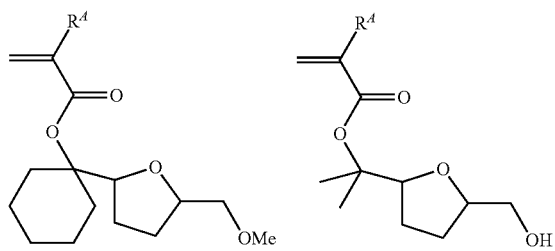
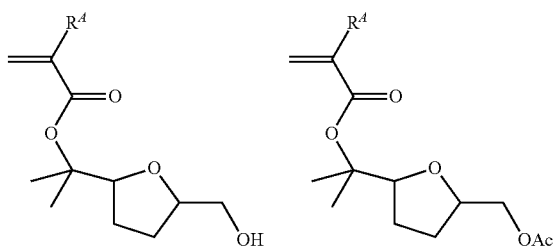
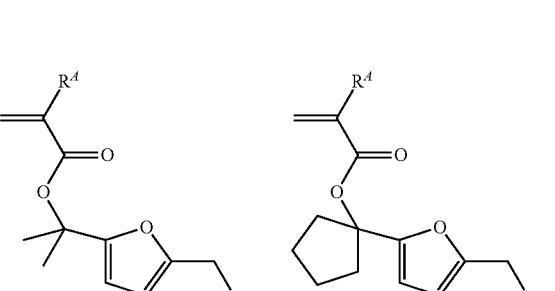

-continued
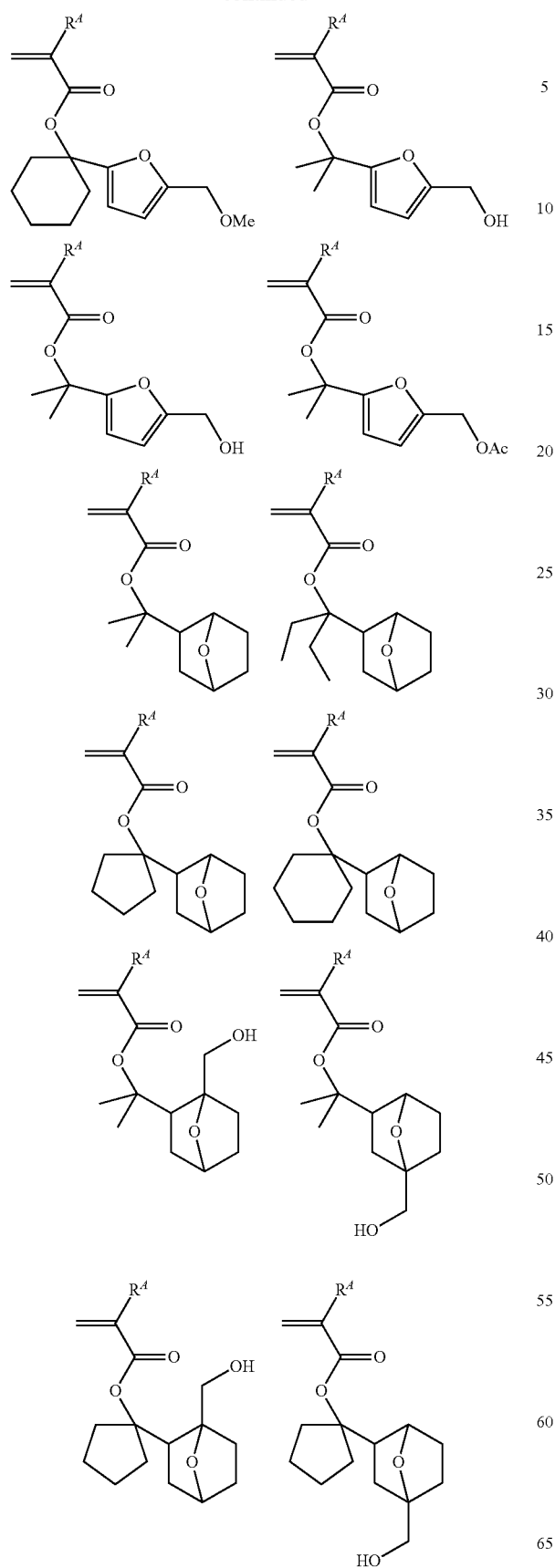
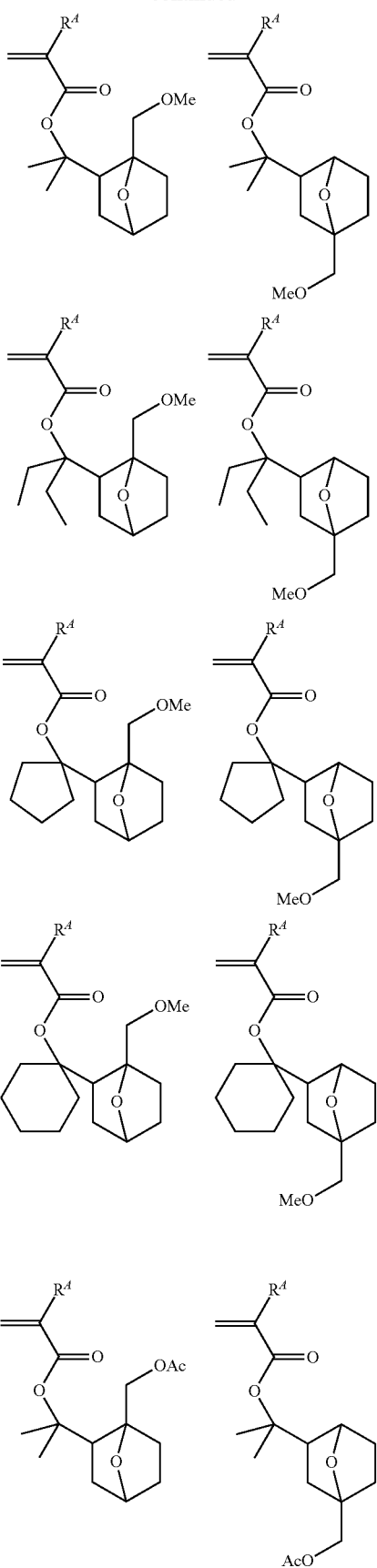

-continued

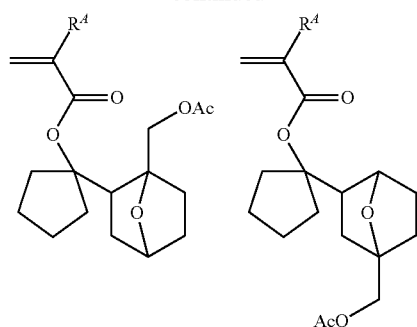

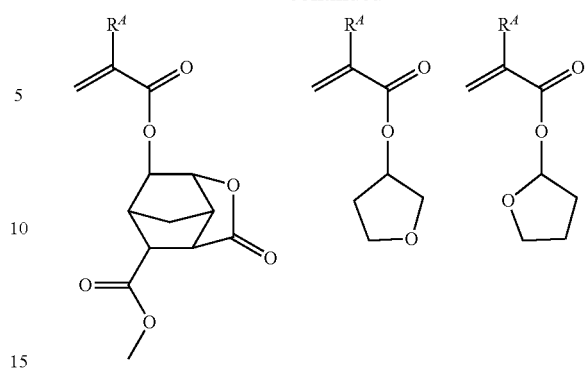

In the base polymer, recurring units (c) having an adhesive group may be incorporated. The adhesive group is selected from hydroxyl, carboxyl, lactone ring, carbonate, thiocarbonate, carbonyl, cyclic acetal, ether, ester, sulfonic acid ester, cyano, amide, —O—C(=O)—S— and —O—C(=O)—NH—.

Examples of the monomer from which recurring units (c) are derived are given below, but not limited thereto. Herein $R^A$ is as defined above.

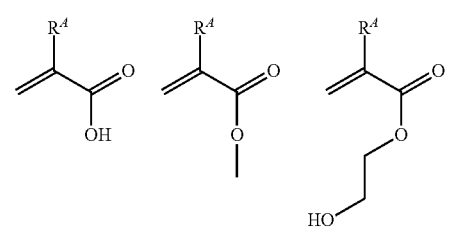

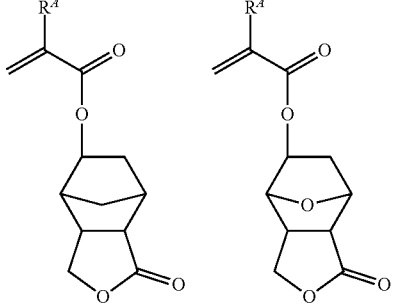

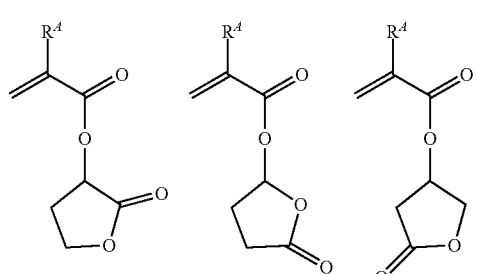

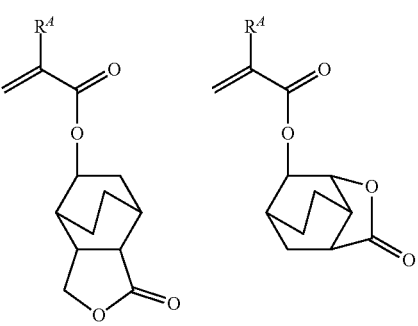

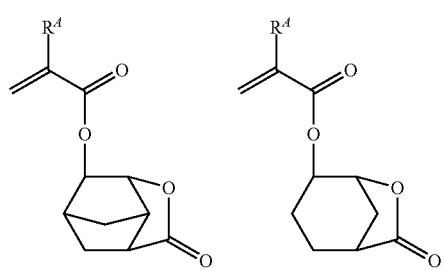

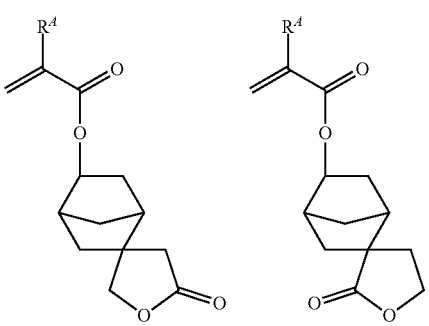

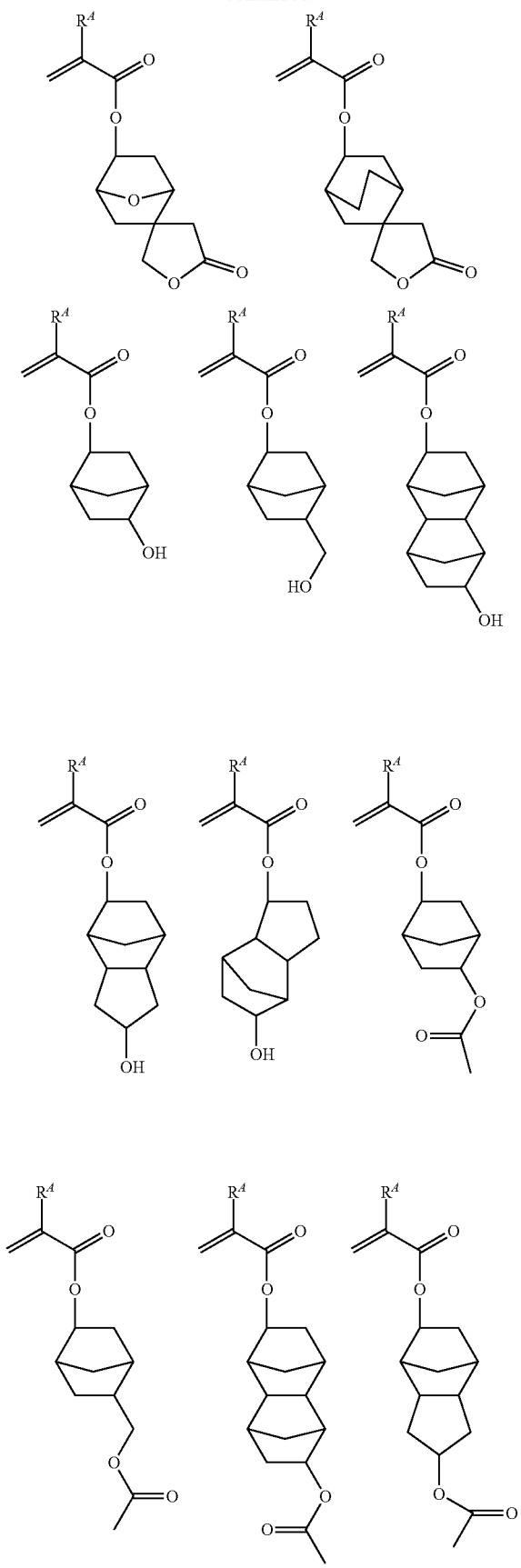
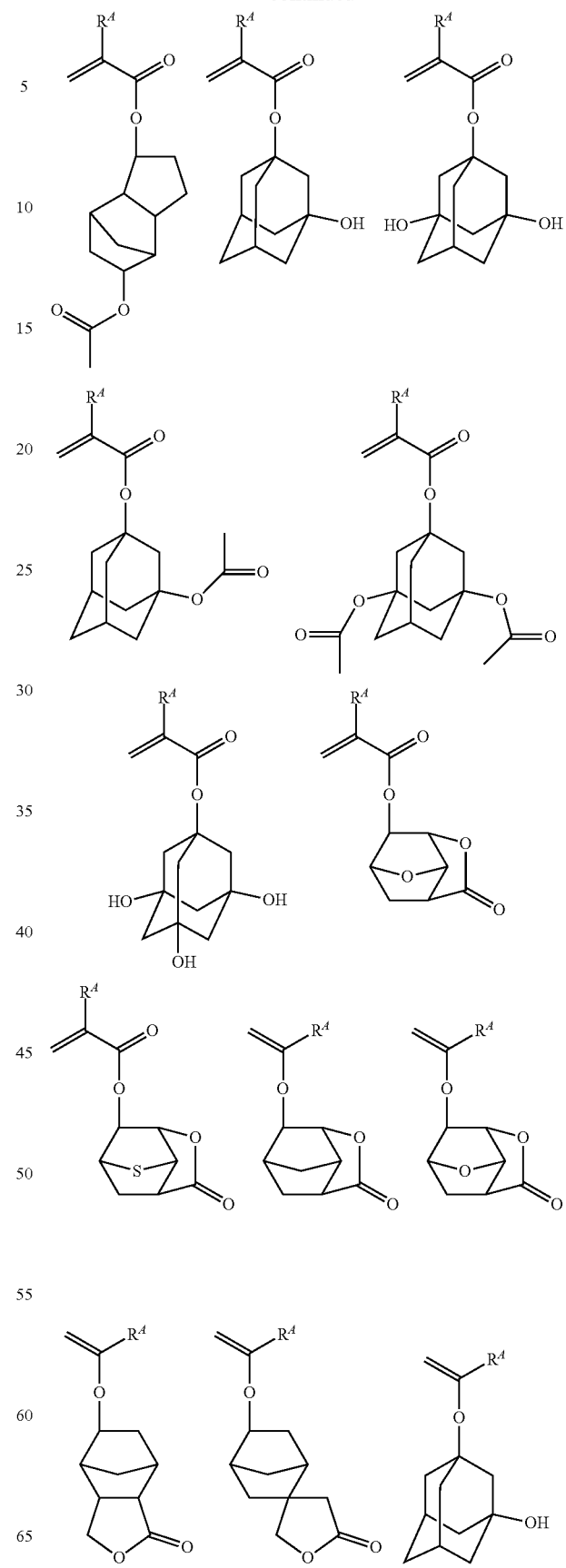

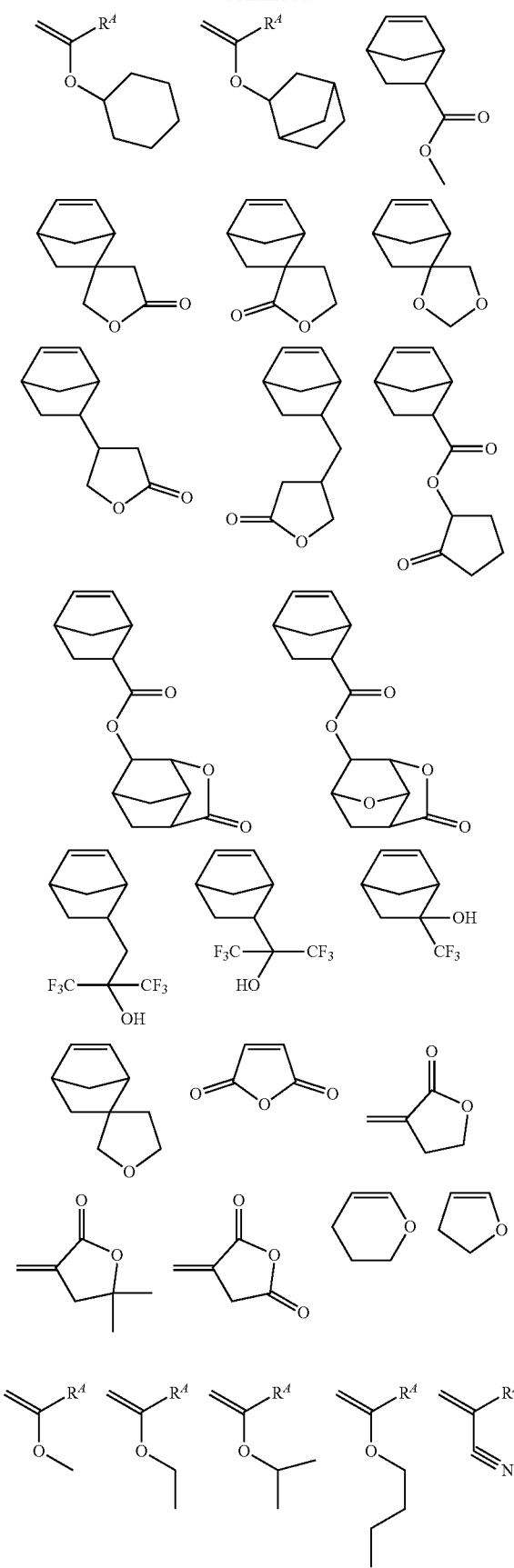
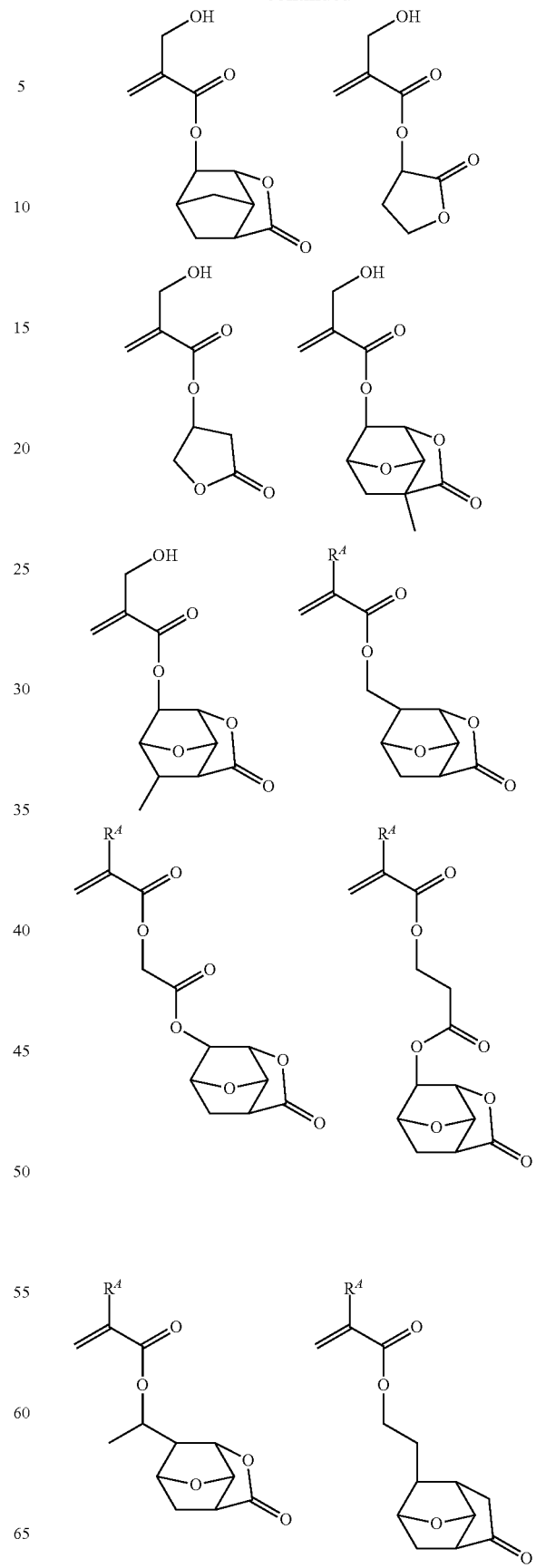

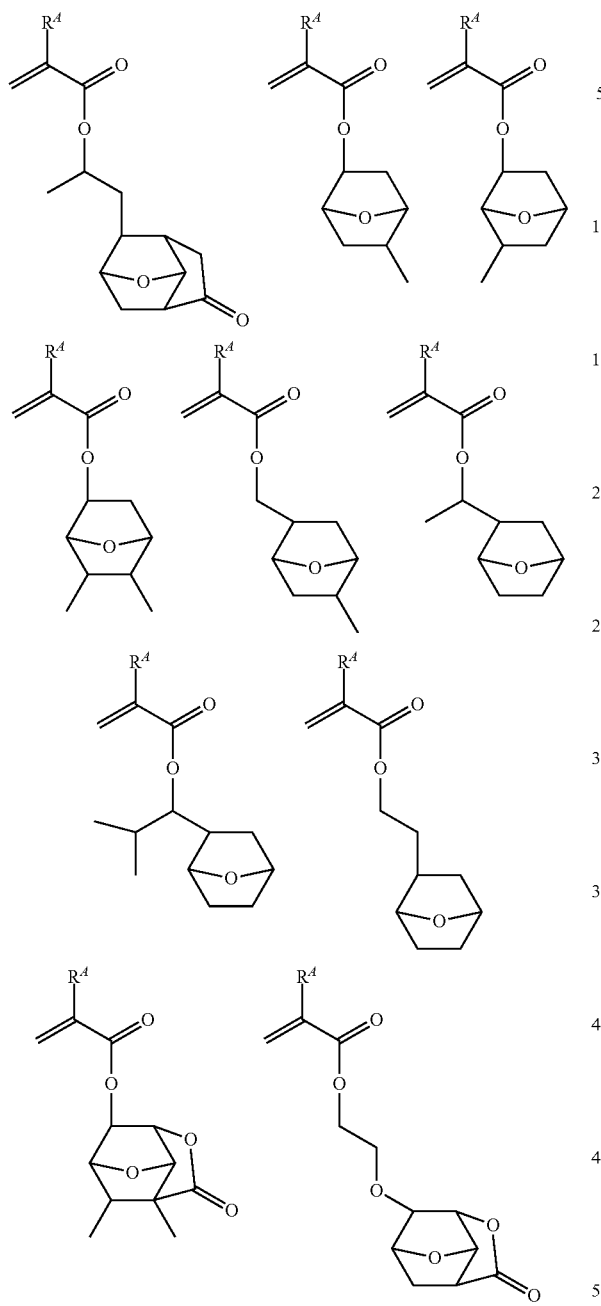
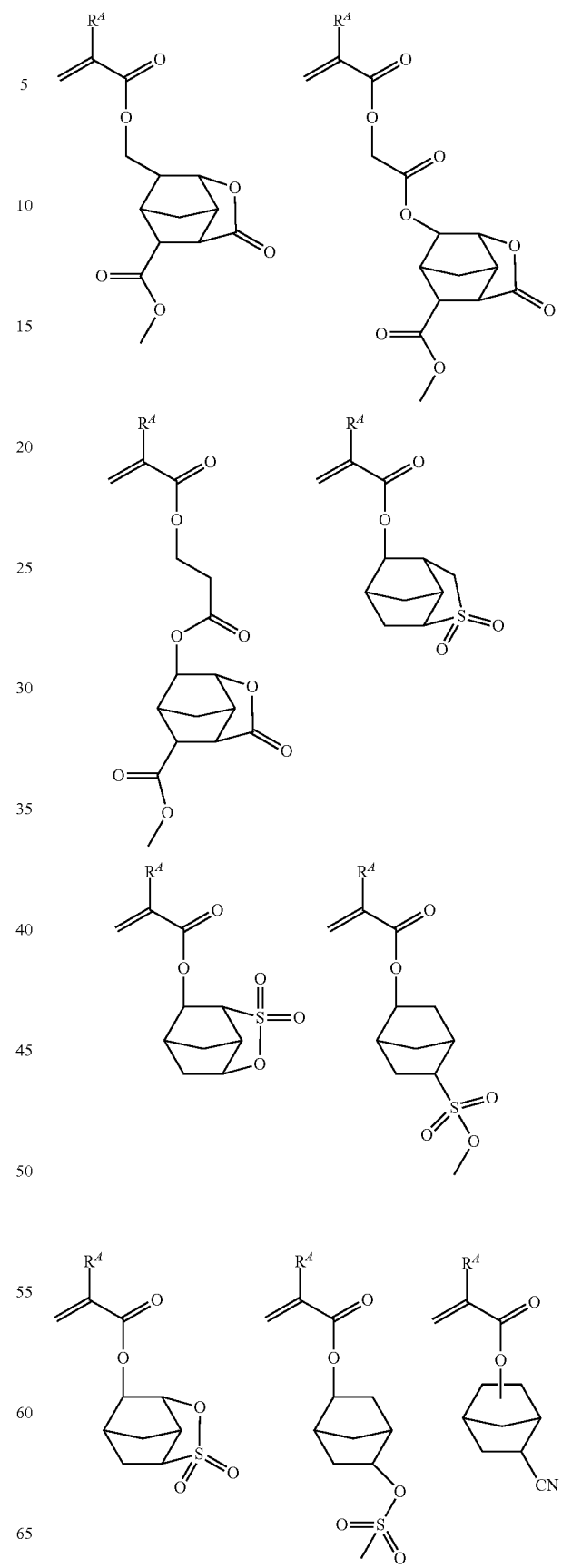

-continued
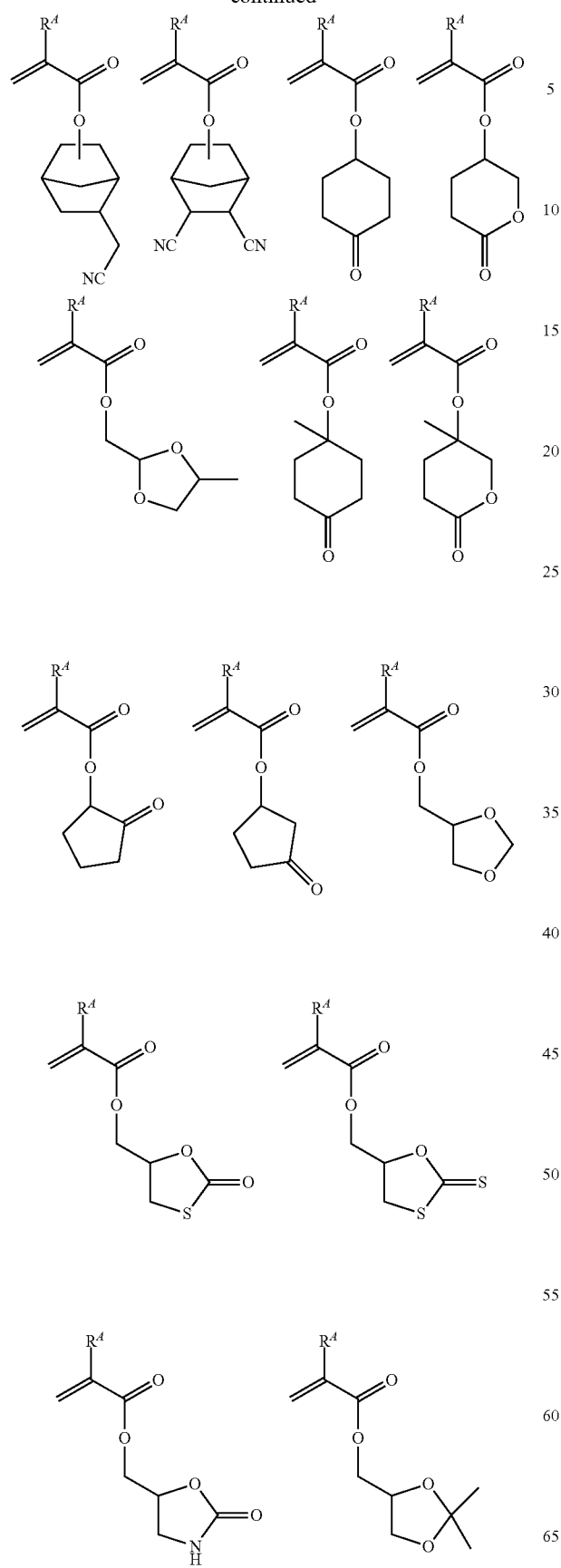
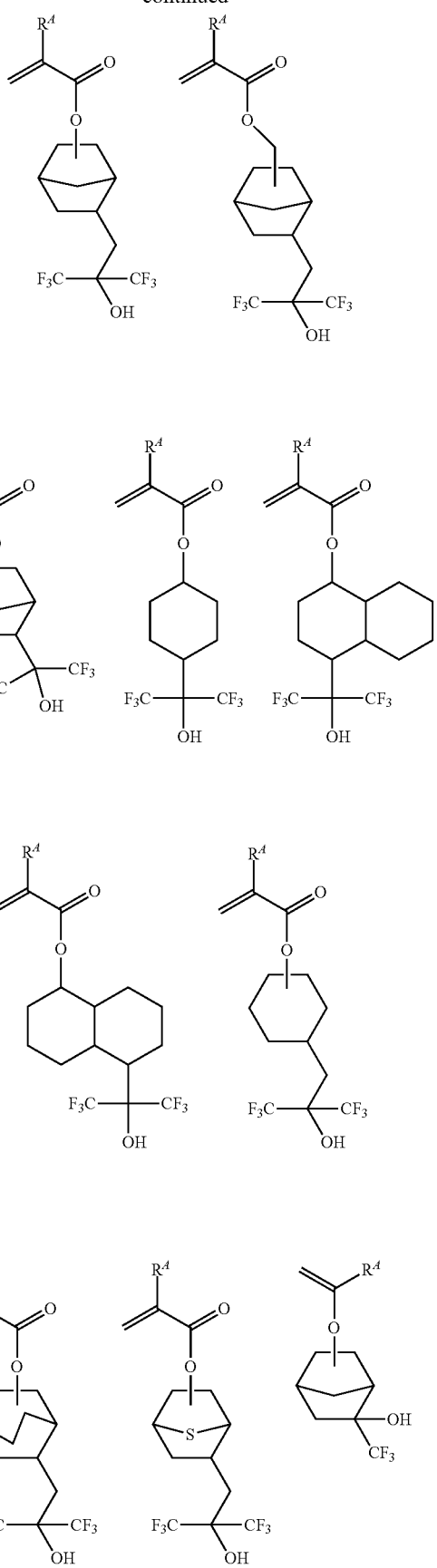

47
-continued
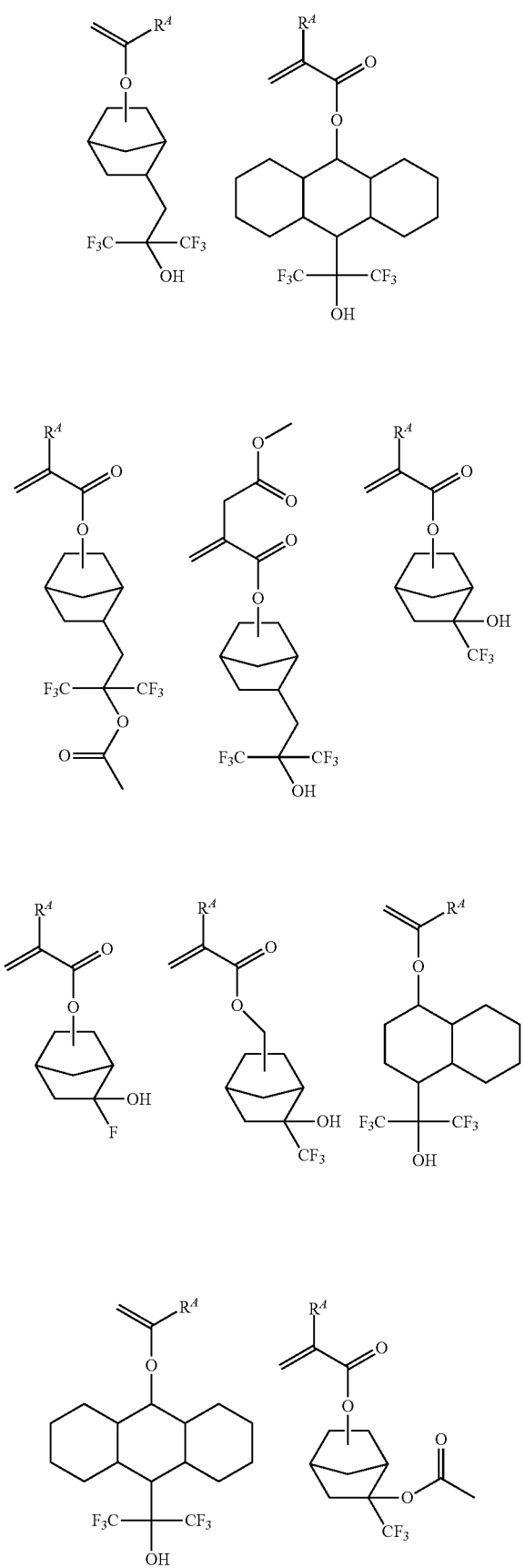
48
-continued
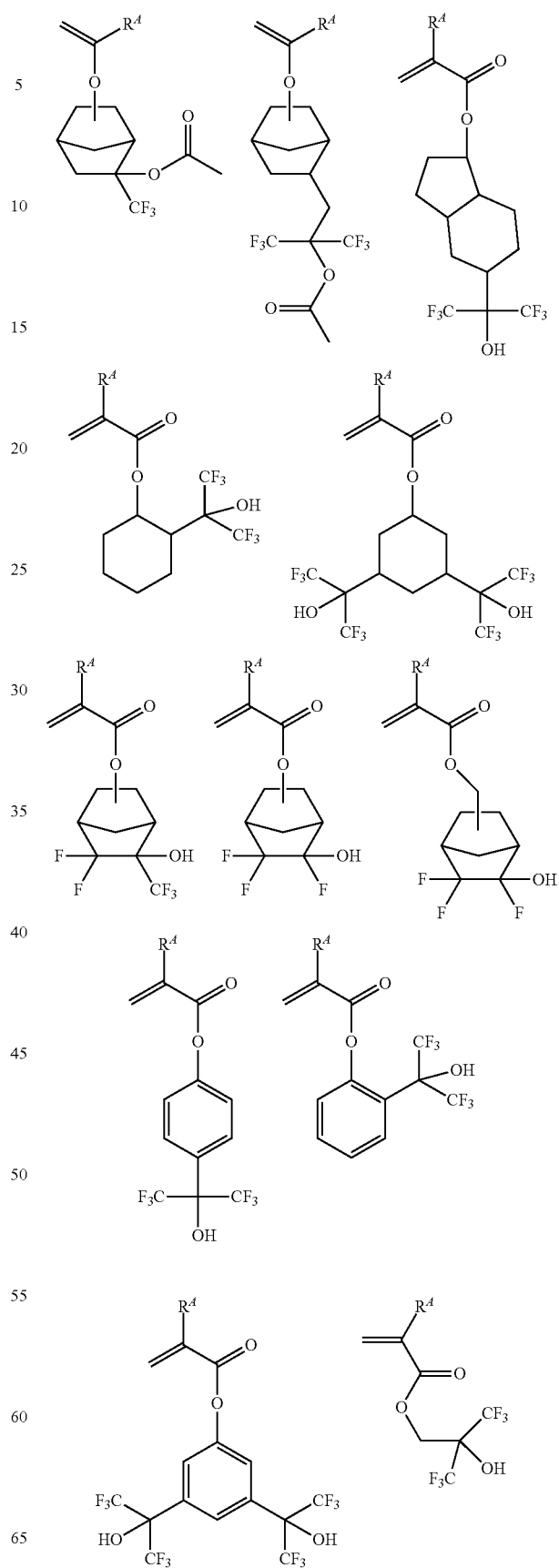

-continued
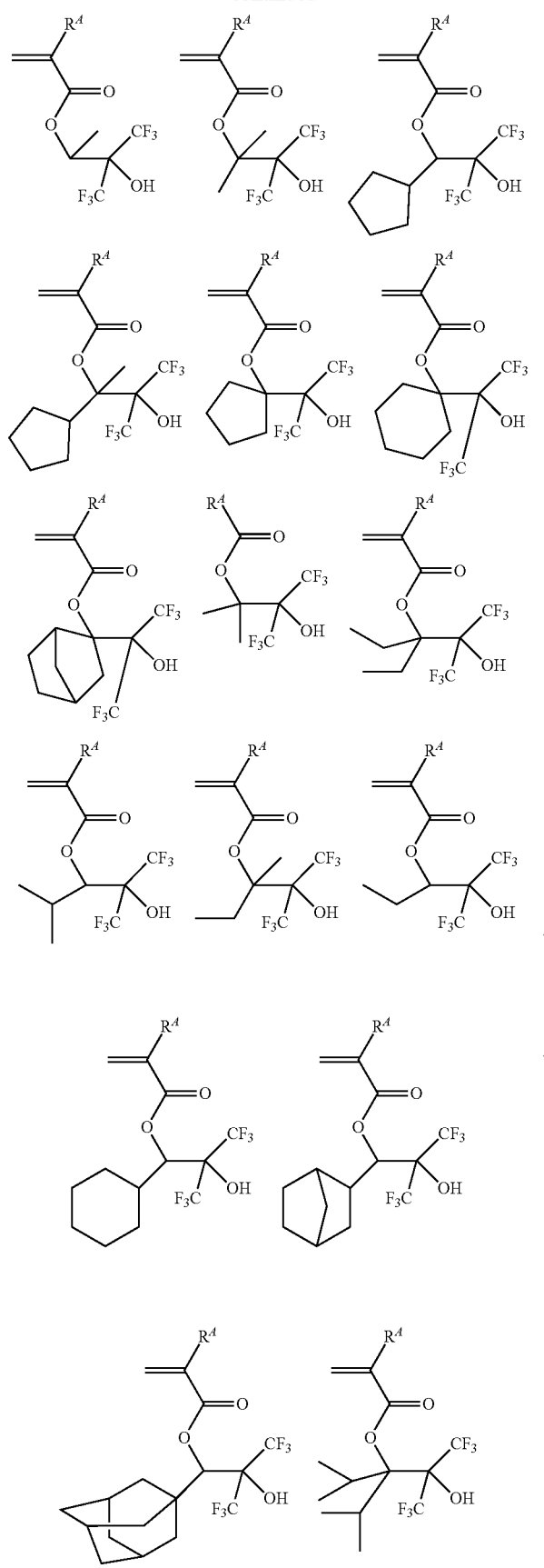
-continued
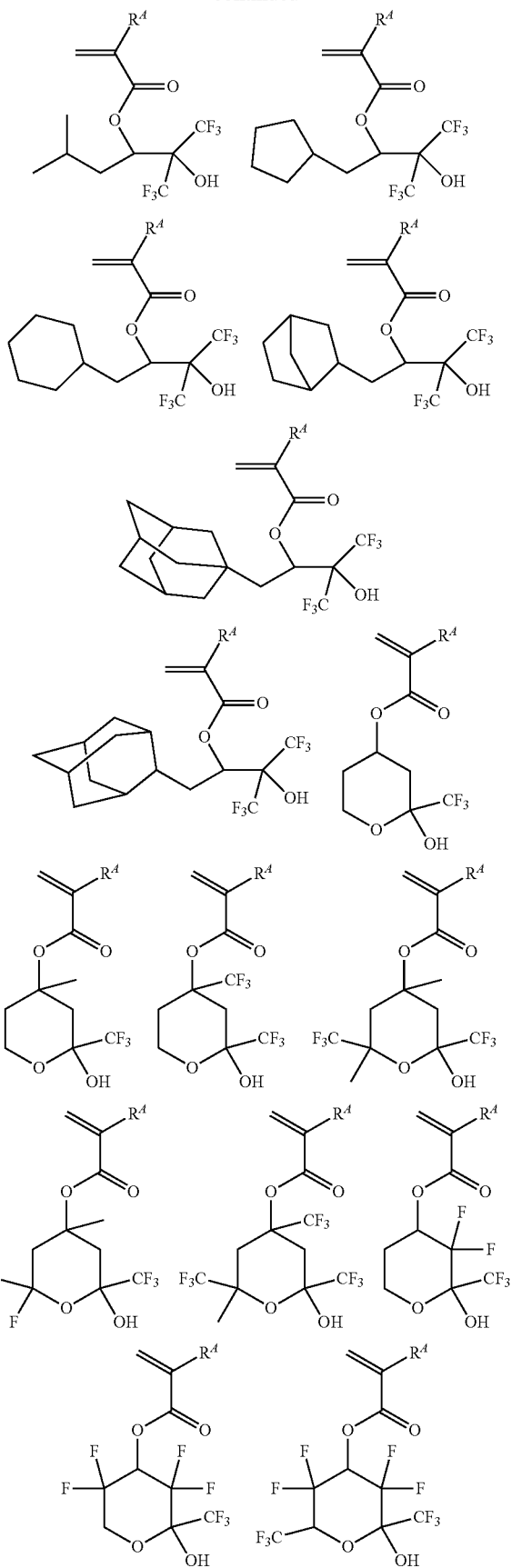

51
-continued
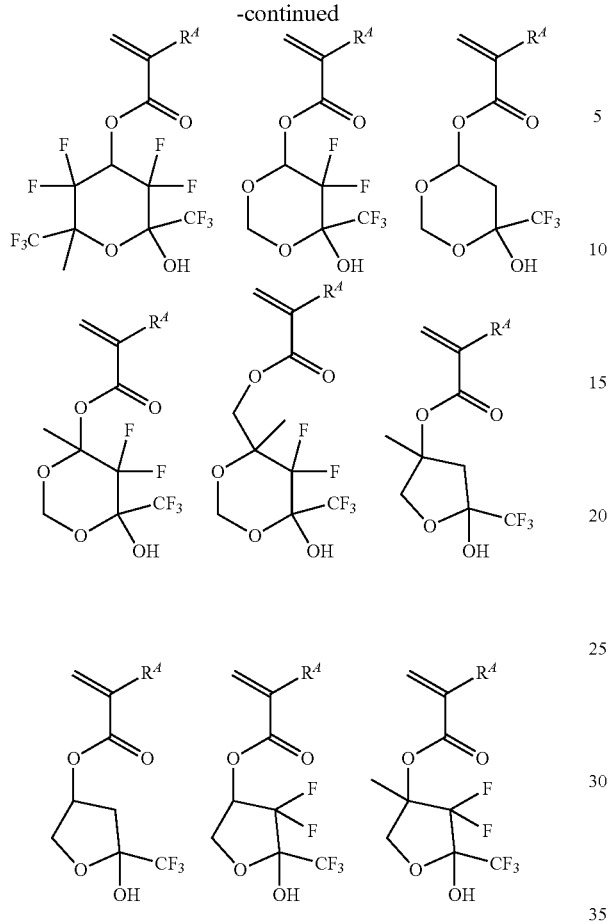
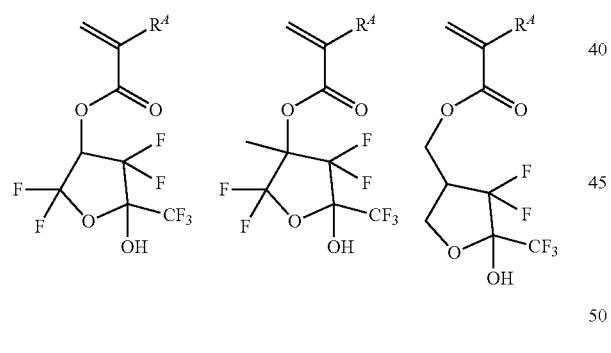
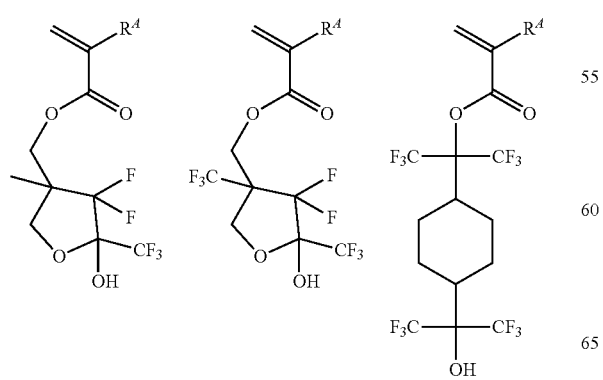
52
-continued
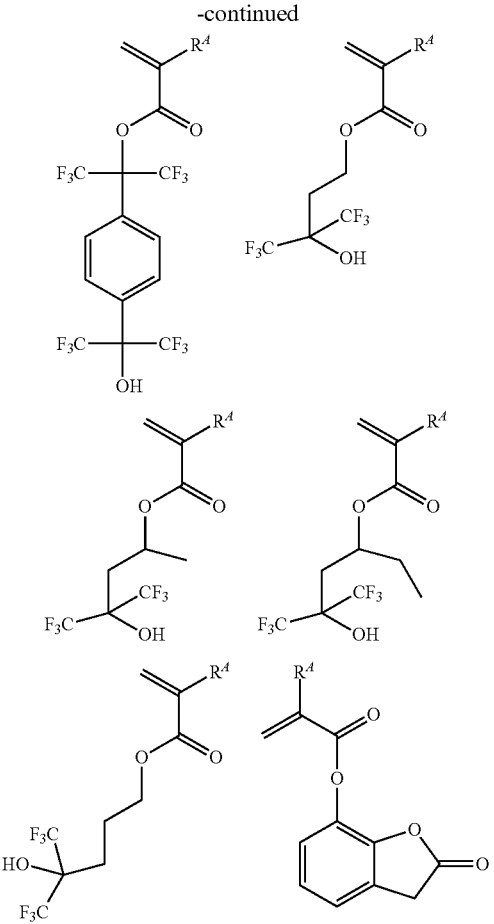

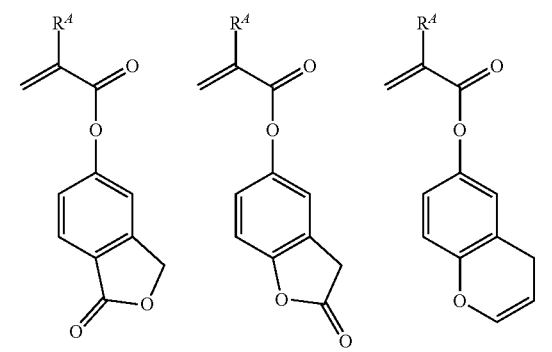
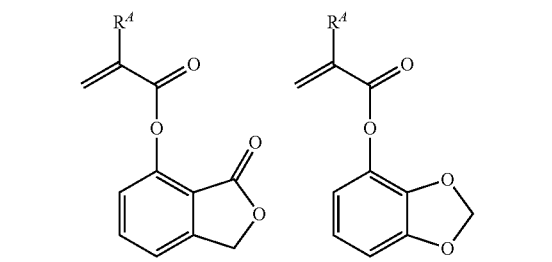
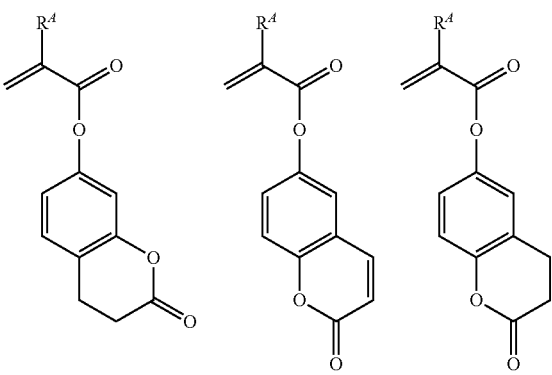
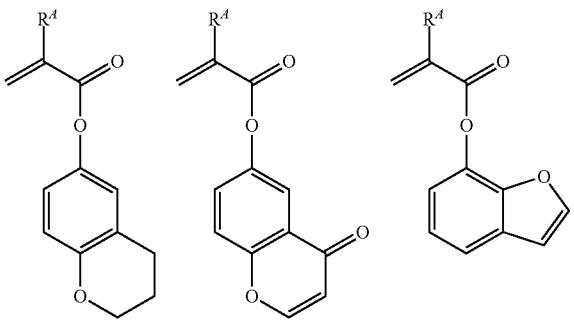
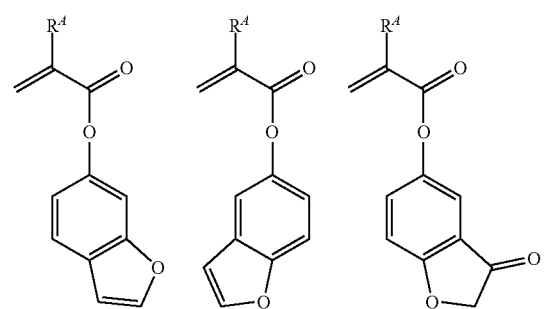
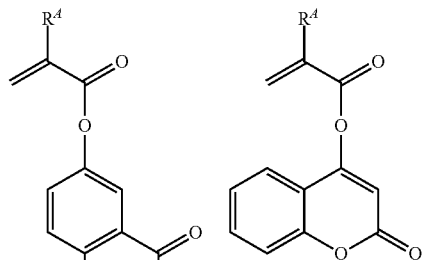
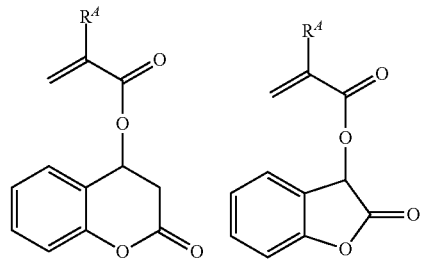
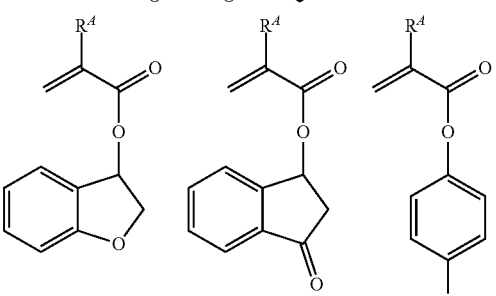
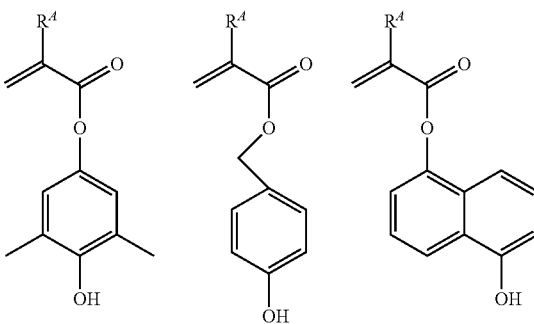
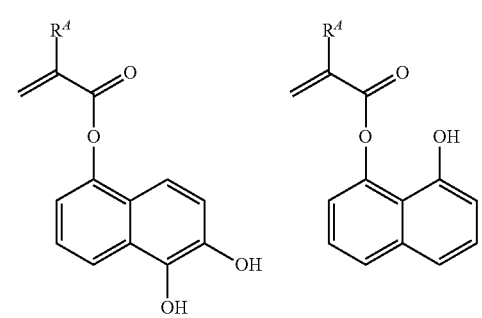

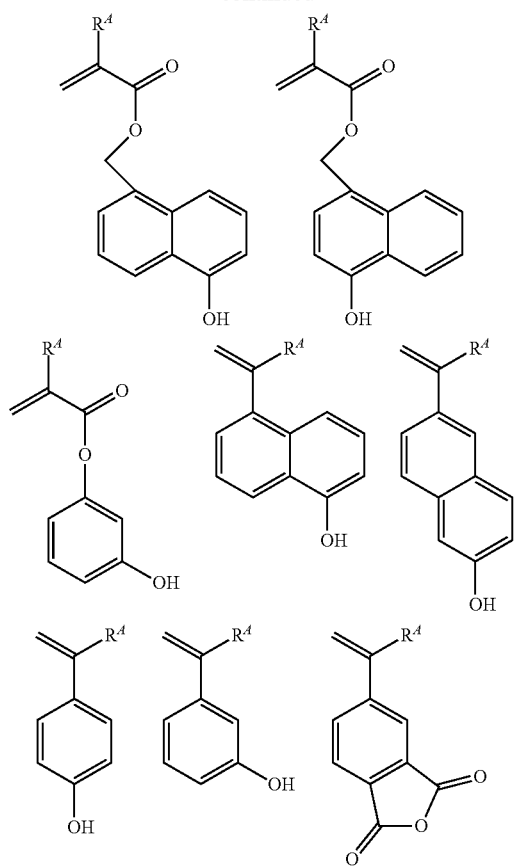
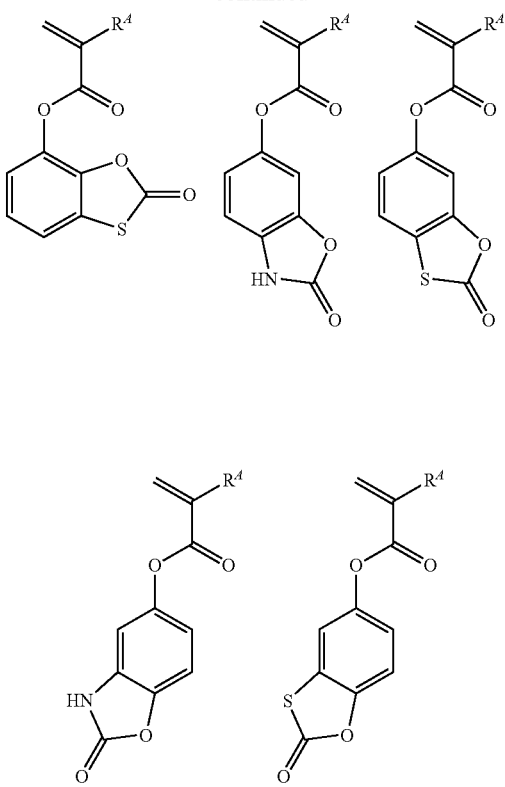

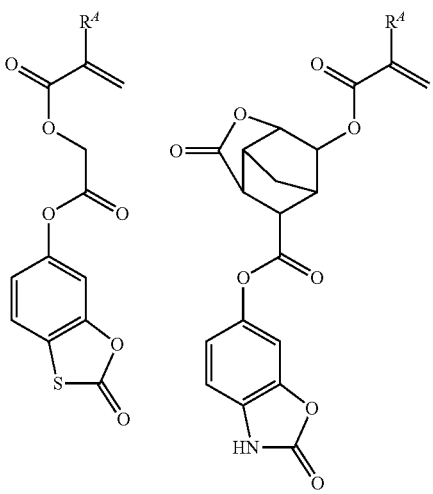
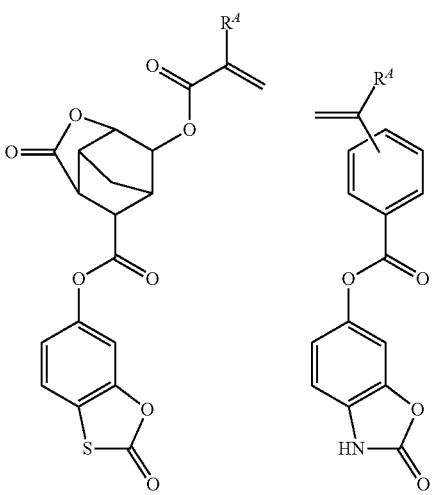
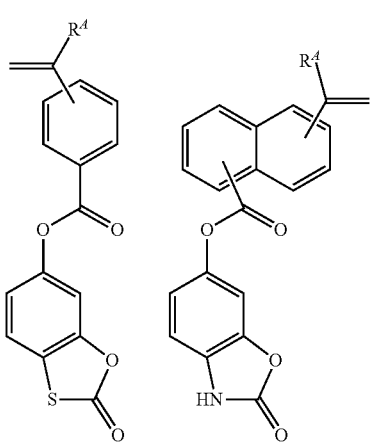

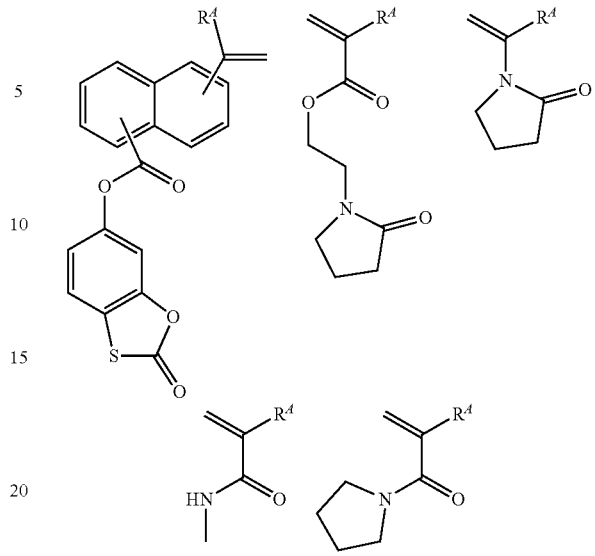

In a further embodiment, recurring units (d) derived from an onium salt having a polymerizable unsaturated bond may be incorporated in the base polymer. The preferred recurring units (d) are recurring units having the following formulae (d1), (d2) and (d3). These units are simply referred to as recurring units (d1), (d2) and (d3), which may be used alone or in combination of two or more types.

(d1)

(d2)

(d3)

In formulae (d1) to (d3), $R^A$ is each independently hydrogen or methyl. $Z^1$ is a single bond, phenylene, —O—$Z^{11}$—, —C(=O)—O—$Z^{11}$— or —C(=O)—NH—$Z^{11}$—, wherein $Z^{11}$ is a $C_1$-$C_6$ alkanediyl group, $C_2$-$C_6$ alkenediyl group, or phenylene group, which may contain a carbonyl moiety, ester bond, ether bond or hydroxyl moiety. $Z^{2A}$ is a single bond or ester bond. $Z^{2B}$ is a single bond or a $C_1$-$C_{12}$ divalent group which may contain an ester bond, ether bond, lactone ring, bromine or iodine. $Z^3$ is a single bond, methylene, ethylene, phenylene, fluorinated phenylene, —O—$Z^{31}$—, —C(=O)—O—$Z^{31}$— or —C(=O)—NH—$Z^{31}$—, wherein $Z^{31}$ is a $C_1$-$C_6$ alkanediyl group, $C_2$-$C_6$ alkenediyl group, or phenylene group, which may contain a carbonyl moiety, ester bond, ether bond or hydroxyl moiety.

In formula (d2), $Rf^4$ to $Rf^4$ are each independently hydrogen, fluorine or trifluoromethyl, at least one of $Rf^4$ to $Rf^4$ being fluorine. Preferably at least one of $Rf^3$ and $Rf^4$ is fluorine, most preferably both $Rf^4$ and $Rf^4$ are fluorine.

In formulae (d1) to (d3), $R^{21}$, to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached. The monovalent hydrocarbon group may be straight, branched or cyclic and examples thereof include $C_1$-$C_{12}$ alkyl, $C_6$-$C_{12}$ aryl, and $C_7$-$C_{20}$ aralkyl groups. In these groups, some or all hydrogen may be substituted by $C_1$-$C_{10}$ alkyl, halogen, trifluoromethyl cyano, nitro, hydroxyl, mercapto, $C_1$-$C_{10}$ alkoxy, $C_2$-$C_{10}$ alkoxycarbonyl, or $C_2$-$C_{10}$ acyloxy moiety, or some carbon may be replaced by a carbonyl moiety, ether bond or ester bond.

Examples of the sulfonium cation in formula (d2) or (d3) are as will be later exemplified for the cation of the sulfonium salt having formula (1-1).

In formula (d1), $M^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluormmethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (K-1) and sulfonate ions having fluorine substituted at α-position and trifluoromethyl at β-position as represented by the formula (K-2).

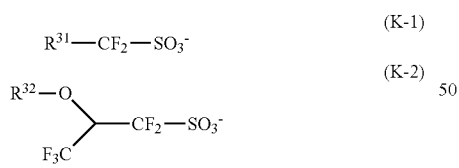

In formula (K-1), $R^{31}$ is hydrogen, or a $C_1$-$C_{20}$ alkyl group, $C_2$-$C_{20}$ alkenyl group, or $C_6$-$C_{20}$ aryl group, which may contain an ether bond, ester bond, carbonyl moiety, lactone ring, or fluorine atom. The alkyl and alkenyl groups may be straight, branched or cyclic.

In formula (K-2). $R^{32}$ is hydrogen, or a $C_1$-$C_{30}$ alkyl group, $C_2$-$C_{30}$ acyl group, $C_2$-$C_{20}$ alkenyl group, $C_6$-$C_{20}$ aryl group or $C_6$-$C_{20}$ aryloxy group, which may contain an ether bond, ester bond, carbonyl moiety or lactone ring. The alkyl, acyl and alkenyl groups may be straight, branched or cyclic.

Examples of the monomer from which recurring unit (d1) is derived are shown below, but not limited thereto. $R^A$ and $M^-$ are as defined above.

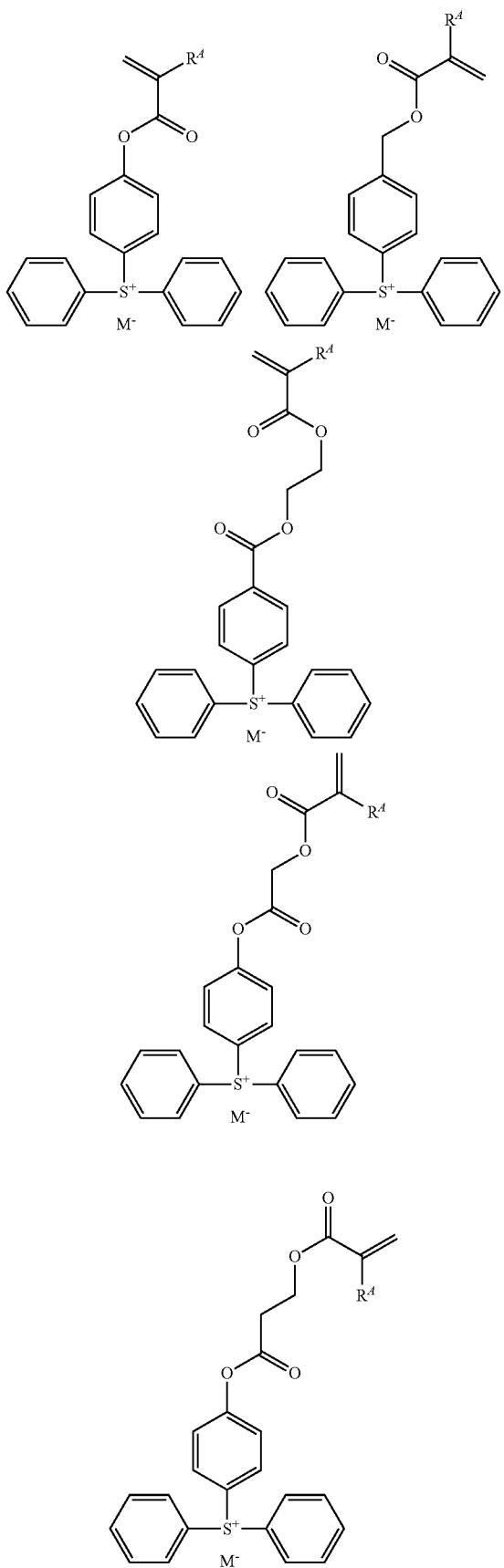

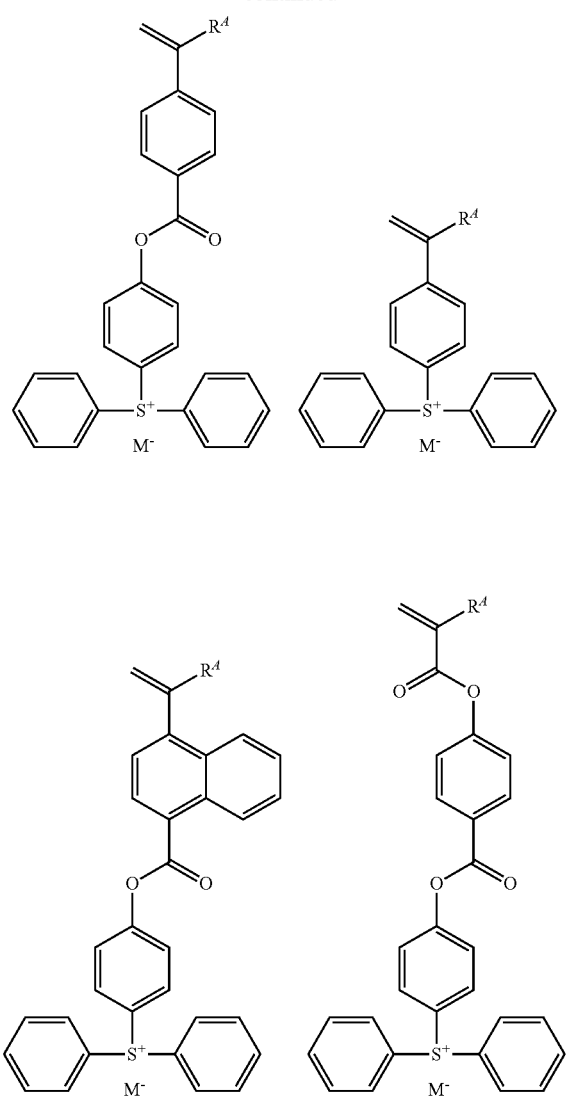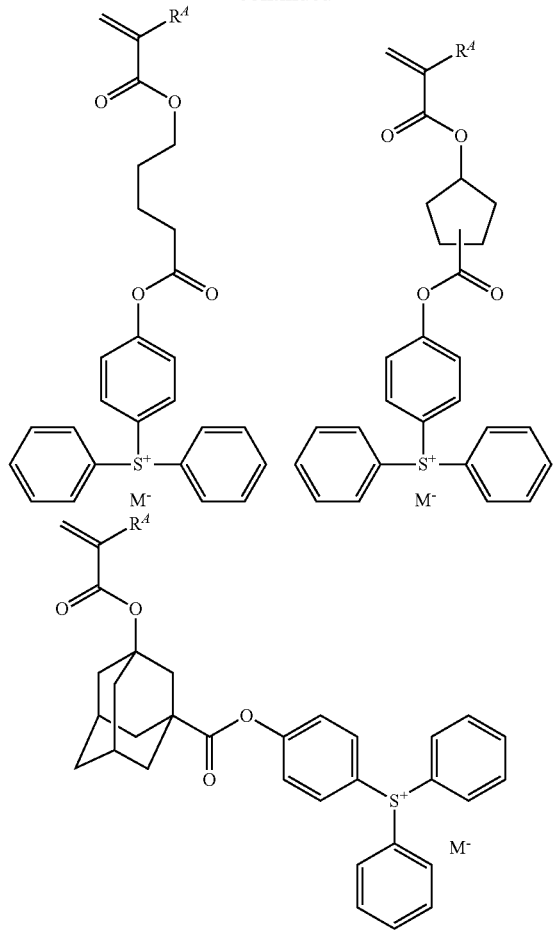
Examples of the monomer from which recurring unit (d2) is derived are shown below, but not limited thereto. $R^A$ is as defined above.
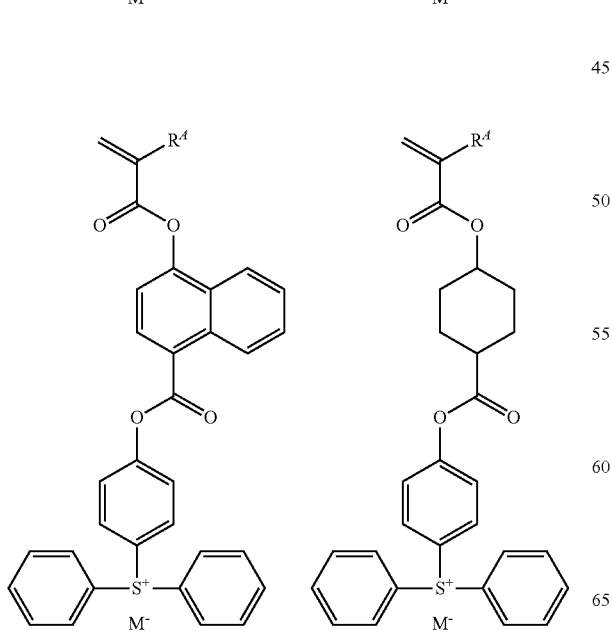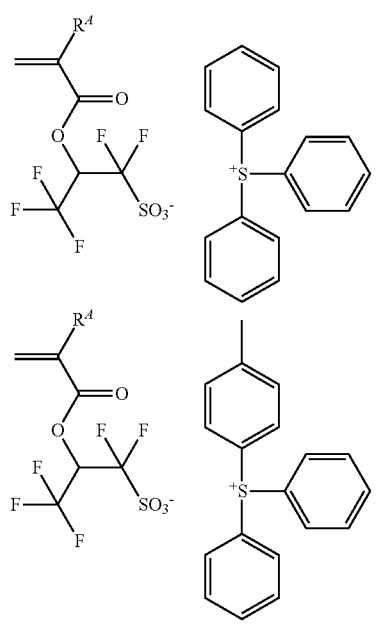

63
-continued
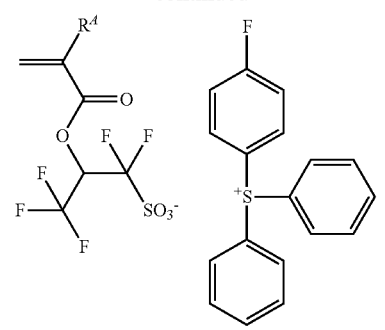
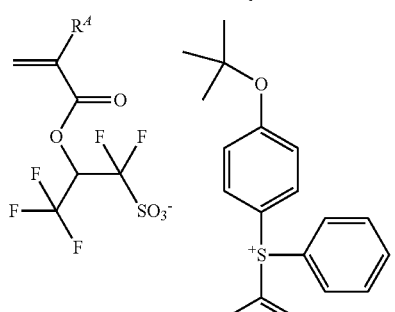
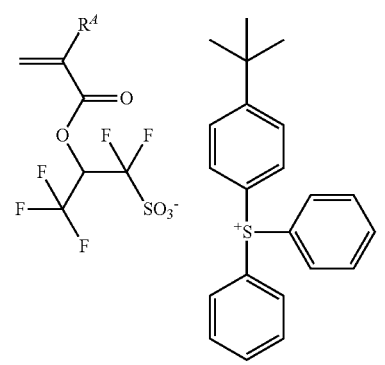
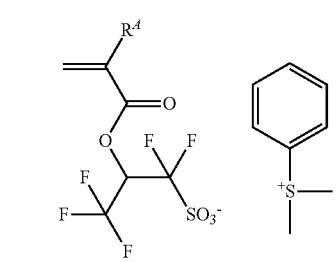
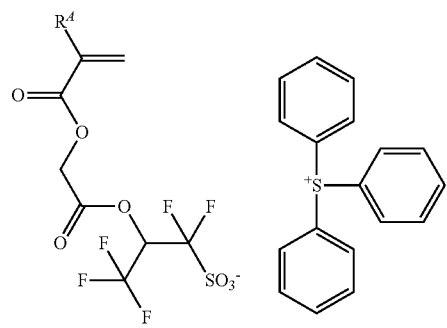
64
-continued
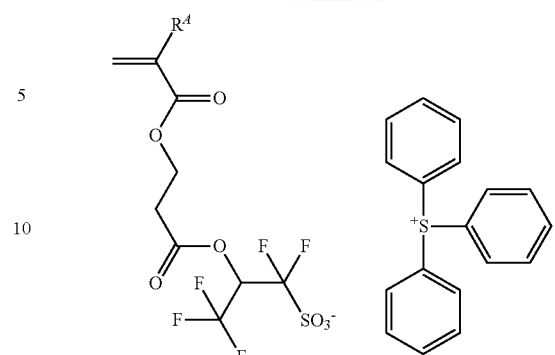
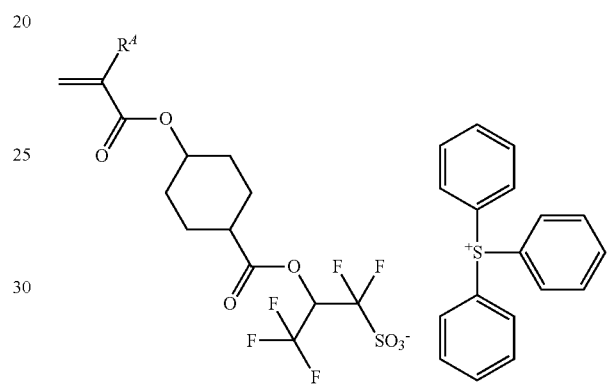
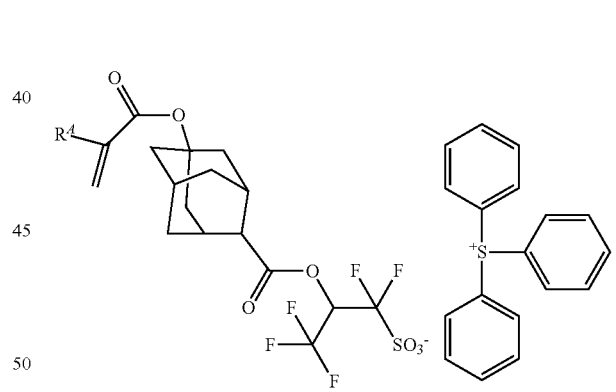
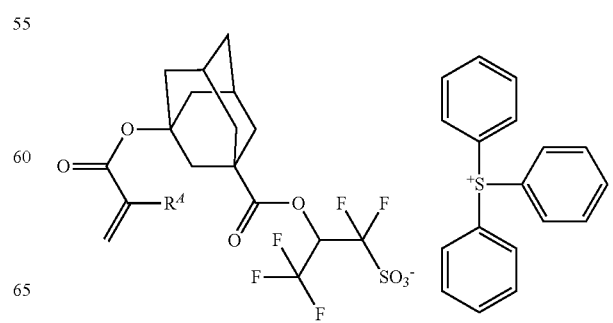

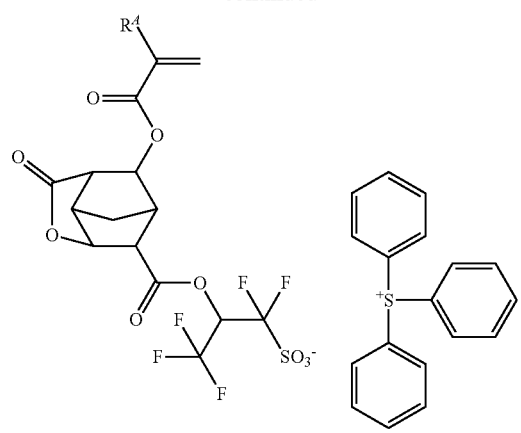
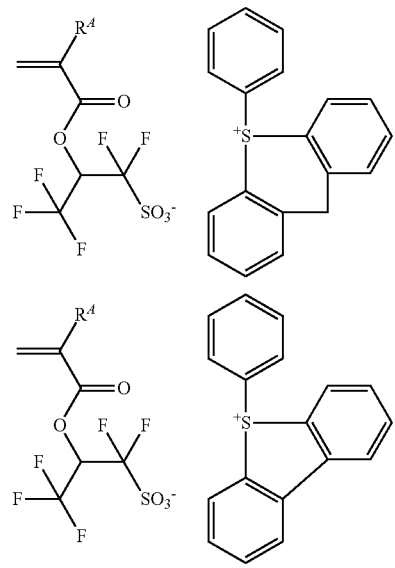
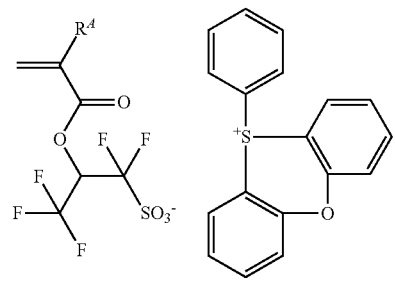
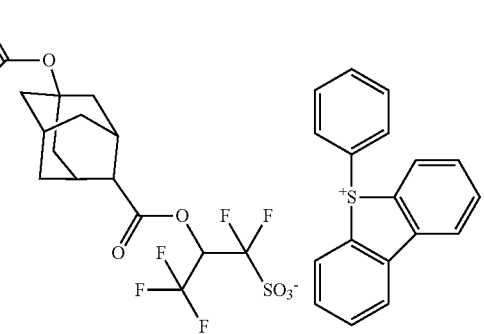
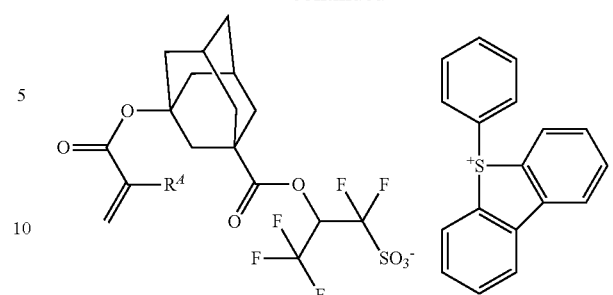
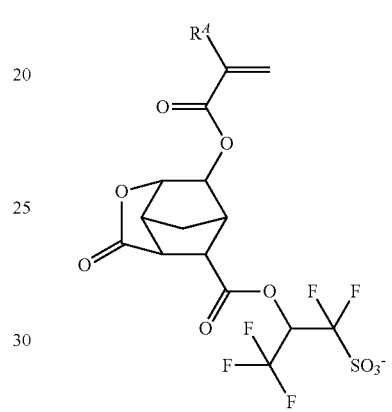
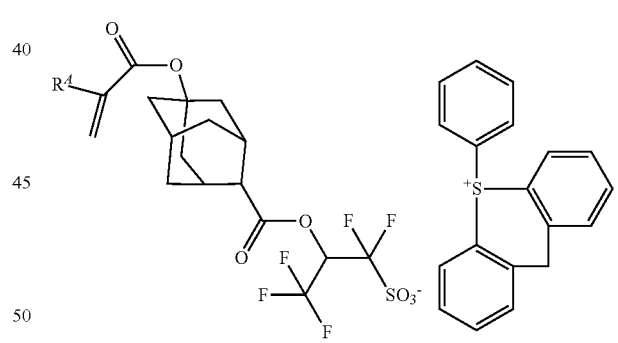
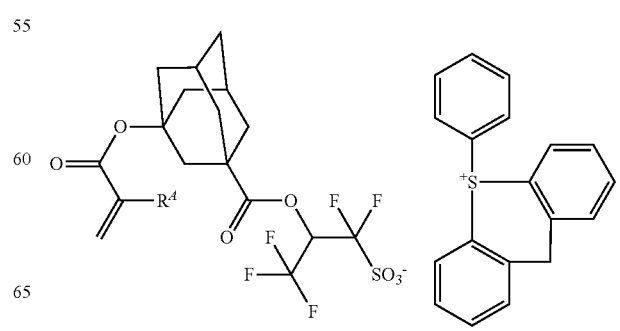

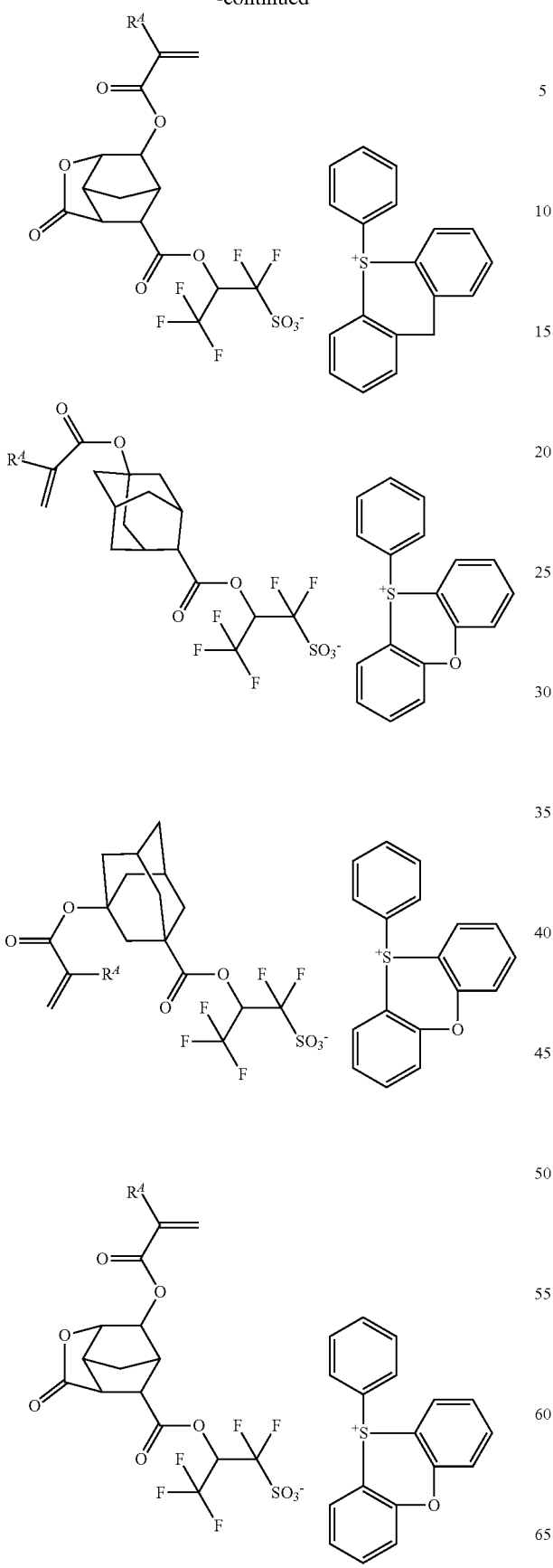
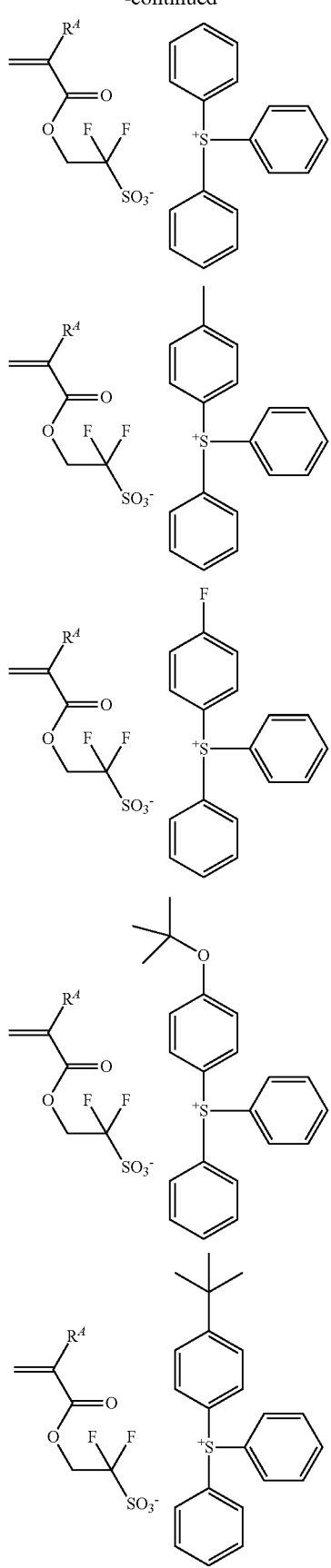

-continued
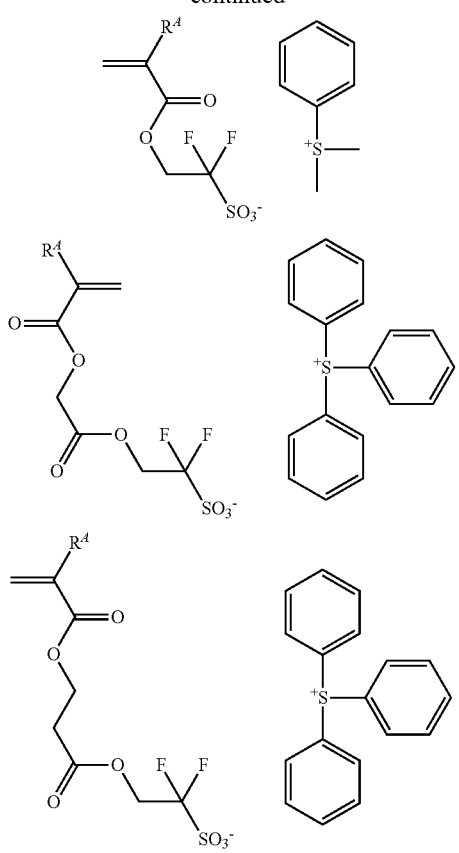
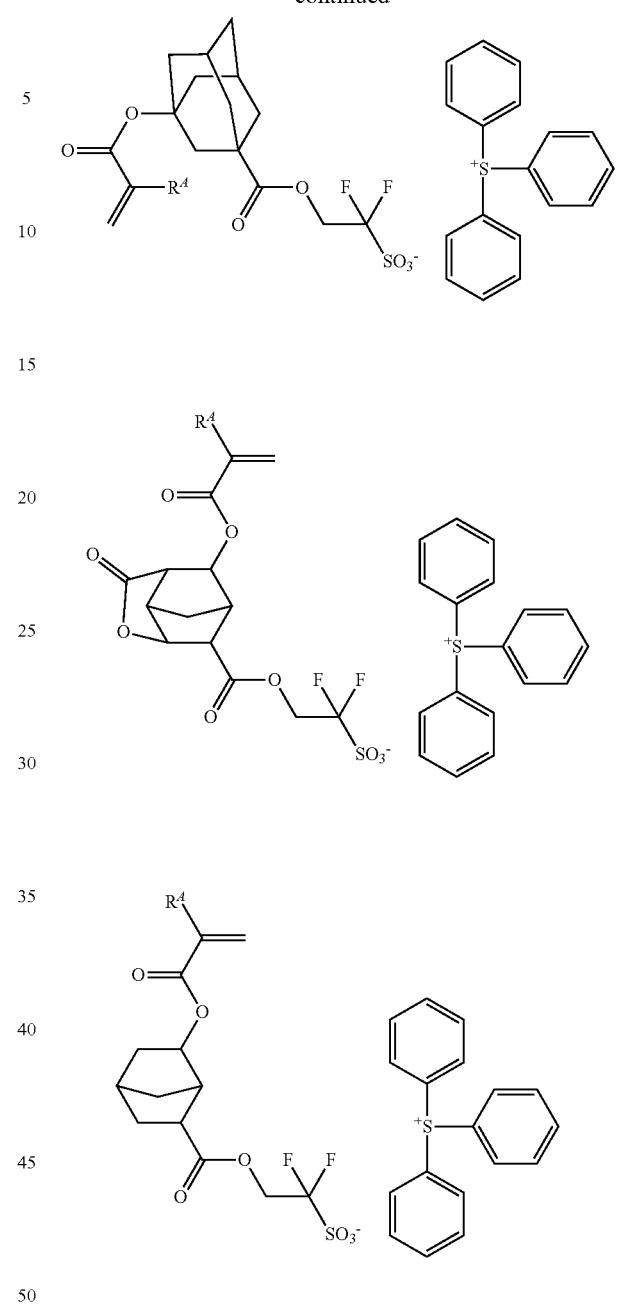
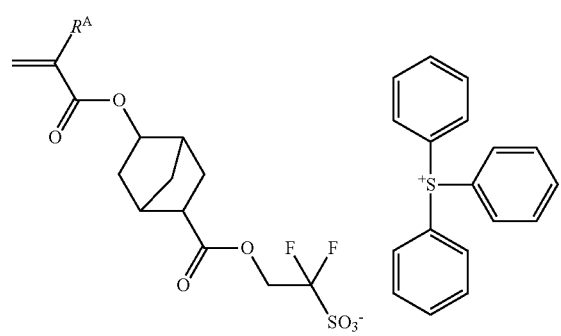
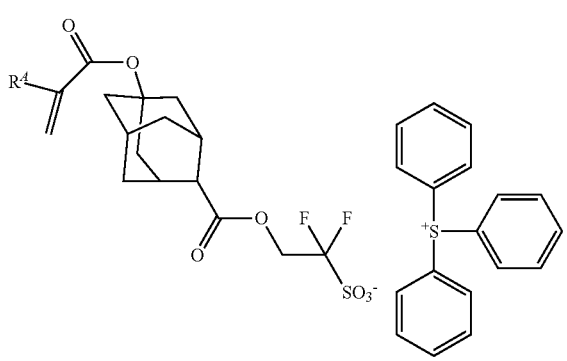
As the monomer from which recurring unit (d2) is derived, compounds having the anions shown below are also preferred. $R^A$ is as defined above.
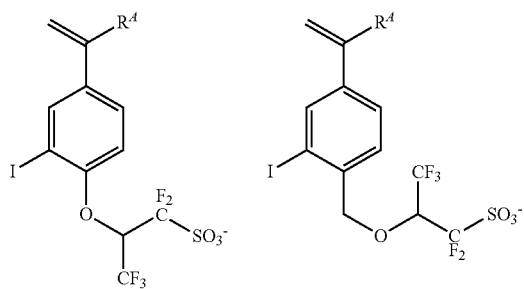

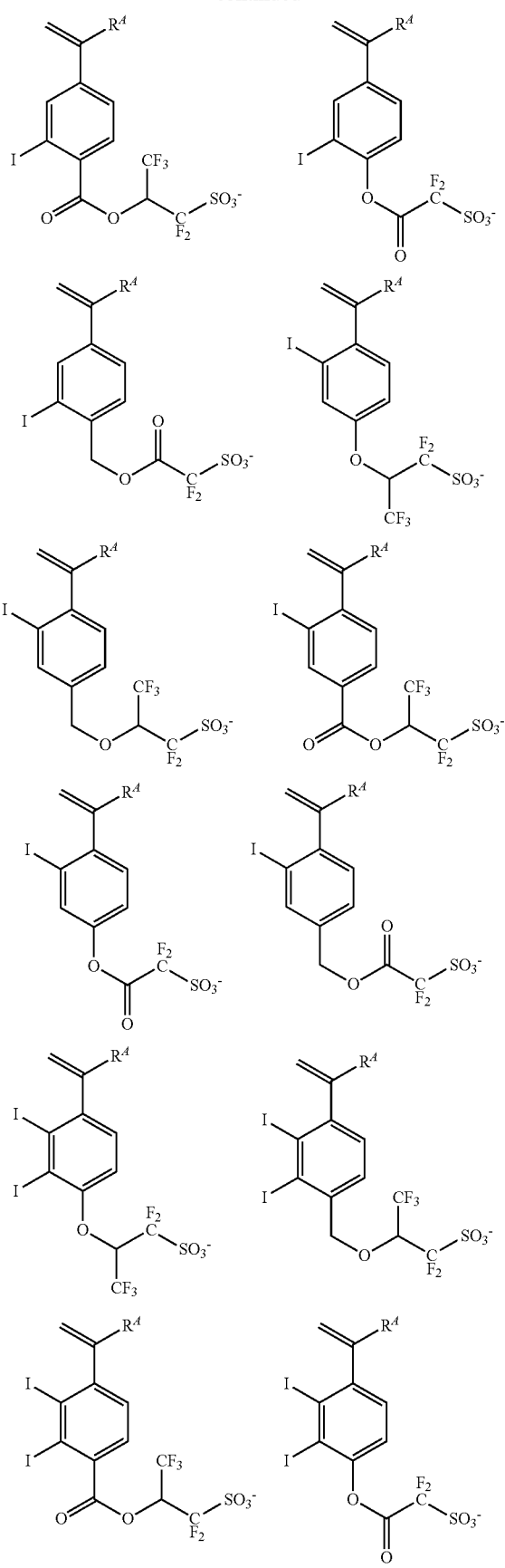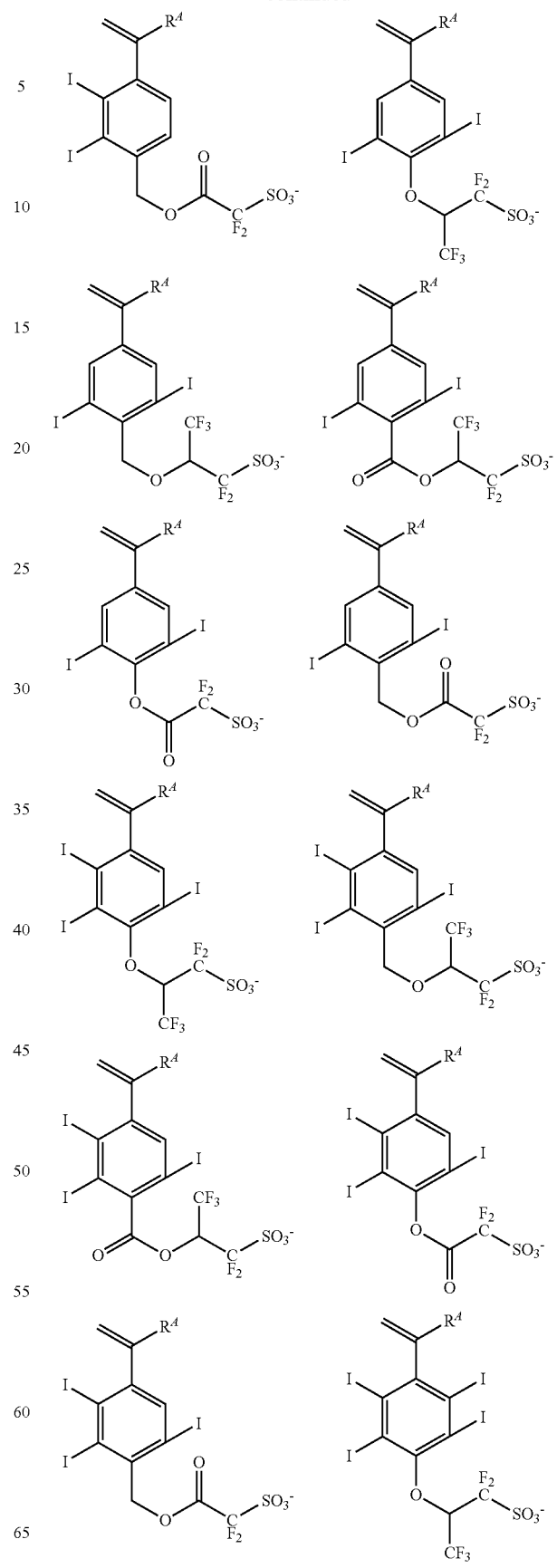

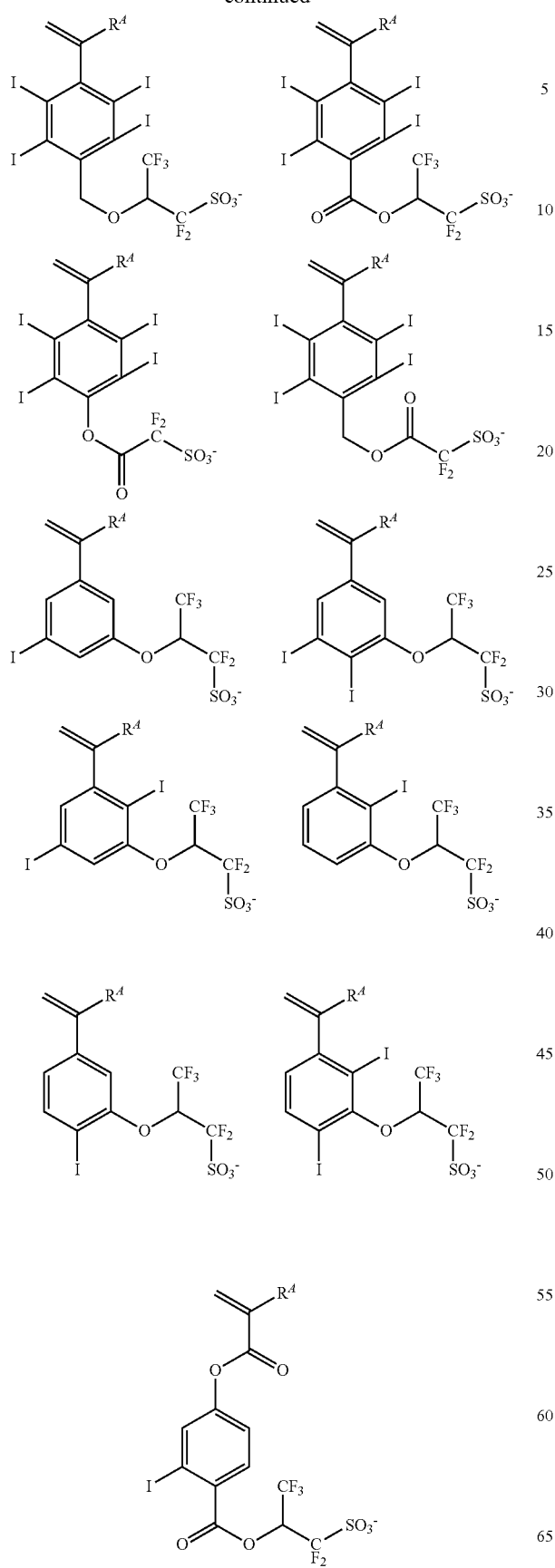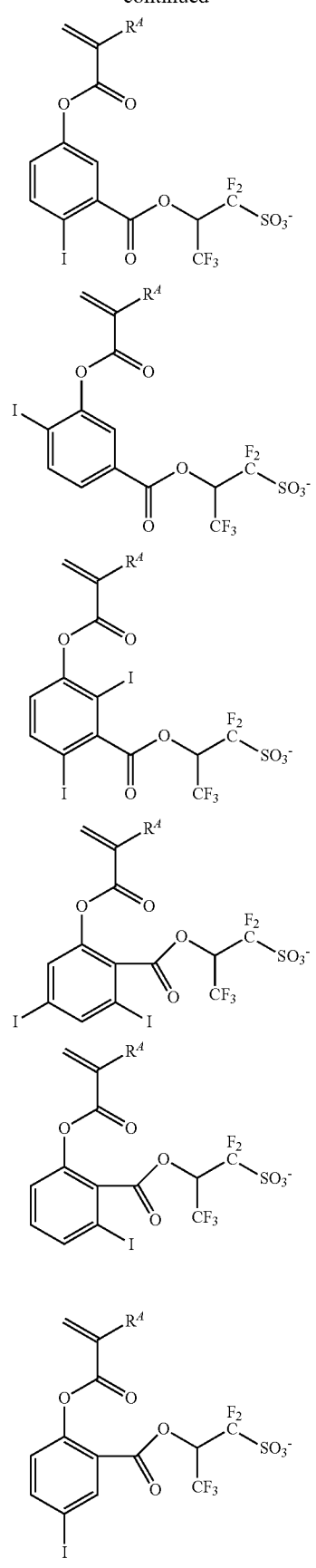

75
-continued
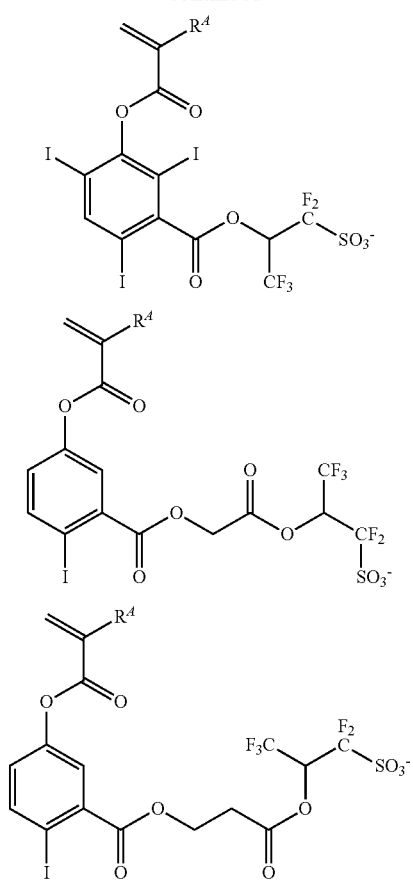
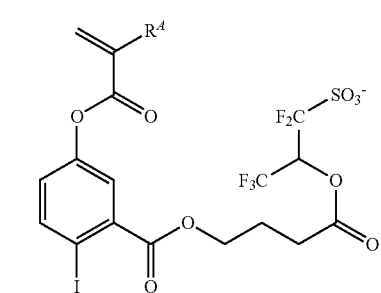
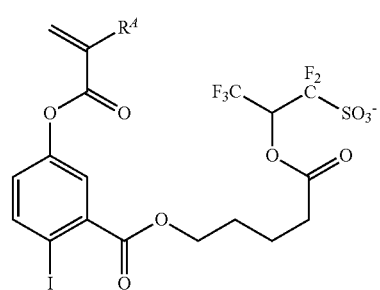
76
-continued
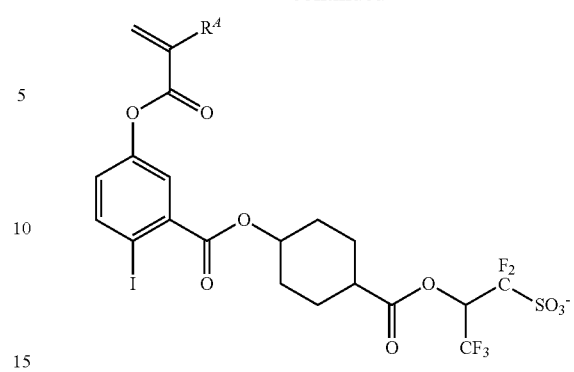
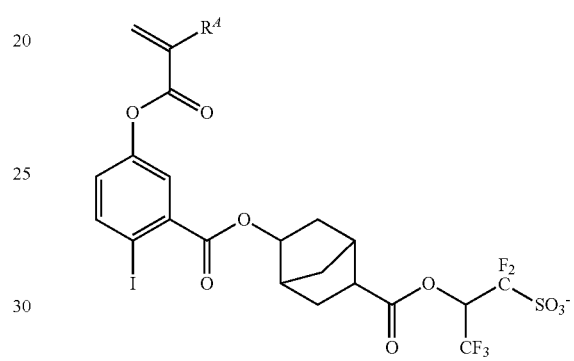
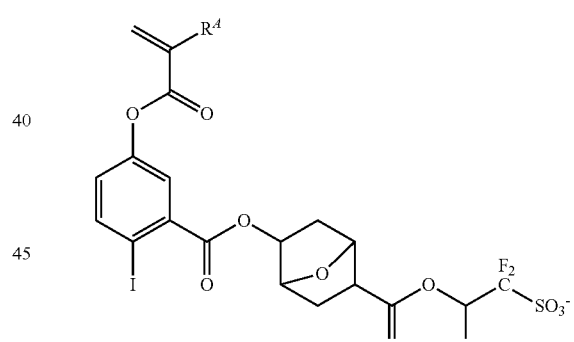
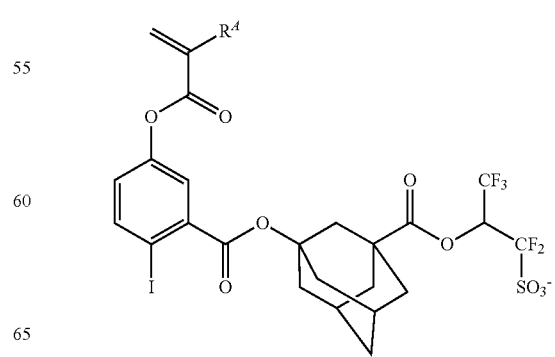

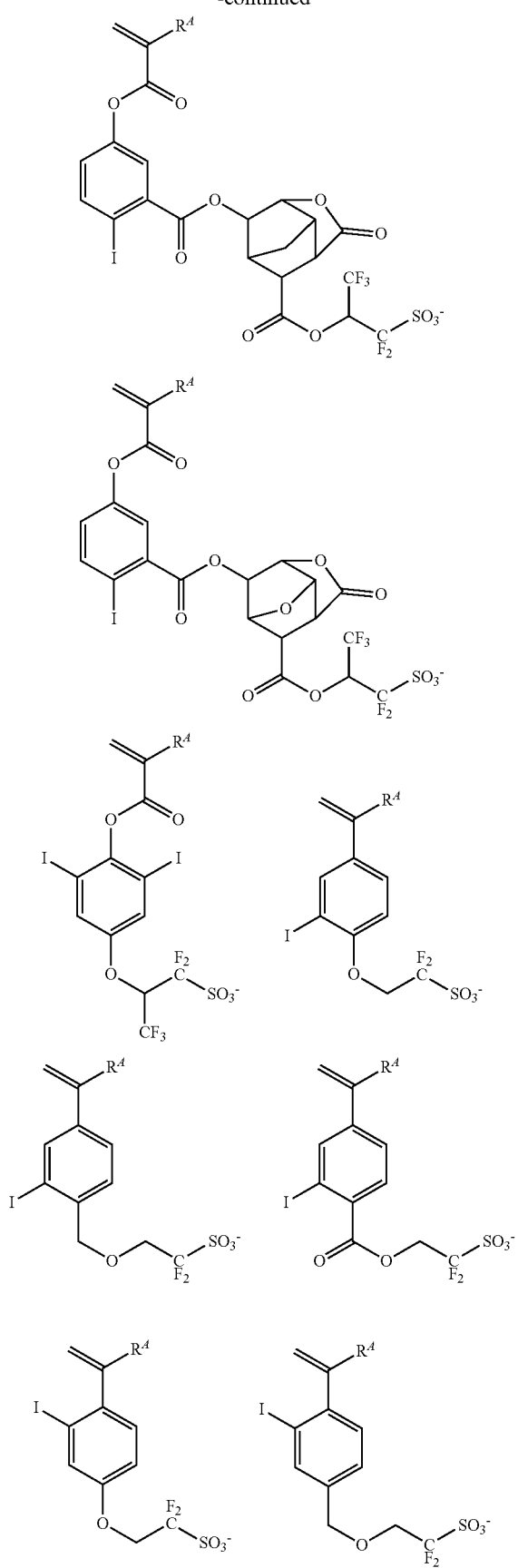
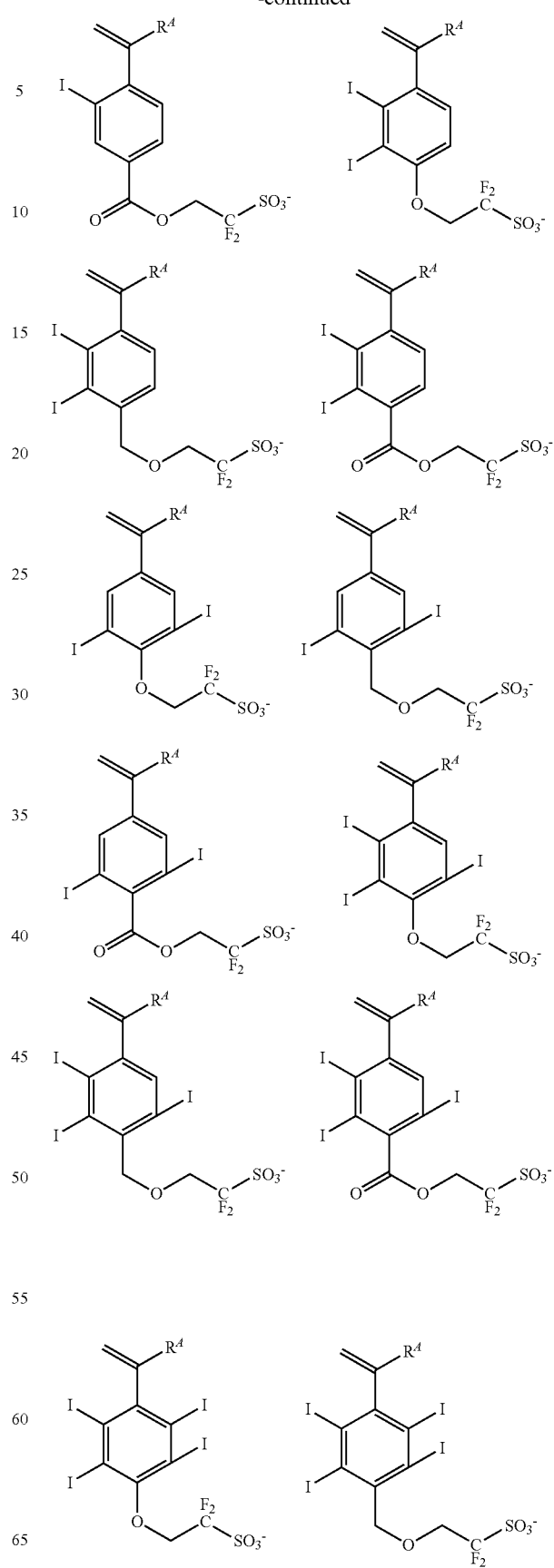

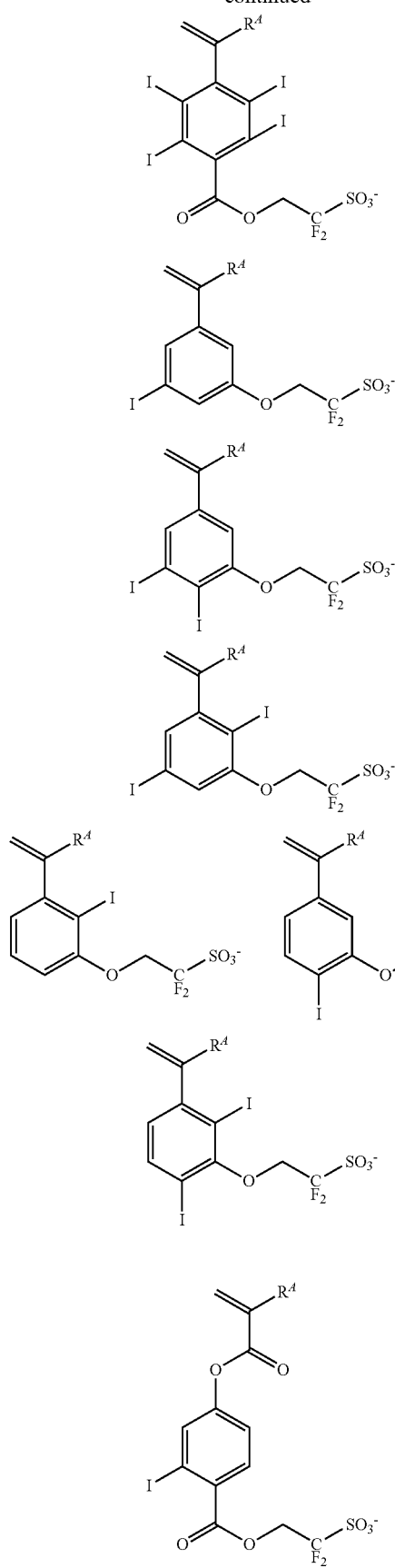
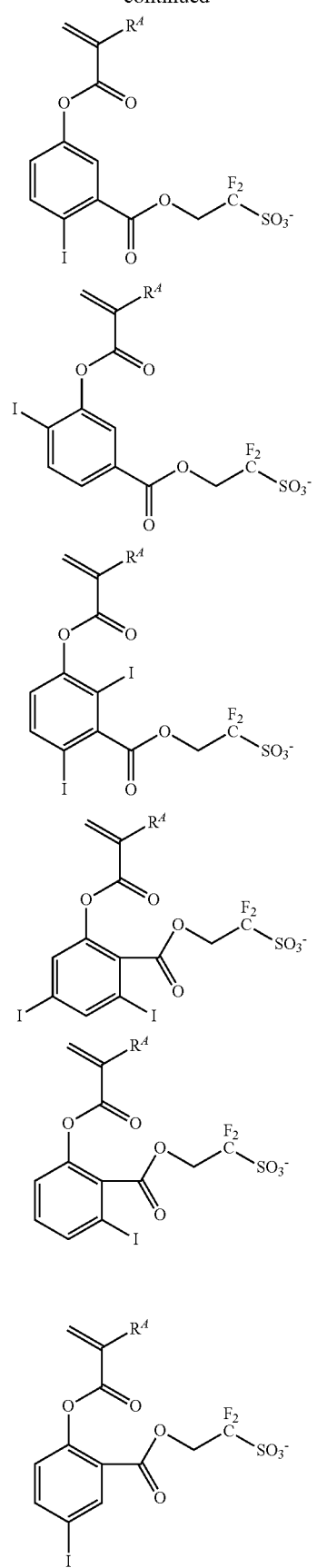

81
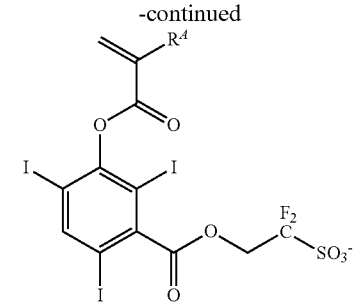
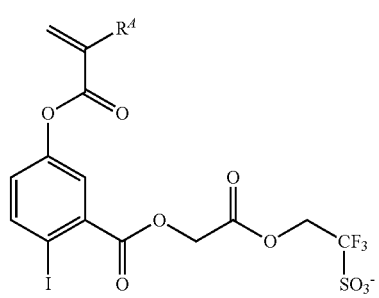
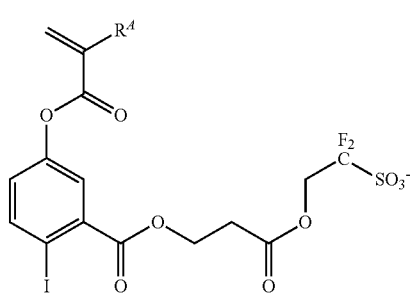
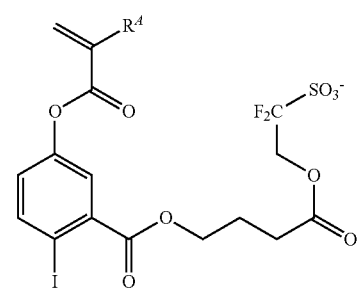
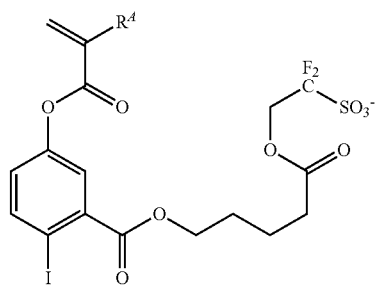
82
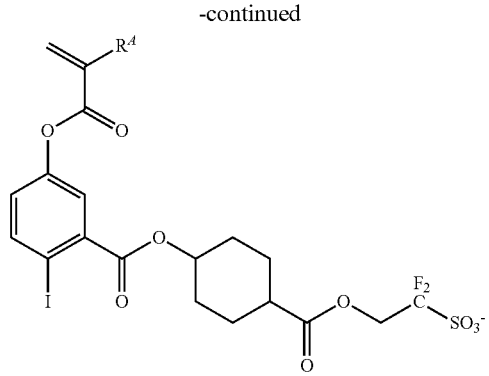
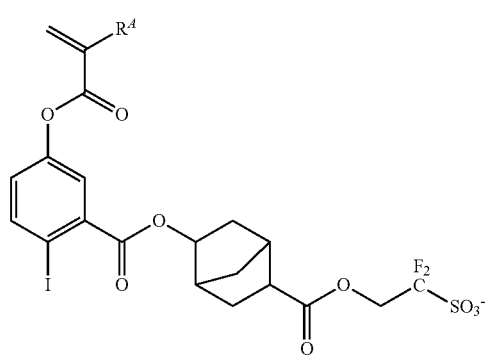
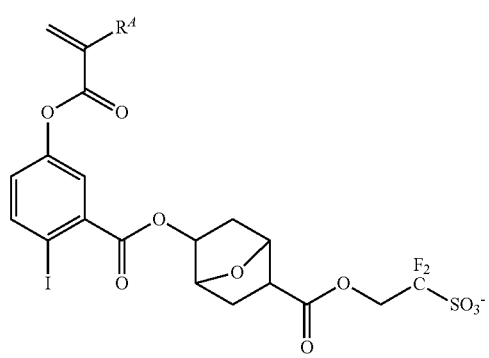
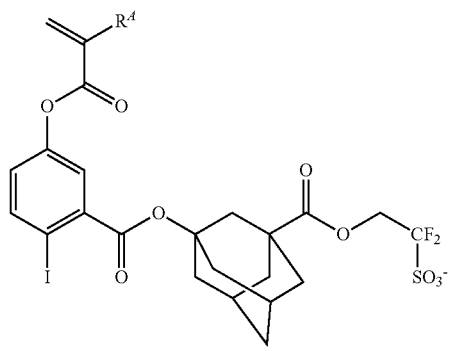

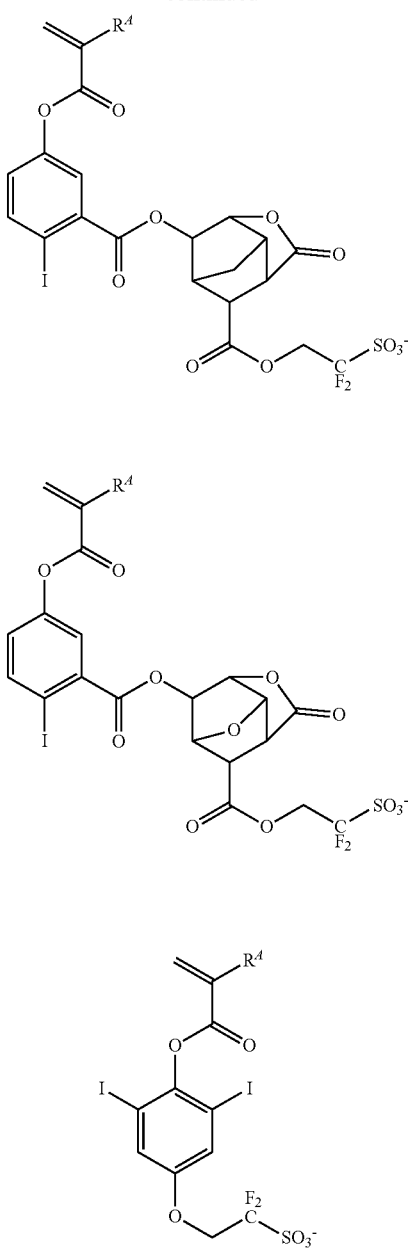
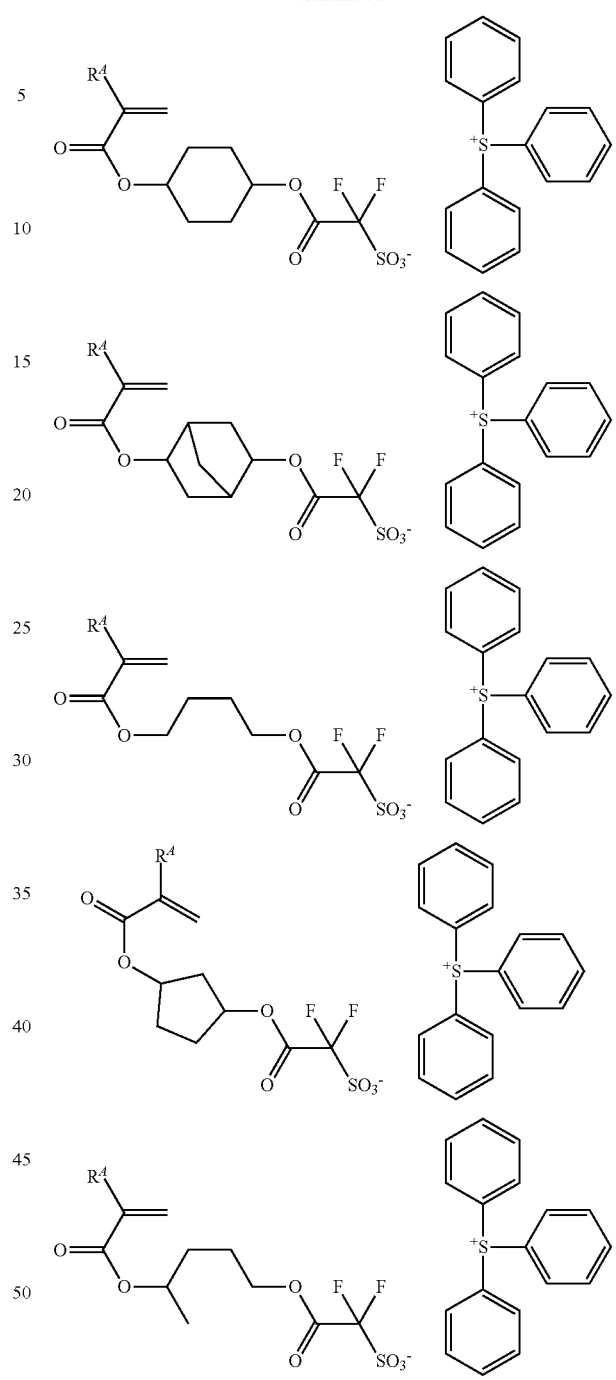
Examples of the monomer from which recurring unit (d3) is derived are shown below, but not limited thereto. $R^A$ is as defined above.
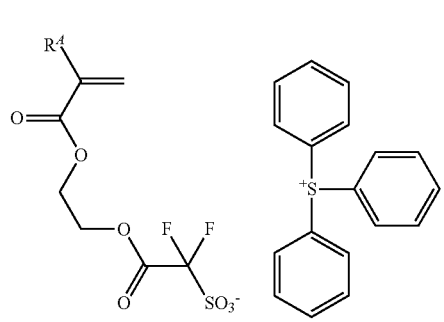
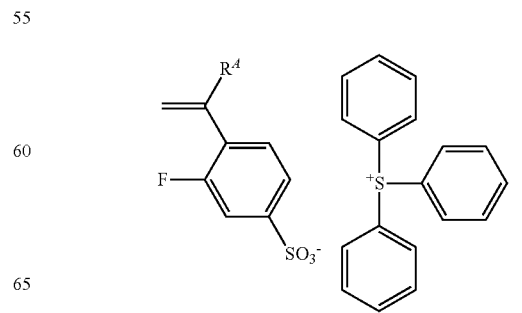

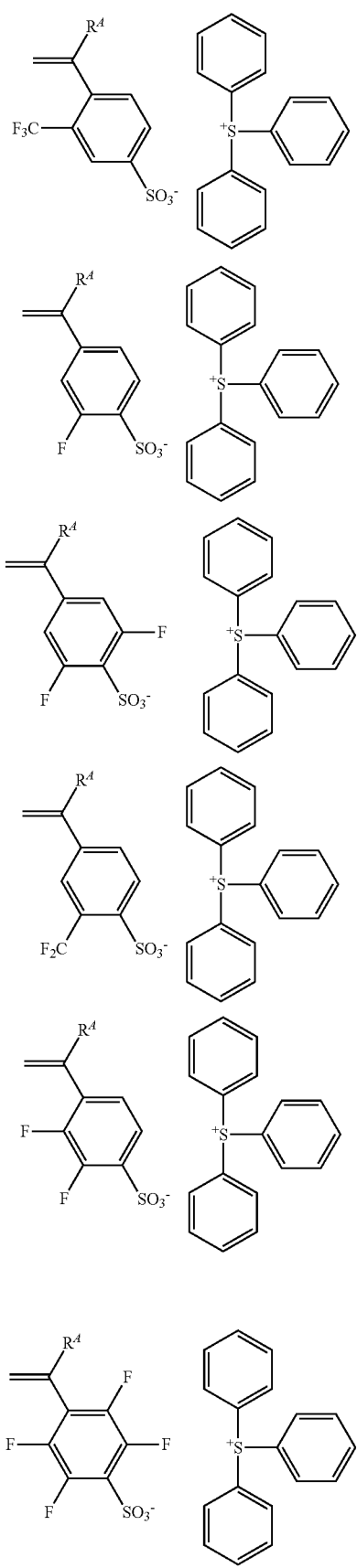
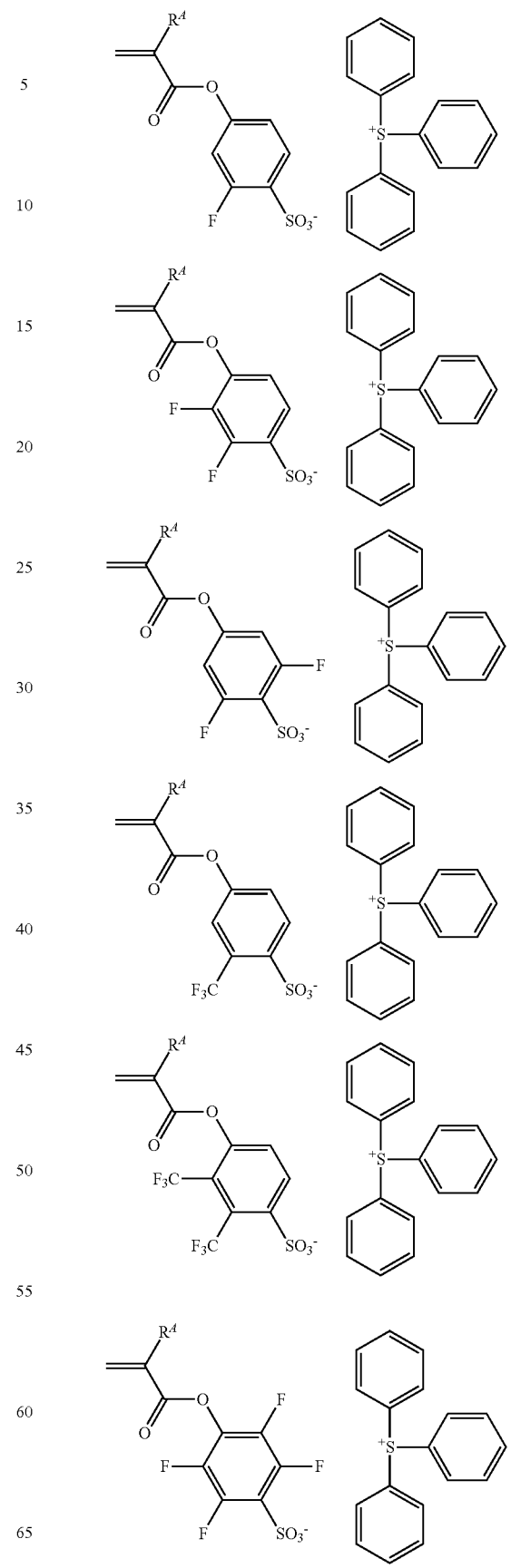

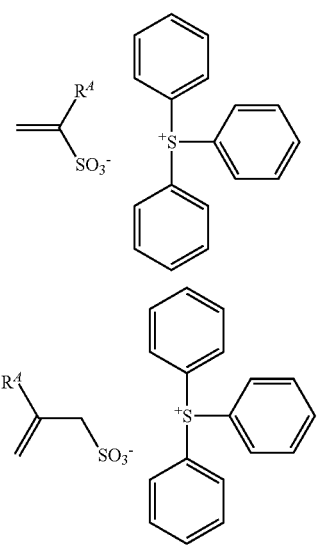

Recurring units (d1) to (d3) have the function of acid generator. The attachment of an acid generator to the polymer main chain is effective in restraining acid diffusion, thereby preventing a reduction of resolution due to blur by acid diffusion. Also LWR is improved since the acid generator is uniformly distributed. When a base polymer comprising recurring units (d) is used, an acid generator of addition type (to be described later) may be omitted.

The base polymer may further include recurring units (e) which contain iodine, but not amino group. Examples of the monomer from which recurring units (e) are derived are shown below, but not limited thereto. $R^4$ is as defined above.

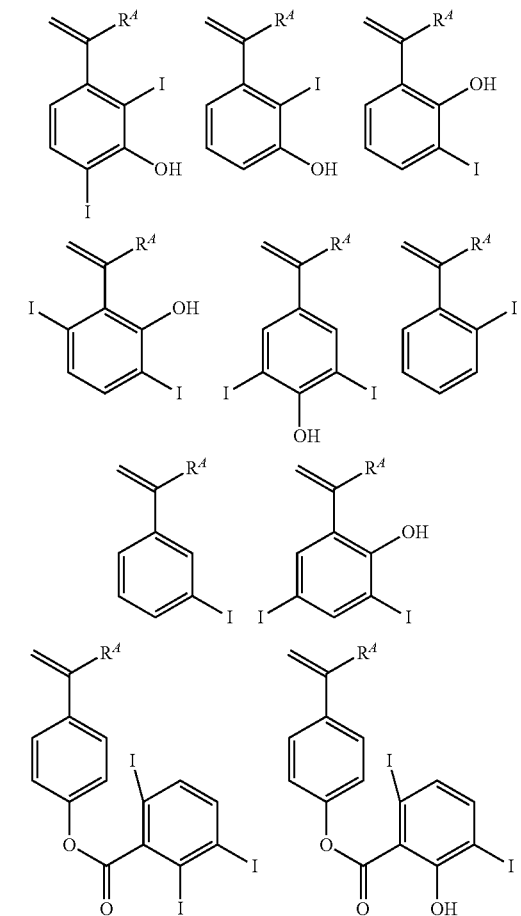

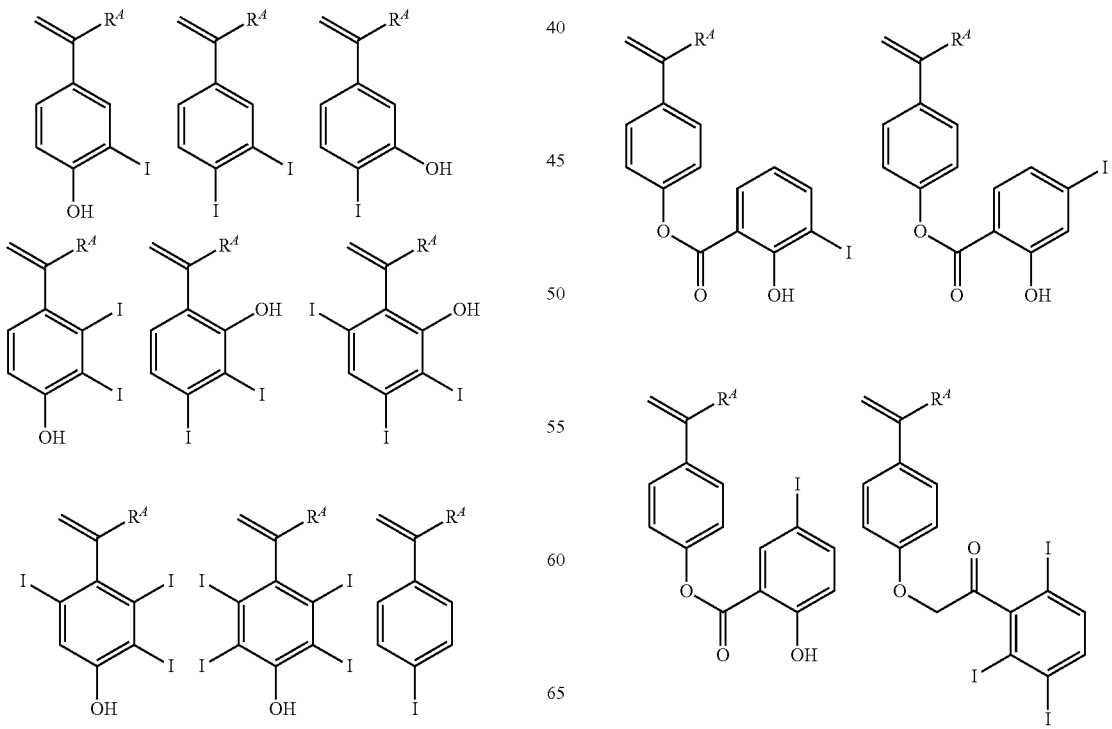

-continued

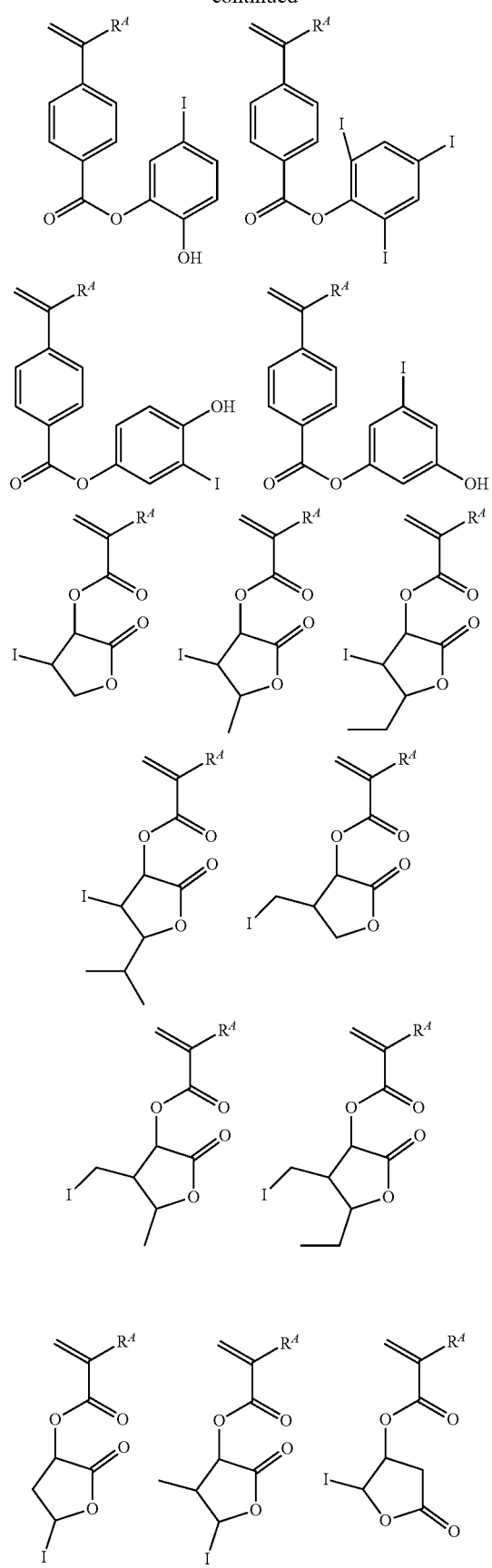

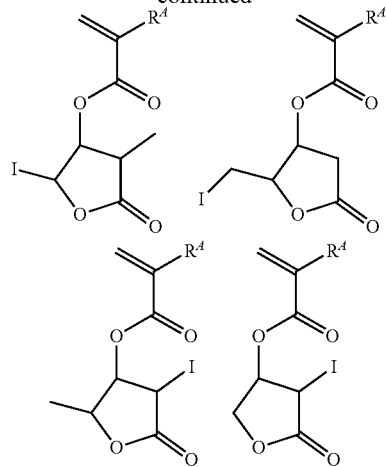

Besides the recurring units described above, further recurring units (f) may be incorporated in the base polymer, which are derived from such monomers as styrene, acenaphthylene, indene, coumarin, and coumarone.

In the base polymer comprising recurring units (a), (b1), (b2), (c), (d1), (d2), (d3), (e), and (f), a fraction of these units is: preferably $0<a<1.0$, $0≤b1≤0.9$, $0≤b2≤0.9$, $0≤b1+b2≤0.9$, $0≤c≤0.9$, $0≤d1≤0.5$, $0≤d2≤0.5$, $0≤d3≤0.5$, $0≤d1+d2+d3≤0.5$, $0≤e≤0.5$, and $0≤f≤0.5$;

more preferably $0.01≤a≤0.8$, $0≤b1≤0.8$, $0≤b2≤0.8$, $0≤b1+b2≤0.8$, $0≤c≤0.8$, $0≤d1≤0.4$, $0≤d2≤0.4$, $0≤d3≤0.4$, $0≤d1+d2+d3≤0.4$, $0≤e≤0.4$, and $0≤f≤0.4$; and even more preferably $0.02≤a≤0.7$, $0≤b1≤0.7$, $0≤b2≤0.7$, $0≤b1+b2≤0.7$, $0≤c≤0.7$, $0≤d1≤0.3$, $0≤d2≤0.3$, $0≤d3≤0.3$, $0≤d1+d2+d3≤0.3$, $0≤0.3$, and $0≤f≤0.3$. Notably, $a+b1+b2+c+d1+d2+d3+e+f=1.0$.

The base polymer may be synthesized by any desired methods, for example, by dissolving one or more monomers selected from the monomers corresponding to the foregoing recurring units in an organic solvent, adding a radical polymerization initiator thereto, and heating for polymerization. Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is 50 to 80° C., and the reaction time is 2 to 100 hours, more preferably 5 to 20 hours.

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

The base polymer may be a blend of two or more polymers which differ in compositional ratio, Mw or Mw/Mn. It may also be a blend of a polymer containing recurring units (a) and a polymer not containing recurring units (a).

Acid Generator

The positive resist composition may contain an acid generator capable of generating a strong acid, also referred to as acid generator of addition type. As used herein, the "strong acid" is a compound having a sufficient acidity to induce deprotection reaction of acid labile groups on the base polymer. The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imidic acid (imide acid) or methide acid are preferred. Suitable PAGs include sulfonium salts, iodonianm salts, sulfonyldiazomethane, N-sulfonyloxyimide, and oxime—O-sulfonate acid generators. Suitable PAGs are as exemplified in U.S. Pat. No. 7,537,880 (JP-A 2008-111103, paragraphs [0122]-[0142]).

Also sulfonium salts having the formula (1-1) and iodonium salts having the formula (1-2) are useful PAGs.

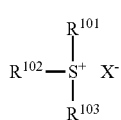

(1-1)

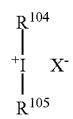

(1-2)

In formulae (1-1) and (1-2), $R^{101}$ to $R^{105}$ are each independently a $C_1$-$C_{20}$ monovalent hydrocarbon group which may contain a heteroatom. Any two of $R^{101}$, $R^{102}$ and $R^{103}$ may bond together to form a ring with the sulfur atom to which they are attached. The monovalent hydrocarbon group may be straight, branched or cyclic, and examples thereof are as exemplified above for $R^{21}$ to $R^{28}$ in formulae (d1) to (d3).

Examples of the cation of the sulfonium salt having formula (1-1) are shown below, but not limited thereto.

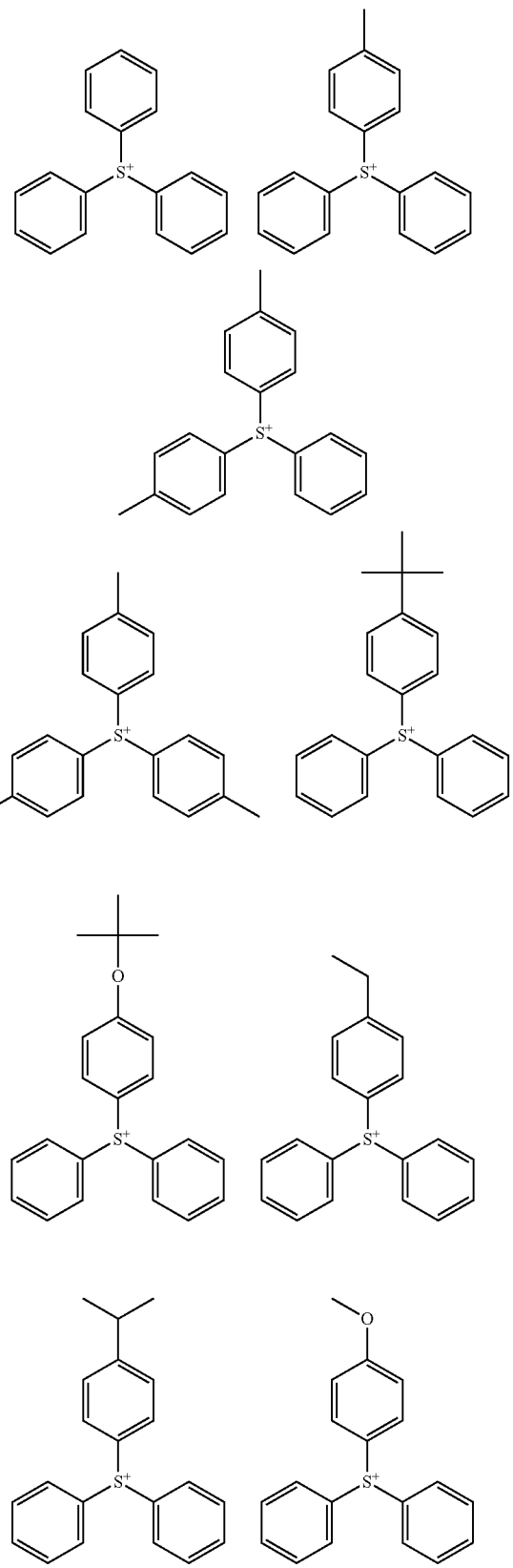

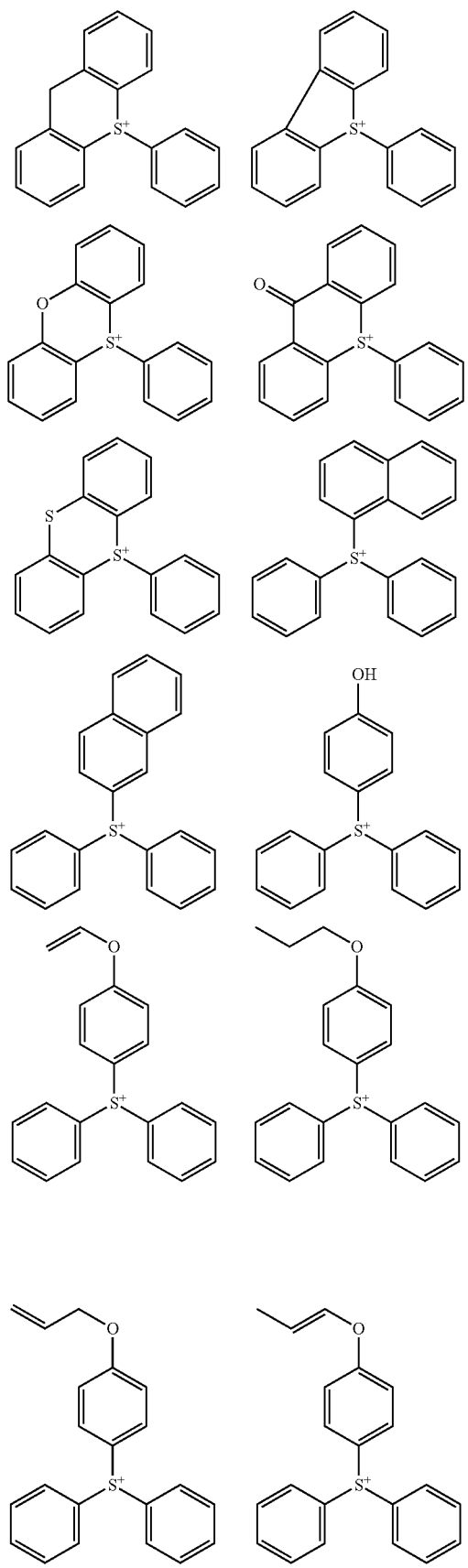
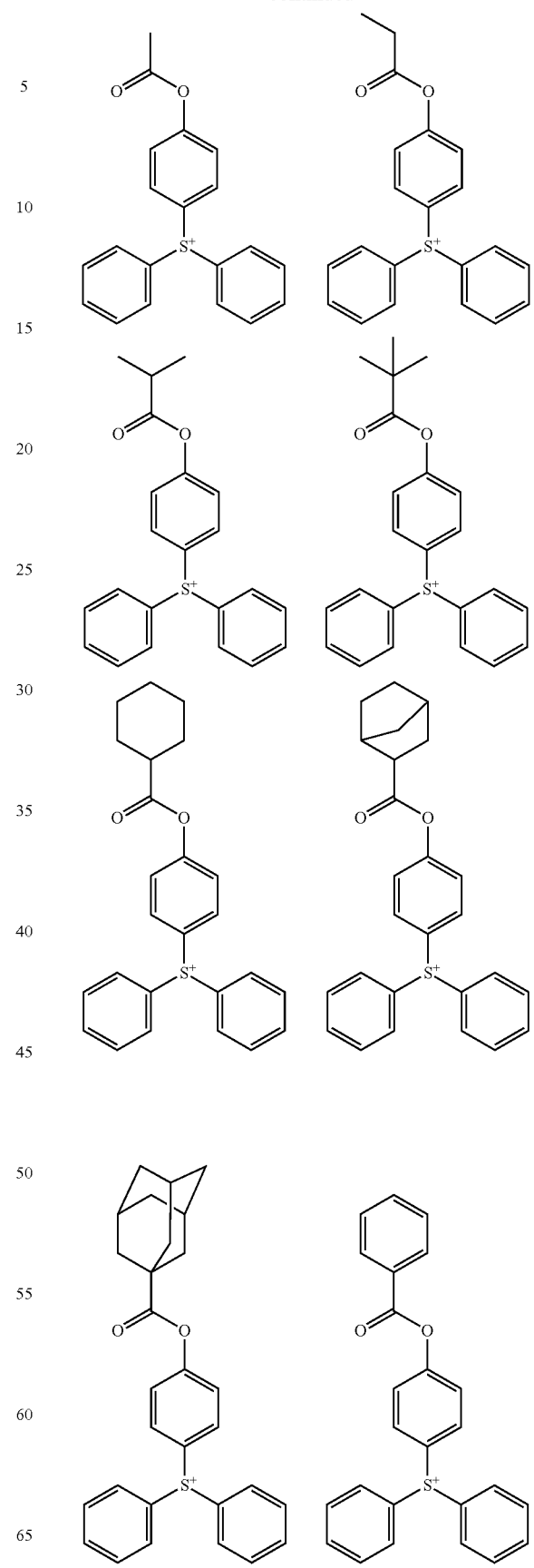

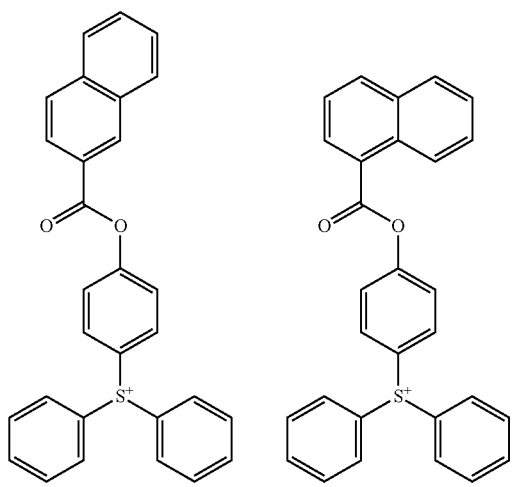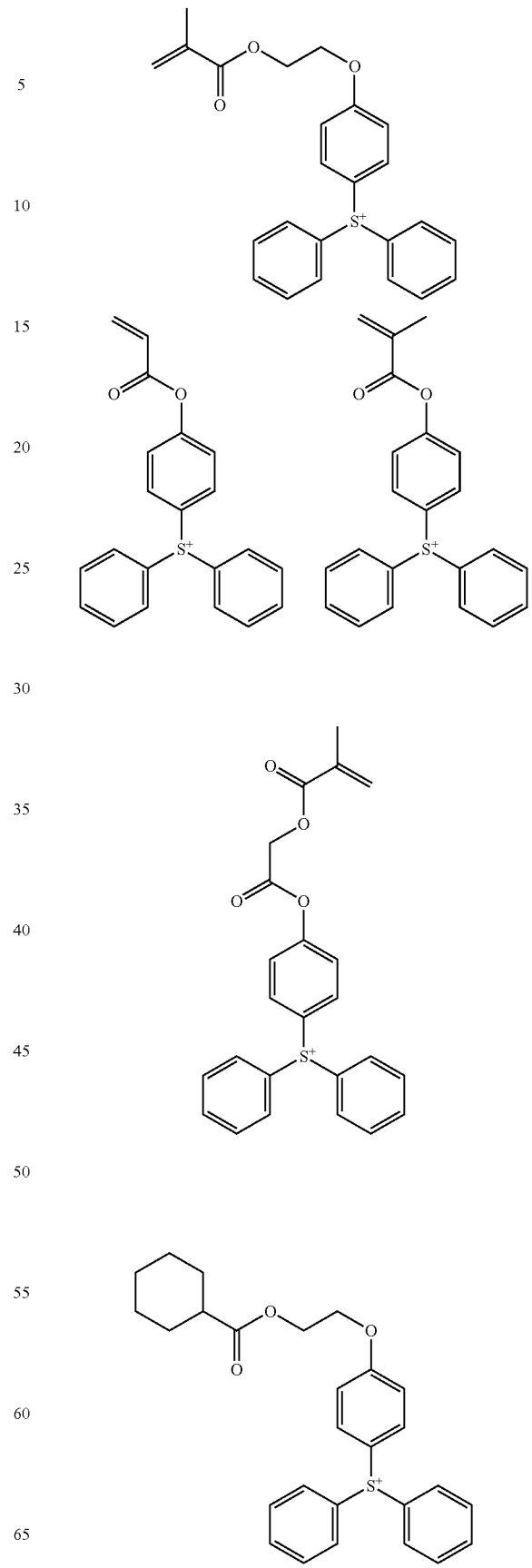

97
-continued
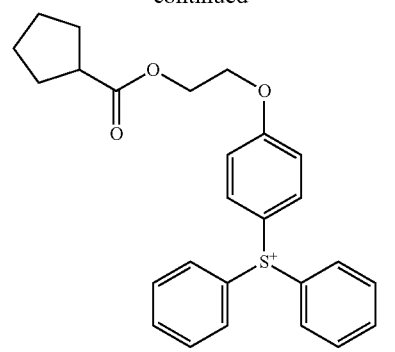
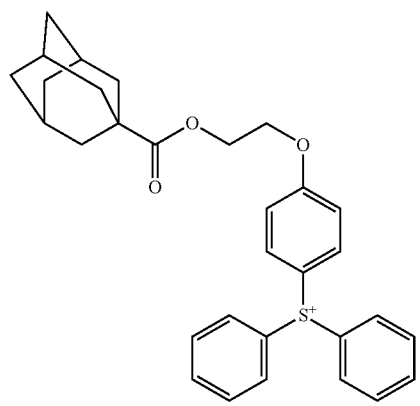
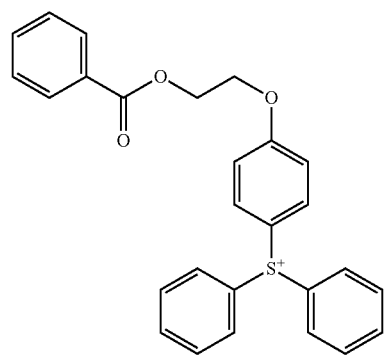
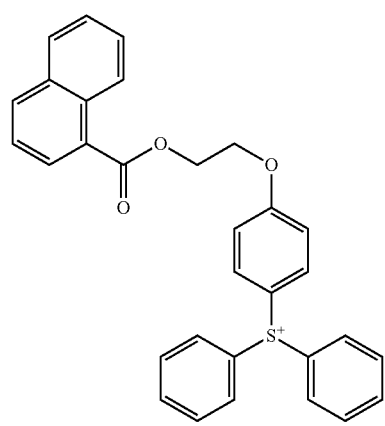
98
-continued
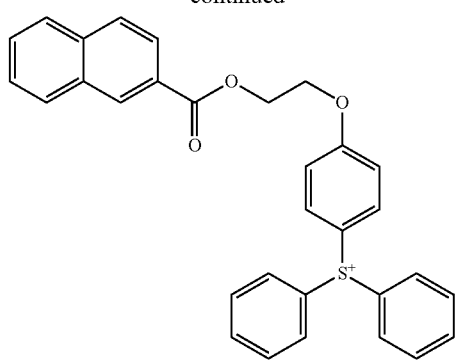
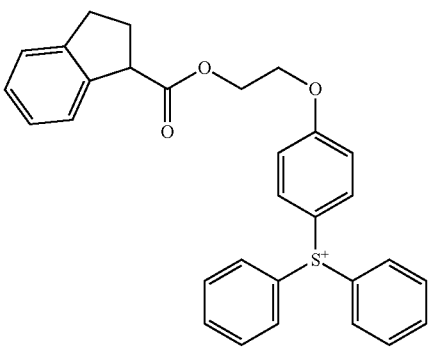
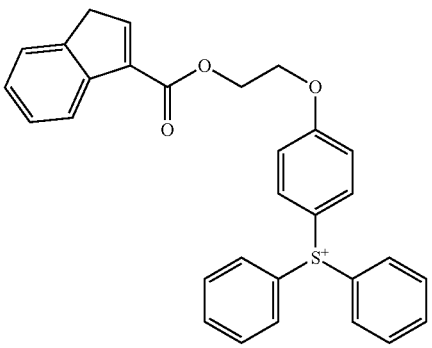
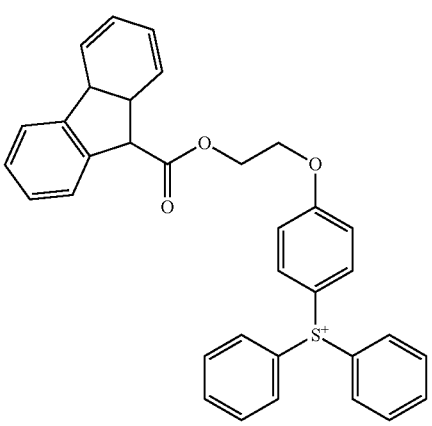

99
-continued
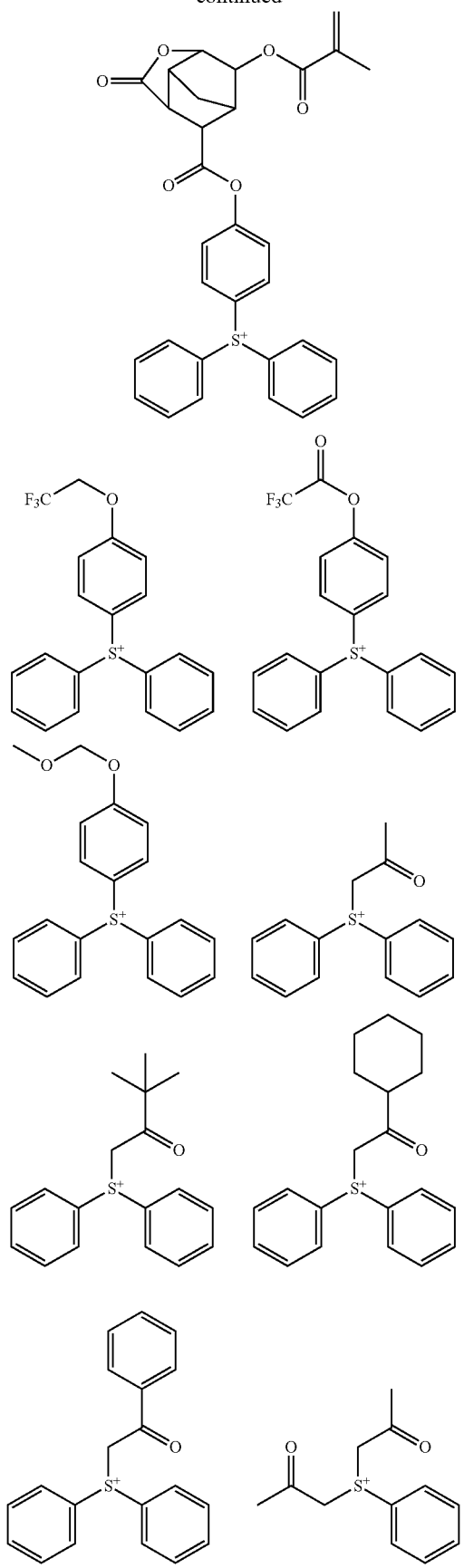
100
-continued
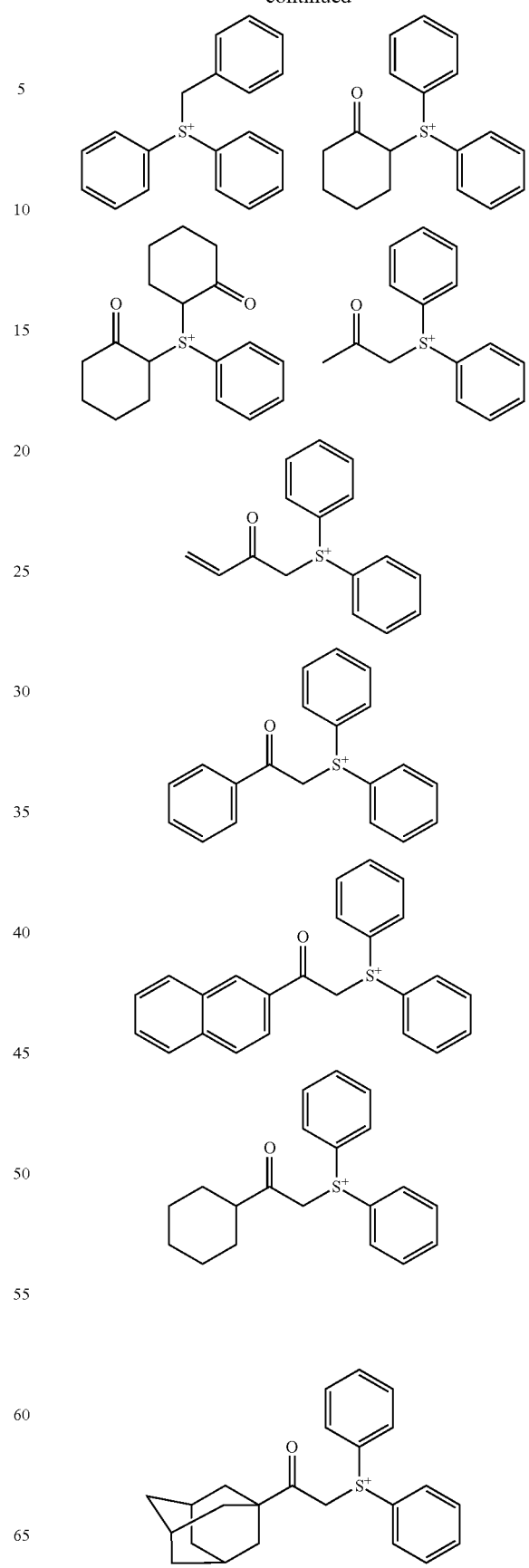

101
-continued
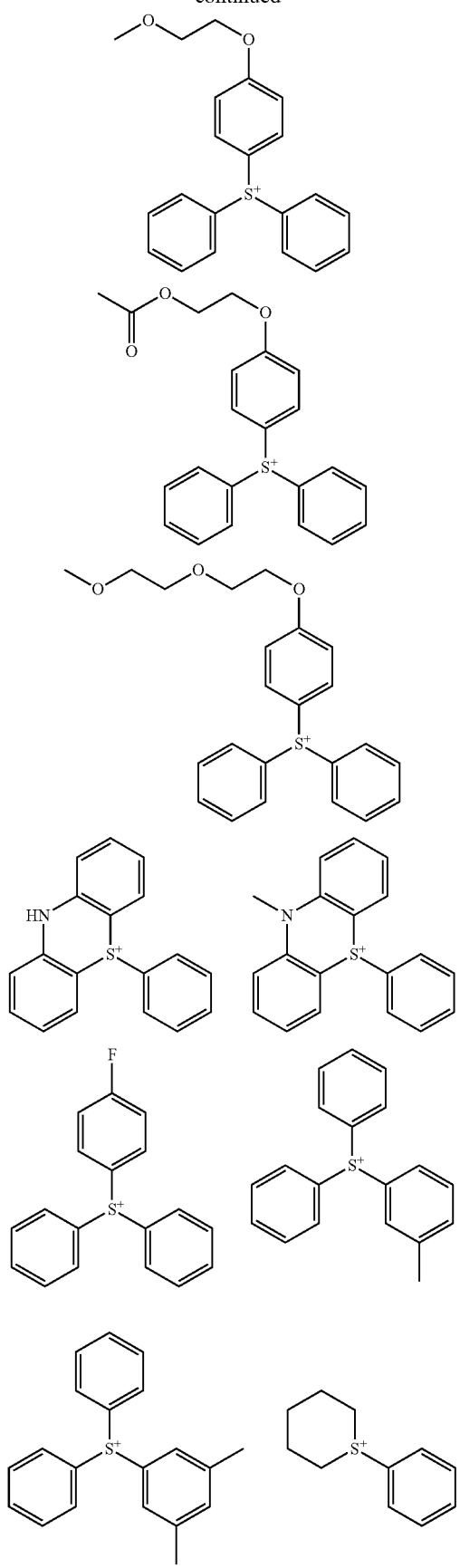
102
-continued
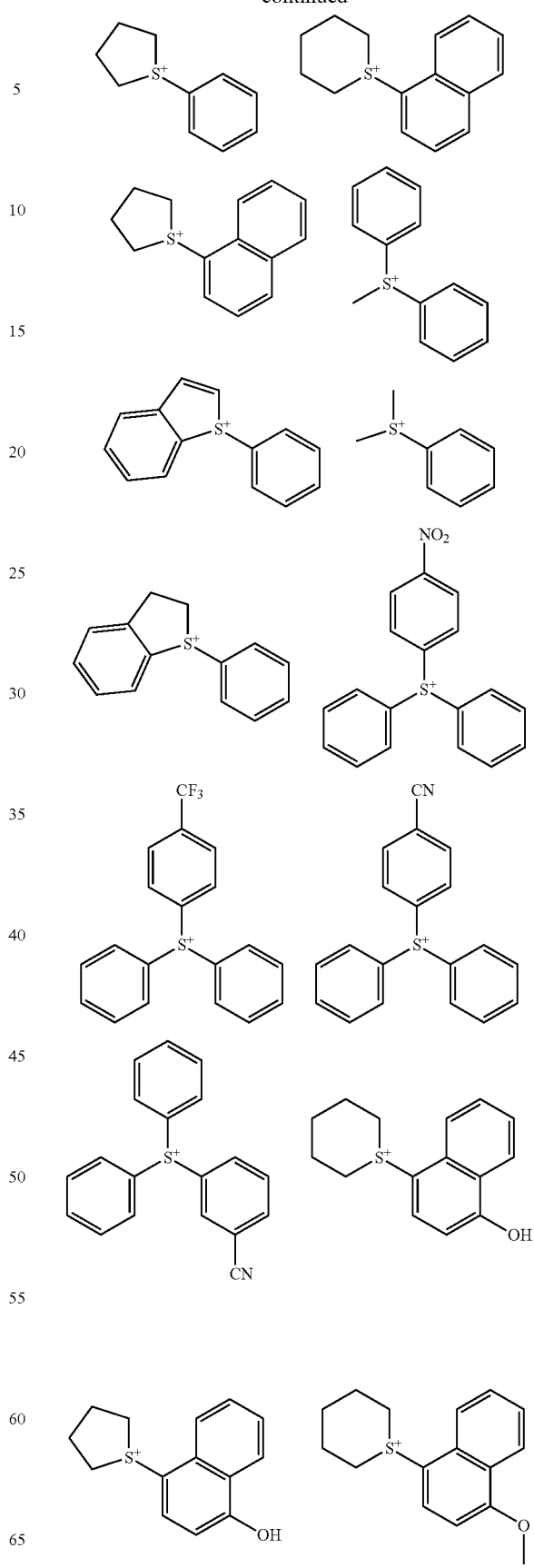

103
-continued
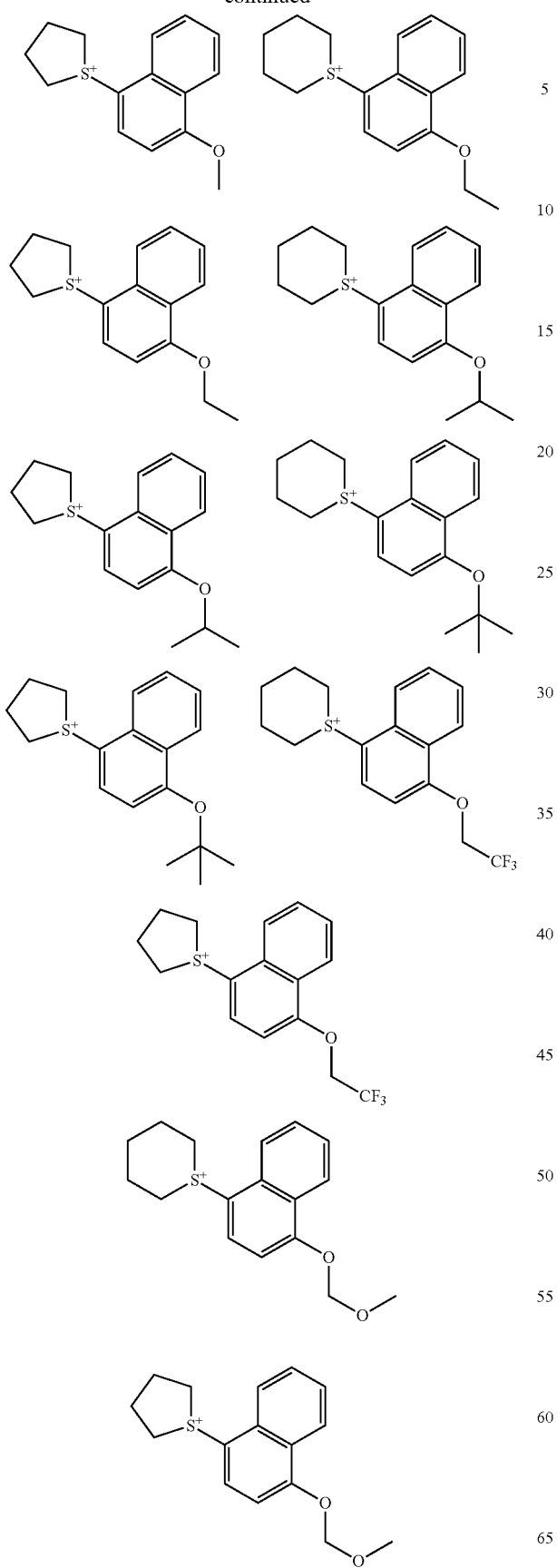
104
-continued
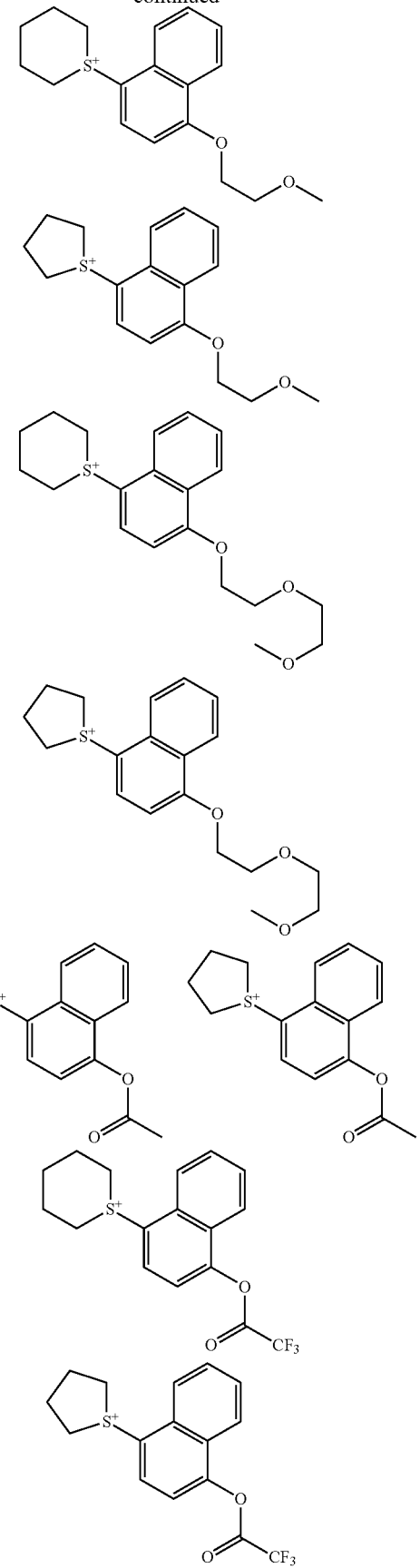

105
-continued
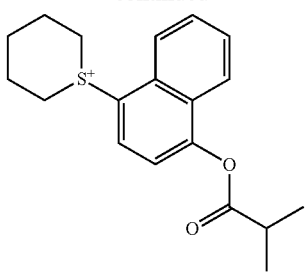
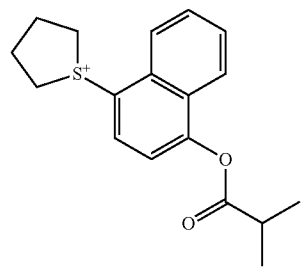
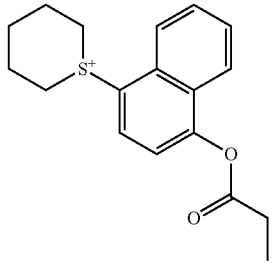
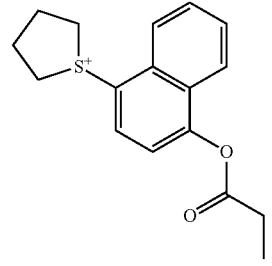
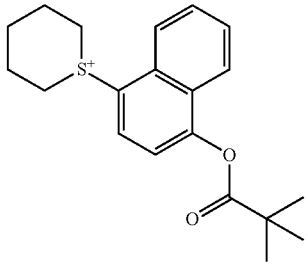
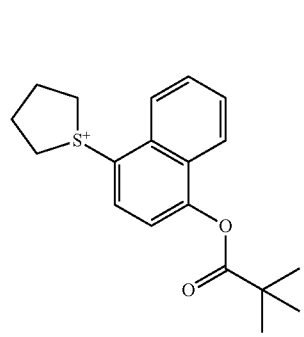
106
-continued
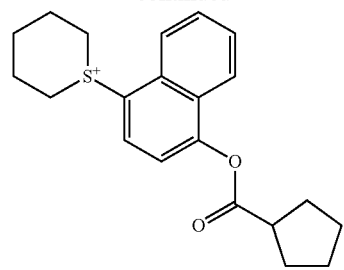
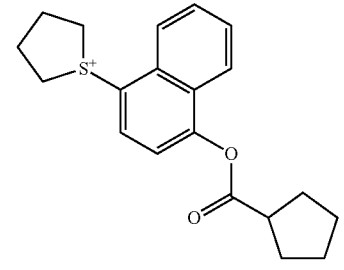
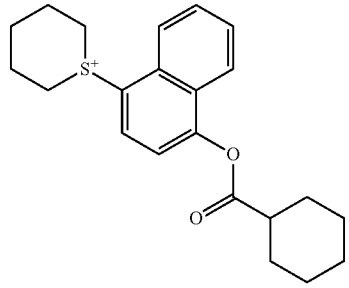
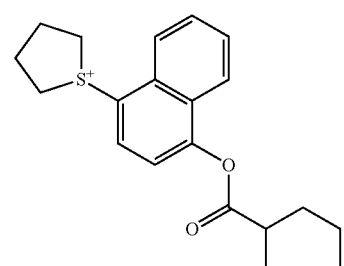
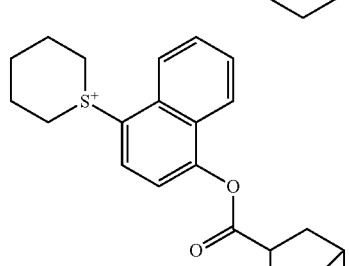
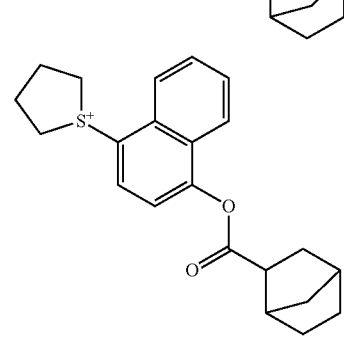

107 -continued
108 -continued
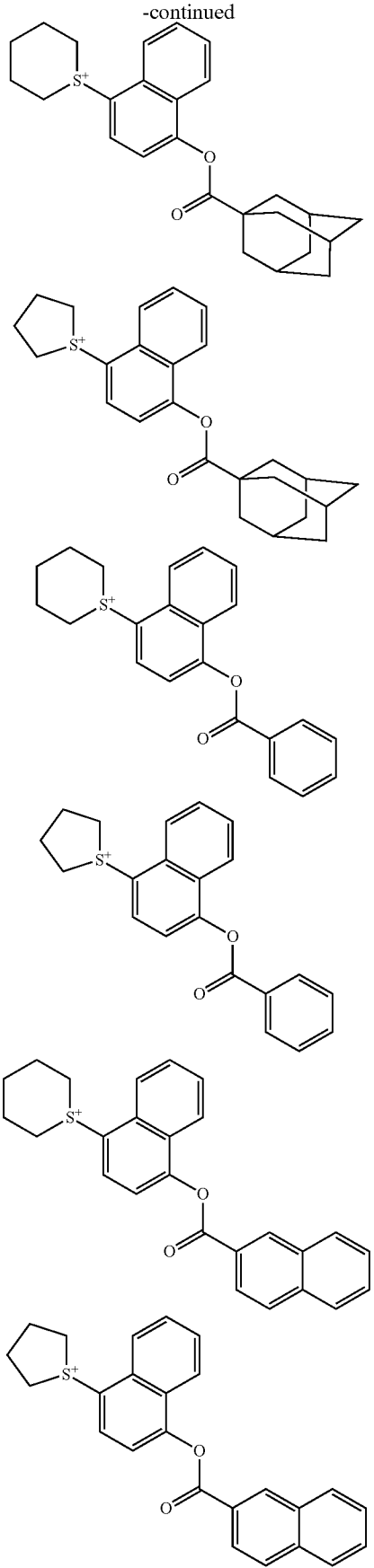
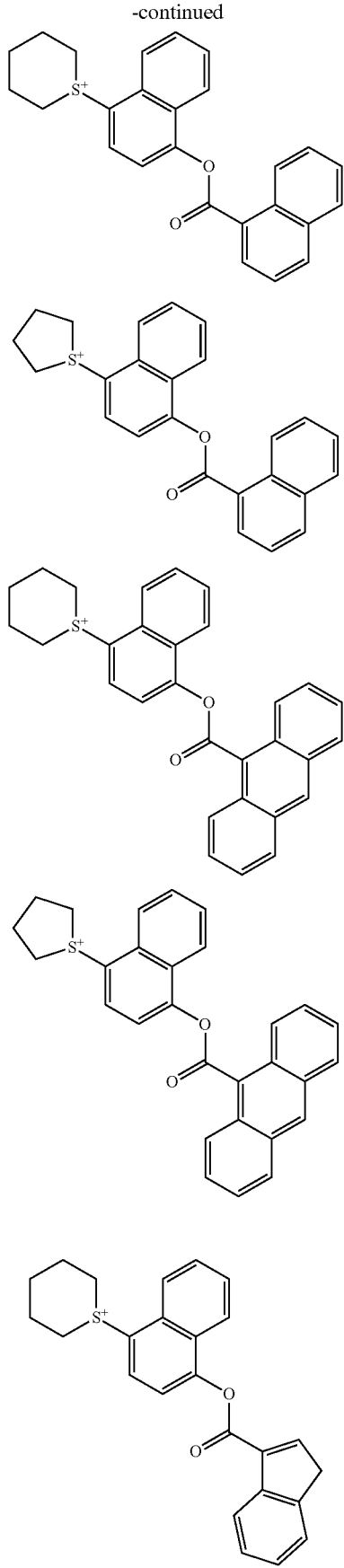

109
-continued
110
-continued
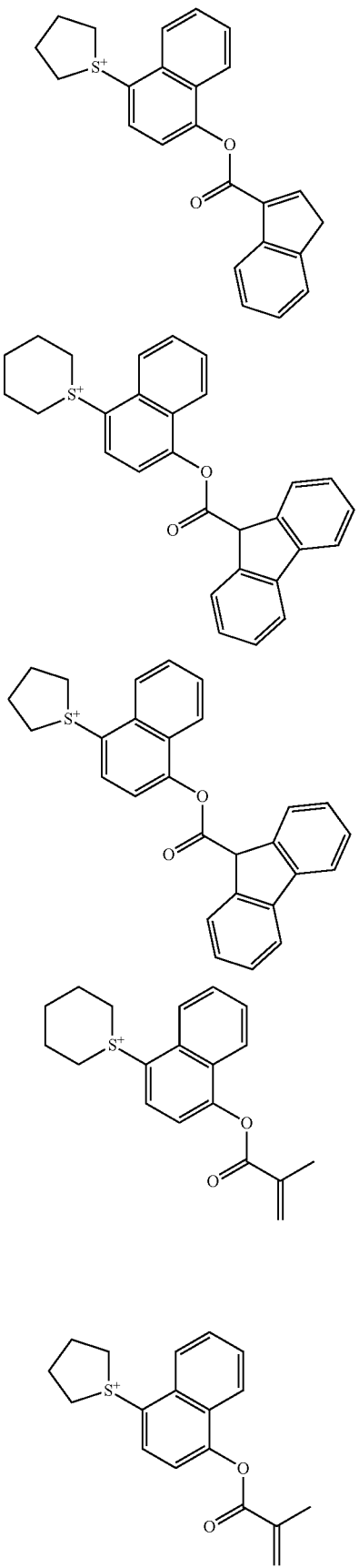
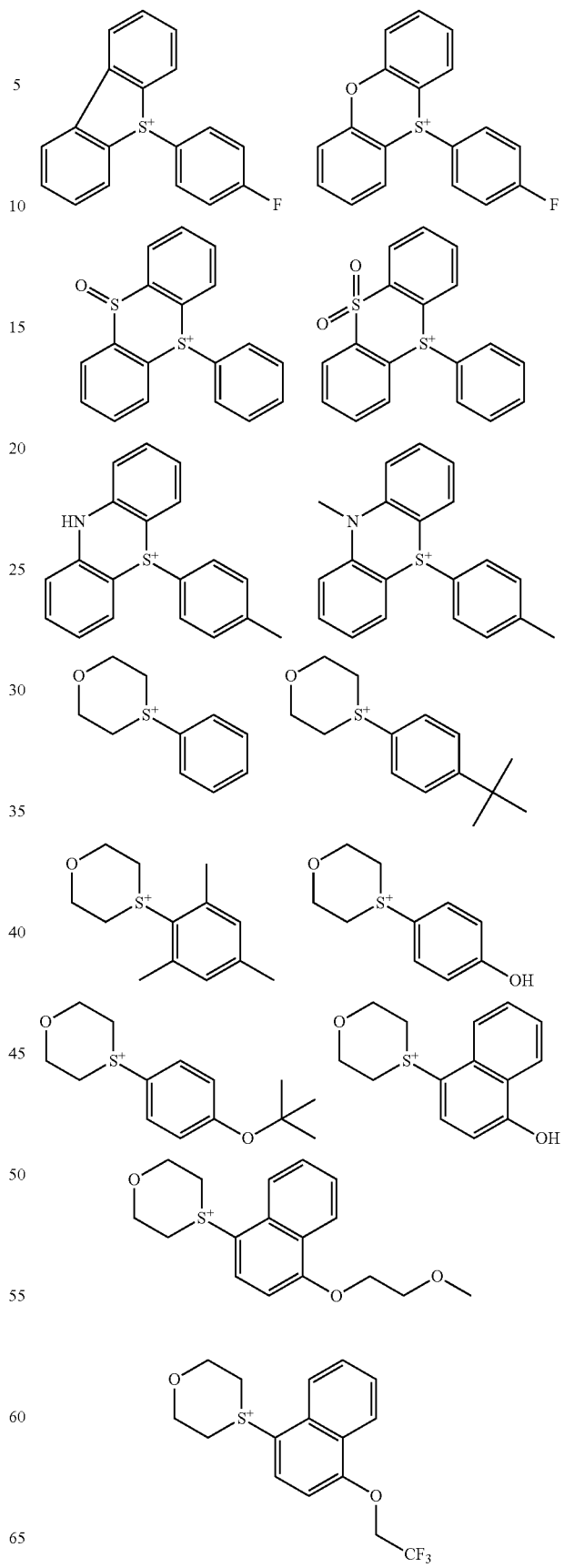

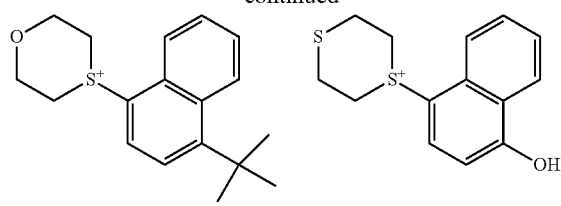
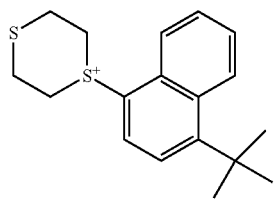
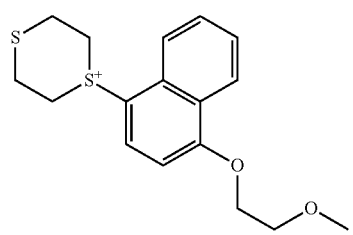
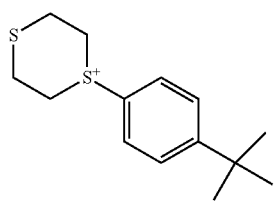
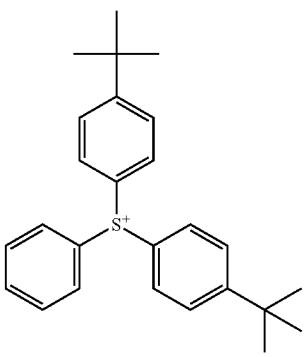
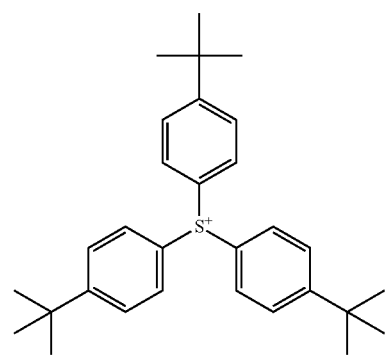
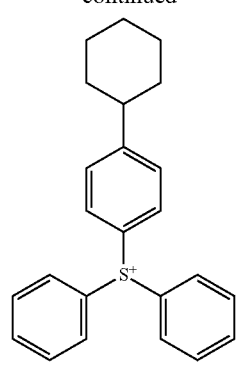
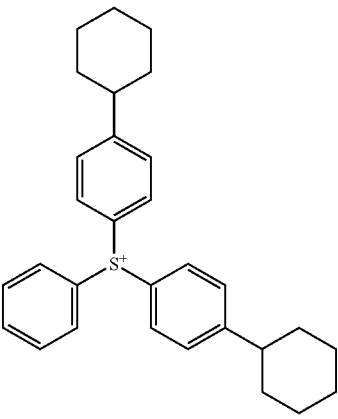
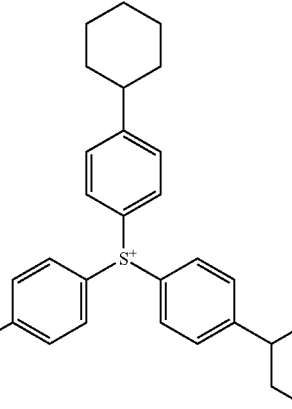
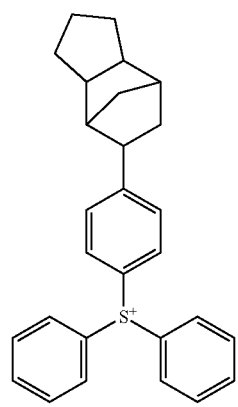

113
-continued
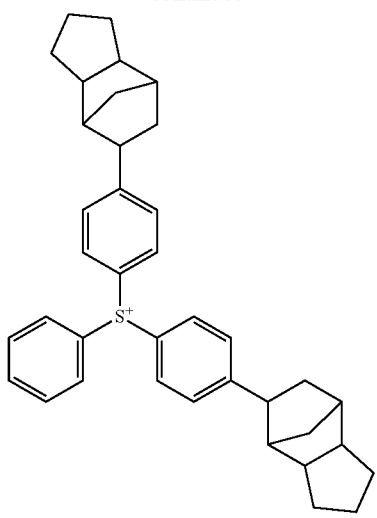
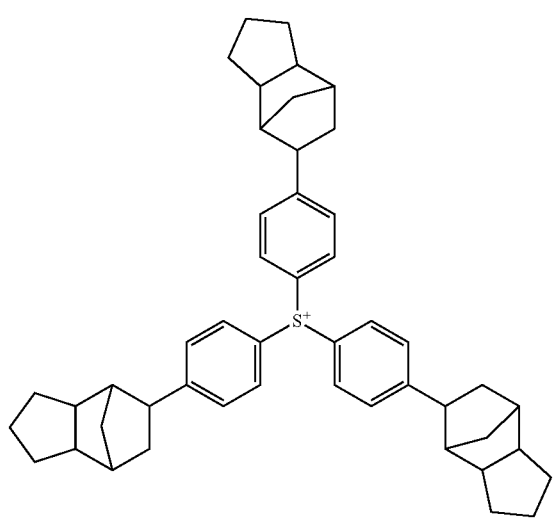
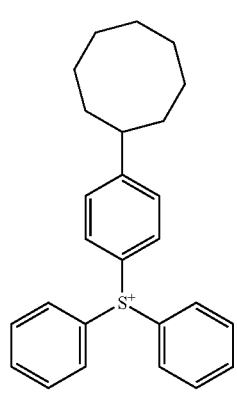
114
-continued
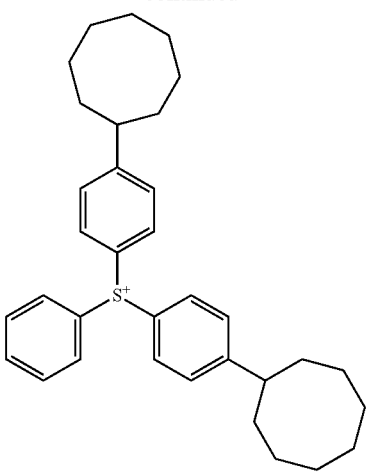
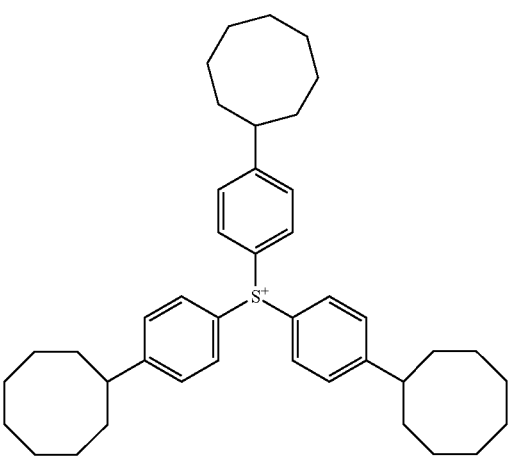
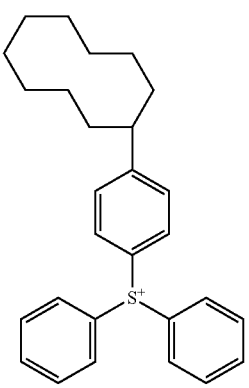

115
-continued
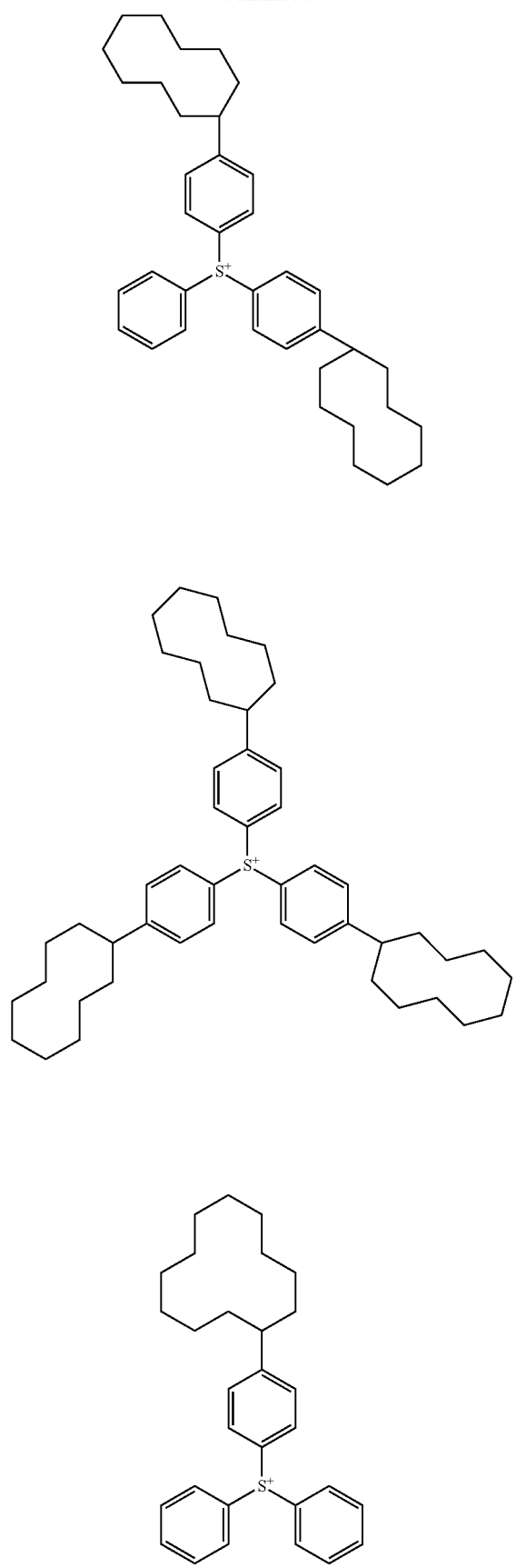
116
-continued
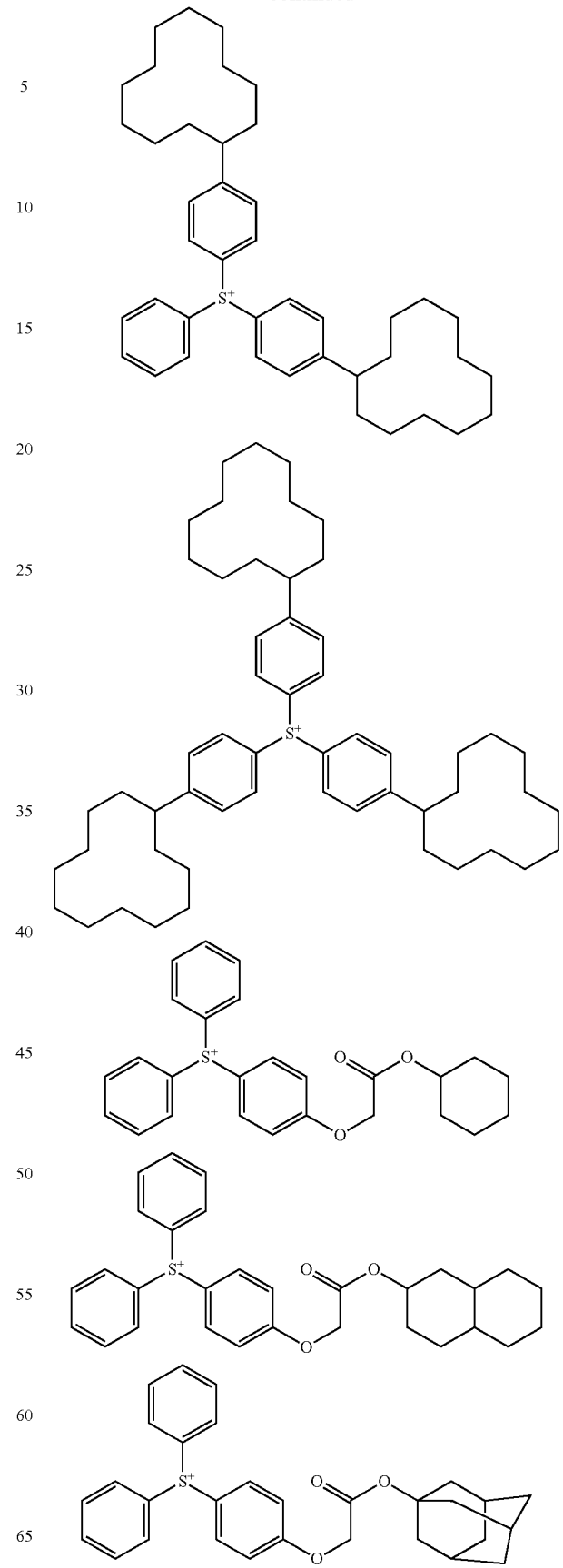

117
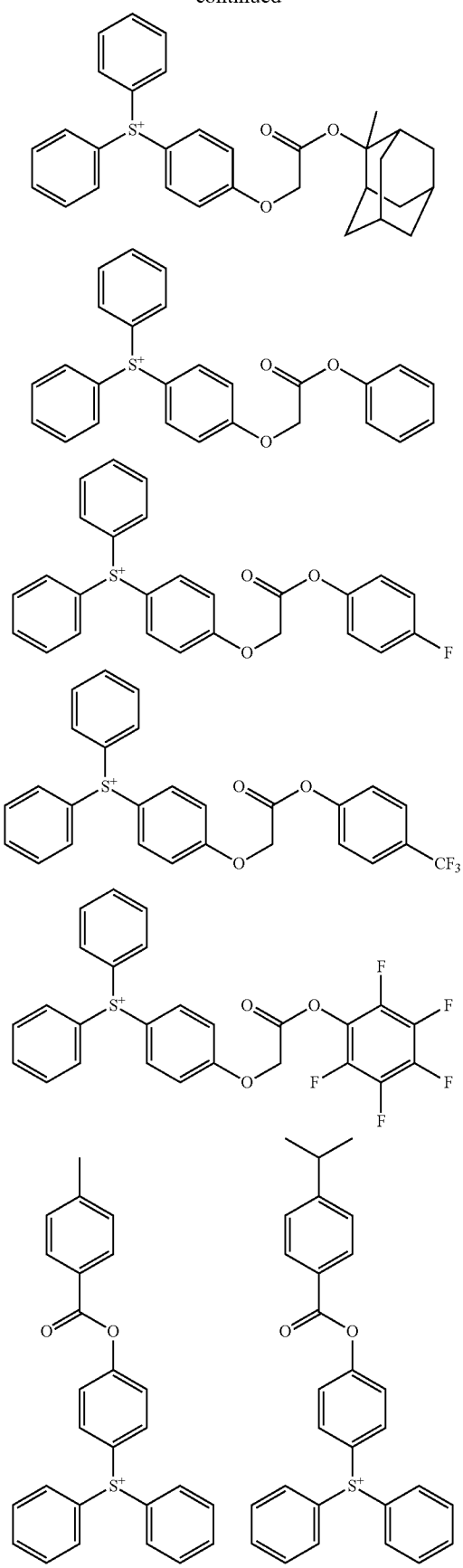
118
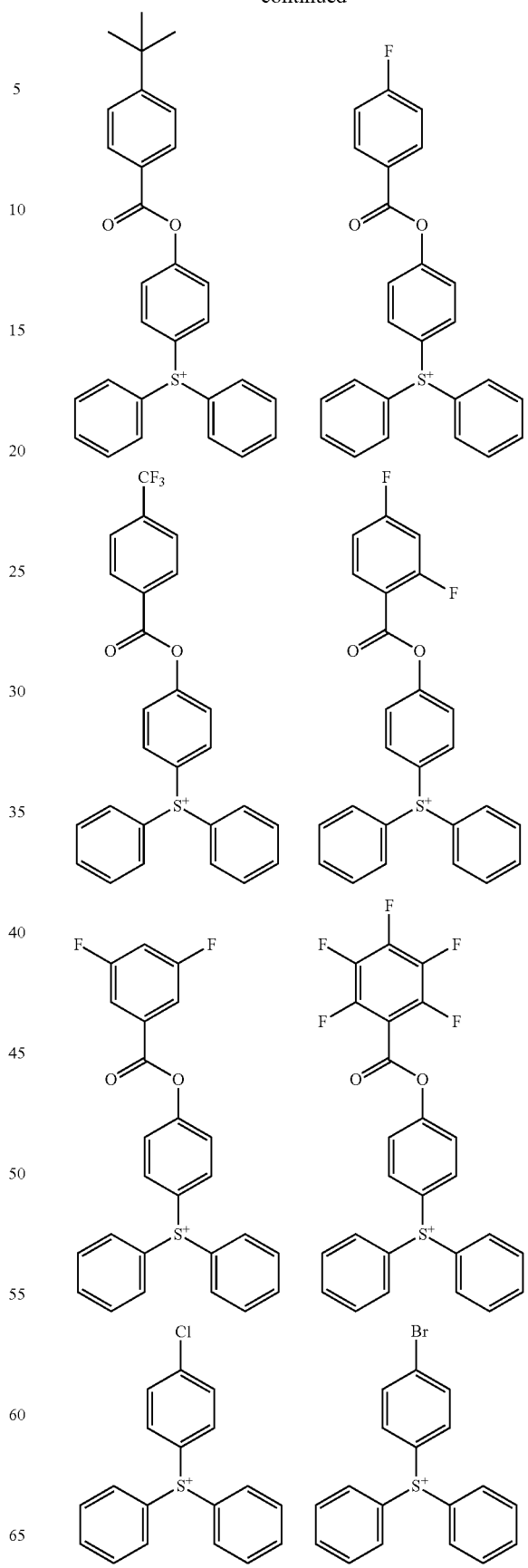

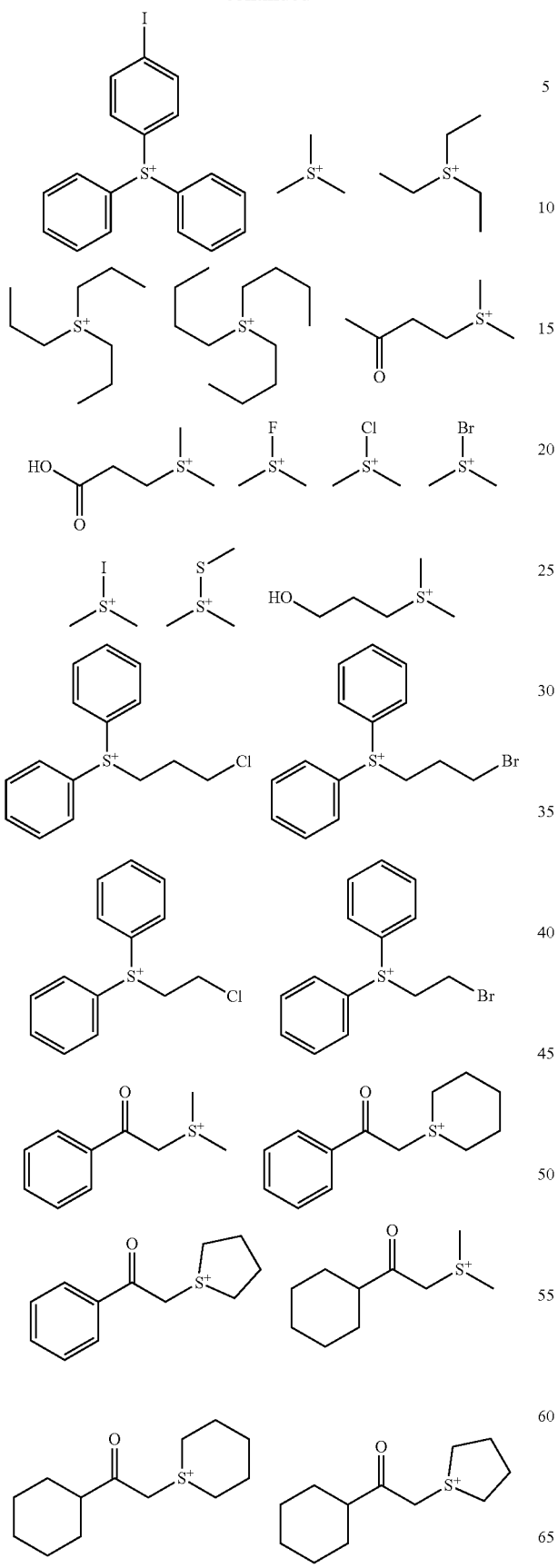
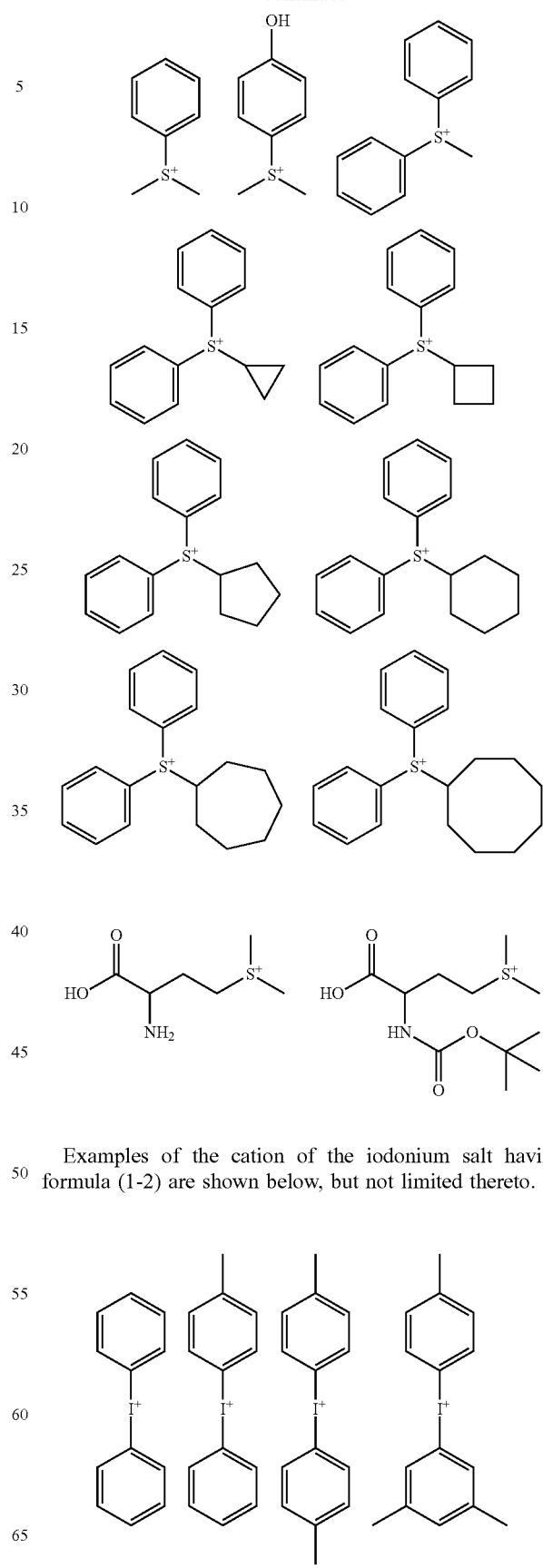
Examples of the cation of the iodonium salt having formula (1-2) are shown below, but not limited thereto.

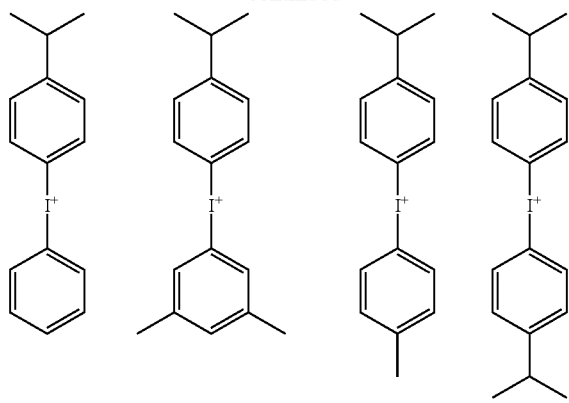
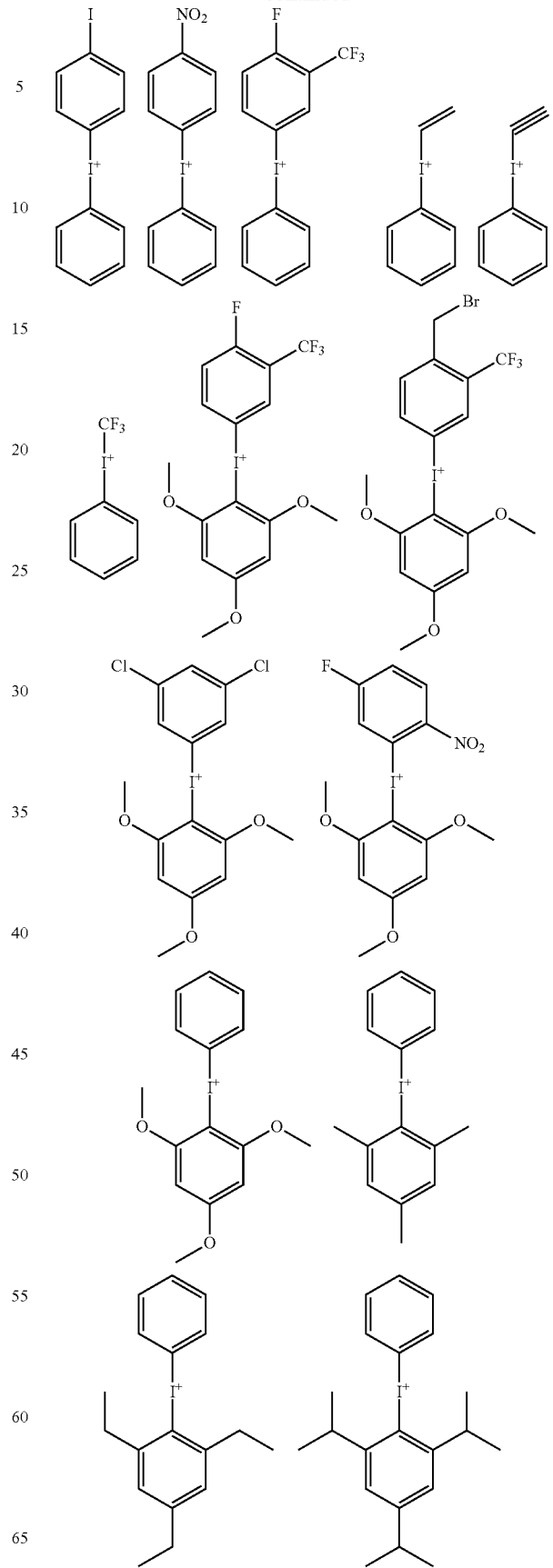

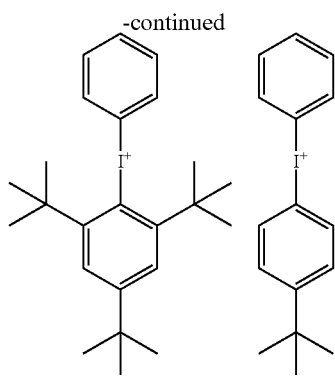

In formulae (1-1) and (1-2). X is an anion selected from the formulae (1A) to (1D).

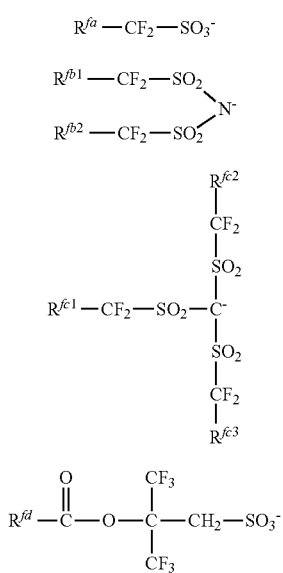

In formula (1A), $R^{fa}$ is fluorine or a $C_1$-$C_{40}$ monovalent hydrocarbon group which may contain a heteroatom. The monovalent hydrocarbon group may be straight, branched or cyclic and examples thereof are as will be exemplified below for $R^{107}$.

Of the anions of formula (1A), a structure having formula (1A') is preferred.

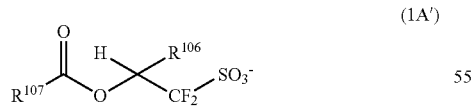

In formula (1A'), $R^{106}$ is hydrogen or trifluoromethyl, preferably trifluoromethyl. $R^{107}$ is a $C_1$-$C_{38}$ monovalent hydrocarbon group which may contain a heteroatom. Suitable heteroatoms include oxygen, nitrogen, sulfur and halogen, with oxygen being preferred. Of the monovalent hydrocarbon groups, those of 6 to 30 carbon atoms are preferred because a high resolution is available in fine pattern formation.

The monovalent hydrocarbon group may be straight, branched or cyclic. Examples thereof include straight or branched alkyl groups such as methyl, ethyl, propyl, isopropyl, butyl, isobutyl, sec-butyl, tert-butyl, pentyl, neopentyl, hexyl, cyclopentyl, hexyl, cyclohexyl, heptyl, 2-ethylhexyl, nonyl, undecyl, tridecyl, pentadecyl, heptadecyl, icosanyl; monovalent saturated alicyclic hydrocarbon groups such as 1-adamantyl, 2-adamantyl, 1-adamantylmethyl, norbornyl, norbornylmethyl, tricyclodecanyl, tetracyclododecanyl, tetracyclododecanylmethyl, dicyclohexyhnethyl; monovalent unsaturated aliphatic hydrocarbon groups such as allyl and 3-cyclohexenyl; aryl groups such as phenyl, 1-naphthyl and 2-naphthyl; aralkyl groups such as benzyl and diphenylmethyl. Exemplary heteroatom-containing monovalent hydrocarbon groups are tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl. Also included are the foregoing groups in which some hydrogen is substituted by a moiety containing a heteroatom such as oxygen, sulfur, nitrogen or halogen, or in which some carbon is replaced by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic anhydride or haloalkyl moiety.

With respect to the synthesis of the sulfonium salt having an anion of formula (1A'), reference is made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the anion having formula (1A) are shown below, but not limited thereto.

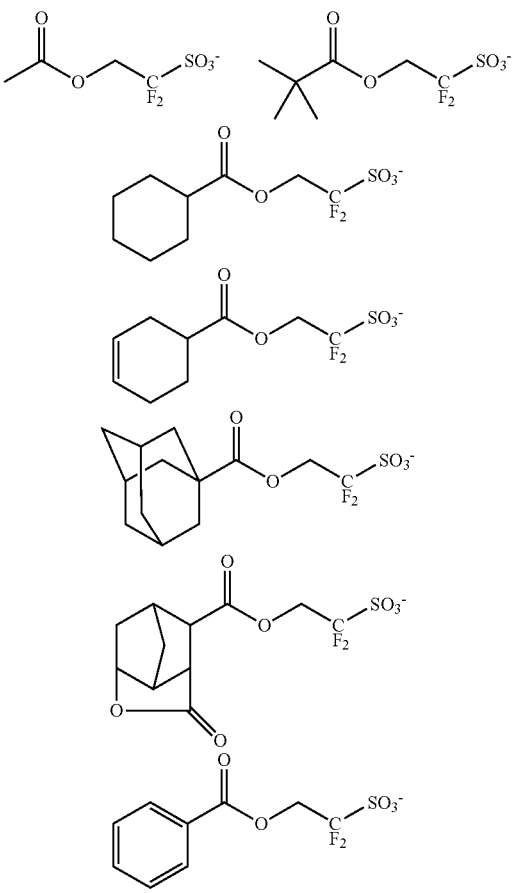

125
-continued
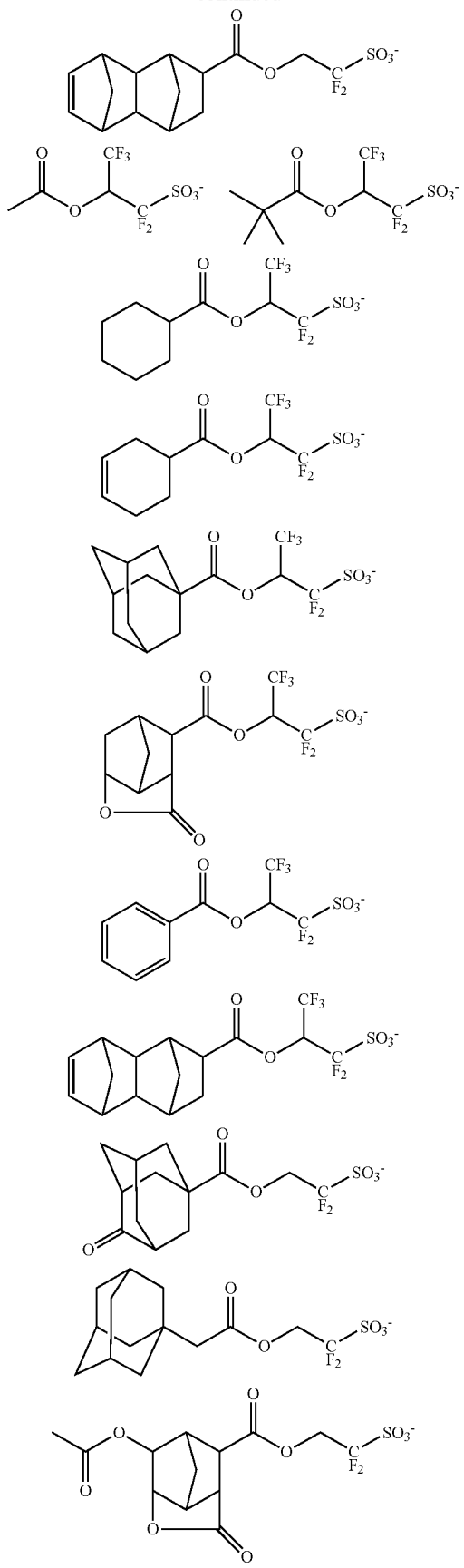
126
-continued
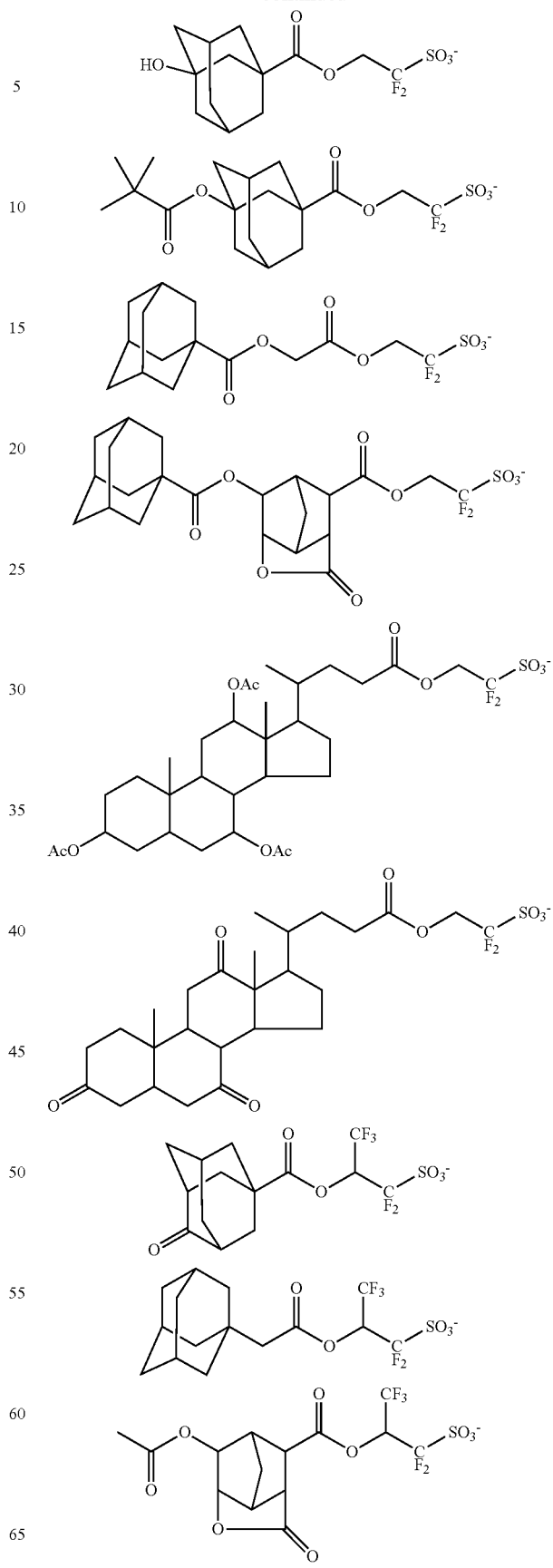

-continued

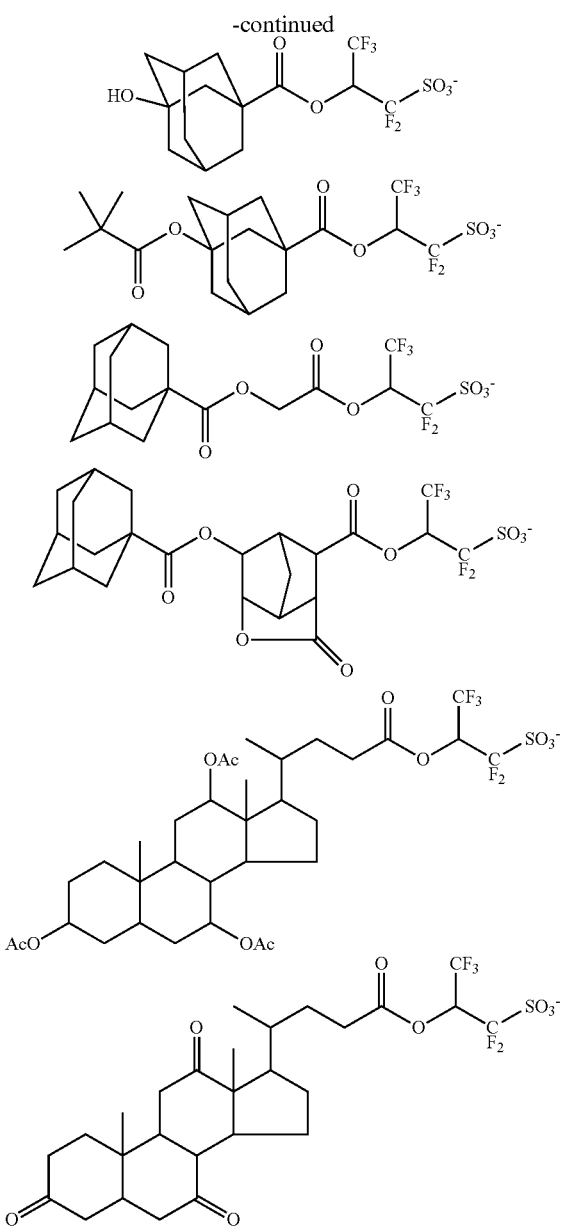

In formula (1B), $R^{fb1}$ and $R^{fb2}$ are each independently fluorine or a $C_1$-$C_{40}$ monovalent hydrocarbon group which may contain a heteroatom. The monovalent hydrocarbon group may be straight, branched or cyclic and examples thereof are as exemplified above for $R^{107}$. Preferably $R^{fb1}$ and $R^{fb2}$ each are fluorine or a straight $C_1$-$C_4$ fluorinated alkyl group. A pair of $R^{fb1}$ and $R^{fb2}$ may bond together to form a ring with the linkage (—$CF_2$—$SO_2$—$N^-$—$SO_2$—$CF_2$—) to which they are attached, and preferably the pair is a fluorinated ethylene or fluorinated propylene group.

In formula (1C), $R^{fc1}$, $R^{fc2}$ and $R^{fc3}$ are each independently fluorine or a $C_1$-$C_{40}$ monovalent hydrocarbon group which may contain a heteroatom. The monovalent hydrocarbon group may be straight, branched or cyclic and examples thereof are as exemplified above for $R^{107}$. Preferably $R^{fc1}$, $R^{fc2}$ and $R^{fc3}$ each are fluorine or a straight $C_1$-$C_4$ fluorinated alkyl group. A pair of $R^{fc1}$ and $R^{fc2}$ may bond together to form a ring with the linkage (—$CF_2$—$SO_2$—$C^-$—$SO_2$—$CF_2$—) to which they are attached, and preferably the pair is a fluorinated ethylene or fluorinated propylene group.

In formula (1D), $R^{fd}$ is a $C_1$-$C_{40}$ monovalent hydrocarbon group which may contain a heteroatom. The monovalent hydrocarbon group may be straight, branched or cyclic and examples thereof are as exemplified above for $R^{107}$.

With respect to the synthesis of the sulfonium salt having an anion of formula (1D), reference is made to JP-A 2010-215608 and JP-A 2014-133723.

Examples of the anion having formula (1D) are shown below, but not limited thereto.

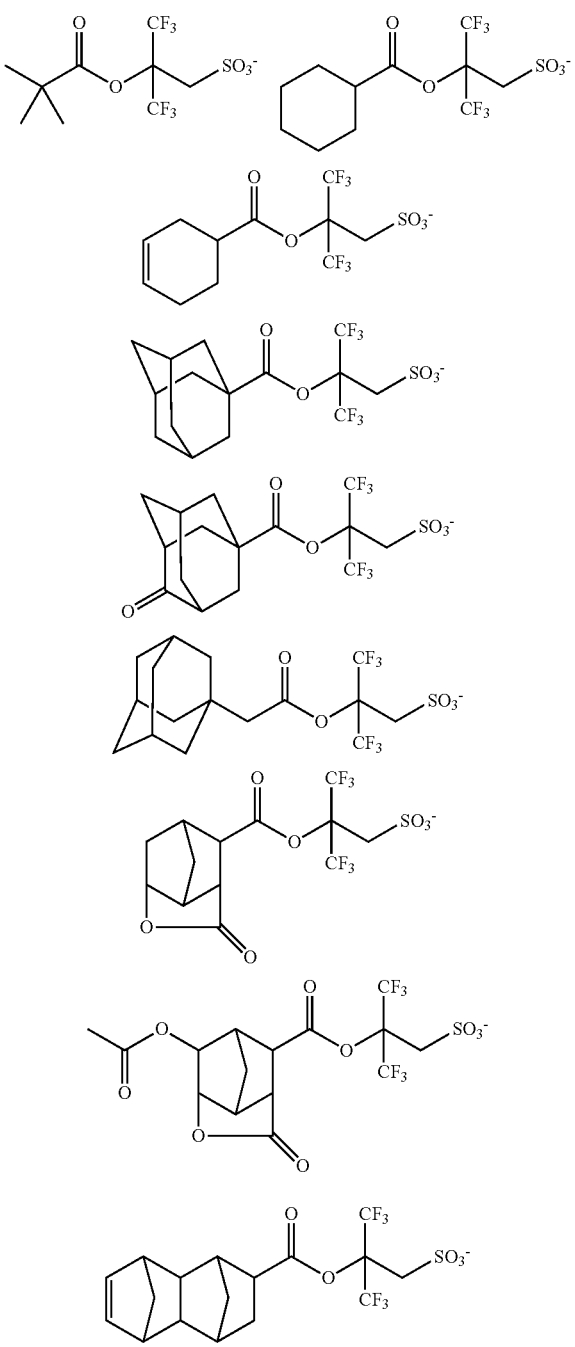

-continued

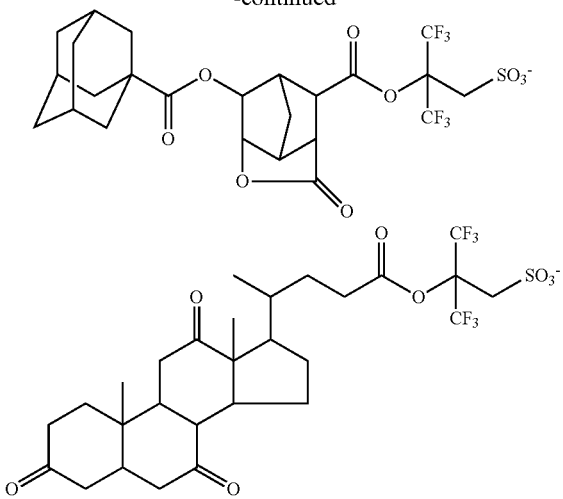

The compound having the anion of formula (1D) has a sufficient acid strength to cleave acid labile groups in the base polymer because it is free of fluorine at α-position of sulfo group, but has two trifluoromethyl groups at β-position. Thus the compound is a useful PAG.

A compound having the formula (2) is also a useful PAG.

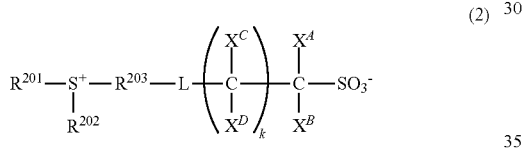

(2)

In formula (2), $R^{201}$ and $R^{202}$ are each independently a $C_1$-$C_{30}$ monovalent hydrocarbon group which may contain a heteroatom. $R^{203}$ is a $C_1$-$C_{30}$ divalent hydrocarbon group which may contain a heteroatom. Any two of $R^{201}$, $R^{202}$ and $R^{203}$ may bond together to form a ring with the sulfur atom to which they are attached. L is a single bond, ether bond or a $C_1$-$C_{20}$ divalent hydrocarbon group which may contain a heteroatom. $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl, and k is an integer of 0 to 3.

The monovalent hydrocarbon group may be straight, branched or cyclic. Examples thereof include straight or branched alkyl groups such as methyl, ethyl, propyl, isopropyl, n-butyl, sec-butyl, tert-butyl, n-pentyl, tert-pentyl, n-hexyl, n-octyl, n-nonyl, n-decyl, 2-ethylhexyl, monovalent saturated cyclic hydrocarbon groups such as cyclopentyl, cyclohexyl, cyclopentylmethyl, cyclopentylethyl, cyclopentylbutyl, cyclohexylmnethyl, cyclohexylethyl, cyclohexylbutyl, norbomyl, oxanorbornyl, tricyclo[5.2.1.0$^{2,6}$]decanyl, adamantyl; aryl groups such as phenyl, naphthyl and anthracenyl. Also included are the foregoing groups in which some hydrogen is substituted by a moiety containing a heteroatom such as oxygen, sulfur, nitrogen or halogen, or in which some carbon is replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride or haloalkyl moiety.

The divalent hydrocarbon group may be straight, branched or cyclic. Examples thereof include straight or branched alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,3-diyl, tetradecane-1,4-diyl, pentadecane-1,15-diyl, hexadecane-1,16-diyl, heptadecane-1,17-diyl; divalent saturated cyclic hydrocarbon groups such as cyclopentanediyl, cyclohexanediyl, norbornanediyl, and adamantanediyl; and divalent unsaturated cyclic hydrocarbon groups such as phenylene and naphthylene. Also included are the foregoing groups in which some hydrogen is substituted by an alkyl group such as methyl, ethyl, propyl, n-butyl or tert-butyl, or in which some hydrogen is substituted by a moiety containing a heteroatom such as oxygen, sulfur, nitrogen or halogen, or in which some carbon is replaced by a moiety containing a heteroatom such as oxygen, sulfur or nitrogen, so that the group may contain a hydroxyl, cyano, carbonyl, ether bond, ester bond, sulfonic acid ester bond, carbonate, lactone ring, sultone ring, carboxylic anhydride or haloalkyl moiety. The preferred heteroatom is oxygen.

Of the PAGs having formula (2), those having formula (2') are preferred.

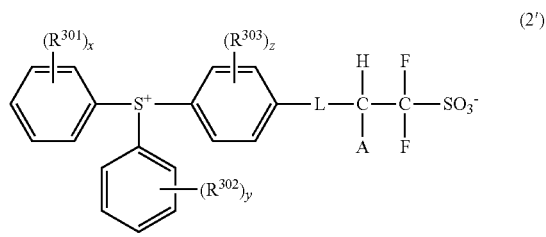

(2')

In formula (2'), L is as defined above. "A" is hydrogen or trifluoromethyl, preferably trifluoromethyl. $R^{301}$, $R^{302}$ and $R^{303}$ are each independently hydrogen or a $C_1$-$C_{20}$ monovalent hydrocarbon group which may contain a heteroatom. The monovalent hydrocarbon group may be straight, branched or cyclic and examples thereof are as exemplified above for $R^{107}$. The subscripts x and y each are an integer of 0 to 5, and z is an integer of 0 to 4.

Examples of the PAG having formula (2) are shown below, but not limited thereto. Herein "A" is as defined above.

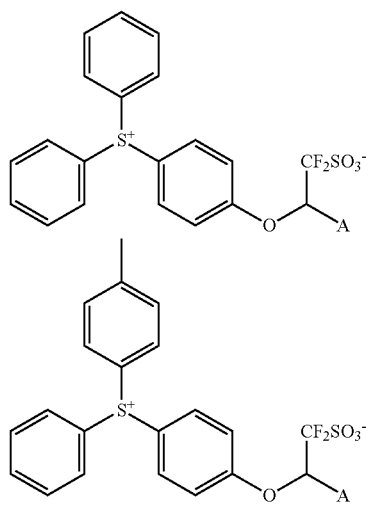

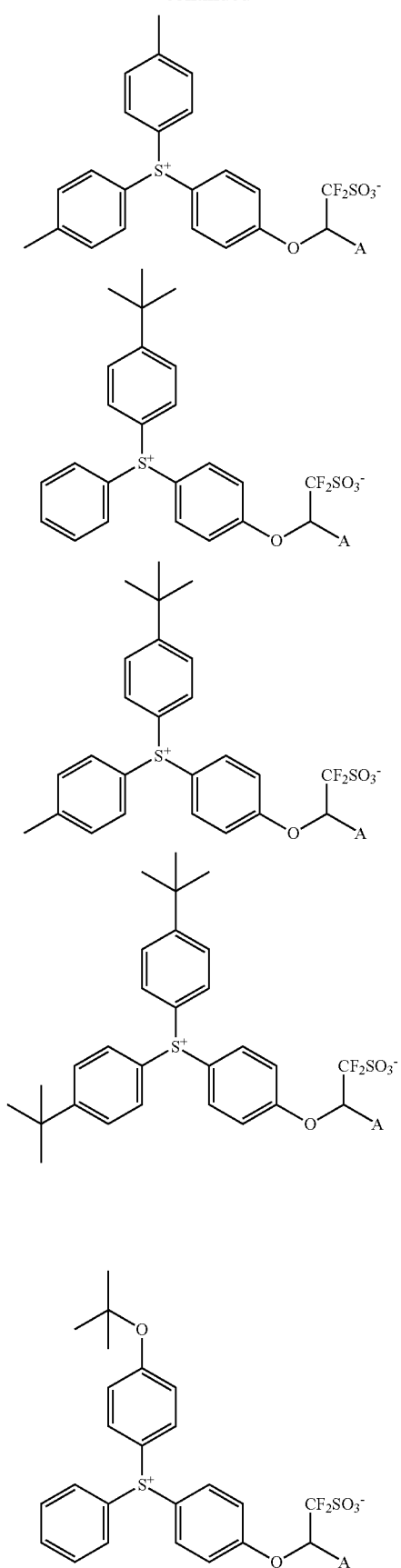
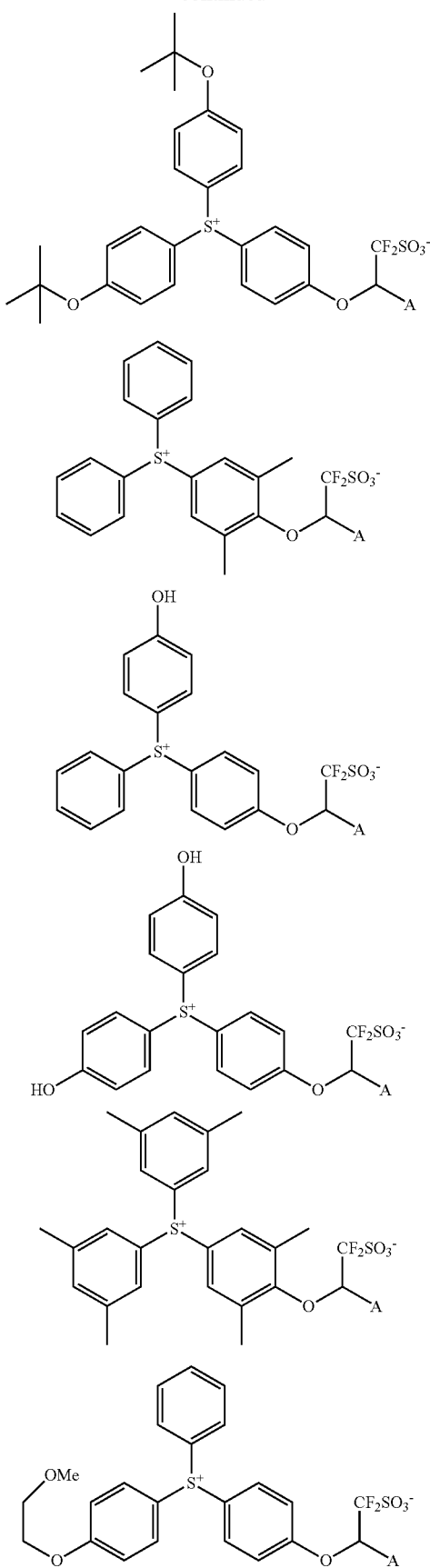

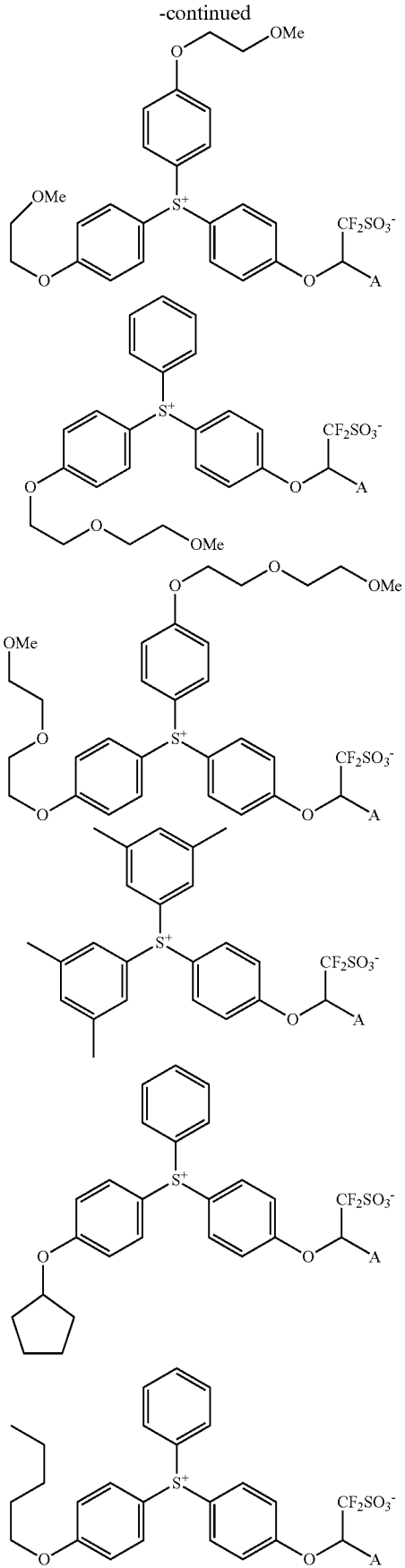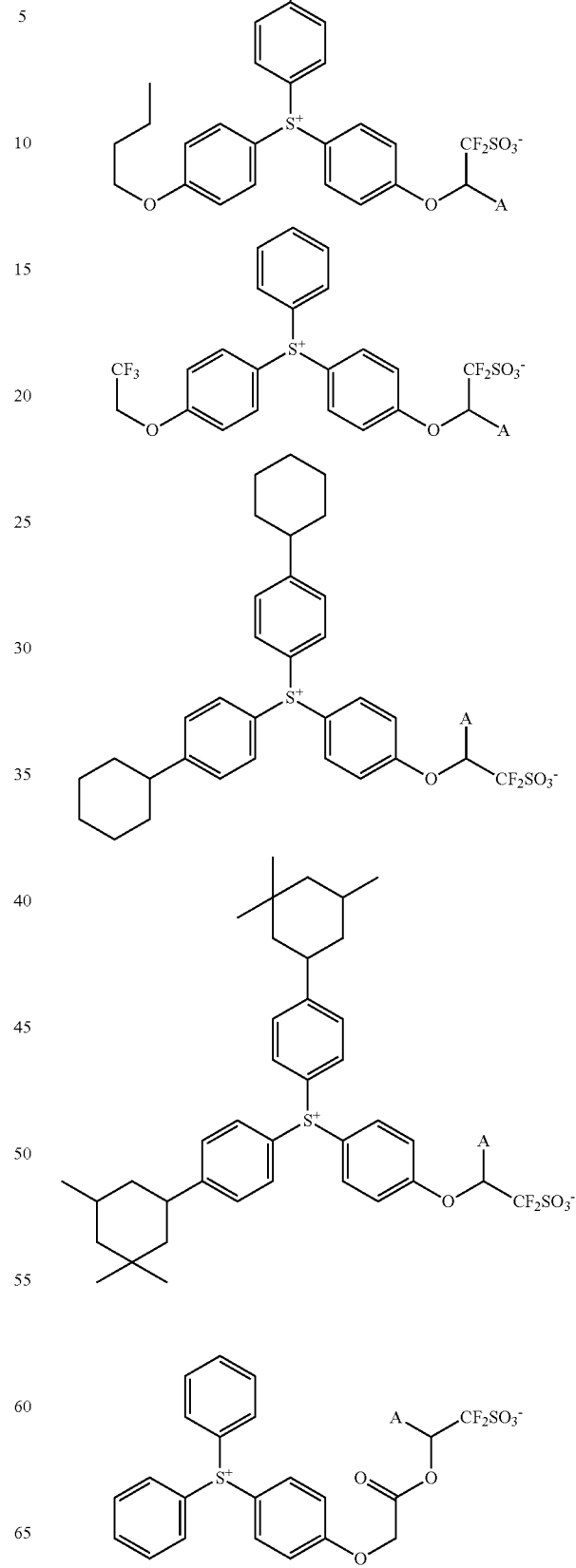

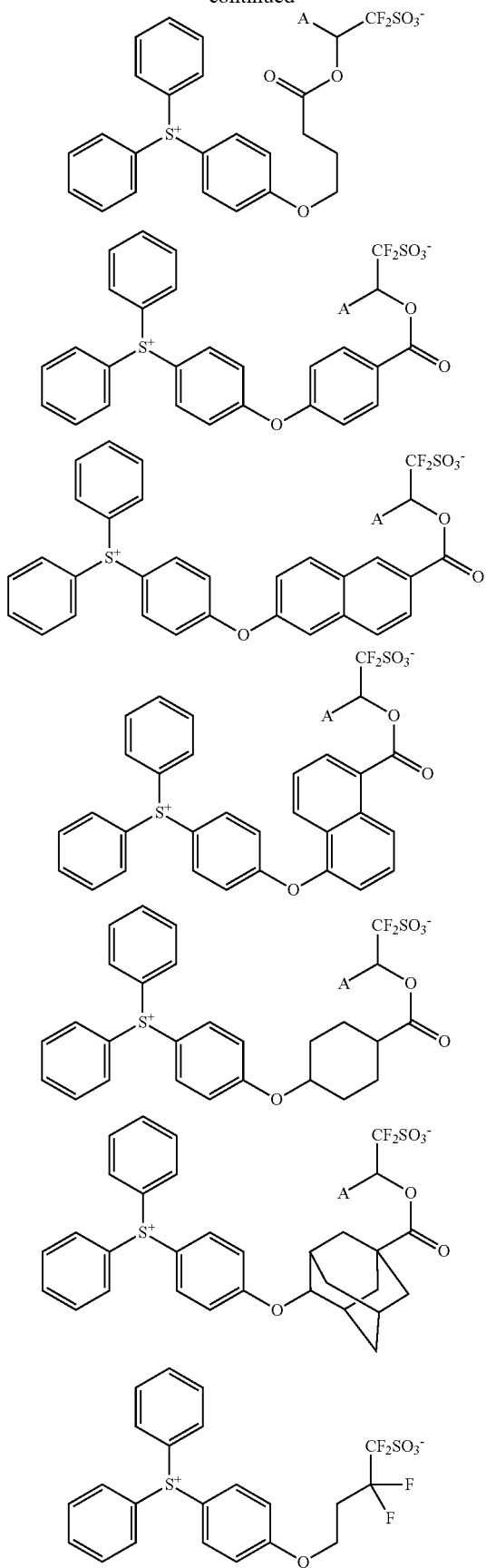
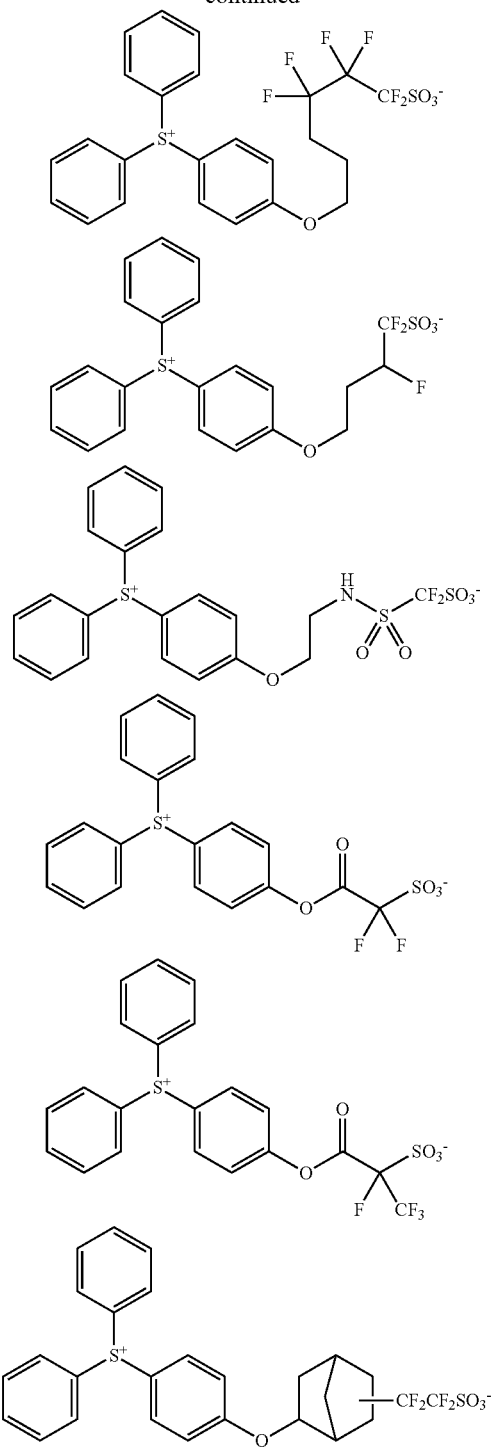

Of the foregoing PAGs, those compounds having an anion of formula (1A') or (1D) are especially preferred because of reduced acid diffusion and high solubility in resist solvent, and those compounds having an anion of formula (2') are especially preferred because of minimized acid diffusion.

Also sulfonium and iodonium salts having an anion containing an iodized or brominated aromatic ring are useful PAGs. These salts typically have the formulae (3-1) and (3-2).

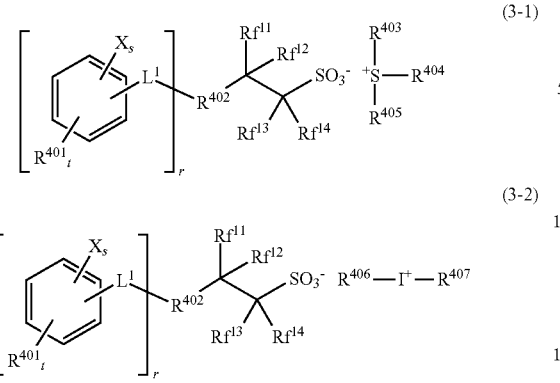

(3-1)

(3-2)

In formulae (3-1) and (3-2), X is iodine or bromine. When s is at least 2, groups X may be identical or different.

$L^1$ is a single bond, ether bond, ester bond, or a $C_1$-$C_6$ alkanediyl group which may contain an ether bond or ester bond. The alkanediyl group may be straight, branched or cyclic.

$R^{401}$ is hydroxyl, carboxyl, fluorine, chlorine, bromine, amino or a $C_1$-$C_{20}$ alkyl group, $C_1$-$C_{20}$ alkoxy group, $C_2$-$C_{10}$ alkoxycarbonyl, $C_2$-$C_{20}$ acyloxy group, or $C_1$-$C_{20}$ alkylsulfonyloxy group, which may contain fluorine, chlorine, bromine, hydroxyl, amino or $C_1$-$C_{10}$ alkoxy moiety, or —$NR^{401A}$—C(=O)—$R^{401B}$ or —$NR^{401A}$—C(=O)—O—$R^{401B}$. $R^{401A}$ is hydrogen or a $C_1$-$C_6$ alkyl group which may contain halogen, hydroxyl, $C_1$-$C_6$ alkoxy, $C_2$-$C_6$ acyl or $C_2$-$C_6$ acyloxy moiety; $R^{401B}$ is a $C_1$-$C_{16}$ alkyl group, $C_2$-$C_6$ alkenyl group or $C_6$-$C_{12}$ aryl group, which may contain halogen, hydroxyl, a $C_1$-$C_6$ alkoxy, $C_2$-$C_6$ acyl or $C_2$-$C_6$ acyloxy moiety. The alkyl, alkoxy, alkoxycarbonyl, acyloxy, acyl and alkenyl groups may be straight, branched or cyclic. When t is at least 2, groups $R^{401}$ may be identical or different.

Inter alia, $R^{401}$ is preferably selected from hydroxyl, —$NR^{401A}$—C(=O)—$R^{401B}$, —$NR^{401A}$—C(=O)—O—$R^{401B}$, fluorine, chlorine, bromine, methyl, and methoxy.

$R^{402}$ is a single bond or a $C_1$-$C_{20}$ divalent linking group in case of r=1, and a $C_1$-$C_{20}$ tri- or tetravalent linking group in case of r=2 or 3. The linking group may contain oxygen, sulfur or nitrogen.

$R^{f11}$ to $R^{f14}$ are each independently hydrogen, fluorine or trifluoromethyl, at least one thereof being fluorine or trifluoromethyl. Also $R^{f11}$ and $R^{f12}$, taken together, may form a carbonyl group. Most preferably both $R^{f11}$ and $R^{f12}$ are fluorine.

$R^{403}$, $R^{404}$, $R^{405}$, $R^{406}$ and $R^{407}$ are each independently a $C_1$-$C_{20}$ monovalent hydrocarbon group which may contain a heteroatom. Any two of $R^{403}$, $R^{404}$ and $R^{405}$ may bond together to form a ring with the sulfur atom to which they are attached. The monovalent hydrocarbon group may be straight, branched or cyclic and examples thereof include $C_1$-$C_{12}$ alkyl groups, $C_2$-$C_{12}$ alkenyl groups, $C_2$-$C_{12}$ alkynyl groups, $C_6$-$C_{20}$ aryl groups, and $C_7$-$C_{12}$ aralkyl groups. In these groups, some or all hydrogen may be substituted by hydroxyl, carboxyl, halogen, cyano, amide, nitro, mercapto, sultone, sulfone, or sulfonium salt-containing moiety, or some carbon may be replaced by an ether bond, ester bond, carbonyl, carbonate or sulfonic acid ester bond.

The subscript r is an integer of 1 to 3. The subscript s is an integer of 1 to 5, and t is an integer of 0 to 3, meeting 1≤s+t≤5. Preferably, s is an integer of 1 to 3, more preferably 2 or 3, and t is an integer of 0 to 2.

The cation moiety in the sulfonium salt having formula (3-1) is as exemplified above for the cation moiety in the sulfonium salt having formula (1-1). The cation moiety in the iodonium salt having formula (3-2) is as exemplified above for the cation moiety in the iodonium salt having formula (1-2).

Examples of the anion moiety in the onium salts having formulae (3-1) and (3-2) are given below, but not limited thereto. Herein X is as defined above.

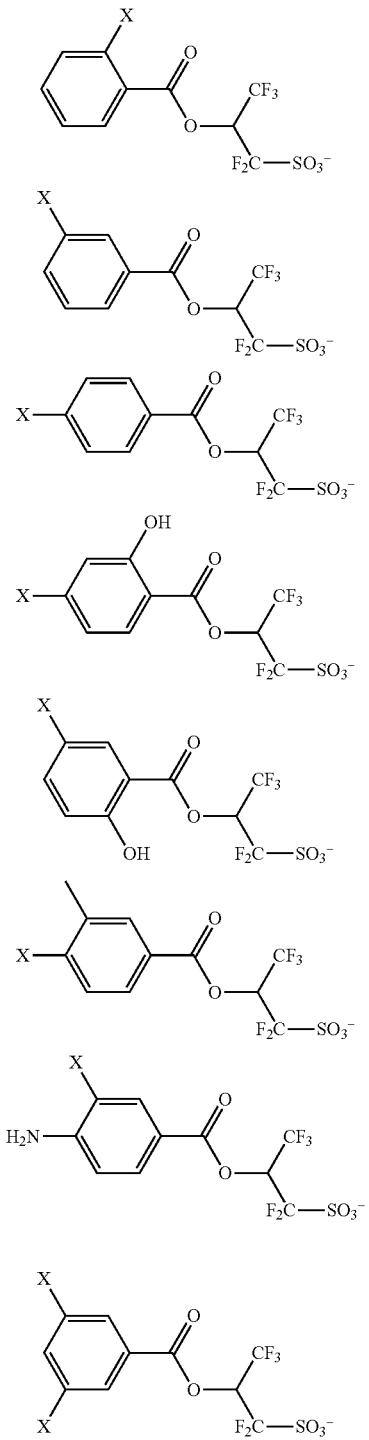

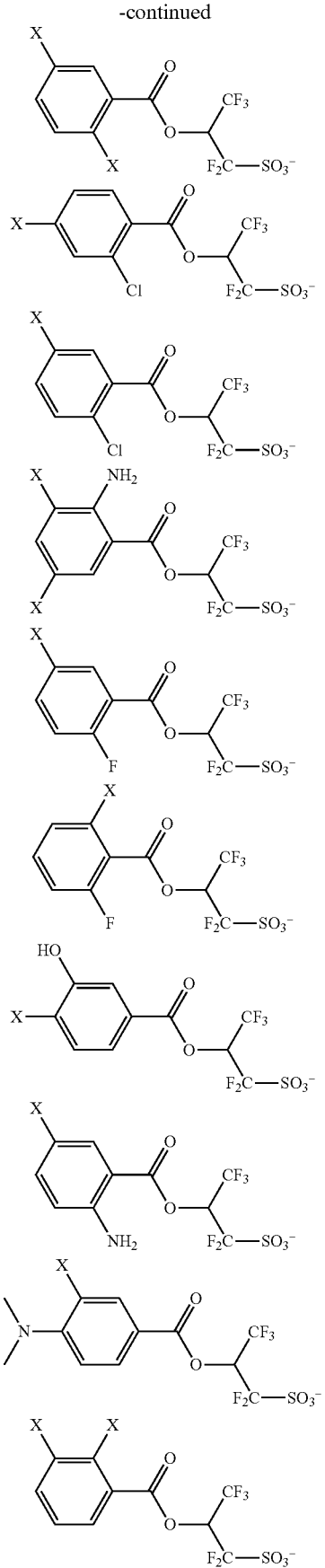
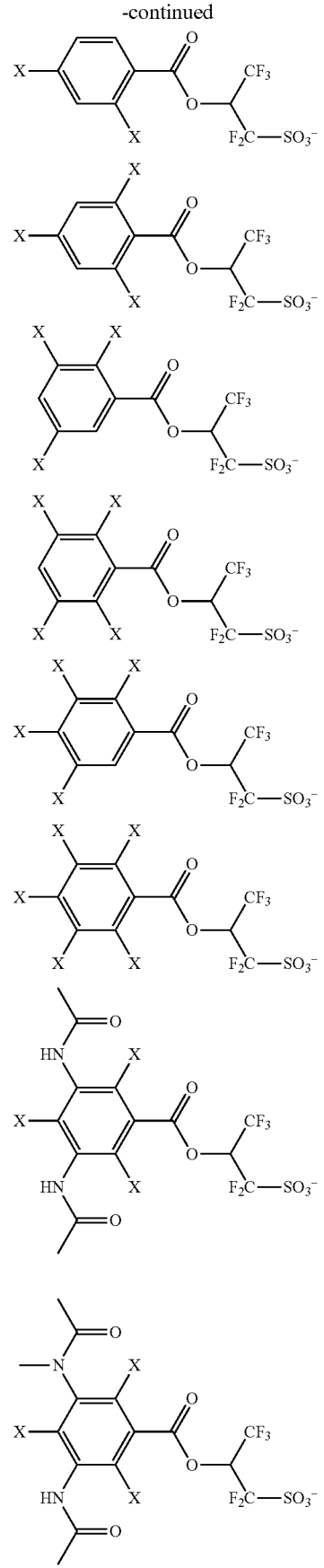

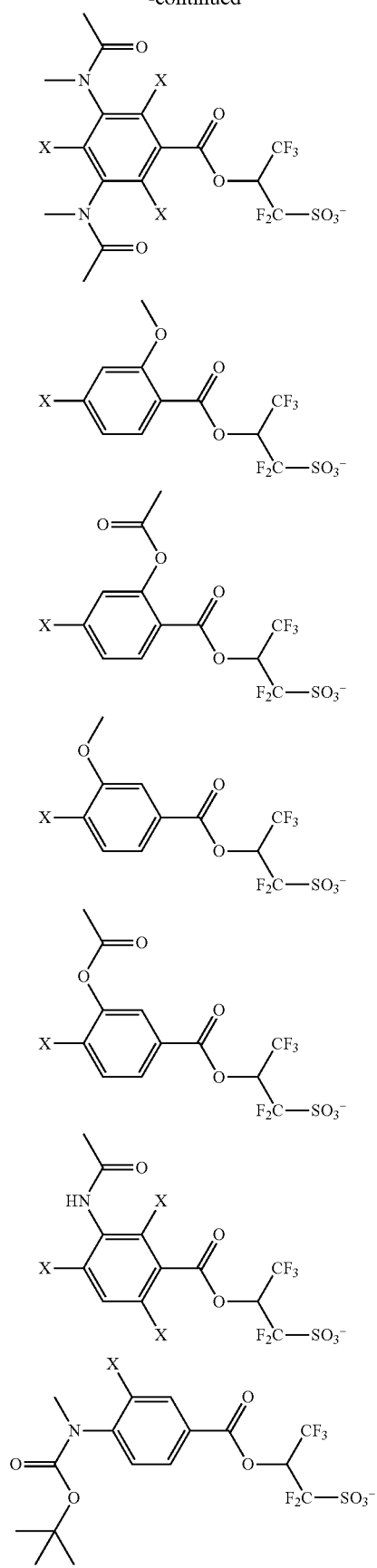
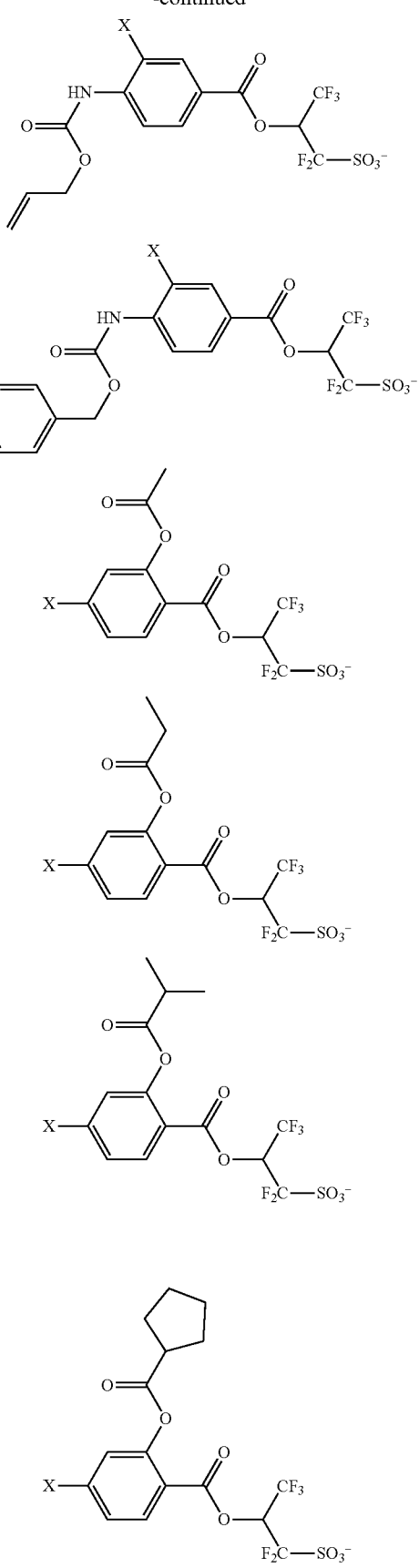

143
-continued
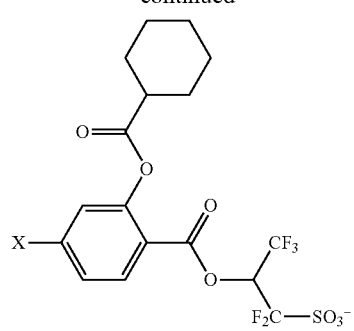
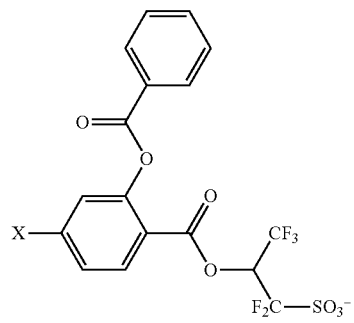
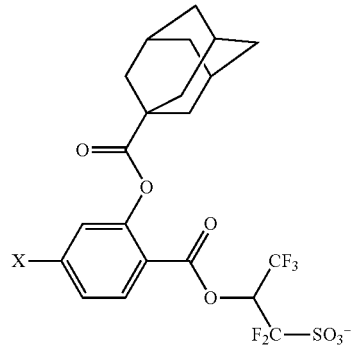
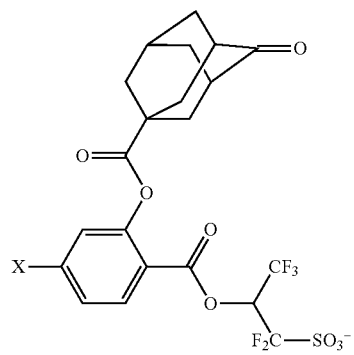
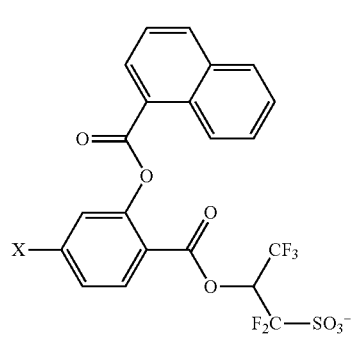
144
-continued
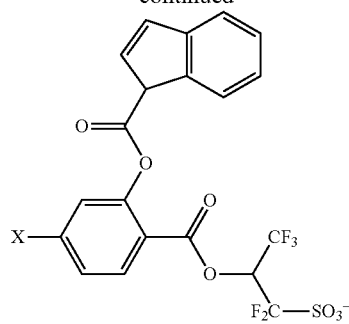
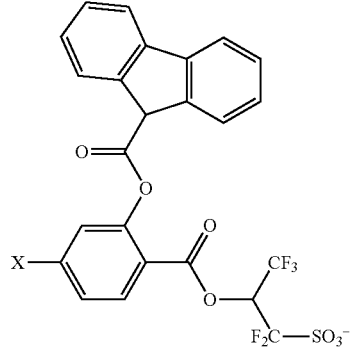
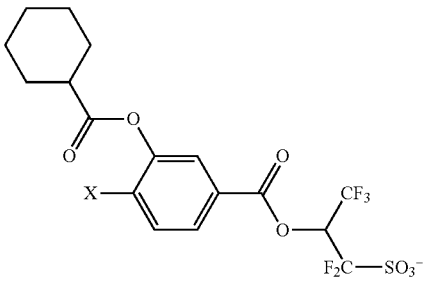
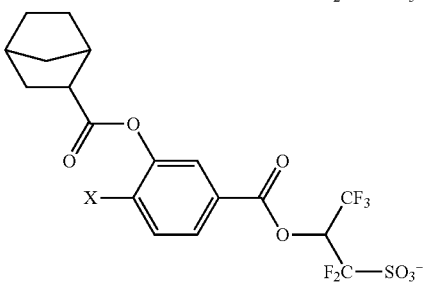
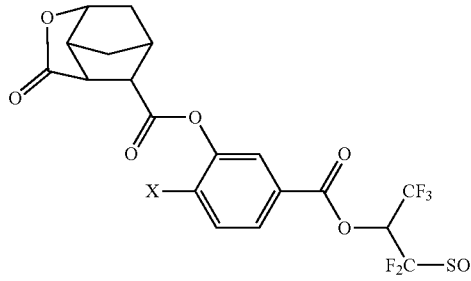
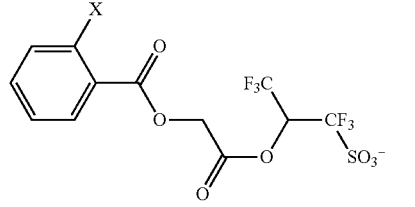

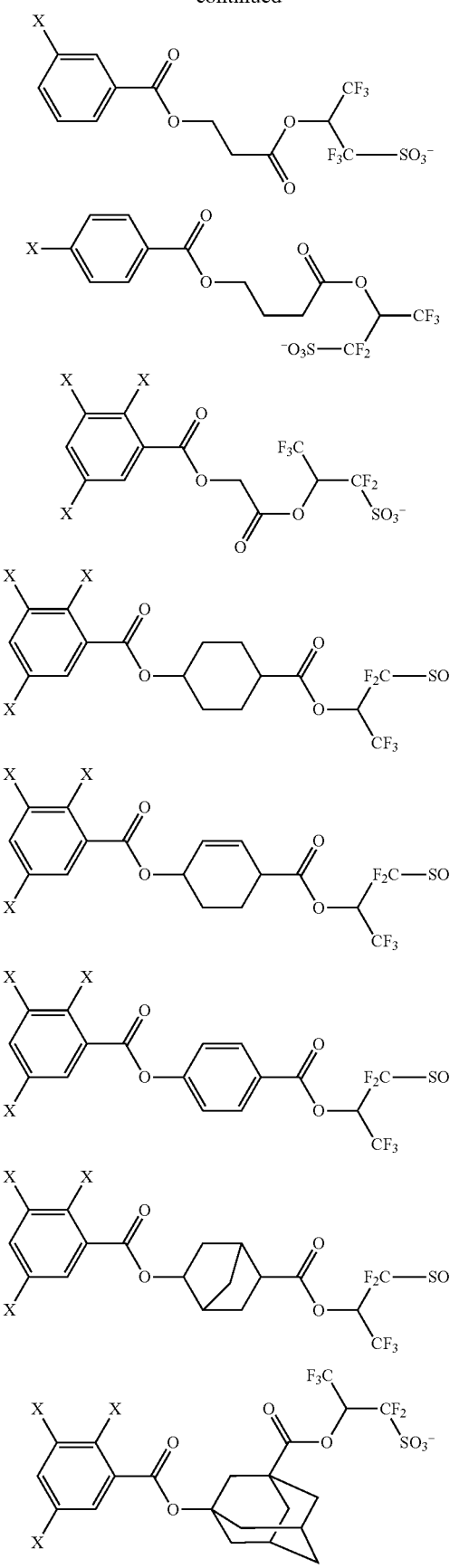
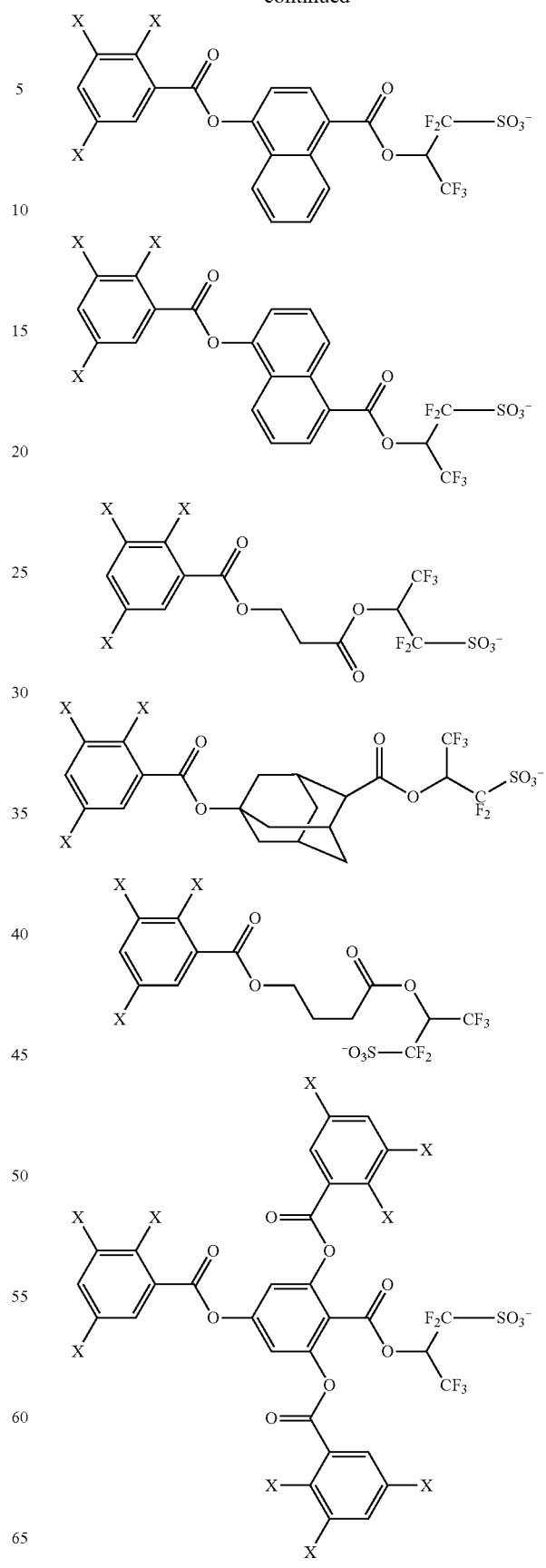

147
-continued
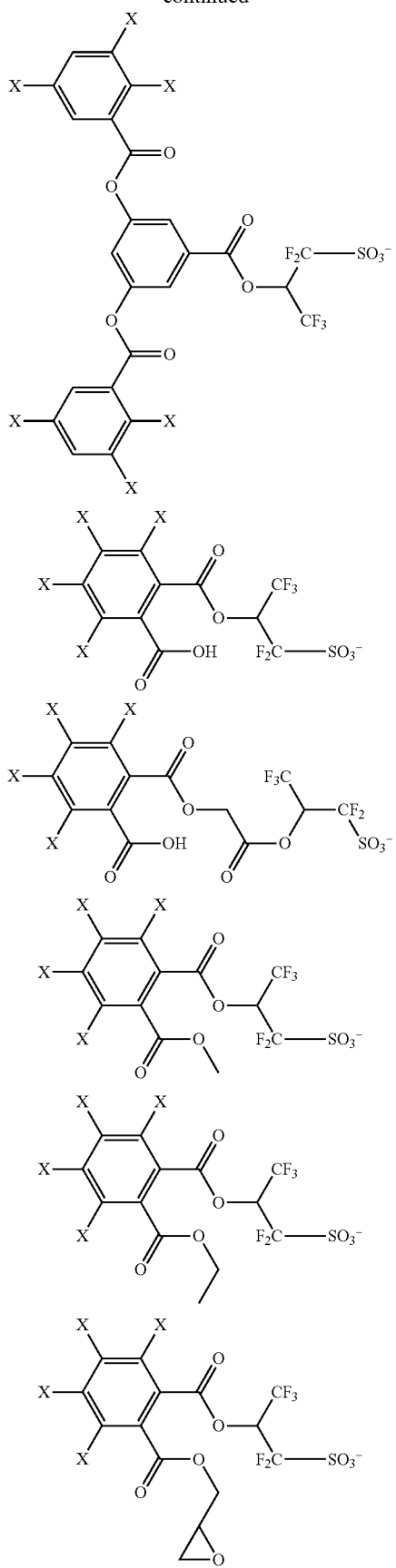
148
-continued
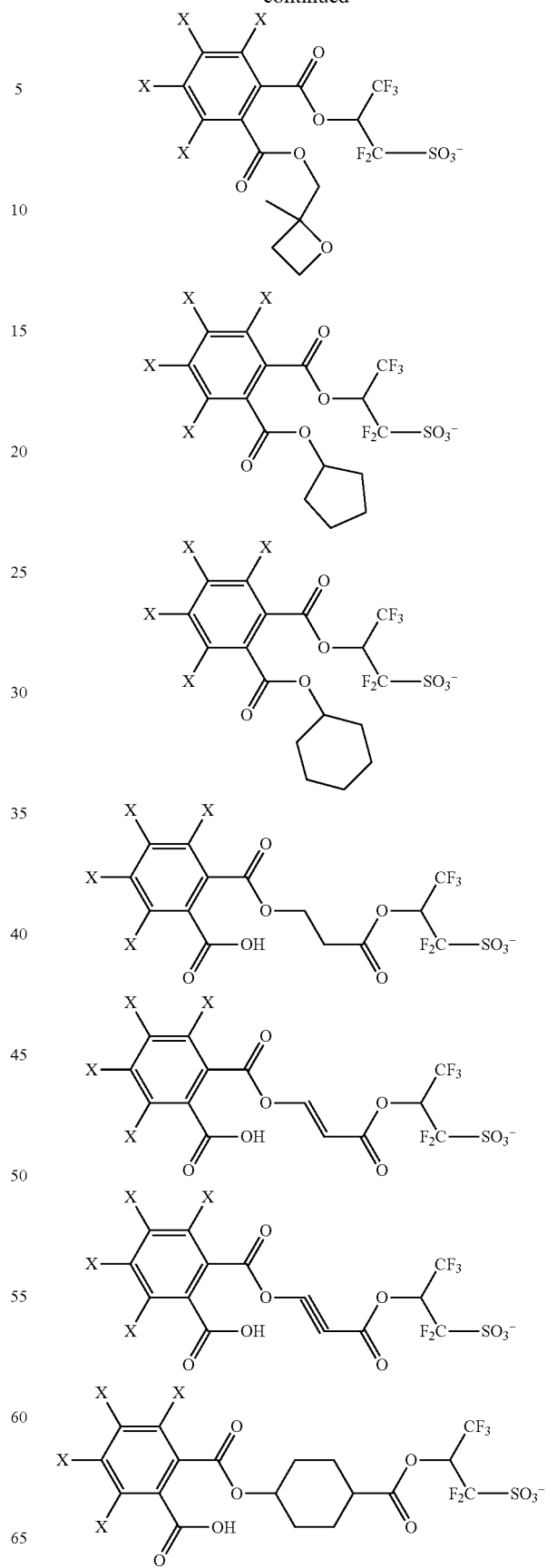

149
-continued
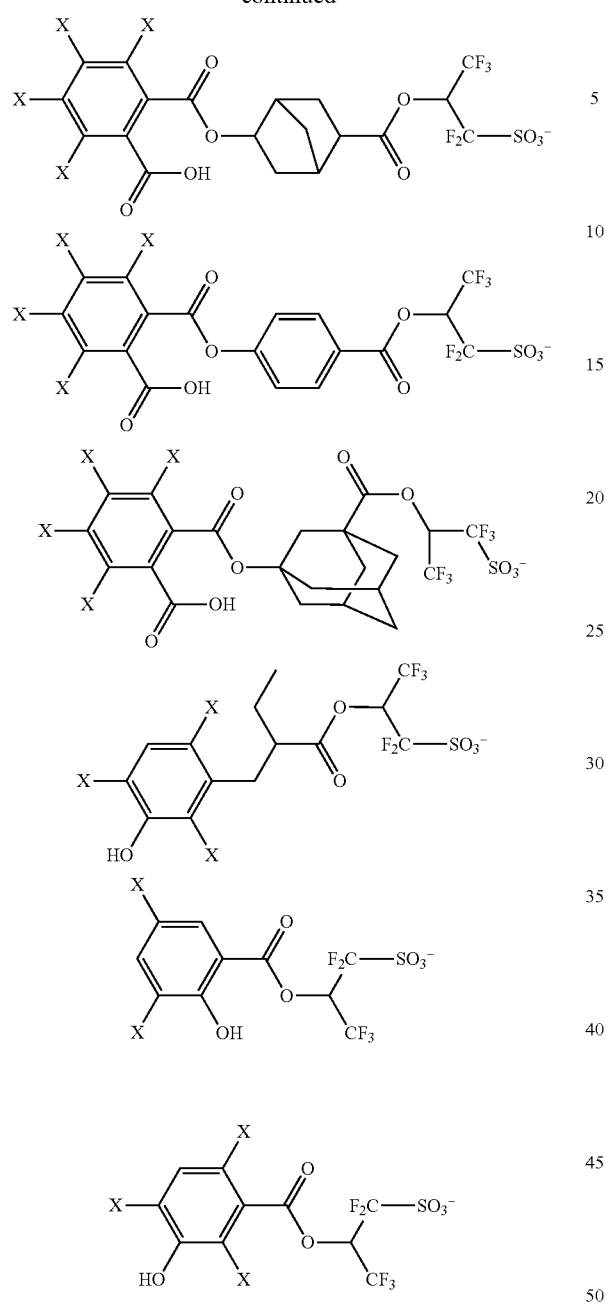
150
-continued
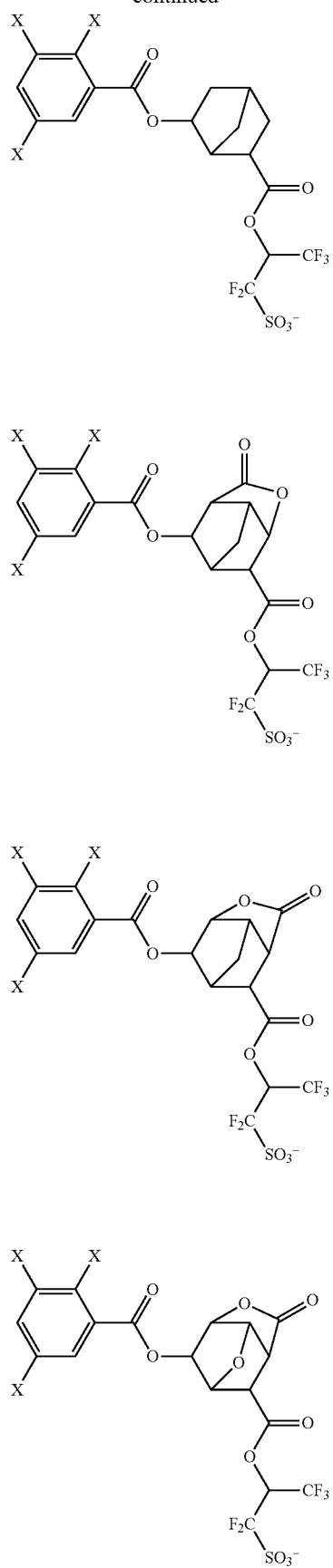

151
-continued
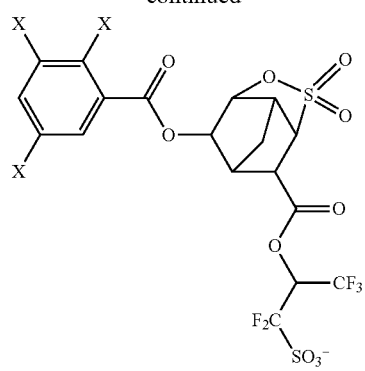
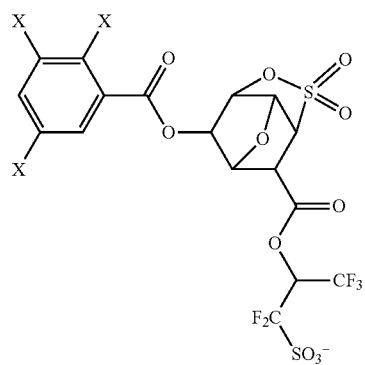
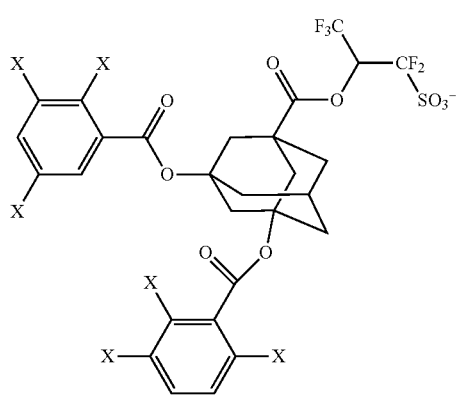
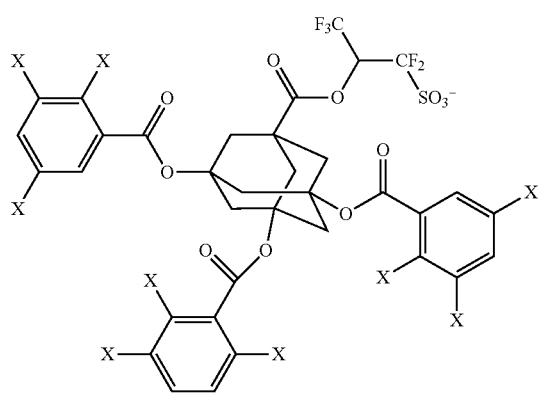
152
-continued
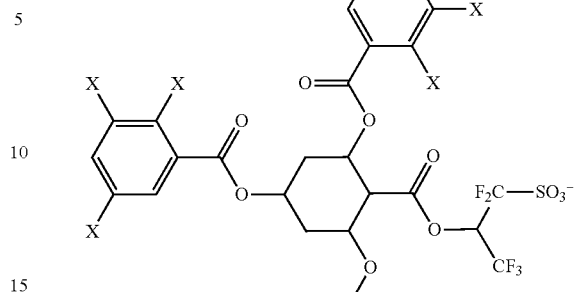
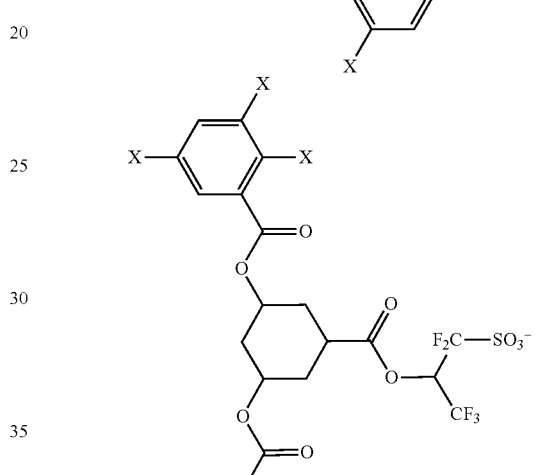
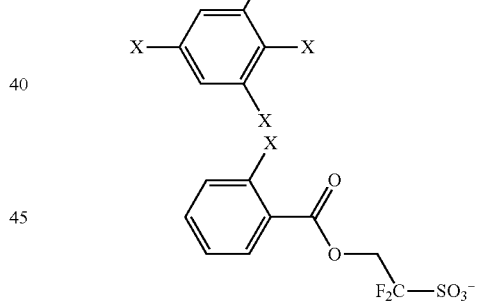
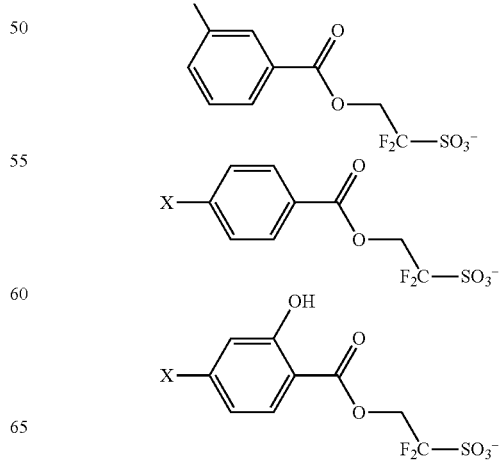

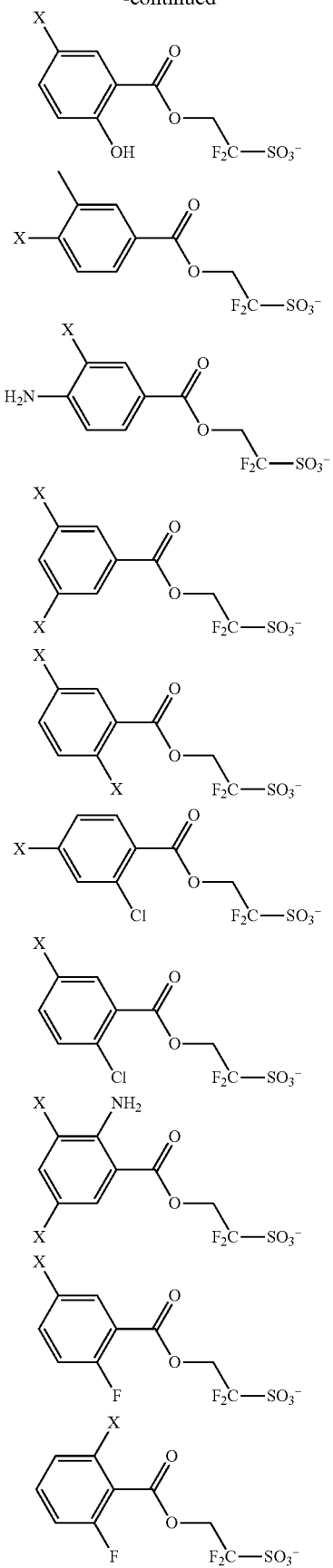
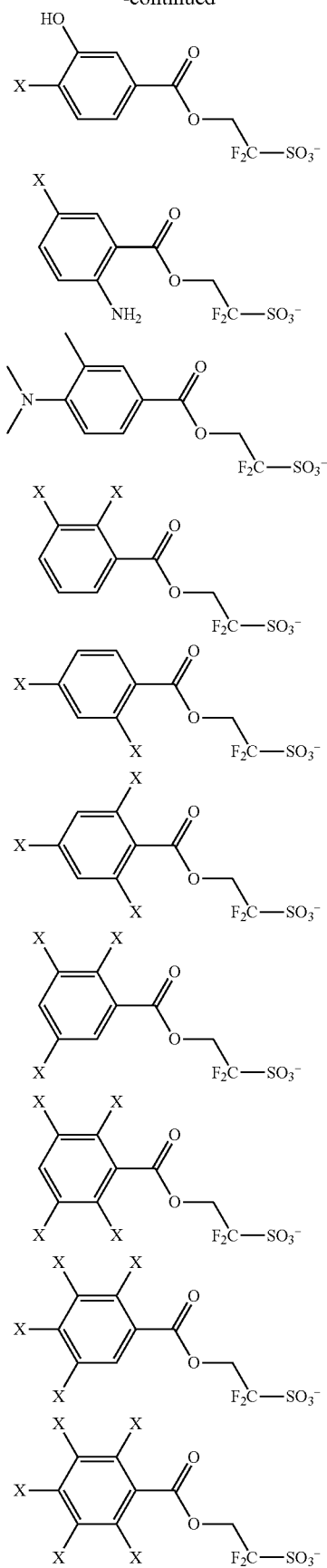

155
-continued
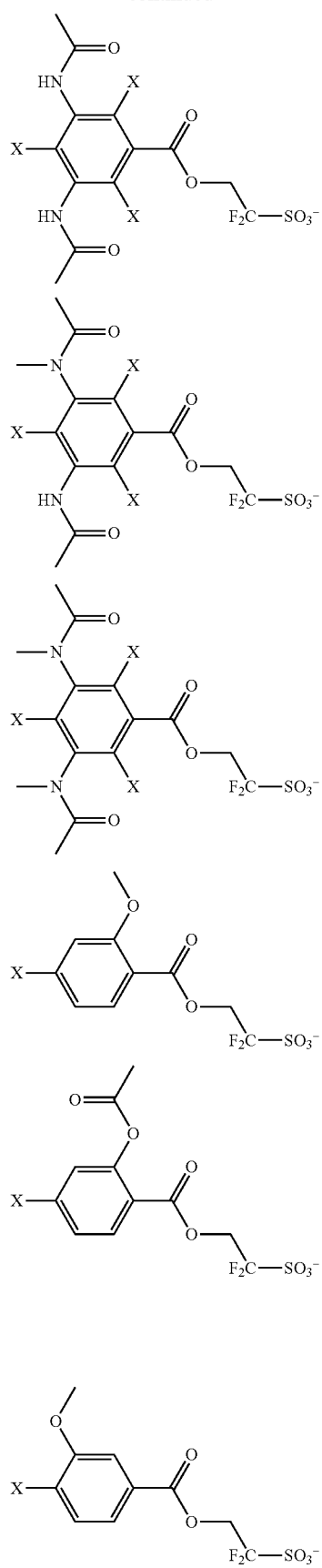
156
-continued
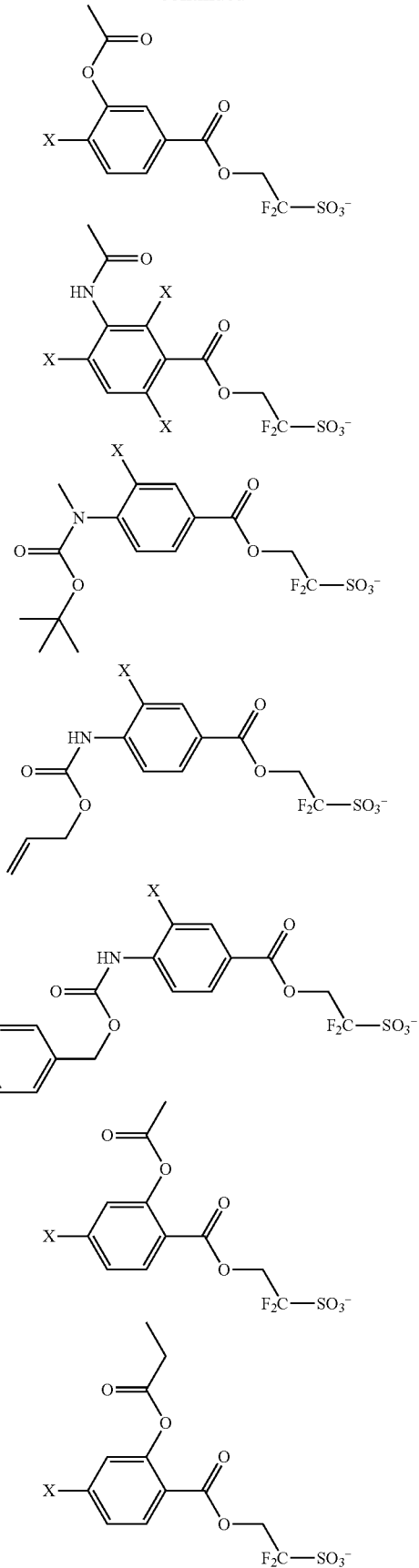

157
-continued
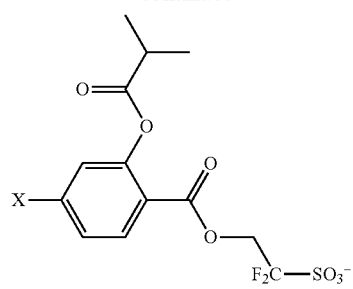
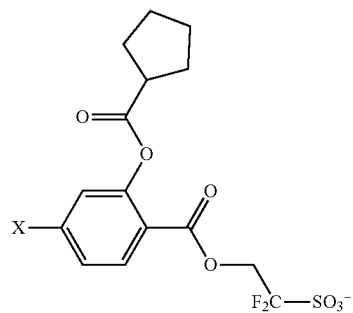
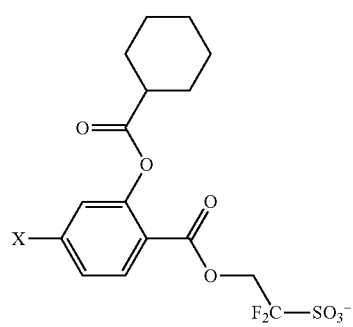
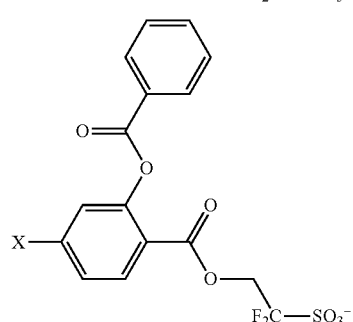
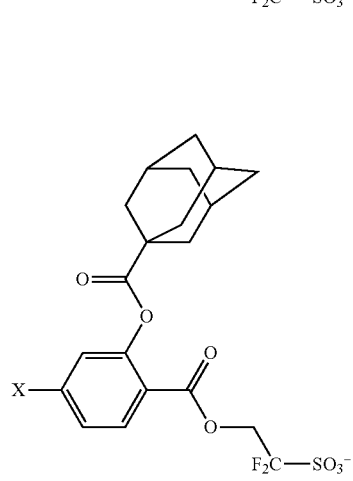
158
-continued
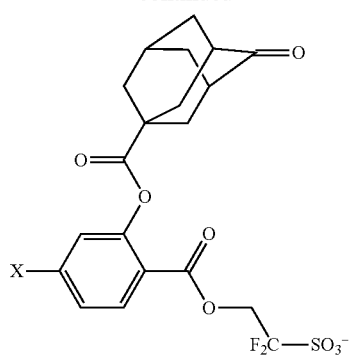
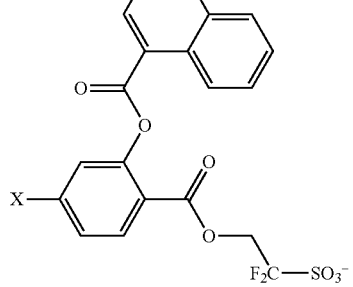
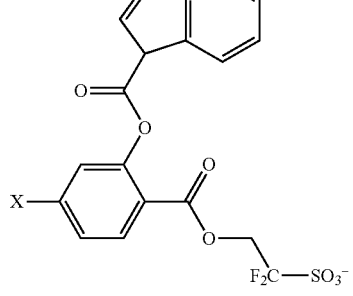
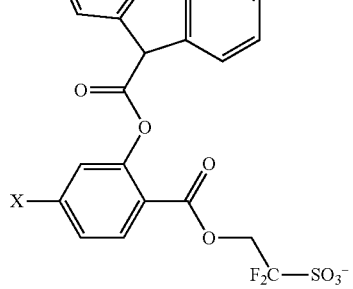
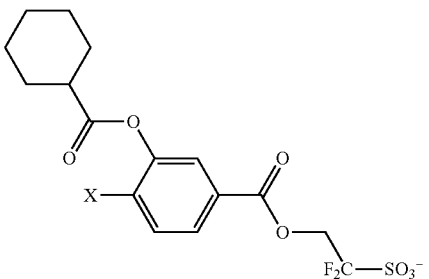

159
-continued
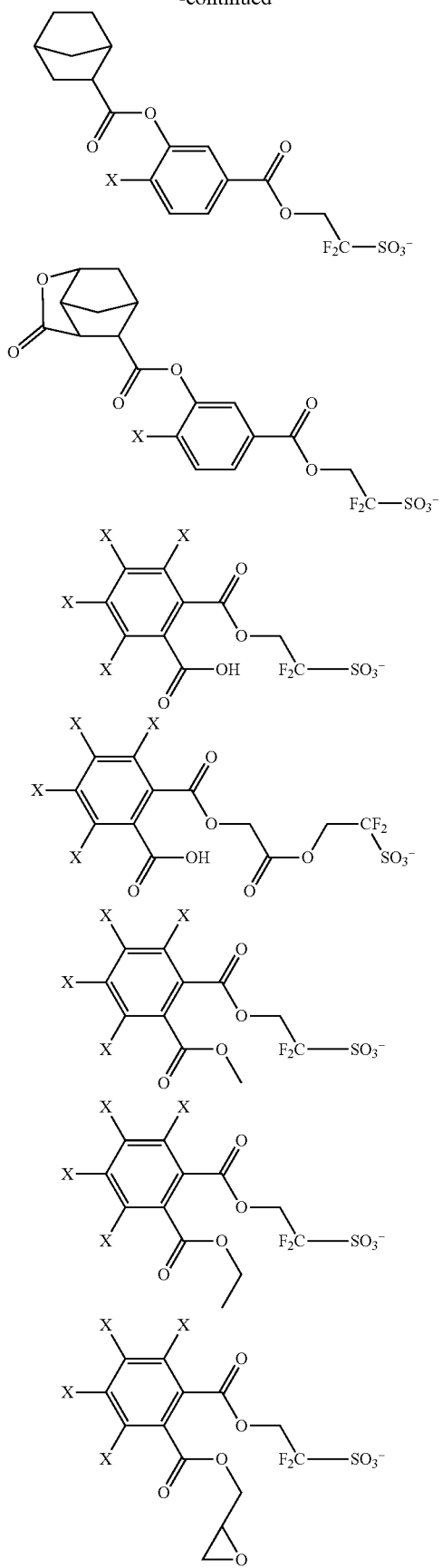
160
-continued
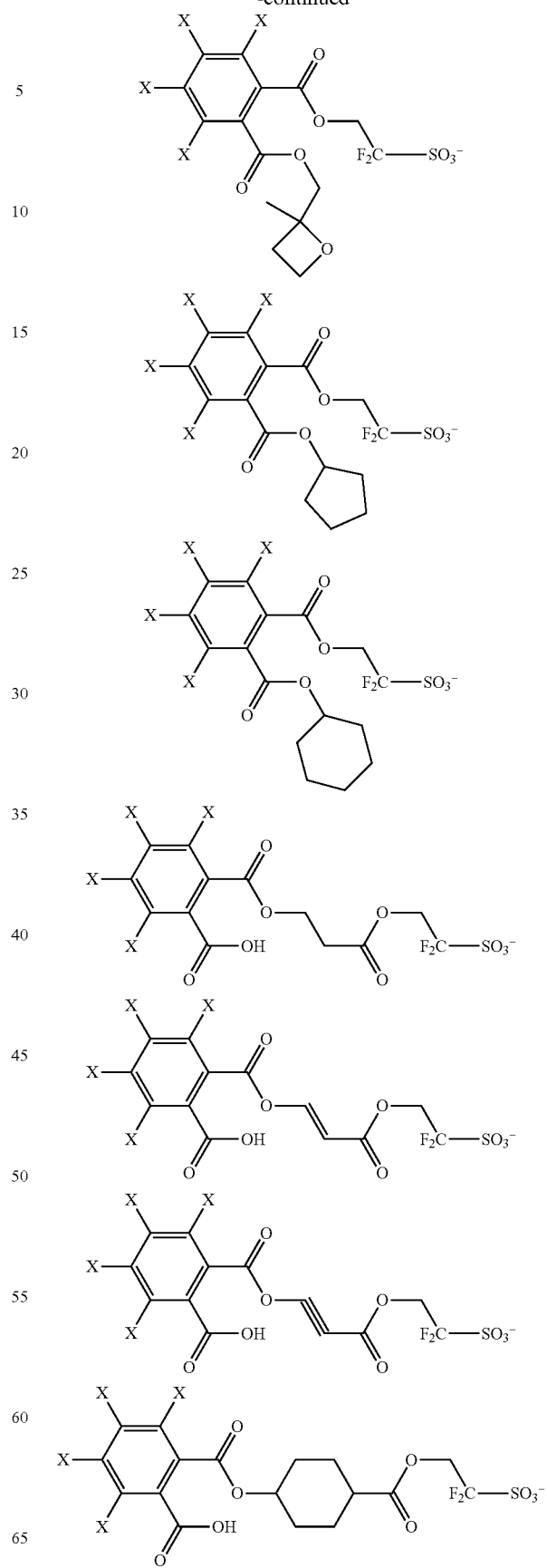

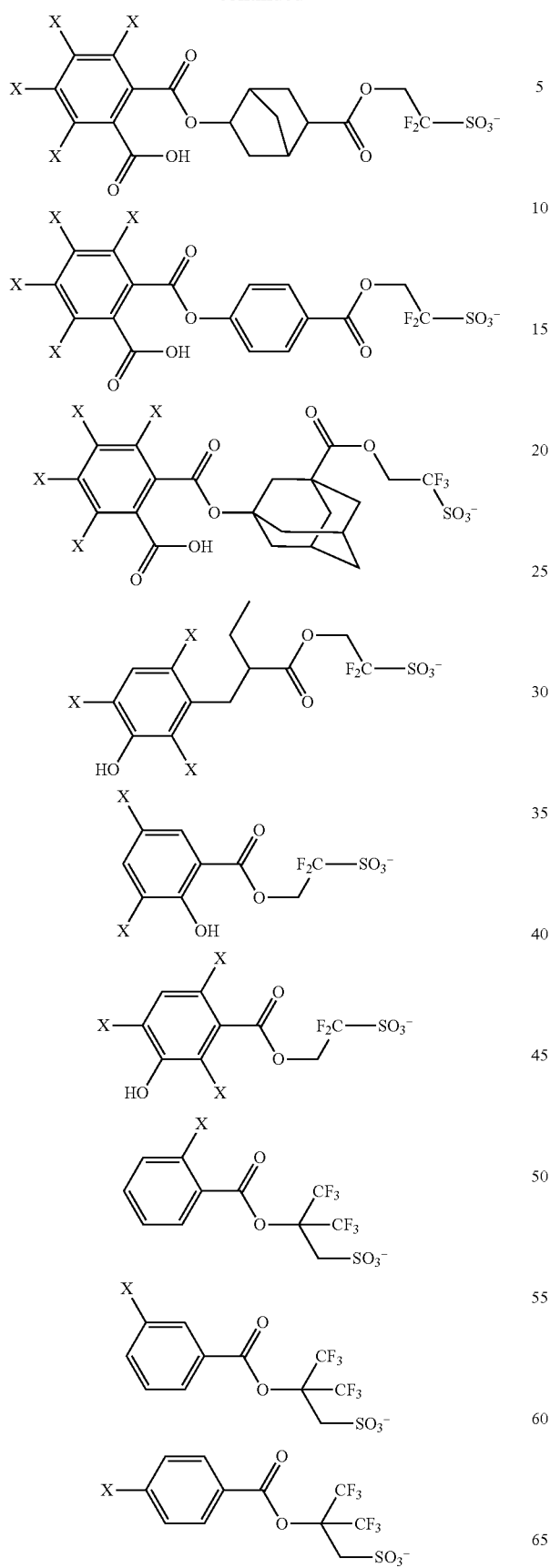
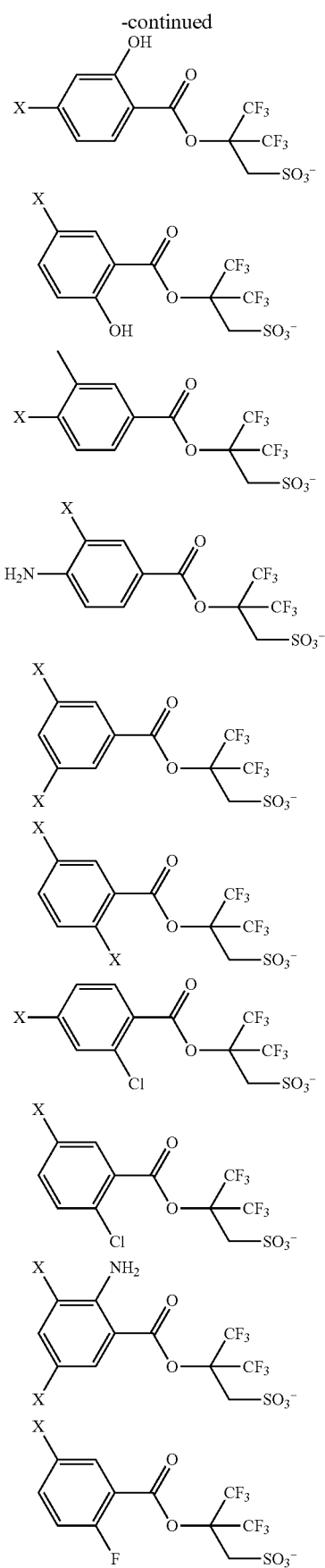

163
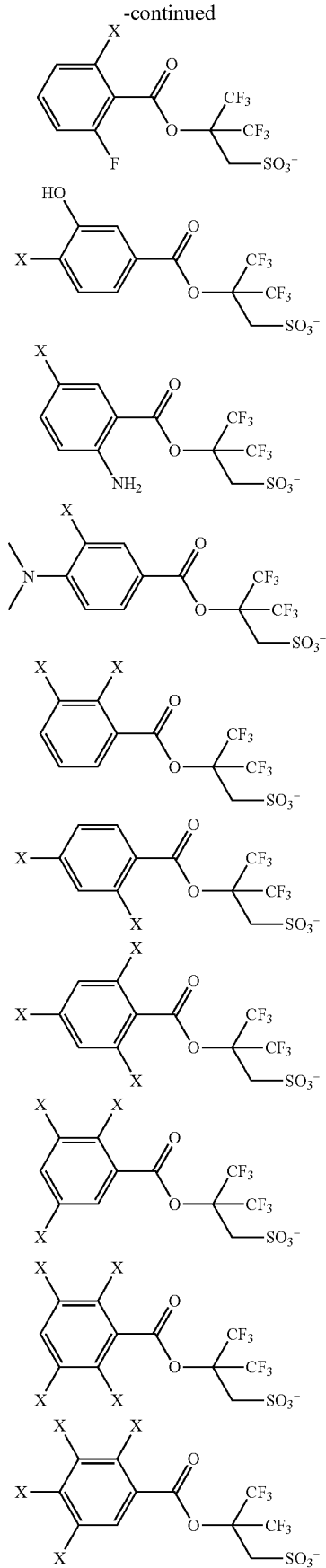
164
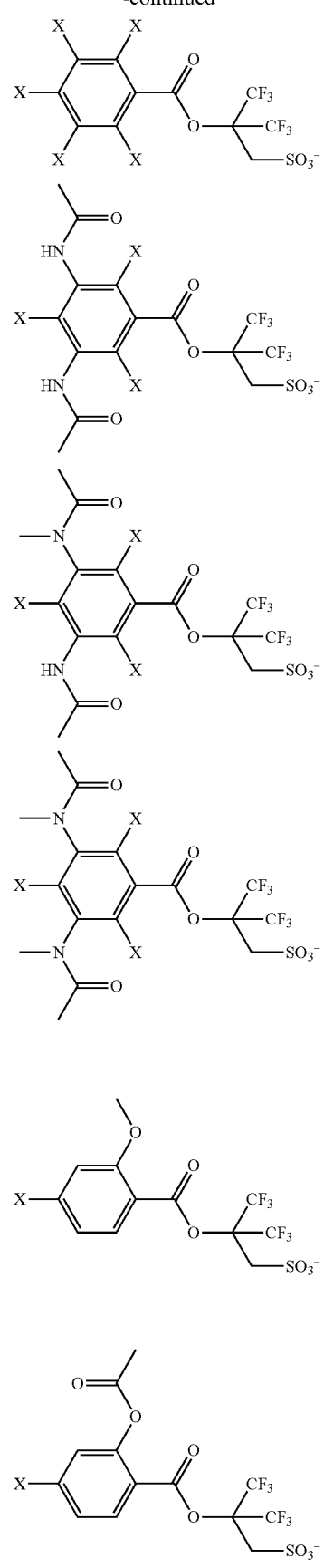

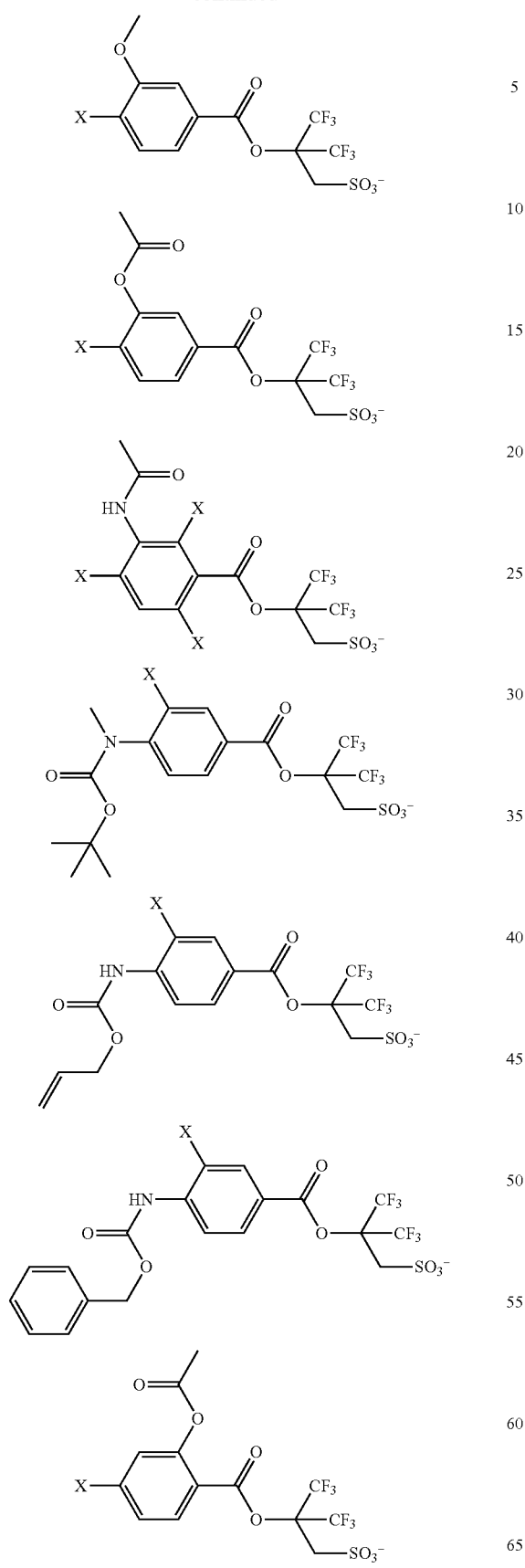
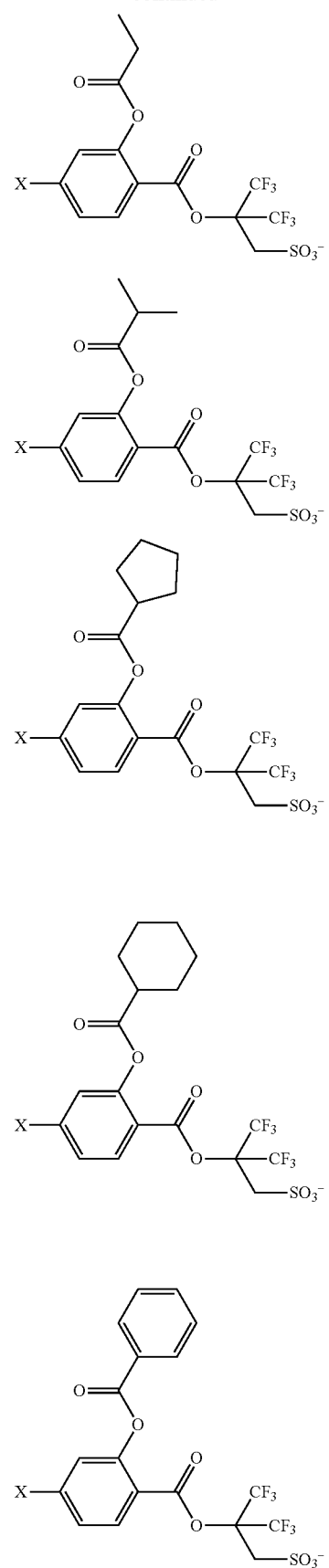

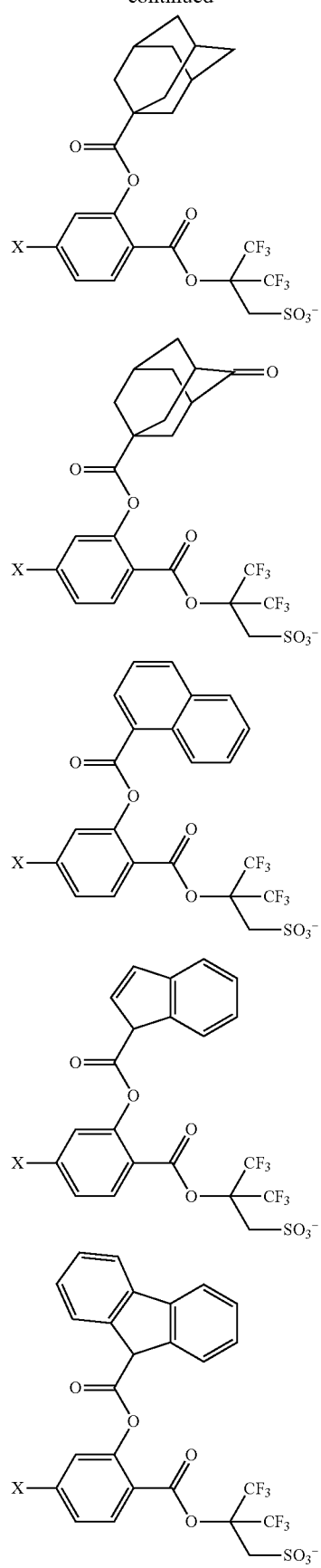
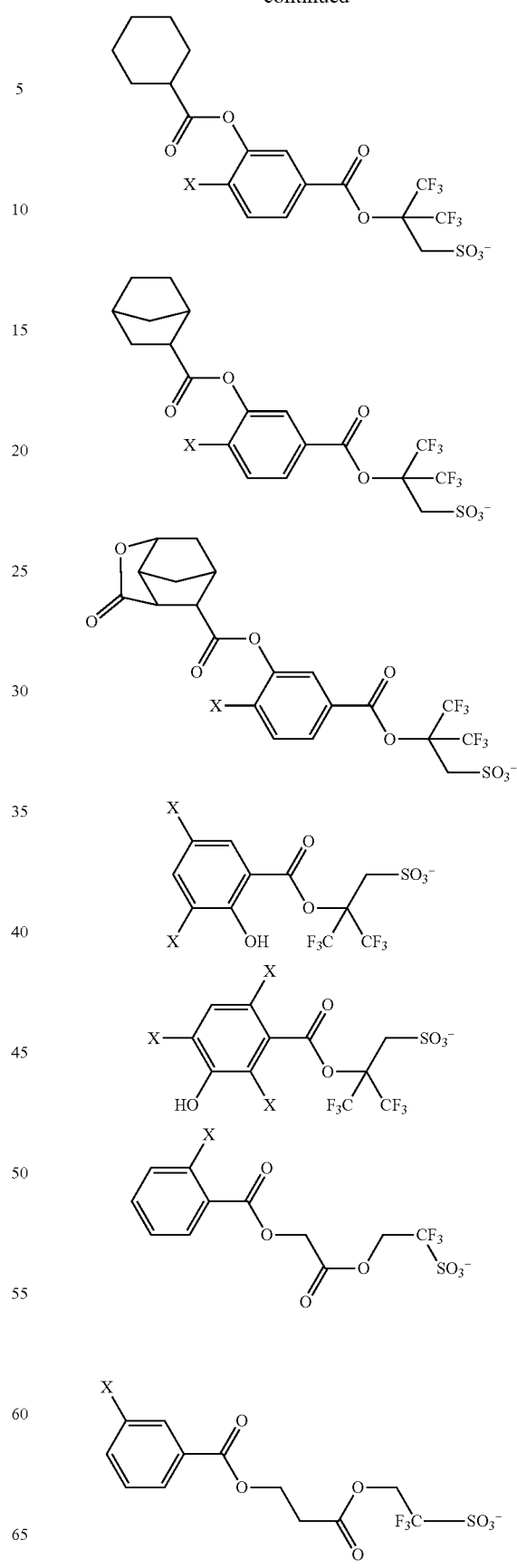

169
-continued
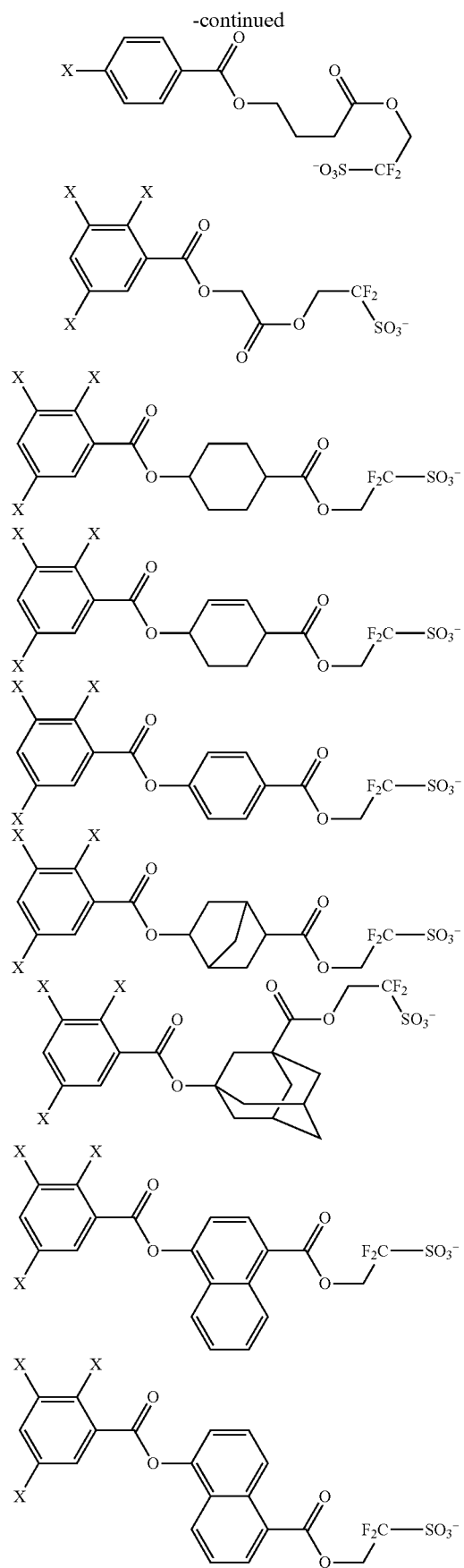
170
-continued
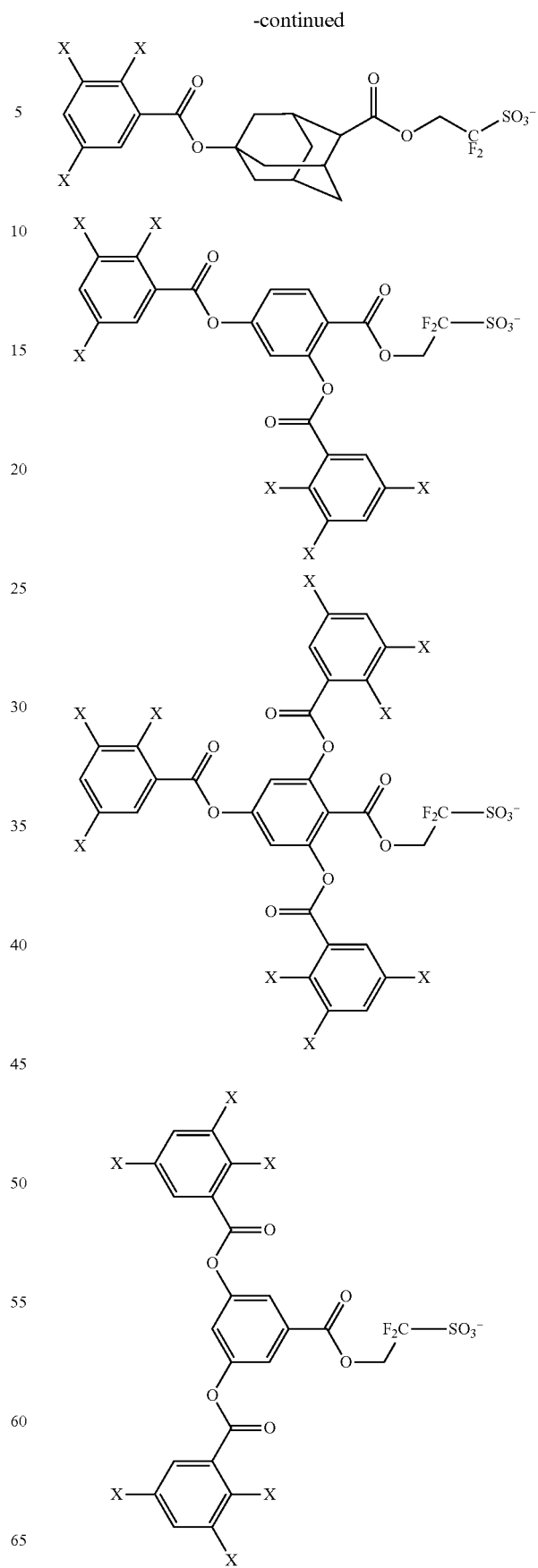

171
-continued
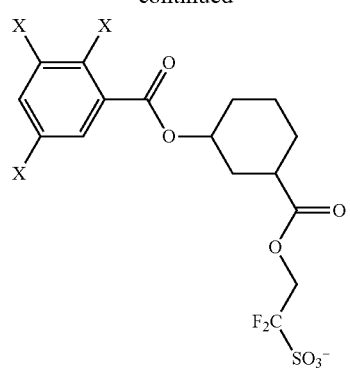
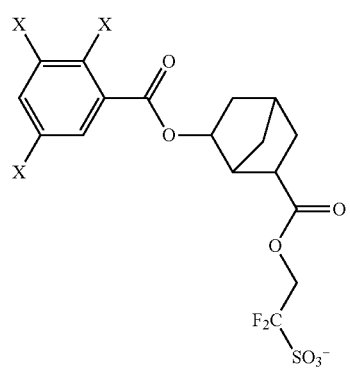
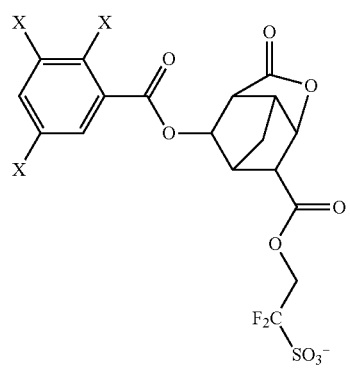
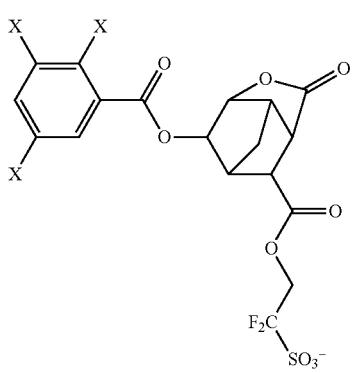
172
-continued
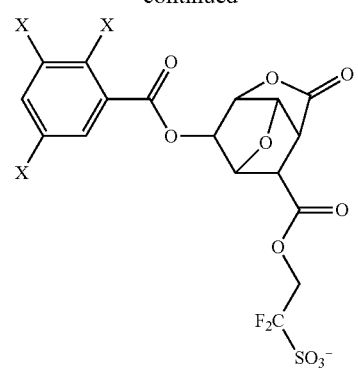
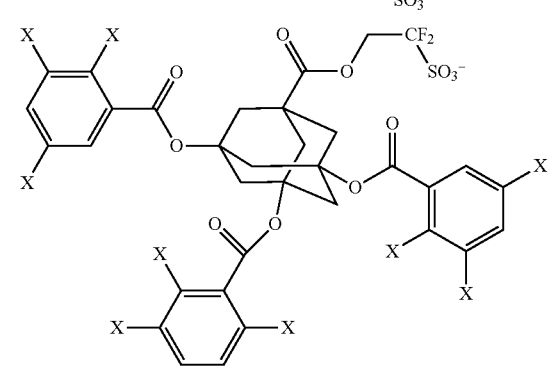
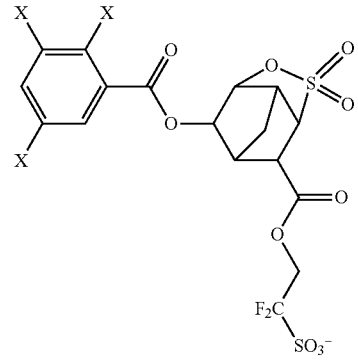
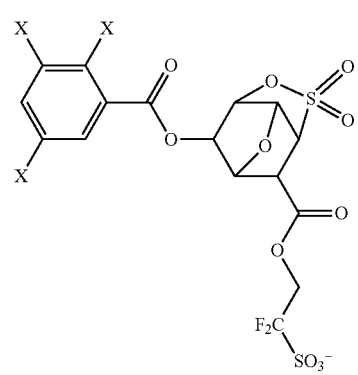

173
-continued
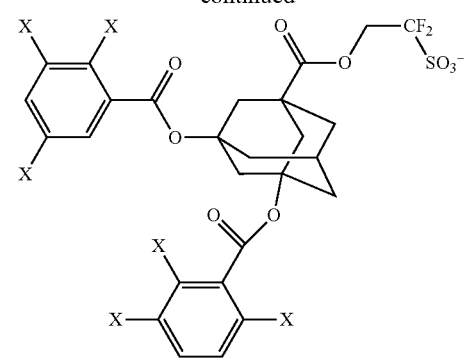
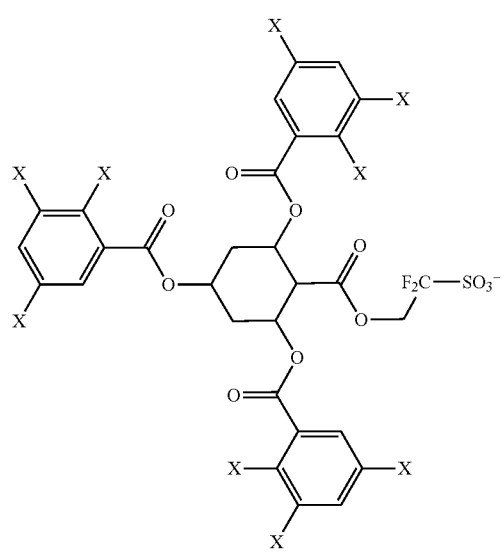
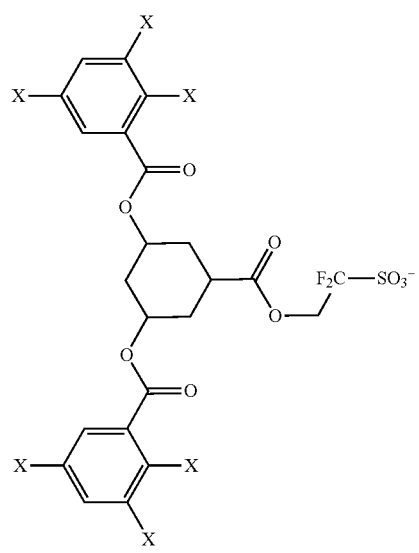
174
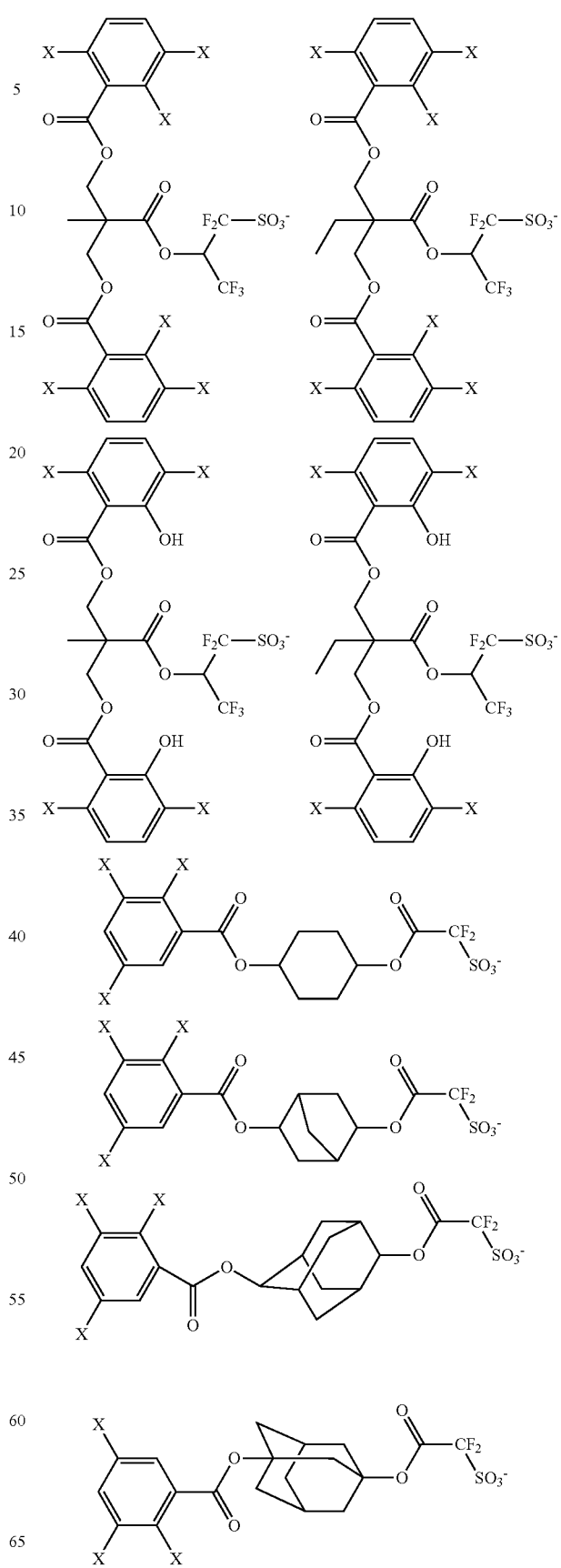

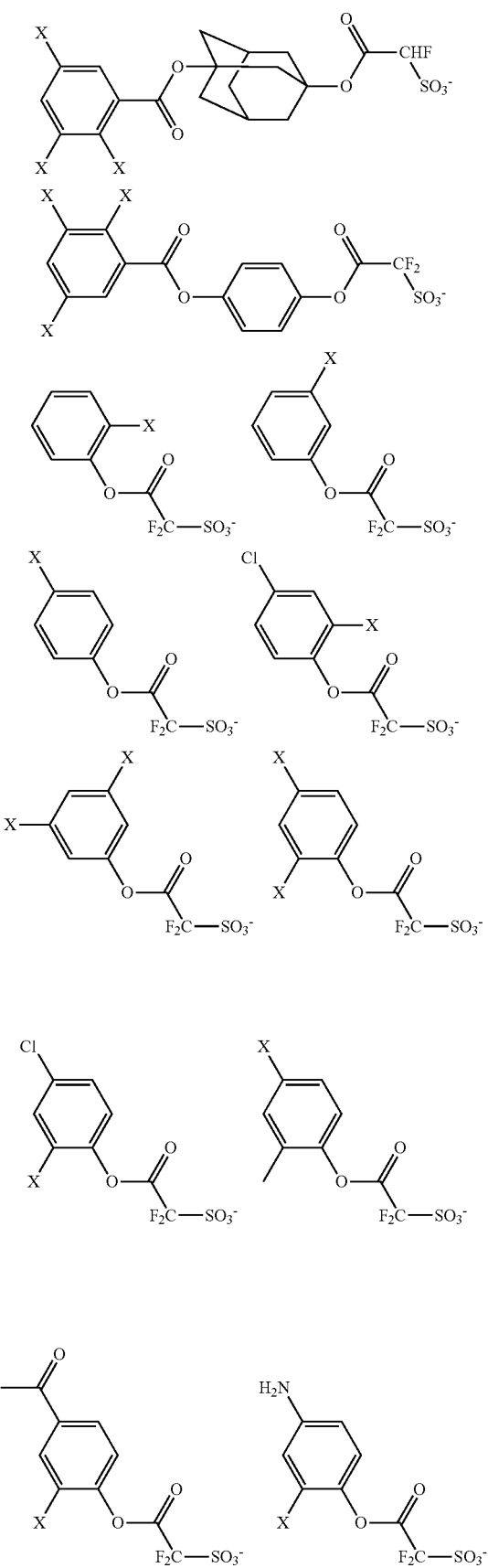
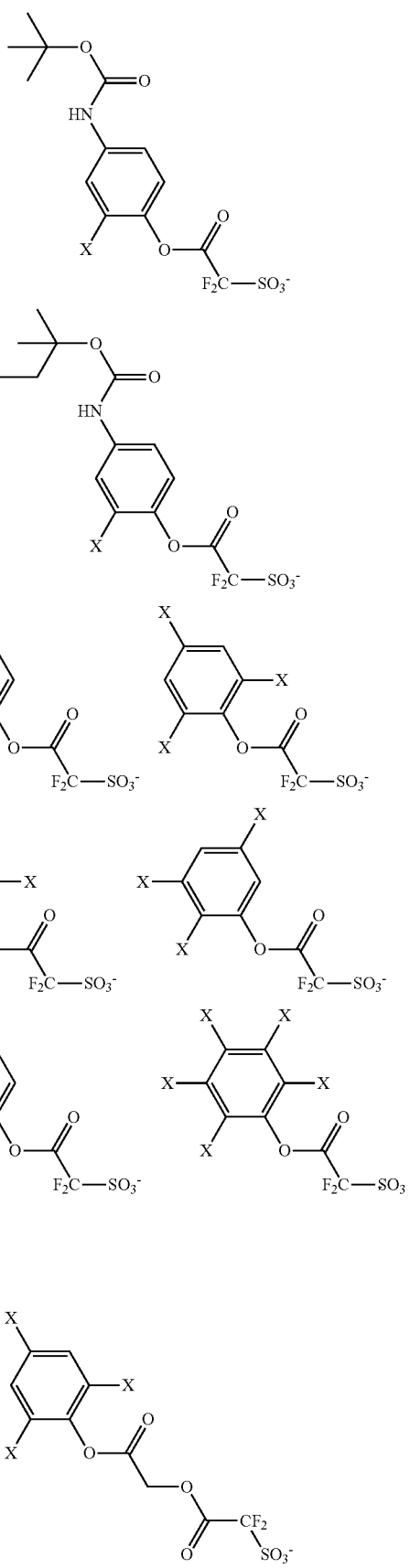

-continued
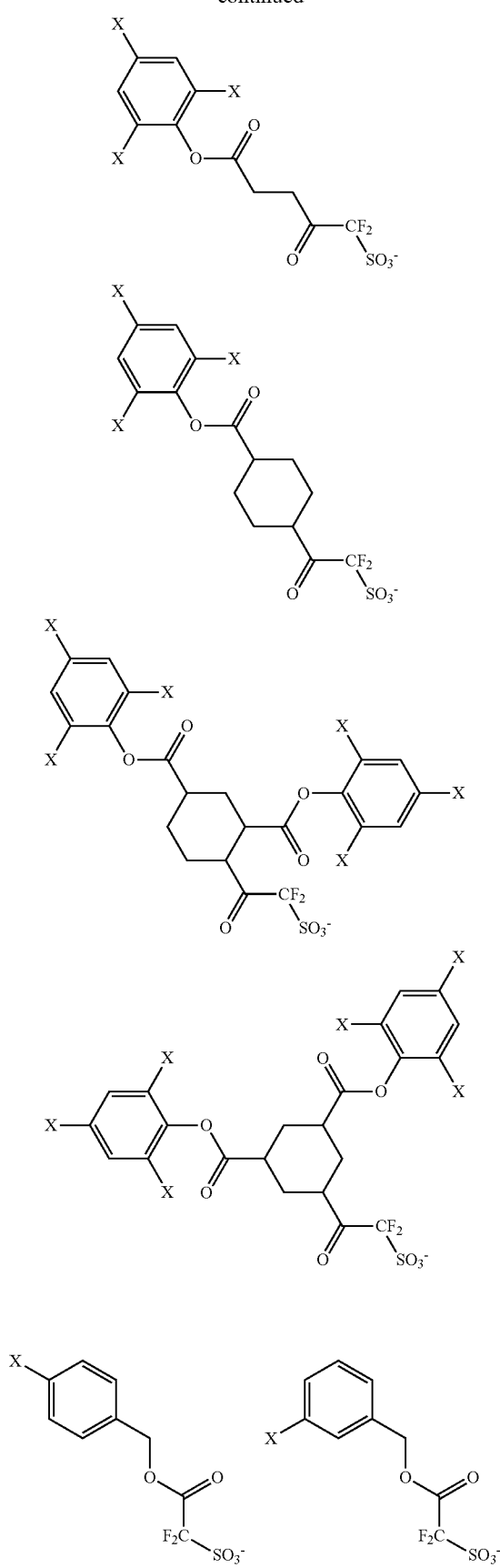
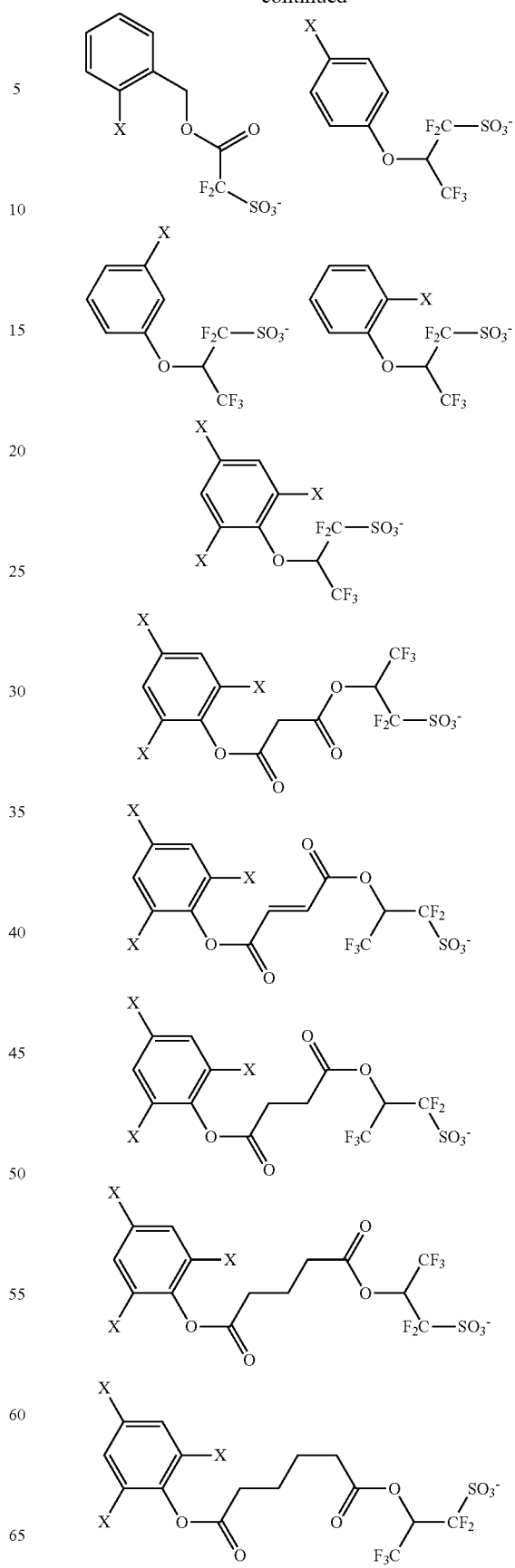

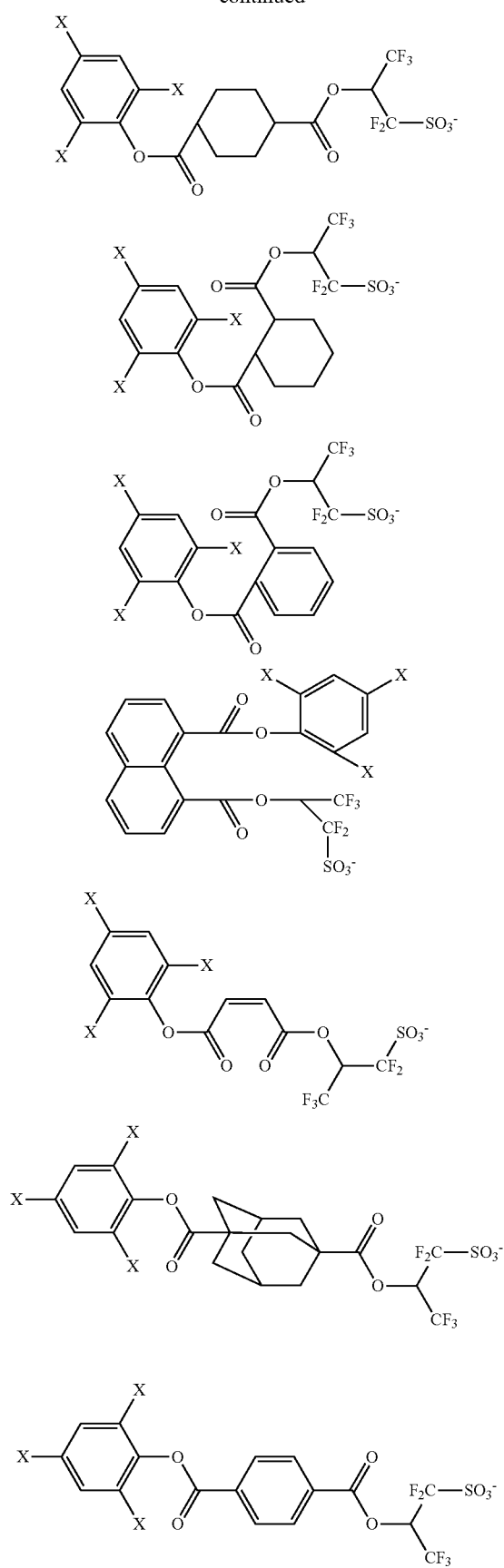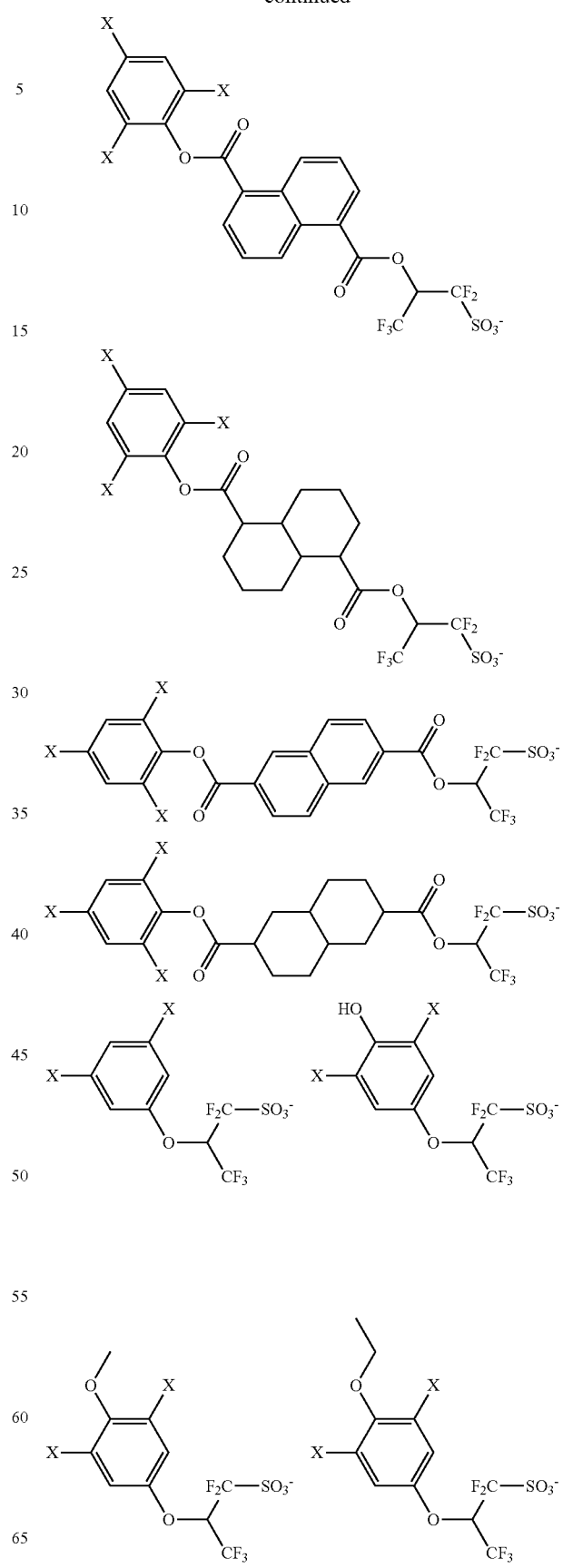

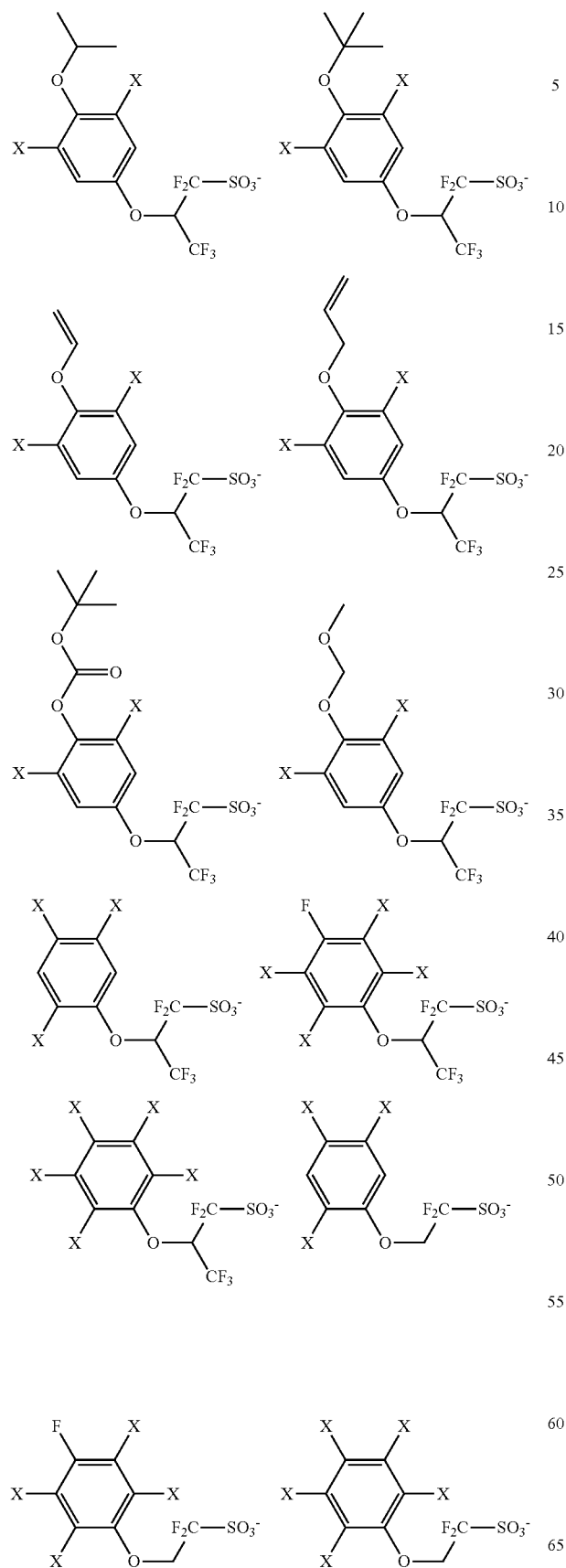
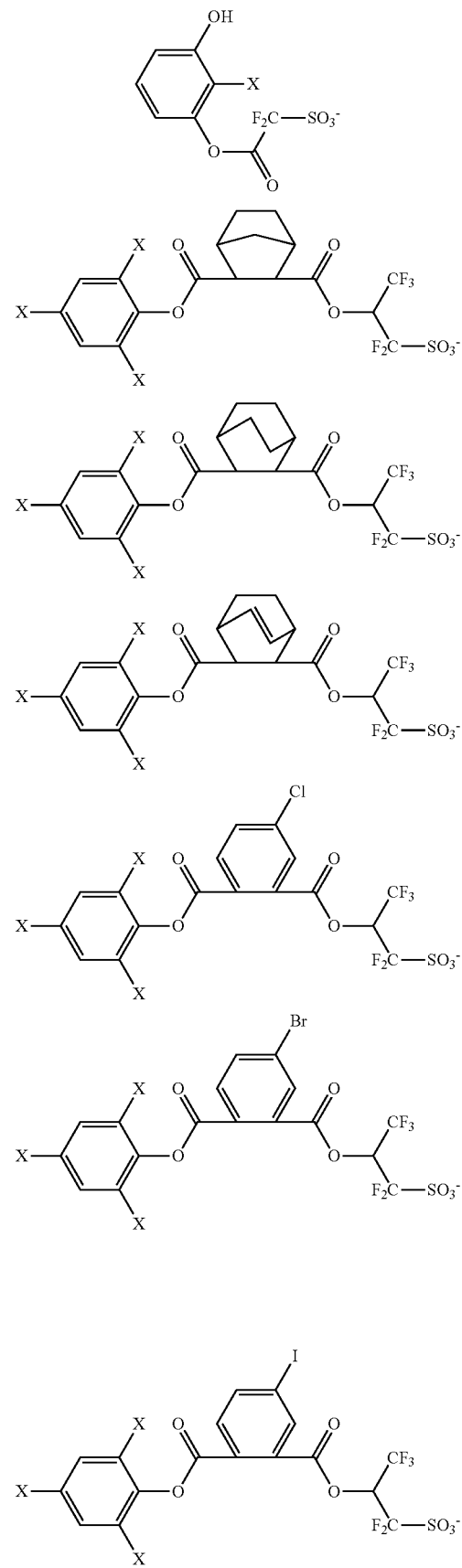

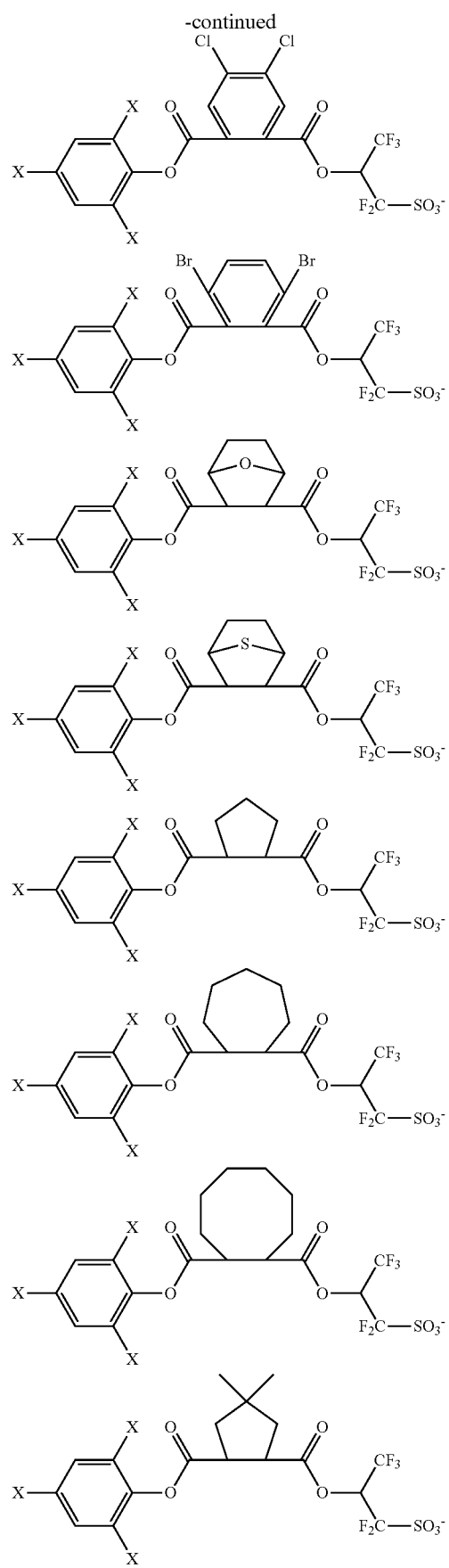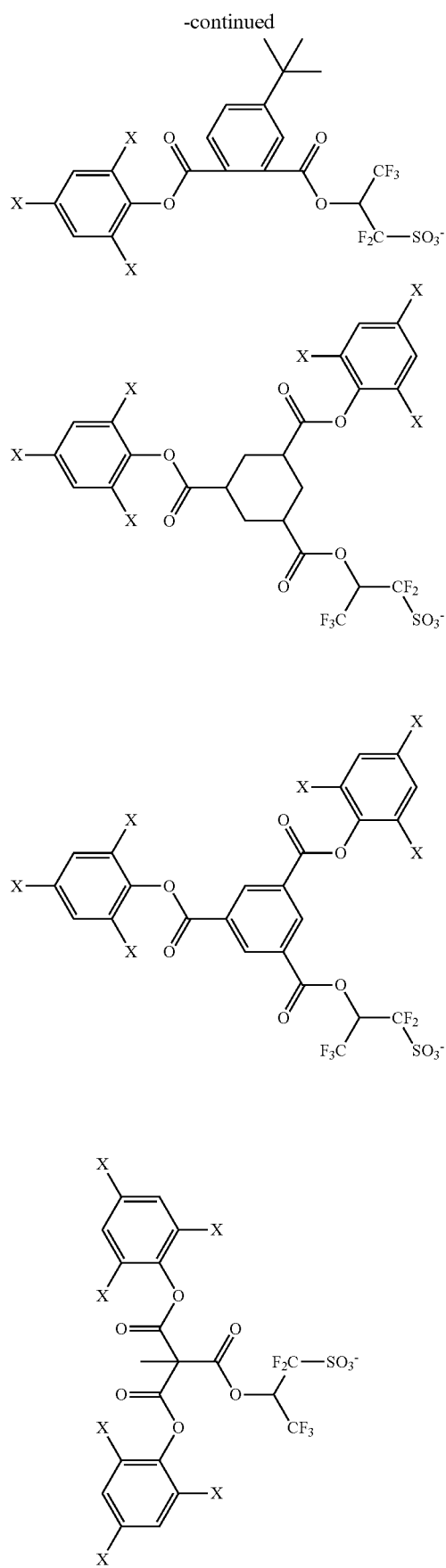

185
-continued
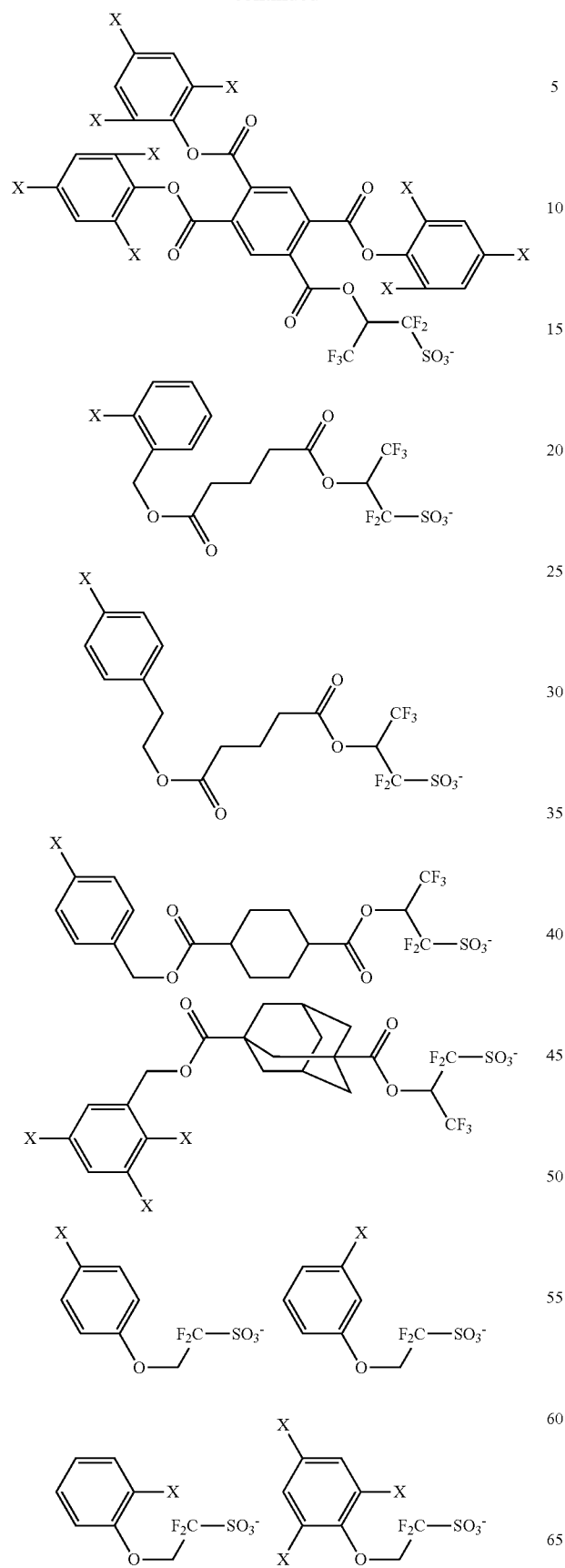
186
-continued
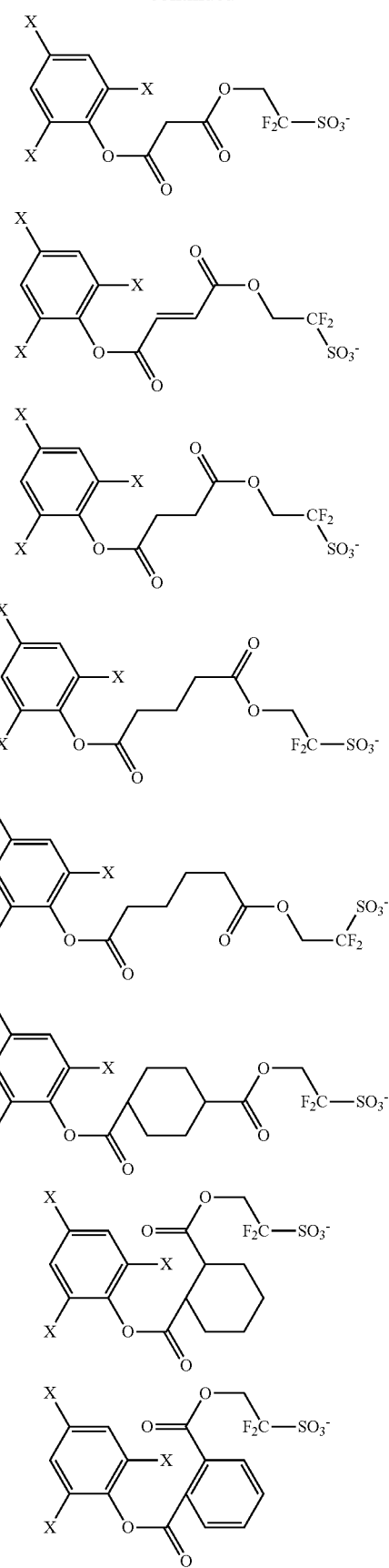

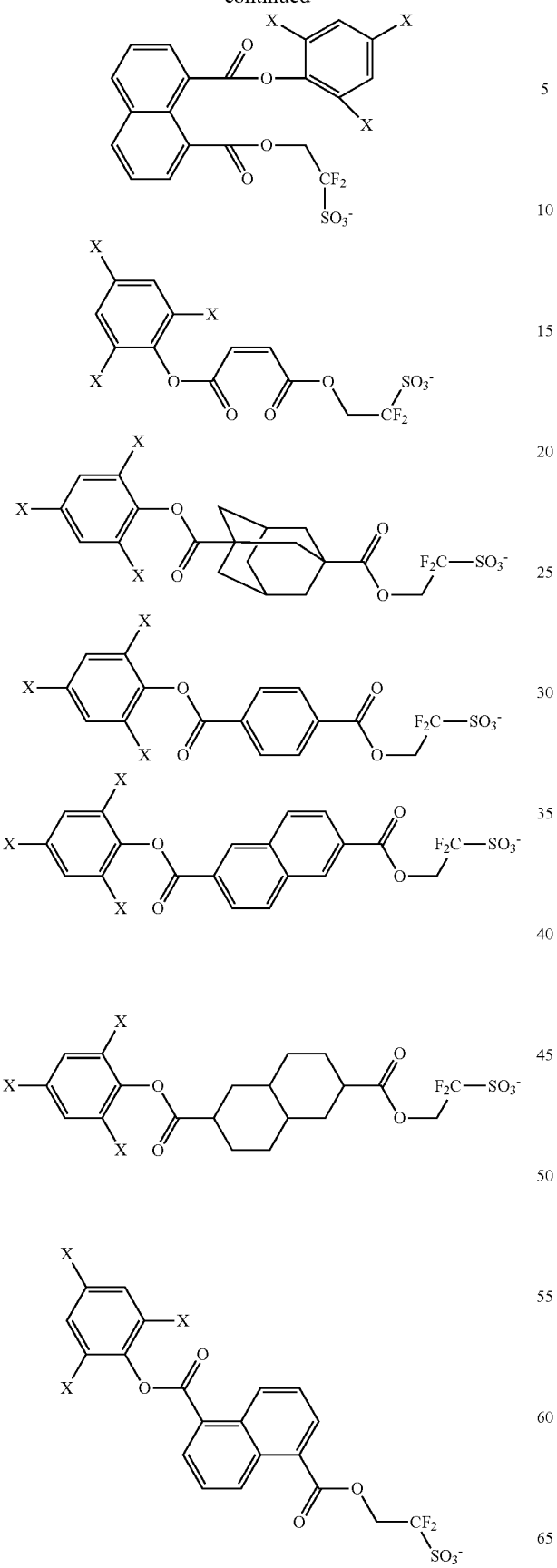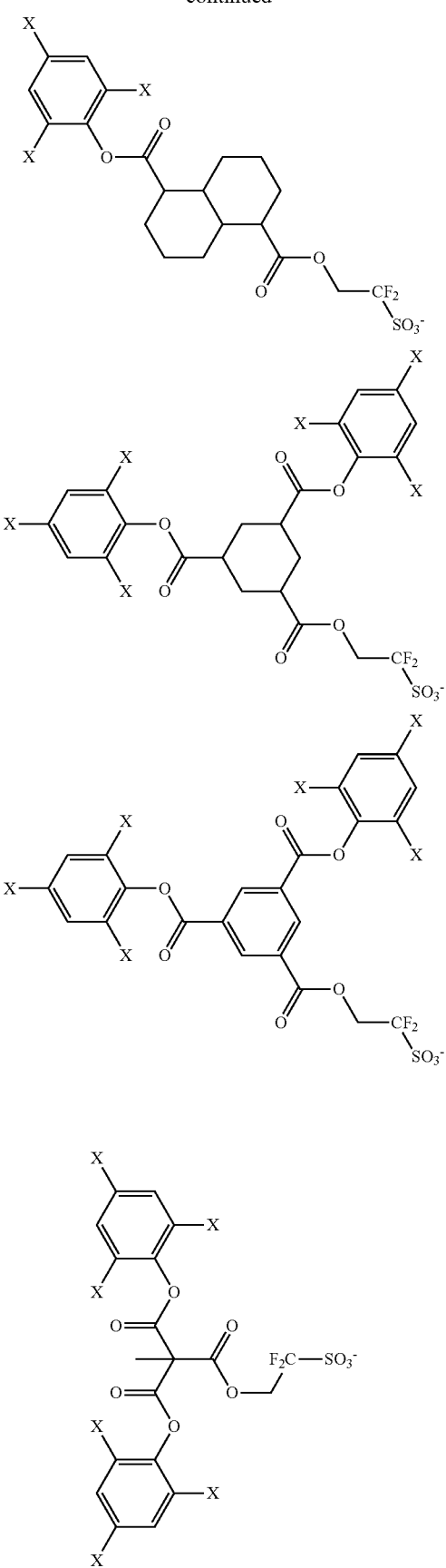

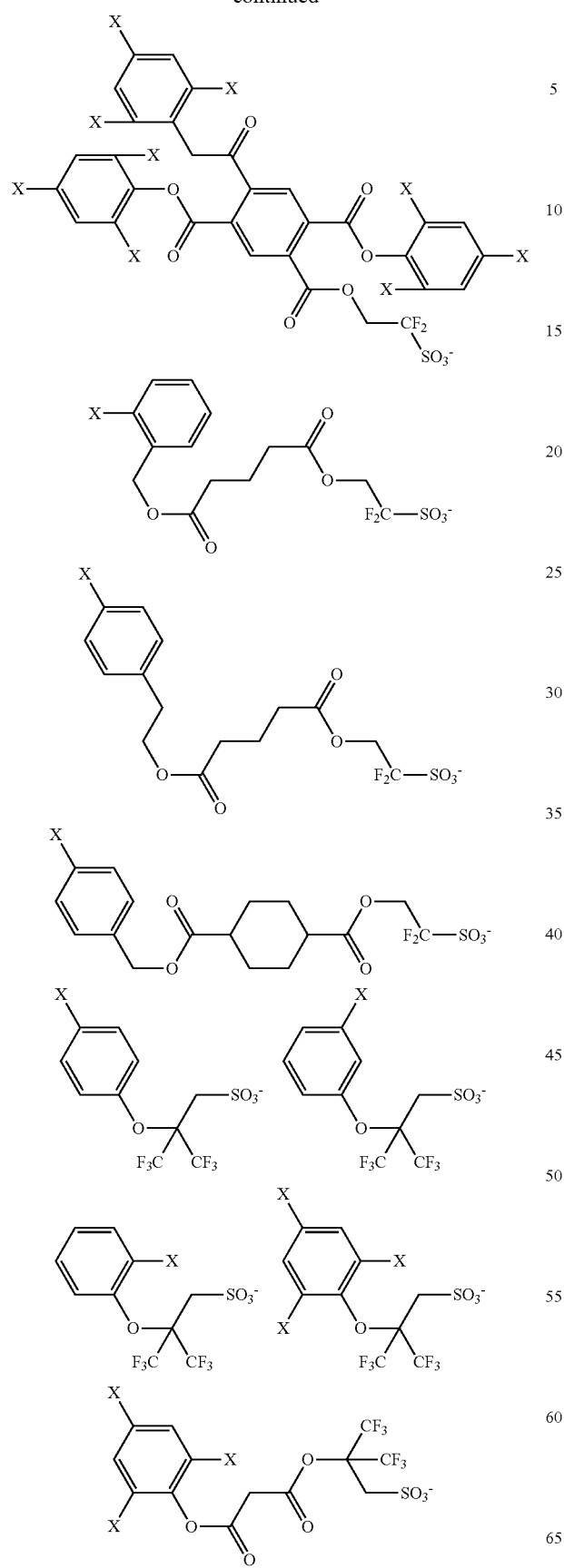
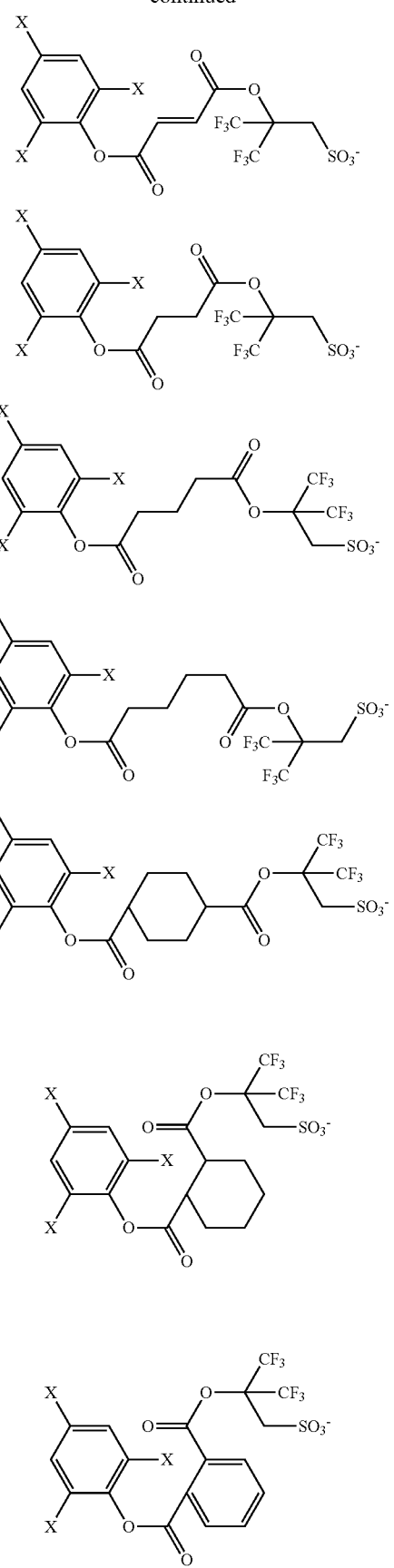

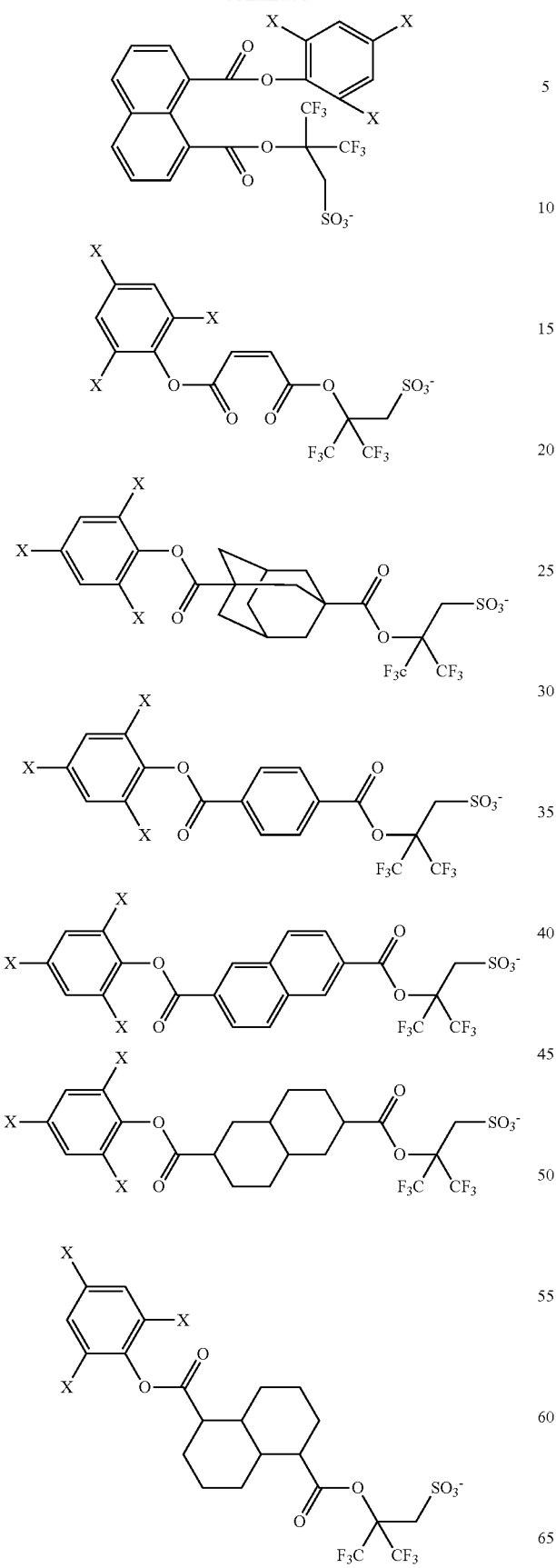
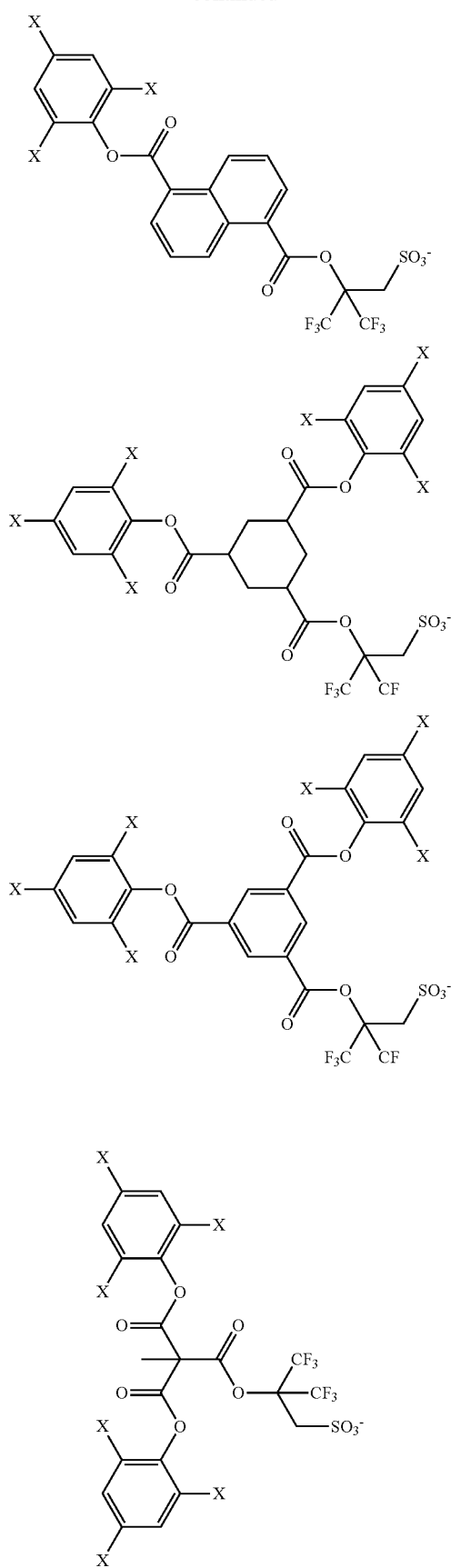

-continued

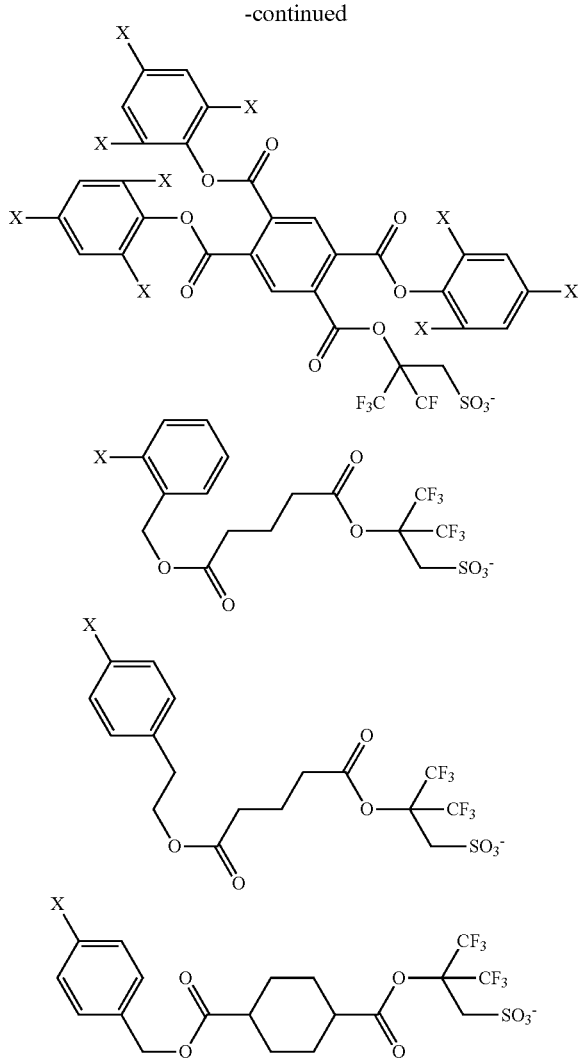

In the positive resist composition, the acid generator of addition type is preferably used in an amount of 0.1 to 50 parts, more preferably 1 to 40 parts by weight per 100 parts by weight of the base polymer. When the base polymer contains recurring units (d1) to (d3) and/or the acid generator of addition type is added, the positive resist composition functions as a chemically amplified positive resist composition.

Organic Solvent

The positive resist composition may contain an organic solvent. The organic solvent is not particularly limited as long as the foregoing components and other components are dissolvable therein. Examples of the organic solvent used herein are described in U.S. Pat. No. 7,537,880 (JP-A 2008-111103, paragraphs [0144]-[0145]). Exemplary solvents include ketones such as cyclohexanone, cyclopentanone, methyl-2-n-pentyl ketone, and 2-heptanone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether, esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate, and lactones such as γ-butyrolactone, and mixtures thereof.

The organic solvent is preferably added in an amount of 100 to 10,000 parts, and more preferably 200 to 8,000 parts by weight per 100 parts by weight of the base polymer.

Quencher

In the positive resist composition, a quencher may be blended. The quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl, ether bond, ester bond, lactone ring, cyano, or sulfonic acid ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Suitable quenchers also include onium salts such as sulfonium salts, iodonium salts and ammonium salts of sulfonic acids which are not fluorinated at α-position and similar onium salts of carboxylic acid, as described in JP-A 2008-158339. While an α-fluorinated sulfonic acid, imide acid, and methide acid are necessary to deprotect the acid labile group of carboxylic acid ester, an α-non-fluorinated sulfonic acid or a carboxylic acid is released by salt exchange with an α-non-fluorinated onium salt. An α-non-fluorinated sulfonic acid and a carboxylic acid function as a quencher because they do not induce deprotection reaction.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

In the resist composition, the quencher is preferably added in an amount of 0 to 5 parts, more preferably 0 to 4 parts by weight per 100 parts by weight of the base polymer. The quenchers may be used alone or in admixture.

Other Components

In addition to the foregoing components, other components such as surfactant and dissolution inhibitor may be blended in any desired combination to formulate a positive resist composition. This positive resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs.

Exemplary surfactants are described in JP-A 2008-111103, paragraphs [0165]-[0166]. Inclusion of a surfactant may improve or control the coating characteristics of the resist composition. The surfactant may be used alone or in admixture. The surfactant is preferably added in an amount of 0.0001 to 10 parts by weight per 100 parts by weight of the base polymer.

The inclusion of a dissolution inhibitor may lead to an increased difference in dissolution rate between exposed and unexposed areas and a further improvement in resolution.

The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

The dissolution inhibitor is preferably added in an amount of 0 to 50 parts, more preferably 5 to 40 parts by weight per 100 parts by weight of the base polymer.

To the resist composition, a water repellency improver may also be added for improving the water repellency on surface of a resist film as spin coated. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. An appropriate amount of the water repellency improver is 0 to 20 parts, preferably 0.5 to 10 parts by weight per 100 parts by weight of the base polymer.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Process

The positive resist composition is used in the fabrication of various integrated circuits. Pattern formation using the resist composition may be performed by well-known lithography processes. The process generally involves coating, exposure, and development. If necessary, any additional steps may be added.

For example, the positive resist composition is first applied onto a substrate on which an integrated circuit is to be formed (e.g., Si, $SiO_2$. SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hotplate at a temperature of 60 to 150° C. for 10 seconds to 30 minutes, preferably at 80 to 120° C. for 30 seconds to 20 minutes. The resulting resist film is generally 0.01 to 2 μm thick.

The resist film is then exposed to a desired pattern of high-energy radiation such as UV, deep-UV, EB, EUV of wavelength 3 to 15 nm, x-ray, soft x-ray, excimer laser light, γ-ray or synchrotron radiation. When UV, deep-UV, EUV, x-ray, soft x-ray, excimer laser light, γ-ray or synchrotron radiation is used as the high-energy radiation, the resist film is exposed thereto through a mask having a desired pattern in a dose of preferably about 1 to 200 m/cm², more preferably about 10 to 100 mJ/cm². When EB is used as the high-energy radiation, the resist film is exposed thereto through a mask having a desired pattern or directly in a dose of preferably about 0.1 to 100 μC/cm², more preferably about 0.5 to 50 μC/cm². It is appreciated that the inventive resist composition is suited in micropatterning using KrF excimer laser, ArF excimer laser, EB, EUV, x-ray, soft x-ray, γ-ray or synchrotron radiation, especially in micropatterning using EB or EUV.

After the exposure, the resist film may be baked (PEB) on a hot plate preferably at 60 to 150'C for 10 seconds to 30 minutes, more preferably at 80 to 120° C. for 30 seconds to 20 minutes.

After the exposure or PEB, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl- 3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. All parts are by weight (pbw). Mw and Mw/Mn are determined by GPC versus polystyrene standards using THF solvent.
[1] Synthesis of Monomers Synthesis Example 1-1

Synthesis of Monomer 1
Monomer 1 of the following formula was prepared by esterification reaction of 5-iodoanthranilic acid with 2-hydroxyethyl methacrylate in triethylamine containing carbodiimide hydrochloride as a condensing agent and 4,4-dimethyiaminopyridine (DMAP) as a catalyst and purifying by silica gel column chromatography.

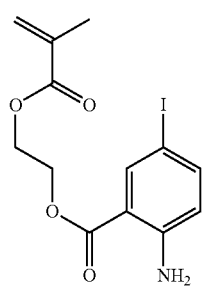

Monomer 1

Synthesis Example 1-2

Synthesis of Monomer 2
Monomer 2 of the following formula was obtained by the same procedure as in Synthesis Example 1-1 aside from using 3,5-diiodoanthranilic acid instead of 5-iodoanthranilic acid.

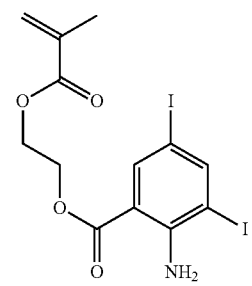

Monomer 2

Synthesis Example 1-3

Synthesis of Monomer 3
Monomer 3 of the following formula was obtained by the same procedure as in Synthesis Example 1-1 aside from using iodopanoic acid instead of 5-iodoanthranilic acid.

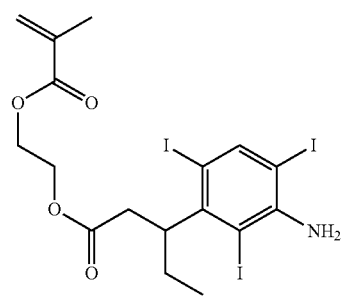

Monomer 3

Synthesis Example 1-4

Synthesis of Monomer 4
Monomer 4 of the following formula was obtained by the same procedure as in Synthesis Example 1-1 aside from using diatrizoic acid instead of 5-iodoanthranilic acid.

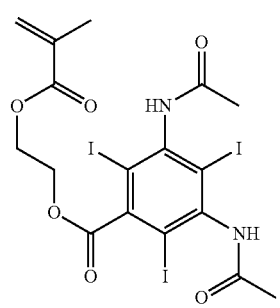

Monomer 4

[2] Synthesis of Polymers

PAG Monomers 1 to 3 and ALG Monomers (i.e., acid labile group-containing monomers) 1 to 3 identified below were used in the synthesis of polymers.

PAG Monomer 1

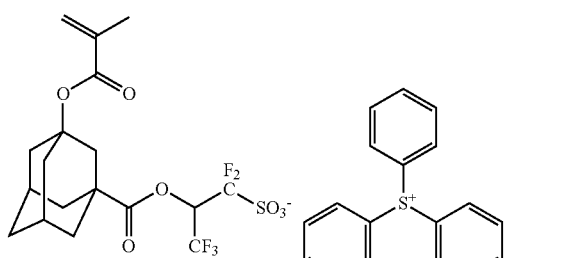

PAG Monomer 2

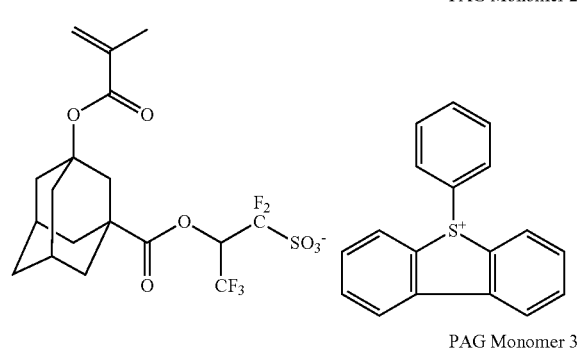

PAG Monomer 3

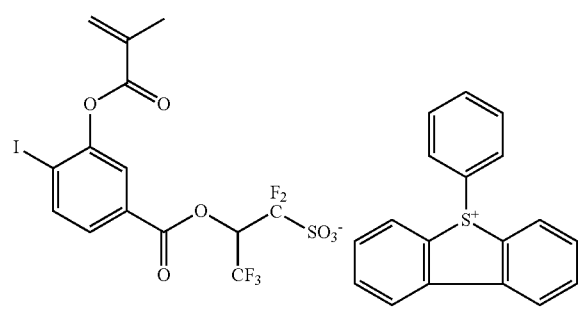

ALG Monomer 1

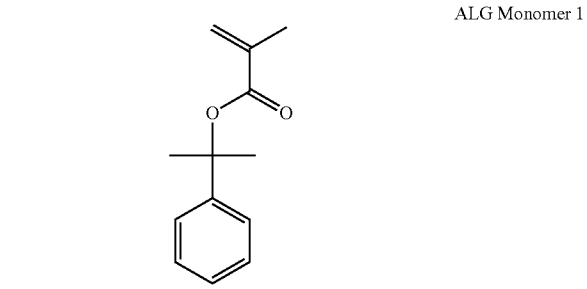

ALG Monomer 2

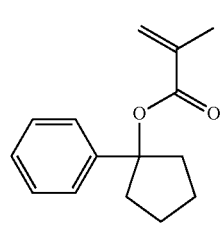

ALG Monomer 3

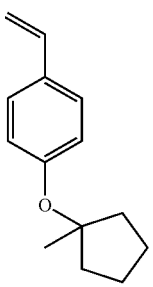

Synthesis Example 2-1

Synthesis of Polymer 1

A 2-L flask was charged with 3.8 g of Monomer 1, 8.4 g of 1-methyl-1-cyclopentyl methacrylate, 4.8 g of 4-hydroxystyrene, and 40 g of tetrahydrofuran (THF) as solvent. The reactor was cooled at −70° C. in nitrogen atmosphere, after which vacuum pumping and nitrogen blow were repeated three times. The reactor was warmed up to room temperature, whereupon 1.2 g of azobisisobutyronitrile (AIBN) was added. The reactor was heated at 60° C., whereupon reaction ran for 15 hours. The reaction solution was poured into 1 L of isopropyl alcohol for precipitation. The precipitated white solid was collected by filtration and vacuum dried at 60° C., yielding Polymer 1. Polymer 1 was analyzed for composition by $^{13}$C- and $^1$H-NMR and for Mw and Mw/Mn by GPC.

Polymer 1

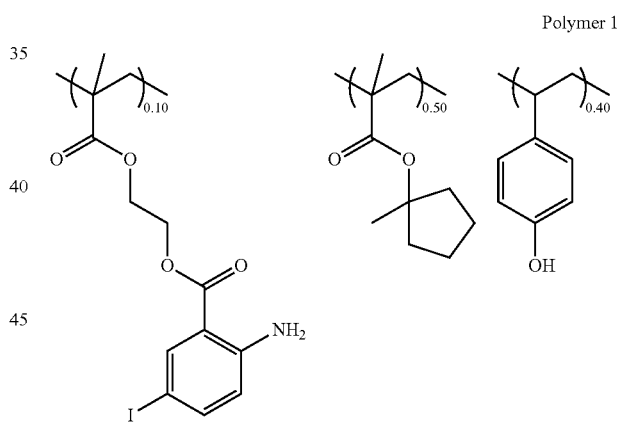

Mw = 7,500
Mw/Mn = 1.61

Synthesis Example 2-2

Synthesis of Polymer 2

A 2-L flask was charged with 5.0 g of Monomer 2, 7.3 g of 1-methyl-1-cyclohexyl methacrylate, 4.2 g of 4-hydroxystyrene, 1.0 g of PAG Monomer 2, and 40 g of THF as solvent. The reactor was cooled at −70° C. in nitrogen atmosphere, after which vacuum pumping and nitrogen blow were repeated three times. The reactor was warmed up to room temperature, whereupon 1.2 g of AIBN was added. The reactor was heated at 60° C., whereupon reaction ran for 15 hours. The reaction solution was poured into 1 L of isopropyl alcohol for precipitation. The precipitated white solid was collected by filtration and vacuum dried at 60° C.,

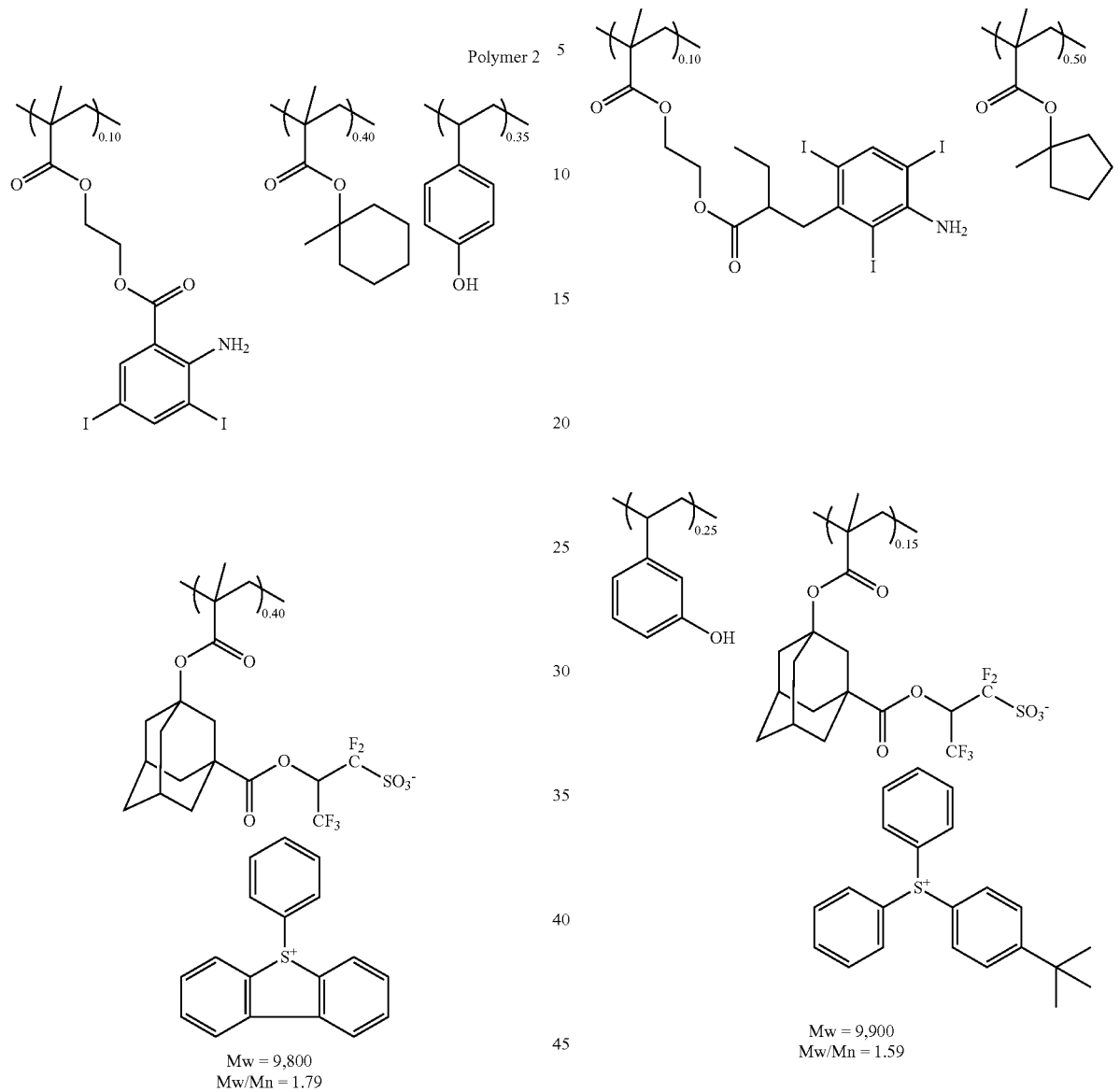

Synthesis Example 2-3

Synthesis of Polymer 3

A 2-L flask was charged with 6.8 g of Monomer 3, 8.4 g of 1-methyl-1-cyclopentyl methacrylate, 3.8 g of 3-hydroxystyrene, 11.9 g of PAG Monomer 1, and 40 g of THF as solvent. The reactor was cooled at −70° C. in nitrogen atmosphere, after which vacuum pumping and nitrogen blow were repeated three times. The reactor was warmed up to room temperature, whereupon 1.2 g of AIBN was added. The reactor was heated at 60° C., whereupon reaction ran for 15 hours. The reaction solution was poured into 1 L of isopropyl alcohol for precipitation. The precipitated white solid was collected by filtration and vacuum dried at 60° C., yielding Polymer 3. Polymer 3 was analyzed for composition by $^{13}$C- and $^1$H-NMR and for Mw and Mw/Mn by GPC.

Synthesis Example 2-4

Synthesis of Polymer 4

A 2-L flask was charged with 6.8 g of Monomer 3, 8.4 g of 1-methyl-1-cyclopentyl methacrylate, 3.8 g of 3-hydroxystyrene, 12.1 g of PAG Monomer 3, and 40 g of THF as solvent. The reactor was cooled at −70° C. in nitrogen atmosphere, after which vacuum pumping and nitrogen blow were repeated three times. The reactor was warmed up to room temperature, whereupon 1.2 g of AIBN was added. The reactor was heated at 60° C., whereupon reaction ran for 15 hours. The reaction solution was poured into 1 L of isopropyl alcohol for precipitation. The precipitated white solid was collected by filtration and vacuum dried at 60° C., yielding Polymer 4. Polymer 4 was analyzed for composition by $^{13}$C- and $^1$H-NMR and for Mw and Mw/Mn by GPC.

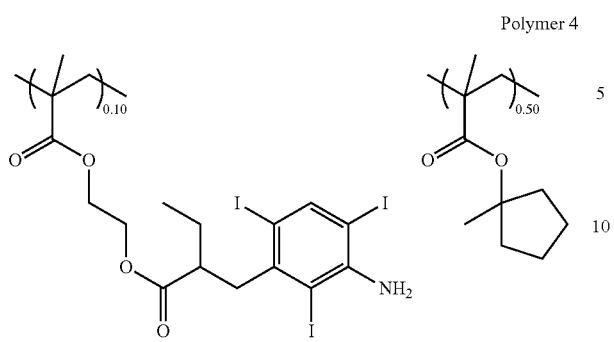

Polymer 4

Mw = 10,300
Mw/Mn = 1.58

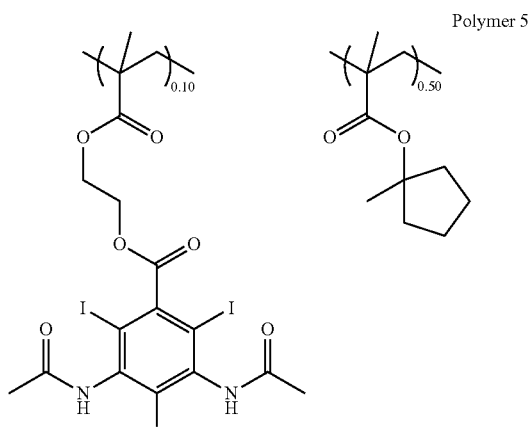

Polymer 5

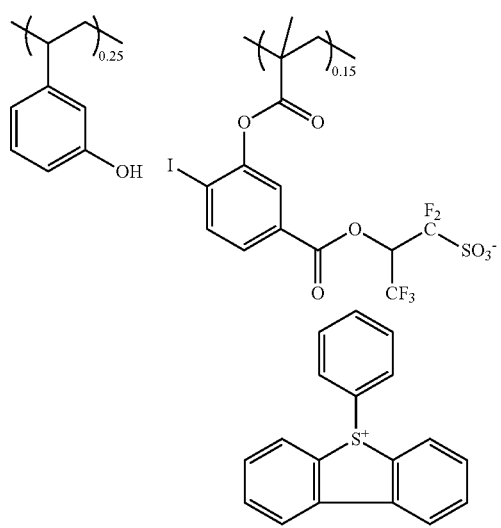

Mw = 10,100
Mw/Mn = 1.53

Synthesis Example 2-5

Synthesis of Polymer 5

A 2-L flask was charged with 7.3 g of Monomer 4, 8.4 g of 1-methyl-1-cyclopentyl methacrylate, 3.8 g of 3-hydroxystyrene, 11.0 g of PAG Monomer 2, and 40 g of THF as solvent. The reactor was cooled at −70° C. in nitrogen atmosphere, after which vacuum pumping and nitrogen blow were repeated three times. The reactor was warmed up to room temperature, whereupon 1.2 g of AIBN was added. The reactor was heated at 60° C., whereupon reaction ran for 15 hours. The reaction solution was poured into 1 L of isopropyl alcohol for precipitation. The precipitated white solid was collected by filtration and vacuum dried at 60° C., yielding Polymer 5. Polymer 5 was analyzed for composition by $^{13}C$- and $^{1}H$-NMR and for Mw and Mw/Mn by GPC.

Synthesis Example 2-6

Synthesis of Polymer 6

A 2-L flask was charged with 7.3 g of Monomer 4, 8.4 g of 1-methyl-1-cyclopentyl methacrylate, 1.8 g of 3-hydroxystyrene, 3.7 g of 3,5-diiodo-4-hydroxystyrene, 12.1 g of PAG Monomer 3, and 40 g of THF as solvent. The reactor was cooled at −70° C. in nitrogen atmosphere, after which vacuum pumping and nitrogen blow were repeated three times. The reactor was warmed up to room temperature, whereupon 1.2 g of AIBN was added. The reactor was heated at 60° C., whereupon reaction ran for 15 hours. The reaction solution was poured into 1 L of isopropyl alcohol for precipitation. The precipitated white solid was collected by filtration and vacuum dried at 60° C., yielding Polymer 6. Polymer 6 was analyzed for composition by $^{13}C$- and $^{1}H$-NMR and for Mw and Mw/Mn by GPC.

Polymer 6

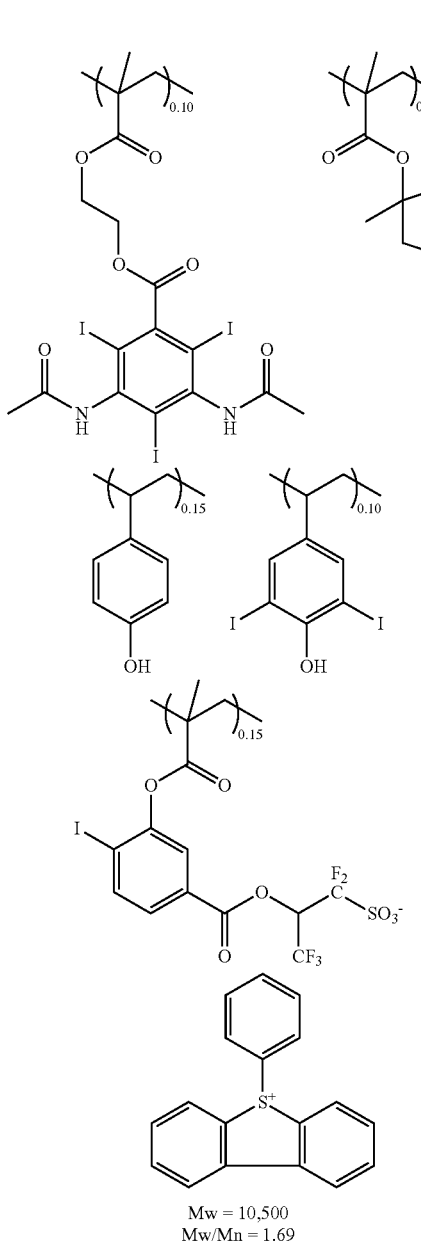

Mw = 10,500
Mw/Mn = 1.69

Synthesis Example 2-7

Synthesis of Polymer 7

A 2-L flask was charged with 5.0 g of Monomer 2, 8.2 g of ALG Monomer 1, 4.2 g of 3-hydroxystyrene, 11.0 g of PAG Monomer 2, and 40 g of THF as solvent. The reactor was cooled at −70° C. in nitrogen atmosphere, after which vacuum pumping and nitrogen blow were repeated three times. The reactor was warmed up to room temperature, whereupon 1.2 g of AIBN was added. The reactor was heated at 60° C., whereupon reaction ran for 15 hours. The reaction solution was poured into 1 L of isopropyl alcohol for precipitation. The precipitated white solid was collected by filtration and vacuum dried at 60° C., yielding Polymer 7. Polymer 7 was analyzed for composition by $^{13}C$- and $^{1}H$-NMR and for Mw and Mw/Mn by GPC.

Polymer 7

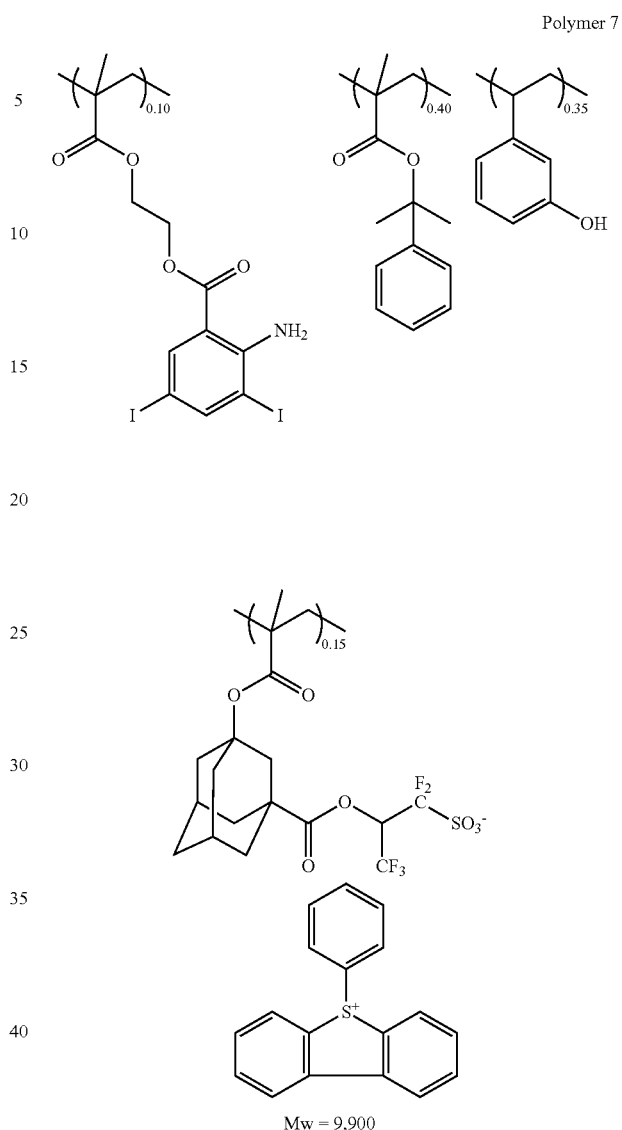

Mw = 9,900
Mw/Mn = 1.89

Synthesis Example 2-8

Synthesis of Polymer 8

A 2-L flask was charged with 5.0 g of Monomer 2, 4.6 g of ALG Monomer 2, 4.0 g of ALG Monomer 3, 4.2 g of 3-hydroxystyrene, 11.0 g of PAG Monomer 2, and 40 g of THF as solvent. The reactor was cooled at −70° C. in nitrogen atmosphere, after which vacuum pumping and nitrogen blow were repeated three times. The reactor was warmed up to room temperature, whereupon 1.2 g of AIBN was added. The reactor was heated at 60° C., whereupon reaction ran for 15 hours. The reaction solution was poured into 1 L of isopropyl alcohol for precipitation. The precipitated white solid was collected by filtration and vacuum dried at 60° C., yielding Polymer 8. Polymer 8 was analyzed for composition by $^{13}C$- and $^{1}H$-NMR and for Mw and Mw/Mn by GPC.

Polymer 8

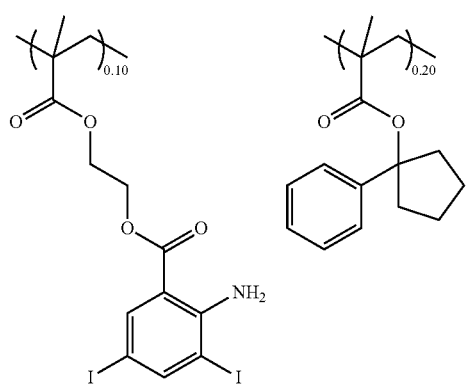

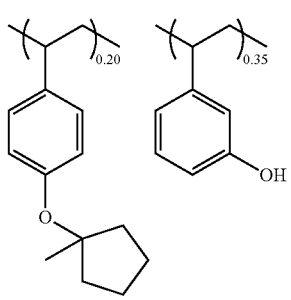

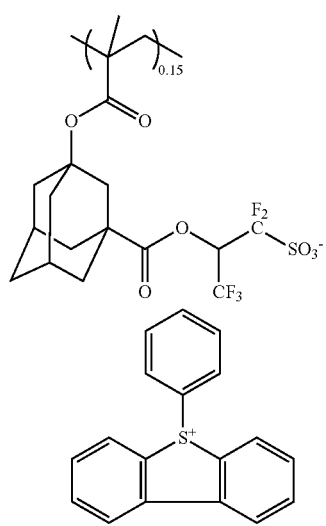

Mw = 9,600
Mw/Mn = 1.81

Comparative Synthesis Example 1

Comparative Polymer 1 was obtained by the same procedure as in Synthesis Example 2-1 except that Monomer 1 was omitted. Comparative Polymer 1 was analyzed for composition by $^{13}$C- and $^1$H-NMR and for Mw and Mw/Mn by GPC.

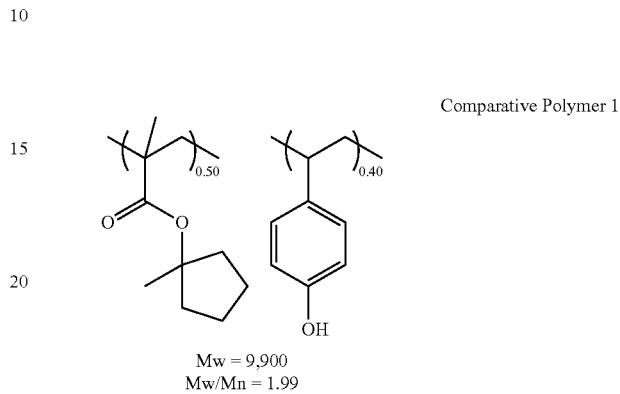

Comparative Polymer 1

Mw = 9,900
Mw/Mn = 1.99

Comparative Synthesis Example 2

Comparative Polymer 2 was obtained by the same procedure as in Synthesis Example 2-1 except that 2-(dimethylamino)ethyl methacrylate was used instead of Monomer 1. Comparative Polymer 2 was analyzed for composition by $^{13}$C- and $^1$H-NMR and for Mw and Mw/Mn by GPC.

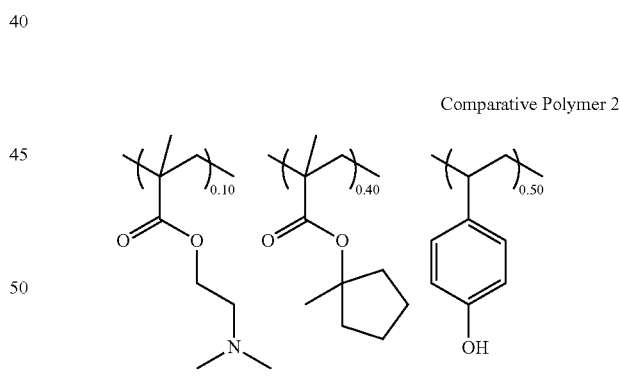

Comparative Polymer 2

Mw = 9,700
Mw/Mn = 1.91

Comparative Synthesis Example 3

Comparative Polymer 3 was obtained by the same procedure as in Synthesis Example 2-2 except that Monomer 2 was omitted and 1-methyl-1-cyclopentyl methacrylate was used instead of 1-methyl-1-cyclohexyl methacrylate. Comparative Polymer 3 was analyzed for composition by $^{13}$C- and $^1$H-NMR and for Mw and Mw/Mn by GPC.

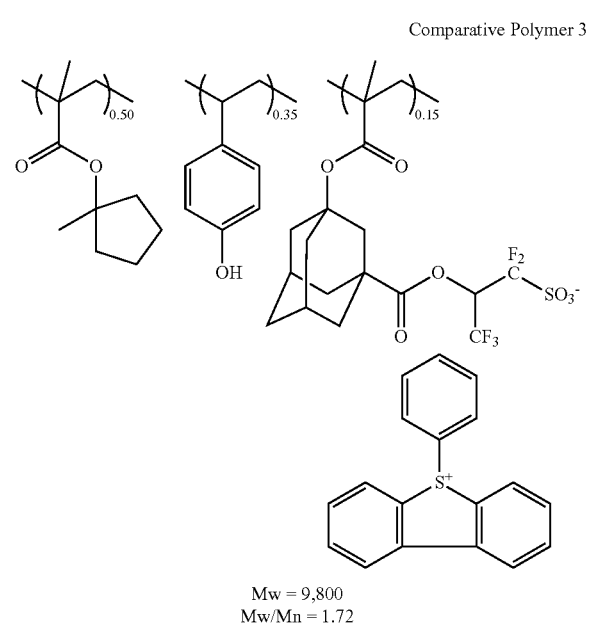

Comparative Polymer 3

Mw = 9,800
Mw/Mn = 1.72

[3] Preparation and Evaluation of Positive Resist Composition

Examples 1 to 12 and Comparative Examples 1 to 3

Positive resist compositions were prepared by dissolving components in a solvent in accordance with the recipe shown in Table 1, and filtering through a filter having a pore size of 0.2 μm. The solvent contained 100 ppm of surfactant FC-4430 (3M). The components in Table 1 are as identified below.

Organic solvents:
PGMEA (propylene glycol monomethyl ether acetate)
DAA (diacetone alcohol)
Acid generator: PAG-1 of the following structural formula
Quencher: Q-1 of the following structural formula

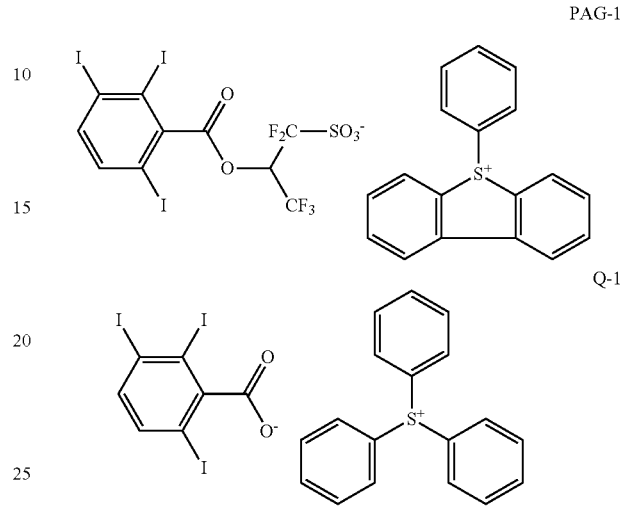

PAG-1

Q-1

EUV Lithography Test

Each of the resist compositions in Table 1 was spin coated on a silicon substrate having a 20-nm coating of silicon-containing spin-on hard mask SHB-A940 (Shin-Etsu Chemical Co., Ltd., Si content 43 wt %) and prebaked on a hotplate at 105° C. for 60 seconds to form a resist film of 60 nm thick. Using an EUV scanner NXE3300 (ASML, NA 0.33, σ0.9/0.6, quadrupole illumination), the resist film was exposed to EUV through a mask bearing a hole pattern at a pitch 46 nm (on-wafer size) and +20% bias. The resist film was baked (PEB) on a hotplate at the temperature shown in Table 1 for 60 seconds and developed in a 2.38 wt % TMAH aqueous solution for 30 seconds to form a hole pattern having a size of 23 nm.

The resist pattern was observed under CD-SEM (CG-5000. Hitachi High-Technologies Corp.). The exposure dose that provides a hole pattern having a size of 23 nm is reported as sensitivity. The size of 50 holes was measured, from which a size variation (30) was computed and reported as CDU.

The resist composition is shown in Table 1 together with the sensitivity and CDU of EUV lithography.

TABLE 1

| | | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 1 | Polymer 1 (100) | PAG-1 (25.0) | — | PGMEA (2,000) DAA (500) | 95 | 29 | 3.0 |
| | 2 | Polymer 2 (100) | — | — | PGMEA (2,000) DAA (500) | 95 | 26 | 2.7 |
| | 3 | Polymer 3 (100) | — | — | PGMEA (2,000) DAA (500) | 95 | 27 | 2.6 |
| | 4 | Polymer 1 (80) Comparative Polymer 1 (20) | — | — | PGMEA (2,000) DAA (500) | 95 | 28 | 2.3 |
| | 5 | Polymer 3 (70) Comparative Polymer 3 (30) | — | — | PGMEA (2,000) DAA (500) | 95 | 28 | 2.6 |

TABLE 1-continued

|  |  | Polymer (pbw) | Acid generator (pbw) | Quencher (pbw) | Organic solvent (pbw) | PEB temp. (° C.) | Sensitivity (mJ/cm²) | CDU (nm) |
|---|---|---|---|---|---|---|---|---|
|  | 6 | Polymer 3 (100) | PAG-1 (10.0) | Q-1 (1.00) | PGMEA (2,000) DAA (500) | 95 | 27 | 2.6 |
|  | 7 | Polymer 4 (100) | — | — | PGMEA (2,000) DAA (500) | 95 | 26 | 2.2 |
|  | 8 | Polymer 5 (100) | — | — | PGMEA (2,000) DAA (500) | 95 | 23 | 2.4 |
|  | 9 | Polymer 6 (100) | — | — | PGMEA (2,000) DAA (500) | 95 | 21 | 2.5 |
|  | 10 | Polymer 7 (100) | — | — | PGMEA (2,000) DAA (500) | 80 | 22 | 2.3 |
|  | 11 | Polymer 8 (100) | — | — | PGMEA (2,000) DAA (500) | 80 | 23 | 2.3 |
|  | 12 | Polymer 8 (100) | — | Q-1 (1.00) | PGMEA (2,000) DAA (500) | 80 | 26 | 2.2 |
| Comparative Example | 1 | Comparative Polymer 1 (100) | PAG-1 (25.0) | Q-1 (3.00) | PGMEA (2,000) DAA (500) | 95 | 30 | 5.6 |
|  | 2 | Comparative Polymer 2 (100) | PAG-1 (25.0) | — | PGMEA (2,000) DAA (500) | 95 | 38 | 4.7 |
|  | 3 | Comparative Polymer 3 (100) | — | Q-1 (3.00) | PGMEA (2,000) DAA (500) | 95 | 35 | 3.9 |

It is demonstrated in Table 1 that positive resist compositions comprising a base polymer comprising recurring units containing iodine and amino offer a high sensitivity and improved CDU.

Japanese Patent Application No. 2018-244436 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A positive resist composition comprising a base polymer comprising recurring units containing an optionally substituted amino group and iodine,
wherein the recurring units containing an optionally substituted amino group and iodine have the formula (a):

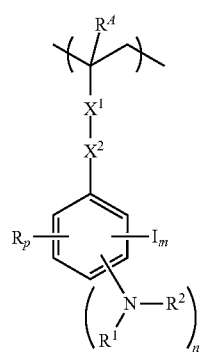

(a)

wherein $R^A$ is hydrogen or methyl, $X^1$ is a single bond, phenylene, naphthylene, or a $C_1$-$C_{12}$ linking group containing an ester bond, ether bond or lactone ring, $X^2$ is a single bond or a $C_1$-$C_{12}$ divalent hydrocarbon group which may contain hydroxyl, ether bond or ester bond, R is hydroxyl, carboxyl, $C_1$-$C_4$ straight or branched alkyl group, $C_1$-$C_4$ straight or branched alkoxy group, $C_2$-$C_5$ straight or branched alkoxycarbonyl group, $C_2$-$C_5$ straight or branched acyl group, $C_2$-$C_5$ straight or branched acyloxy group, or halogen exclusive of iodine, $R^1$ and $R^2$ are each independently hydrogen, $C_1$-$C_6$ alkyl group, $C_2$-$C_6$ alkenyl group, $C_2$-$C_6$ alkynyl group, $C_2$-$C_7$ acyl group, $C_2$-$C_7$ alkoxycarbonyl group, $C_2$-$C_7$ alkenyloxycarbonyl group, $C_2$-$C_7$ alkynyloxycarbonyl group, $C_7$-$C_{12}$ aryloxycarbonyl group, or $C_8$-$C_{12}$ aralkyloxycarbonyl group, $R^1$ and $R^2$ may bond together to form a ring with the nitrogen atom to which they are attached, the ring may contain an ether bond, m is an integer of 1 to 4, n is 1 or 2, p is an integer of 0 to 3, and 2≤m+n+p≤5.

2. The resist composition of claim 1 wherein the base polymer further comprises recurring units having a carboxyl group substituted with an acid labile group and/or recurring units having a phenolic hydroxyl group substituted with an acid labile group.

3. The resist composition of claim 2 wherein the recurring units having a carboxyl group substituted with an acid labile group and the recurring units having a phenolic hydroxyl group substituted with an acid labile group are recurring units having the formula (b1) and recurring units having the formula (b2), respectively,

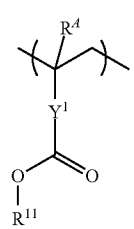

(b1)

-continued (b2)

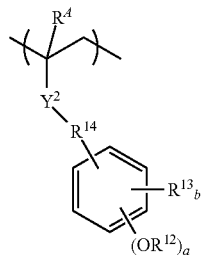

wherein $R^A$ is each independently hydrogen or methyl, $Y^1$ is a single bond, phenylene, naphthylene, or a $C_1$-$C_{12}$ linking group containing an ester bond, ether bond or lactone ring, $Y^2$ is a single bond, ester bond or amide bond, $R^{11}$ and $R^{12}$ are each independently an acid labile group, $R^{13}$ is fluorine, trifluoromethyl, cyano, or a $C_1$-$C_6$ alkyl group, $R^{14}$ is a single bond or $C_1$-$C_6$ straight or branched alkanediyl group in which some carbon may be replaced by an ether or ester bond, a is 1 or 2, and b is an integer of 0 to 4.

4. The resist composition of claim 1 wherein the base polymer further comprises recurring units (c) containing an adhesive group selected from the group consisting of hydroxyl, carboxyl, lactone ring, carbonate, thiocarbonate, carbonyl, cyclic acetal, ether bond, ester bond, sulfonic acid ester bond, cyano, amide, —O—C(=O)—S—, and —O—C(=O)—NH—.

5. The resist composition of claim 1 wherein the base polymer further comprises recurring units of at least one type selected from recurring units having the formulae (d1) to (d3):

(d1)

(d2)

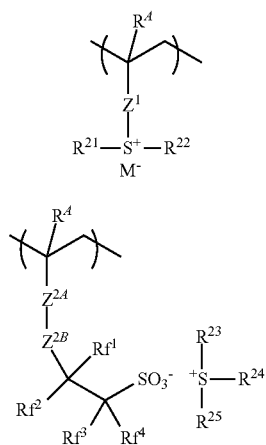

(d3)

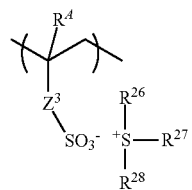

wherein $R^A$ is each independently hydrogen or methyl,
$Z^1$ is a single bond, phenylene, —O—$Z^{11}$—, —C(=O)—O—$Z^{11}$— or —C(=O)—NH—$Z^{11}$—, $Z^{11}$ is a $C_1$-$C_6$ alkanediyl group, $C_2$-$C_6$ alkenediyl group or phenylene group, which may contain a carbonyl moiety, ester bond, ether bond or hydroxyl moiety,
$Z^{2A}$ is a single bond or ester bond, $Z^{2B}$ is a single bond or $C_1$-$C_{12}$ divalent group which may contain an ester bond, ether bond, lactone ring, bromine or iodine,
$Z^3$ is a single bond, methylene, ethylene, phenylene, fluorinated phenylene, —O—$Z^{31}$—, —C(=O)—O—$Z^{31}$— or —C(=O)—NH—$Z^{31}$—, $Z^{31}$ is a $C_1$-$C_6$ alkanediyl group, $C_2$-$C_6$ alkenediyl group or phenylene group, which may contain a carbonyl moiety, ester bond, ether bond or hydroxyl moiety,
$Rf^1$ to $Rf^4$ are each independently hydrogen, fluorine or trifluoromethyl, at least one thereof being fluorine,
$R^{21}$ to $R^{28}$ are each independently a $C_1$-$C_{20}$ monovalent hydrocarbon group which may contain a heteroatom, any two of $R^{23}$, $R^{24}$ and $R^{25}$ or any two of $R^{26}$, $R^{27}$ and $R^{28}$ may bond together to form a ring with the sulfur atom to which they are attached, and
$M^-$ is a non-nucleophilic counter ion.

6. The resist composition of claim 1, further comprising an acid generator.

7. The resist composition of claim 1, further comprising an organic solvent.

8. The resist composition of claim 1, further comprising a quencher.

9. The resist composition of claim 1, further comprising a surfactant.

10. The resist composition of claim 1 wherein $X^2$ is a $C_1$-$C_{12}$ divalent hydrocarbon group which may contain hydroxyl, ether bond or ester bond.

11. A pattern forming process comprising the steps of applying the resist composition of claim 1 to form a resist film on a substrate, exposing the resist film to high-energy radiation, and developing the exposed resist film in a developer.

12. The process of claim 11 wherein the high-energy radiation is i-line, KrF excimer laser, ArF excimer laser, EB or EUV of wavelength 3 to 15 nm.

* * * * *